(12) United States Patent
Bisson et al.

(10) Patent No.: US 8,216,803 B2
(45) Date of Patent: Jul. 10, 2012

(54) COMPOSITIONS AND METHODS FOR REDUCING H₂S LEVELS IN FERMENTED BEVERAGES

(75) Inventors: Linda F. Bisson, Davis, CA (US);
Angela Linderholm, Davis, CA (US);
Kevin L. Dietzel, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 109 days.

(21) Appl. No.: 12/530,825

(22) PCT Filed: Mar. 13, 2008

(86) PCT No.: PCT/US2008/056847
§ 371 (c)(1),
(2), (4) Date: Nov. 9, 2009

(87) PCT Pub. No.: WO2008/115759
PCT Pub. Date: Sep. 25, 2008

(65) Prior Publication Data
US 2010/0143536 A1    Jun. 10, 2010

Related U.S. Application Data

(60) Provisional application No. 60/918,616, filed on Mar. 16, 2007, provisional application No. 60/959,366, filed on Jul. 12, 2007.

(51) Int. Cl.
*C12P 1/00* (2006.01)
*C12P 7/06* (2006.01)
*C12P 1/02* (2006.01)
*A23B 4/12* (2006.01)
*C12C 1/00* (2006.01)
*C12G 11/00* (2006.01)

(52) U.S. Cl. .............. 435/41; 435/161; 435/171; 426/7; 426/11; 426/15; 426/16

(58) Field of Classification Search ........................ None
See application file for complete search history.

(56) References Cited

U.S. PATENT DOCUMENTS

| | | | |
|---|---|---|---|
| 5,858,764 | A | 1/1999 | Osinga et al. |
| 6,133,041 | A | 10/2000 | Park |
| 6,140,108 | A | 10/2000 | Mortimer et al. |

OTHER PUBLICATIONS http://www.broadinstitute.org/regev/orthogroups/aln/5/2/OG4252-aa-og.aln, Sep. 19, 2011.*
Kumar et al., Large-Scale Mutagenesis of the Yeast Genome Using a Tn7-Derived Multipurpose Transposon; Genome Research, vol. 14, pp. 1975-1986, 2004.*
Kumar et al., Large-Scale Mutagenesis of the Yeast Genome Using a Tn7-Derived Multipurpose Transposon; Genome Research, vol. 14, pp. 1975-1986, supplemental materials, 2004.*
http://www.yeastgenome.org/cgi-bin/getSeq?seq=YFR030W&flankl=0&flankr=0&map=n3map, Sep. 19, 2011.*
http://www.ncbi.nlm.nih.gov/protein/YP_003232916.1, 2010.*
International Search Report and Written Opinion from PCT/US2008/056847, mailed Sep. 2, 2008 (7 pages).
GenBank Accession No. EF058164, (Version EF058164.1); Nov. 20, 2006. (3 pages) *Saccharomyces cerevisiae* isolate UCD932 sulfite reductase alpha subunit (*MET10*) gene, complete cds.
GenBank Accession No. EF058165, (Version EF058165.1); Nov. 20, 2006. (3 pages) *Saccharomyces cerevisiae* isolate UCD938 sulfite reductase alpha subunit (*MET10*) gene, complete cds.
GenBank Accession No. EF058166 (Version EF058166.1); Nov. 20, 2006. (3 pages) *Saccharomyces cerevisiae* isolate UCD939 sulfite reductase alpha subunit (*MET10*) gene, complete cds.
GenBank Accession No. EF058167, (Version EF058167.1); Nov. 20, 2006. (3 pages) *Saccharomyces cerevisiae* isolate UCD940 sulfite reductase alpha subunit (*MET10*) gene, complete cds.
GenBank Accession No. EF058168, (Version EF058168.1); Nov. 20, 2006. (3 pages) *Saccharomyces cerevisiae* isolate UCD942 sulfite reductase alpha subunit (*MET10*) gene, complete cds.
GenBank Accession No. EF058169 (Version EF058169.1); Nov. 20, 2006. (3 pages) *Saccharomyces cerevisiae* isolate UCD956 sulfite reductase alpha subunit (*MET10*) gene, complete cds.
GenBank Accession No. EF058170 (Version EF058170.1); Nov. 20, 2006. (3 pages) *Saccharomyces cerevisiae* isolate UCD920 sulfite reductase alpha subunit (*MET10*) gene, complete cds.
GenBank Accession No. EF058171 (Version EF058171.1); Nov. 20, 2006. (3 pages) *Saccharomyces cerevisiae* isolate UCD957 sulfite reductase alpha subunit (*MET10*) gene, complete cds.
GenBank Accession No. EF058172 (Version EF058172.1); Nov. 20, 2006. (3 pages) *Saccharomyces cerevisiae* isolate UCD934 sulfite reductase alpha subunit (*MET10*) gene, complete cds.
GenBank Accession No. EF058173 (Version EF058173.1); Nov. 20, 2006. (3 pages) *Saccharomyces cerevisiae* isolate UCD950 sulfite reductase alpha subunit (*MET10*) gene, complete cds.
Linderholm, A.L.; "Defining the genetic basis of hydrogen sulfideproduction by *Saccharomyces cerevisiae*"; Ph.D. dissertation; University of California, Davis, 2006. *Abstract/Summary only*. ProQuest document ID: 1273108651.
Linderholm et al.; "Identification of Genes Impacting Hydrogen Sulfide Formation in *Saccharomyces cerevisiae*"; *Appl. Envir. Micriobiol.*; 74(5): 1418-1427 (Mar. 2008)) *ePub on* Jan. 11, 2008.
Spiropoulos et al.; "MET17 and hydrogen sulfide formation in *Saccharomyces cerevisiae*; "*Appl. Envir. Microbiol.*; 66(10): 4421-4426 (2000).
Sutherland et al.; "Subunit and cofactor binding of *Saccharomyces cerevisiae* sulfite reductase—towards developing wine yeast with lowered ability to produce hydrogen sulfide"; *Aus. J. Grape Wine Res.*; 9: 186-193 (2003).

(Continued)

*Primary Examiner* — Celine Qian
*Assistant Examiner* — Addison D Ault
(74) *Attorney, Agent, or Firm* — Weaver Austin Villeneuve & Sampson LLP

(57) ABSTRACT

The present invention provides compositions and methods for reducing H₂S levels in fermented beverages.

25 Claims, 34 Drawing Sheets

OTHER PUBLICATIONS

Hansen et al. "Two Divergent *MET10* Genes, One from *Saccharomyces cerevisae* and One from *Saccharomyes carlsbergensis*, Encode the alpha Subunit of Sulfite Reductase and Specify Potential Binding Sites for FAD and NADPH", *J. Bacteriol*, Oct. 1994, 176(19): pp. 6050-6058.

Linderholm et al. "Identification of *MET10-932* and Characterization as an Allele Reducing Hydrogen Sulfide Formation in Wine Strains of *Saccharomyces cerevisiae*", Applied and Environmental Microbiology, Dec. 2010, vol. 76, No. 23, p. 7699-7707.

Office Action for Chinese Patent Application No. 200880008551.5 mailed Apr. 27, 2011.

Office Action for European Patent Application No. 08743850.3 mailed Jan. 11, 2011.

Office Action for European Patent Application No. 08743850.3 mailed May 30, 2011.

Office Action for New Zealand Patent Application No. 579569 mailed Sep. 8, 2010.

Office Action for Russian Patent Application No. 2009138248 mailed Nov. 24, 2011.

* cited by examiner

Figure 2A

```
             10         20         30         40
        ....|....| ....|....| ....|....| ....|....|
S288c   ATGCCAGTTG AGTTTGCTAC CAATCCTTTT GGCGAGGCCA
UCD522  ATGCCAGTTG AGTTTGCTAC CAATCCTTTT GGCGAGGCCA
UCD932  ATGCCAGTTG AGTTTGCTAC CAATCCTTTT GGCGAGGCCA
UCD934  ATGCCAGTTG AGTTTGCTAC CAATCCTTTT GGCGAGGCCA
UCD938  ATGCCAGTTG AGTTTGCTAC CAATCCTTTT GGCGAGGCCA
UCD939  ATGCCAGTTG AGTTTGCTAC CAATCCTTTT GGCGAGGCCA
UCD940  ATGCCAGTTG AGTTTGCTAC CAATCCTTTT GGCGAGGCCA
UCD942  ATGCCAGTTG AGTTTGCTAC CAATCCTTTT GGCGAGGCCA
UCD950  ATGCCAGTTG AGTTTGCTAC CAATCCTTTT GGCGAGGCCA
UCD956  ATGCCAGTTG AGTTTGCTAC CAATCCTTTT GGCGAGGCCA
UCD957  ATGCCAGTTG AGTTTGCTAC CAATCCTTTT GGCGAGGCCA 50         60         70         80
        ....|....| ....|....| ....|....| ....|....|
S288c   AAAATGCAAC TTCACTGCCA AAATATGGTA CACCCGTAAC
UCD522  AAAATGCAAC TTCACTGCCA AAATATGGTA CACCCGTAAC
UCD932  AAAATGCAAC TTCACTGCCA AAATATGGTA CACCCGTAAC
UCD934  AAAATGCAAC TTCACTGCCA AAATATGGTA CACCCGTAAC
UCD938  AAAATGCAAC TTCACTGCCA AAATATGGTA CACCCGTAAC
UCD939  AAAATGCAAC TTCACTGCCA AAATATGGTA CACCCGTAAC
UCD940  AAAATGCAAC TTCACTGCCA AAATATGGTA CACCCGTAAC
UCD942  AAAATGCAAC TTCACTGCCA AAATATGGTA CACCCGTAAC
UCD950  AAAATGCAAC TTCACTGCCA AAATATGGTA CACCCGTAAC
UCD956  AAAATGCAAC TTCACTGCCA AAATATGGTA CACCCGTAAC
UCD957  AAAATGCAAC TTCACTGCCA AAATATGGTA CACCCGTAAC 90        100        110        120
        ....|....| ....|....| ....|....| ....|....|
S288c   TGCCATTTCA TCTGTGCTGT TCAATAACGT GGACTCCATT
UCD522  TGCCATTTCA TCTGTGCTGT TCAATAACGT GGACTCCATT
UCD932  TGCCATTTCA TCTGTGCTGT TCAATAACGT GGACTCCATT
UCD934  TGCCATTTCA TCTGTGCTGT TCAATAACGT GGACTCCATT
UCD938  TGCCATTTCA TCTGTGCTGT TCAATAACGT GGACTCCATT
UCD939  TGCCATTTCA TCTGTGCTGT TCAATAACGT GGACTCCATT
UCD940  TGCCATTTCA TCTGTGCTGT TCAATAACGT GGACTCCATT
UCD942  TGCCATTTCA TCTGTGCTGT TCAATAACGT GGACTCCATT
UCD950  TGCCATTTCA TCTGTGCTGT TCAATAACGT GGACTCCATT
UCD956  TGCCATTTCA TCTGTGCTGT TCAATAACGT GGACTCCATT
UCD957  TGCCATTTCA TCTGTGCTGT TCAATAACGT GGACTCCATT
```

*Figure 2B*

```
                    130        140        150        160
                ....|....| ....|....| ....|....| ....|....|
        S288c   TTTGCTTACA AGTCCTTTTC TCAACCCGAT TTGCTACACC
        UCD522  TTTGCTTACA AGTCCTTTTC TCAACCCGAT TTGTTACACC
        UCD932  TTTGCTTACA AGTCCTTTTC TCAACCCGAT TTGTTACACC
        UCD934  TTTGCTTACA AGTCCTTTTC TCAACCCGAT TTGTTACACC
        UCD938  TTTGCTTACA AGTCCTTTTC TCAACCCGAT TTGTTACACC
        UCD939  TTTGCTTACA AGTCCTTTTC TCAACCCGAT TTGTTACACC
        UCD940  TTTGCTTACA AGTCCTTTTC TCAACCCGAT TTGTTACACC
        UCD942  TTTGCTTACA AGTCCTTTTC TCAACCCGAT TTGTTACACC
        UCD950  TTTGCTTACA AGTCCTTTTC TCAACCCGAT TTGTTACACC
        UCD956  TTTGCTTACA AGTCCTTTTC TCAACCCGAT TTGTTACACC
        UCD957  TTTGCTTACA AGTCCTTTTC TCAACCCGAT TTGTTACACC 170        180        190        200
                ....|....| ....|....| ....|....| ....|....|
        S288c   AAGATCTAAA AAAATGGTCT GAAAAGCGTG GTAACGAATC
        UCD522  AAGATCTAAA AAAATGGTCT GAAAAGCGTG GTAACGAATC
        UCD932  AAGATCTAAA AAAATGGTCT GAAAAGCGTG GTAACGAATC
        UCD934  AAGATCTAAA AAAATGGTCT GAAAAGCGTG GTAACGAATC
        UCD938  AAGATCTAAA AAAATGGTCT GAAAAGCGTG GTAACGAATC
        UCD939  AAGATCTAAA AAAATGGTCT GAAAAGCGTG GTAACGAATC
        UCD940  AAGATCTAAA AAAATGGTCT GAAAAGCGTG GTAACGAATC
        UCD942  AAGATCTAAA AAAATGGTCT GAAAAGCGTG GTAACGAATC
        UCD950  AAGATCTAAA AAAATGGTCT GAAAAGCGTG GTAACGAATC
        UCD956  AAGATCTAAA AAAATGGTCT GAAAAGCGTG GTAACGAATC
        UCD957  AAGATCTAAA AAAATGGTCT GAAAAGCGTG GTAACGAATC 210        220        230        240
                ....|....| ....|....| ....|....| ....|....|
        S288c   ACGTGGGAAG CCATTTTTCC AAGAGCTGGA TATCAGATCT
        UCD522  ACGTGGGAAG CCATTTTTCC AAGAGCTGGA TATCAGATCT
        UCD932  ACGTGGGAAG CCATTTTTCC AAGAGCTGGA TATCAGATCT
        UCD934  ACGTGGGAAG CCATTTTTCC AAGAGCTGGA TATCAGATCT
        UCD938  ACGTGGGAAG CCATTTTTCC AAGAGCTGGA TATCAGATCT
        UCD939  ACGTGGGAAG CCATTTTTCC AAGAGCTGGA TATCAGATCT
        UCD940  ACGTGGGAAG CCATTTTTCC AAGAGCTGGA TATCAGATCT
        UCD942  ACGTGGGAAG CCATTTTTCC AAGAGCTGGA TATCAGATCT
        UCD950  ACGTGGGAAG CCATTTTTCC AAGAGCTGGA TATCAGATCT
        UCD956  ACGTGGGAAG CCATTTTTCC AAGAGCTGGA TATCAGATCT
        UCD957  ACGTGGGAAG CCATTTTTCC AAGAGCTGGA TATCAGATCT
```

Figure 2C

```
              250         260         270         280
         ....|....|  ....|....|  ....|....|  ....|....|
S288c    GGCGCTGGTT  TGGCTCCTTT  AGGGTTTTCT  CATGGATTGA
UCD522   GGCGCTGGTT  TGGCTCCTTT  AGGGTTTTCT  CATGGATTGA
UCD932   GGCGCTGGTT  TGGCTCCTTT  AGGGTTTTCT  CATGGATTGA
UCD934   GGCGCTGGTT  TGGCTCCTTT  AGGGTTTTCT  CATGGATTGA
UCD938   GGCGCTGGTT  TGGCTCCTTT  AGGGTTTTCT  CATGGATTGA
UCD939   GGCGCTGGTT  TGGCTCCTTT  AGGGTTTTCT  CATGGATTGA
UCD940   GGCGCTGGTT  TGGCTCCTTT  AGGGTTTTCT  CATGGATTGA
UCD942   GGCGCTGGTT  TGGCTCCTTT  AGGGTTTTCT  CATGGATTGA
UCD950   GGCGCTGGTT  TGGCTCCTTT  AGGGTTTTCT  CATGGATTGA
UCD956   GGCGCTGGTT  TGGCTCCTTT  AGGGTTTTCT  CATGGATTGA
UCD957   GGCGCTGGTT  TGGCTCCTTT  AGGGTTTTCT  CATGGATTGA 290         300         310         320
         ....|....|  ....|....|  ....|....|  ....|....|
S288c    AGAACACTAC  AGCAATTGTT  GCTCCAGGGT  TTTCGCTGCC
UCD522   AGAACACTAC  AGCAATTGTT  GCTCCAGGGT  TTTCGCTGCC
UCD932   AGAACACTAC  AGCAATTGTT  GCTCCAGGGT  TTTCGCTGCC
UCD934   AGAACACTAC  AGCAATTGTT  GCTCCAGGGT  TTTCGCTGCC
UCD938   AGAACACTAC  AGCAATTGTT  GCTCCAGGGT  TTTCGCTGCC
UCD939   AGAACACTAC  AGCAATTGTT  GCTCCAGGGT  TTTCGCTGCC
UCD940   AGAACACTAC  AGCAATTGTT  GCTCCAGGGT  TTTCGCTGCC
UCD942   AGAACACTAC  AGCAATTGTT  GCTCCAGGGT  TTTCGCTGCC
UCD950   AGAACACTAC  AGCAATTGTT  GCTCCAGGGT  TTTCGCTGCC
UCD956   AGAACACTAC  AGCAATTGTT  GCTCCAGGGT  TTTCGCTGCC
UCD957   AGAACACTAC  AGCAATTGTT  GCTCCAGGGT  TTTCGCTGCC 330         340         350         360
         ....|....|  ....|....|  ....|....|  ....|....|
S288c    ATACTTCATT  AACTCTTTGA  AAACCGTCTC  TCATGATGGT
UCD522   ATACTTCATT  AACTCTTTGA  AAACCGTCTC  TCATGATGGT
UCD932   ATACTTCATT  AACTCTTTGA  AAACCGTCTC  TCATGATGGT
UCD934   ATACTTCATT  AACTCTTTGA  AAACCGTCTC  TCATGATGGT
UCD938   ATACTTCATT  AACTCTTTGA  AAACCGTCTC  TCATGATGGT
UCD939   ATACTTCATT  AACTCTTTGA  AAACCGTCTC  TCATGATGGT
UCD940   ATACTTCATT  AACTCTTTGA  AAACCGTCTC  TCATGATGGT
UCD942   ATACTTCATT  AACTCTTTGA  AAACCGTCTC  TCATGATGGT
UCD950   ATACTTCATT  AACTCTTTGA  AAACCGTCTC  TCATGATGGT
UCD956   ATACTTCATT  AACTCTTTGA  AAACCGTCTC  TCATGATGGT
UCD957   ATACTTCATT  AACTCTTTGA  AAACCGTCTC  TCATGATGGT
```

Figure 2D

```
                 370        380        390        400
            ....|....| ....|....| ....|....| ....|....|
S288c       AAGTTTCTTT TGAATGTTGG TGCTTTAAAC TACGACAATG
UCD522      AAGTTTCTTT TGAATGTTGG TGCTTTAAAC TACGACAATG
UCD932      AAGTTTCTTT TGAATGTTGG TGCTTTAAAC TACGACAATG
UCD934      AAGTTTCTTT TGAATGTTGG TGCTTTAAAC TACGACAATG
UCD938      AAGTTTCTTT TGAATGTTGG TGCTTTAAAC TACGACAATG
UCD939      AAGTTTCTTT TGAATGTTGG TGCTTTAAAC TACGACAATG
UCD940      AAGTTTCTTT TGAATGTTGG TGCTTTAAAC TACGACAATG
UCD942      AAGTTTCTTT TGAATGTTGG TGCTTTAAAC TACGACAATG
UCD950      AAGTTTCTTT TGAATGTTGG TGCTTTAAAC TACGACAATG
UCD956      AAGTTTCTTT TGAATGTTGG TGCTTTAAAC TACGACAATG
UCD957      AAGTTTCTTT TGAATGTTGG TGCTTTAAAC TACGACAATG 410        420        430        440
            ....|....| ....|....| ....|....| ....|....|
S288c       CTACCGGCTC TGTCACCAAC GATTATGTAA CCGCATTGGA
UCD522      CTACCGGCTC TGTCACCAAC GATTATGTAA CCGCATTGGA
UCD932      CTAACGGCTC TGTCACCAAC GATTATGTAA CCGCATTGGA
UCD934      CTACCGGCTC TGTCACCAAC GATTATGTAA CCGCATTGGA
UCD938      CTAACGGCTC TGTCACCAAC GATTATGTAA CCGCATTGGA
UCD939      CTACCGGCTC TGTCACCAAC GATTATGTAA CCGCATTGGA
UCD940      CTAMCGGCTC TGTCACCAAC GATTATGTAA CCGCATTGGA
UCD942      CTAACGGCTC TGTCACCAAC GATTATGTAA CCGCATTGGA
UCD950      CTACCGGCTC TGTCACCAAC GATTATGTAA CCGCATTGGA
UCD956      CTACCGGCTC TGTCACCAAC GATTATGTAA CCGCATTGGA
UCD957      CTACCGGCTC TGTCACCAAC GATTATGTAA CCGCATTGGA 450        460        470        480
            ....|....| ....|....| ....|....| ....|....|
S288c       TGCTGCTTCC AAGCTGAAGT ATGGTGTCGT GACTCCGATT
UCD522      TGCTGCTTCC AAGCTGAAGT ATGGTGTCGT GACTCCGATT
UCD932      TGCTGCTTCC AAGCTGAAGT ATGGTGTCGT GACTCCGATT
UCD934      TGCTGCTTCC AAGCTGAAGT ATGGTGTCGT GACTCCGATT
UCD938      TGCTGCTTCC AAGCTGAAGT ATGGTGTCGT GACTCCGATT
UCD939      TGCTGCTTCC AAGCTGAAGT ATGGTGTCGT GACTCCGATT
UCD940      TGCTGCTTCC AAGCTGAAGT ATGGTGTCGT GACTCCGATT
UCD942      TGCTGCTTCC AAGCTGAAGT ATGGTGTCGT GACTCCGATT
UCD950      TGCTGCTTCC AAGCTGAAGT ATGGTGTCGT GACTCCGATT
UCD956      TGCTGCTTCC AAGCTGAAGT ATGGTGTCGT GACTCCGATT
UCD957      TGCTGCTTCC AAGCTGAAGT ATGGTGTCGT GACTCCGATT
```

*Figure 2E*

```
              490        500        510        520
         ....|....| ....|....| ....|....| ....|....|
S288c    TCCGCTAACG AGGTACAAAG TGTCGCCTTA CTGGCATTGG
UCD522   TCCGCTAACG AGGTACAAAG TGTCGCCTTA CTGACATTGG
UCD932   TCCGCTAACG AGGTACAAAG TGTCGCCTTA CTGACATTGG
UCD934   TCCGCTAACG AGGTACAAAG TGTCGCCTTA CTGGCATTGG
UCD938   TCCGCTAACG AGGTACAAAG TGTCGCCTTA CTGACATTGG
UCD939   TCCGCTAACG AGGTACAAAG TGTCGCCTTA CTGRCATTGG
UCD940   TCCGCTAACG AGGTACAAAG TGTCGCCTTA CTGACATTGG
UCD942   TCCGCTAACG AGGTACAAAG TGTCGCCTTA CTGACATTGG
UCD950   TCCGCTAACG AGGTACAAAG TGTCGCCTTA CTGGCATTGG
UCD956   TCCGCTAACG AGGTACAAAG TGTCGCCTTA CTGACATTGG
UCD957   TCCGCTAACG AGGTACAAAG TGTCGCCTTA CTGGCATTGG 530        540        550        560
         ....|....| ....|....| ....|....| ....|....|
S288c    CGATTGCCAC TTTCAGTAAT AACTCCGGAG CTATCAATTT
UCD522   CGATTGCCAC TTTCAGTAAT AACTCCGGAG CTATCAATTT
UCD932   CGATTGCCAC TTTCAGTAAT AACTCCGGAG CTATCAATTT
UCD934   CGATTGCCAC TTTCAGTAAT AACTCCGGAG CTATCAATTT
UCD938   CGATTGCCAC TTTCAGTAAT AACTCCGGAG CTATCAATTT
UCD939   CGATTGCCAC TTTCAGTAAT AACTCCGGAG CTATCAATTT
UCD940   CGATTGCCAC TTTCAGTAAT AACTCCGGAG CTATCAATTT
UCD942   CGATTGCCAC TTTCAGTAAT AACTCCGGAG CTATCAATTT
UCD950   CGATTGCCAC TTTCAGTAAT AACTCCGGAG CTATCAATTT
UCD956   CGATTGCCAC TTTCAGTAAT AACTCCGGAG CTATCAATTT
UCD957   CGATTGCCAC TTTCAGTAAT AACTCCGGAG CTATCAATTT 570        580        590        600
         ....|....| ....|....| ....|....| ....|....|
S288c    ATTTGACGGA TTAAACTACT CGAAAACCGT CTTGCCGTTG
UCD522   ATTTGACGGA TTAAACTACT CGAAAACCGT CTTGCCGTTG
UCD932   ATTTGACGGA TTAAACTACT CGAAAACCGT CTTGCCGTTG
UCD934   ATTTGACGGA TTAAACTACT CGAAAACCGT CTTGCCGTTG
UCD938   ATTTGACGGA TTAAACTACT CGAAAACCGT CTTGCCGTTG
UCD939   ATTTGACGGA TTAAACTACT CGAAAACCGT CTTGCCGTTG
UCD940   ATTTGACGGA TTAAACTACT CGAAAACCGT CTTGCCGTTG
UCD942   ATTTGACGGA TTAAACTACT CGAAAACCGT CTTGCCGTTG
UCD950   ATTTGACGGA TTAAACTACT CGAAAACCGT CTTGCCGTTG
UCD956   ATTTGACGGA TTAAACTACT CGAAAACCGT CTTGCCGTTG
UCD957   ATTTGACGGA TTAAACTACT CGAAAACCGT CTTGCCGTTG
```

*Figure 2F*

```
                610        620        630        640
           ....|....| ....|....| ....|....| ....|....|
S288c      GTCGAATCTG TTCCTGAGGC ATCTATTTTG GCAAAACTAT
UCD522     GTCGAATCTG TTCCTGAGGC ATCTATTTTG GCAAAACTAT
UCD932     GTCGAATCTG TTCCTGAGGC ATCTATTTTG GCAAAACTAT
UCD934     GTCGAATCTG TTCCTGAGGC ATCTATTTTG GCAAAACTAT
UCD938     GTCGAATCTG TTCCTGAGGC ATCTATTTTG GCAAAACTAT
UCD939     GTCGAATCTG TTCCTGAGGC ATCTATTTTG GCAAAACTAT
UCD940     GTCGAATCTG TTCCTGAGGC ATCTATTTTG GCAAAACTAT
UCD942     GTCGAATCTG TTCCTGAGGC ATCTATTTTG GCAAAACTAT
UCD950     GTCGAATCTG TTCCTGAGGC ATCTATTTTG GCAAAACTAT
UCD956     GTCGAATCTG TTCCTGAGGC ATCTATTTTG GCAAAACTAT
UCD957     GTCGAATCTG TTCCTGAGGC ATCTATTTTG GCAAAACTAT 650        660        670        680
           ....|....| ....|....| ....|....| ....|....|
S288c      CCAAAGTTAT TGCACCAGAT GCTGCCTTTG ATGATGTCTT
UCD522     CCAAAGTTAT TGCACCAGAT GCTGCCTTTG ATGATGTCTT
UCD932     CCAAAGTTAT TGCACCAGAT GCTGCCTTTG ATGATGTCTT
UCD934     CCAAAGTTAT TGCACCAGAT GCTGCCTTTG ATGATGTCTT
UCD938     CCAAAGTTAT TGCACCAGAT GCTGCCTTTG ATGATGTCTT
UCD939     CCAAAGTTAT TGCACCAGAT GCTGCCTTTG ATGATGTCTT
UCD940     CCAAAGTTAT TGCACCAGAT GCTGCCTTTG ATGATGTCTT
UCD942     CCAAAGTTAT TGCACCAGAT GCTGCCTTTG ATGATGTCTT
UCD950     CCAAAGTTAT TGCACCAGAT GCTGCCTTTG ATGATGTCTT
UCD956     CCAAAGTTAT TGCACCAGAT GCTGCCTTTG ATGATGTCTT
UCD957     CCAAAGTTAT TGCACCAGAT GCTGCCTTTG ATGATGTCTT 690        700        710        720
           ....|....| ....|....| ....|....| ....|....|
S288c      GGATAAGTTT AATGAATTGA CTGGATTGAG ACTACATAAT
UCD522     GGATAAGTTT AATGAATTGA CTGGATTGAG ACTACATAAT
UCD932     GGATAAGTTT AATGAATTGA CTGGATTGAG ACTACATAAT
UCD934     GGATAAGTTT AATGAATTGA CTGGATTGAG ACTACATAAT
UCD938     GGATAAGTTT AATGAATTGA CTGGATTGAG ACTACATAAT
UCD939     GGATAAGTTT AATGAATTGA CTGGATTGAG ACTACATAAT
UCD940     GGATAAGTTT AATGAATTGA CTGGATTGAG ACTACATAAT
UCD942     GGATAAGTTT AATGAATTGA CTGGATTGAG ACTACATAAT
UCD950     GGATAAGTTT AATGAATTGA CTGGATTGAG ACTACATAAT
UCD956     GGATAAGTTT AATGAATTGA CTGGATTGAG ACTACATAAT
UCD957     GGATAAGTTT AATGAATTGA CTGGATTGAG ACTACATAAT
```

*Figure 2G*

```
              730        740        750        760
         ....|....| ....|....| ....|....| ....|....|
S288c    TTCCAATACT TTGGTGCTCA GGATGCTGAA ACTGTGTTTA
UCD522   TTCCAATACT TTGGTGCTCA GGATGCTGAA ACTGTGTTTA
UCD932   TTCCAATACT TTGGTGCTCA GGATGCTGAA ACTGTGTTTA
UCD934   TTCCAATACT TTGGTGCTCA GGATGCTGAA ACTGTGTTTA
UCD938   TTCCAATACT TTGGTGCTCA GGATGCTGAA ACTGTGTTTA
UCD939   TTCCAATACT TTGGTGCTCA GGATGCTGAA ACTGTGTTTA
UCD940   TTCCAATACT TTGGTGCTCA GGATGCTGAA ACTGTGTTTA
UCD942   TTCCAATACT TTGGTGCTCA GGATGCTGAA ACTGTGTTTA
UCD950   TTCCAATACT TTGGTGCTCA GGATGCTGAA ACTGTGTTTA
UCD956   TTCCAATACT TTGGTGCTCA GGATGCTGAA ACTGTGTTTA
UCD957   TTCCAATACT TTGGTGCTCA GGATGCTGAA ACTGTGTTTA 770        780        790        800
         ....|....| ....|....| ....|....| ....|....|
S288c    TCACTTATGG GTCTTTAGAA TCCGAATTGT TCAACTCTGC
UCD522   TCACTTATGG GTCTTTAGAA TCCGAATTGT TCAACTCTGC
UCD932   TCACTTATGG GTCTTTAGAA TCCGAATTGT TCAACTCTGC
UCD934   TCACTTATGG GTCTTTAGAA TCCGAATTGT TCAACTCTGC
UCD938   TCACTTATGG GTCTTTAGAA TCCGAATTGT TCAACTCTGC
UCD939   TCACTTATGG GTCTTTAGAA TCCGAATTGT TCAACTCTGC
UCD940   TCACTTATGG GTCTTTAGAA TCCGAATTGT TCAACTCTGC
UCD942   TCACTTATGG GTCTTTAGAA TCCGAATTGT TCAACTCTGC
UCD950   TCACTTATGG GTCTTTAGAA TCCGAATTGT TCAACTCTGC
UCD956   TCACTTATGG GTCTTTAGAA TCCGAATTGT TCAACTCTGC
UCD957   TCACTTATGG GTCTTTAGAA TCCGAATTGT TCAACTCTGC 810        820        830        840
         ....|....| ....|....| ....|....| ....|....|
S288c    GATTAGTGGT AATAATTCCA AAATCGGGTT AATCAACGTC
UCD522   GATTAGTGGT AATAATTCCA AAATCGGGTT AATCAACGTC
UCD932   GATTAGTGGT AATAATTCCA AAATCGGGTT AATCAACGTC
UCD934   GATTAGTGGT AATAATTCCA AAATCGGGTT AATCAACGTC
UCD938   GATTAGTGGT AATAATTCCA AAATCGGGTT AATCAACGTC
UCD939   GATTAGTGGT AATAATTCCA AAATCGGGTT AATCAACGTC
UCD940   GATTAGTGGT AATAATTCCA AAATCGGGTT AATCAACGTC
UCD942   GATTAGTGGT AATAATTCCA AAATCGGGTT AATCAACGTC
UCD950   GATTAGTGGT AATAATTCCA AAATCGGGTT AATCAACGTC
UCD956   GATTAGTGGT AATAATTCCA AAATCGGGTT AATCAACGTC
UCD957   GATTAGTGGT AATAATTCCA AAATCGGGTT AATCAACGTC
```

*Figure 2H*

```
                 850        860        870        880
            ....|....| ....|....| ....|....| ....|....|
   S288c    AGAGTGCCAT TACCTTTTAA CGTTGCTAAG TTTGTCACTC
   UCD522   AGAGTACCAT TACCTTTTAA CGTTGCTAAG TTTGTCACTC
   UCD932   AGAGTACCAT TACCTTTTAA CGTTGCTAAG TTTGTCACTC
   UCD934   AGAGTACCAT TACCTTTTAA CGTTGCTAAG TTTGTCACTC
   UCD938   AGAGTACCAT TACCTTTTAA CGTTGCTAAG TTTGTCACTC
   UCD939   AGAGTACCAT TACCTTTTAA CGTTGCTAAG TTTGTCACTC
   UCD940   AGAGTACCAT TACCTTTTAA CGTTGCTAAG TTTGTCACTC
   UCD942   AGAGTACCAT TACCTTTTAA CGTTGCTAAG TTTGTCACTC
   UCD950   AGAGTACCAT TACCTTTTAA CGTTGCTAAG TTTGTCACTC
   UCD956   AGAGTACCAT TACCTTTTAA CGTTGCTAAG TTTGTCACTC
   UCD957   AGAGTACCAT TACCTTTTAA CGTTGCTAAG TTTGTCACTC 890        900        910        920
            ....|....| ....|....| ....|....| ....|....|
   S288c    ACGTTCCATC CACTACCAAA CAAATTGTTG TTATAGGCCA
   UCD522   ACGTTCCATC CACTACCAAA CAAATTGTTG TTATAGGCCA
   UCD932   ACGTTCCATC CACTACCAAA CAAATTGTTG TTATAGGCCA
   UCD934   ACGTTCCATC CACTACCAAA CAAATTGTTG TTATAGGCCA
   UCD938   ACGTTCCATC CACTACCAAA CAAATTGTTG TTATAGGCCA
   UCD939   ACGTTCCATC CACTACCAAA CAAATTGTTG TTATAGGCCA
   UCD940   ACGTTCCATC CACTACCAAA CAAATTGTTG TTATAGGCCA
   UCD942   ACGTTCCATC CACTACCAAA CAAATTGTTG TTATAGGCCA
   UCD950   ACGTTCCATC CACTACCAAA CAAATTGTTG TTATAGGCCA
   UCD956   ACGTTCCATC CACTACCAAA CAAATTGTTG TTATAGGCCA
   UCD957   ACGTTCCATC CACTACCAAA CAAATTGTTG TTATAGGCCA 930        940        950        960
            ....|....| ....|....| ....|....| ....|....|
   S288c    AACTTTGGAT GGTTCTTCGC CTTCTTTCTT GAGATCTCAA
   UCD522   AACTTTGGAT GGTTCTTCGC CTTCTTTCTT GAGATCTCAA
   UCD932   AACTTTGGAT GGTTCTTCGC CTTCTTTCTT GAGATCTCAA
   UCD934   AACTTTGGAT GGTTCTTCGC CTTCTTTCTT GAGATCTCAA
   UCD938   AACTTTGGAT GGTTCTTCGC CTTCTTTCTT GAGATCTCAA
   UCD939   AACTTTGGAT GGTTCTTCGC CTTCTTTCTT GAGATCTCAA
   UCD940   AACTTTGGAT GGTTCTTCGY CTTCTTTCTT GAGATCTCAA
   UCD942   AACTTTGGAT GGTTCTTCGC CTTCTTTCTT GAGATCTCAA
   UCD950   AACTTTGGAT GGTTCTTCGC CTTCTTTCTT GAGATCTCAA
   UCD956   AACTTTGGAT GGTTCTTCGC CTTCTTTCTT GAGATCTCAA
   UCD957   AACTTTGGAT GGTTCTTCGC CTTCTTTCTT GAGATCTCAA
```

*Figure 2I*

```
              970        980        990       1000
          ....|....| ....|....| ....|....| ....|....|
S288c     GTTTCAGCCG CCTTATTTTA CCACGGCCGC ACCTCAATTA
UCD522    GTTTCAGCCG CCTTATTTTA CCACGGCCGC ACCTCAATTA
UCD932    GTTTCAGCCG CCTTATTTTA CCACGGCCGC ACCTCAATTA
UCD934    GTTTCAGCCG CCTTATTTTA CCACGGCCGC ACCTCAATTA
UCD938    GTTTCAGCCG CCTTATTTTA CCACGGCCGC ACCTCAATTA
UCD939    GTTTCAGCCG CCTTATTTTA CCACGGCCGC ACCTCAATTA
UCD940    GTTTCAGCCG CCTTATTTTA CCACGGCCGC ACCTCAATTA
UCD942    GTTTCAGCCG CCTTATTTTA CCACGGCCGC ACCTCAATTA
UCD950    GTTTCAGCCG CCTTATTTTA CCACGGCCGC ACCTCAATTA
UCD956    GTTTCAGCCG CCTTATTTTA CCACGGCCGC ACCTCAATTA
UCD957    GTTTCAGCCG CCTTATTTTA CCACGGCCGC ACCTCAATTA 1010       1020       1030       1040
          ....|....| ....|....| ....|....| ....|....|
S288c     GCGTTTCTGA GTACATCTAT CAACCAGATT TCATTTGGTC
UCD522    GCGTTTCTGA GTACATCTAT CAACCAGATT TCATTTGGTC
UCD932    GCGTTTCTGA GTACATCTAT CAACCAGATT TCATTTGGTC
UCD934    GCGTTTCTGA GTACATCTAT CAACCAGATT TCATTTGGTC
UCD938    GCGTTTCTGA GTACATCTAT CAACCAGATT TCATTTGGTC
UCD939    GCGTTTCTGA GTACATCTAT CAACCAGATT TCATTTGGTC
UCD940    GCGTTTCTGA GTACATCTAT CAACCAGATT TCATTTGGTC
UCD942    GCGTTTCTGA GTACATCTAT CAACCAGATT TCATTTGGTC
UCD950    GCGTTTCTGA GTACATCTAT CAACCAGATT TCATTTGGTC
UCD956    GCGTTTCTGA GTACATCTAT CAACCAGATT TCATTTGGTC
UCD957    GCGTTTCTGA GTACATCTAT CAACCAGATT TCATTTGGTC 1050       1060       1070       1080
          ....|....| ....|....| ....|....| ....|....|
S288c     CCCAAAAGCT GTCAAATCAA TTGTATCGTC ATTCATCCCT
UCD522    CCCAAAAGCT GTCAAATCAA TTGTATCGTC ATTCATCCCT
UCD932    CCCAAAAGCT GTCAAATCAA TTGTATCGTC ATTCATCCCT
UCD934    CCCAAAAGCT GTCAAATCAA TTGTATCGTC ATTCATCCCT
UCD938    CCCAAAAGCT GTCAAATCAA TTGTATCGTC ATTCATCCCT
UCD939    CCCAAAAGCT GTCAAATCAA TTGTATCGTC ATTCATCCCT
UCD940    CCCAAAAGCT GTCAAATCAA TTGTATCGTC ATTCATCCCT
UCD942    CCCAAAAGCT GTCAAATCAA TTGTATCGTC ATTCATCCCT
UCD950    CCCAAAAGCT GTCAAATCAA TTGTATCGTC ATTCATCCCT
UCD956    CCCAAAAGCT GTCAAATCAA TTGTATCGTC ATTCATCCCT
UCD957    CCCAAAAGCT GTCAAATCAA TTGTATCGTC ATTCATCCCT
```

Figure 2J

```
               1090       1100       1110       1120
           ....|....| ....|....| ....|....| ....|....|
S288c      GAATTCACTT ACAATGCCGA TTCATCTTTC GGCGAAGGAT
UCD522     GAATTCACTT ACAATGCCGA TTCATCTTTC GGCGAAGGAT
UCD932     GAATTCACTT ACAATGCCGA TTCATCTTTC GGCGAAGGAT
UCD934     GAATTCACTT ACAATGCCGA TTCATCTTTC GGCGAAGGAT
UCD938     GAATTCACTT ACAATGCCGA TTCATCTTTC GGCGAAGGAT
UCD939     GAATTCACTT ACAATGCCGA TTCATCTTTC GGCGAAGGAT
UCD940     GAATTCACTT ACAATGCCGA TTCATCTTTC GGCGAAGGAT
UCD942     GAATTCACTT ACAATGCCGA TTCATCTTTC GGCGAAGGAT
UCD950     GAATTCACTT ACAATGCCGA TTCATCTTTC GGCGAAGGAT
UCD956     GAATTCACTT ACAATGCCGA TTCATCTTTC GGCGAAGGAT
UCD957     GAATTCACTT ACAATGCCGA TTCATCTTTC GGCGAAGGAT 1130       1140       1150       1160
           ....|....| ....|....| ....|....| ....|....|
S288c      TCATTTATTG GGCCTCTGAT AAGAGTATCA ATATTGATGT
UCD522     TCATTTATTG GGCCTCTGAT AAGAGTATCA ATATTGATGT
UCD932     TCATTTATTG GGCCTCTGAT AAGAGTATCA ATATTGATGT
UCD934     TCATTTATTG GGCCTCTGAT AAGAGTATCA ATATTGATGT
UCD938     TCATTTATTG GGCCTCTGAT AAGAGTATCA ATATTGATGT
UCD939     TCATTTATTG GGCCTCTGAT AAGAGTATCA ATATTGATGT
UCD940     TCATTTATTG GGCCTCTGAT AAGAGTATCA ATATTGATGT
UCD942     TCATTTATTG GGCCTCTGAT AAGAGTATCA ATATTGATGT
UCD950     TCATTTATTG GGCCTCTGAT AAGAGTATCA ATATTGATGT
UCD956     TCATTTATTG GGCCTCTGAT AAGAGTATCA ATATTGATGT
UCD957     TCATTTATTG GGCCTCTGAT AAGAGTATCA ATATTGATGT 1170       1180       1190       1200
           ....|....| ....|....| ....|....| ....|....|
S288c      TGCCTCCAAA CTTGTGAAAG CTCTGTCTTT GGAAGATGGG
UCD522     TGCCTCCAAA CTTGTGAAAG CTCTGTCTTT GGAAGATGGG
UCD932     TGCCTCCAAA CTTGTGAAAG CTCTGTCTTT GGAAGATGGG
UCD934     TGCCTCCAAA CTTGTGAAAG CTCTGTCTTT GGAAGATGGG
UCD938     TGCCTCCAAA CTTGTGAAAG CTCTGTCTTT GGAAGATGGG
UCD939     TGCCTCCAAA CTTGTGAAAG CTCTGTCTTT GGAAGATGGG
UCD940     TGCCTCCAAA CTTGTGAAAG CTCTGTCTTT GGAAGATGGG
UCD942     TGCCTCCAAA CTTGTGAAAG CTCTGTCTTT GGAAGATGGG
UCD950     TGCCTCCAAA CTTGTGAAAG CTCTGTCTTT GGAAGATGGG
UCD956     TGCCTCCAAA CTTGTGAAAG CTCTGTCTTT GGAAGATGGG
UCD957     TGCCTCCAAA CTTGTGAAAG CTCTGTCTTT GGAAGATGGG
```

Figure 2K

```
              1210       1220       1230       1240
              ....|....| ....|....| ....|....| ....|....|
S288c         AAATTTGTGT CTTTGAGAAC GAAATTTGAT AACTTGGCTA
UCD522        AAATTTGTGT CTTTGAGAAC GAAATTTGAT AACTTGGCTA
UCD932        AAATTTGTGT CTTTGAGAAC GAAATTTGAT AACTTGGCTA
UCD934        AAATTTGTGT CTTTGAGAAC GAAATTTGAT AACTTGGCTA
UCD938        AAATTTGTGT CTTTGAGAAC GAAATTTGAT AACTTGGCTA
UCD939        AAATTTGTGT CTTTGAGAAC GAAATTTGAT AACTTGGCTA
UCD940        AAATTTGTGT CTTTGAGAAC GAAATTTGAT AACTTGGCTA
UCD942        AAATTTGTGT CTTTGAGAAC GAAATTTGAT AACTTGGCTA
UCD950        AAATTTGTGT CTTTGAGAAC GAAATTTGAT AACTTGGCTA
UCD956        AAATTTGTGT CTTTGAGAAC GAAATTTGAT AACTTGGCTA
UCD957        AAATTTGTGT CTTTGAGAAC GAAATTTGAT AACTTGGCTA 1250       1260       1270       1280
              ....|....| ....|....| ....|....| ....|....|
S288c         ATGCTGGTAC CTTCCAAGCT CAATTTGTGA CCTCGAAAGA
UCD522        ATGCTGGTAC CTTCCAAGCT CAATTTGTGA CCTCGAARGA
UCD932        ATGCTGGTAC CTTCCAAGCT CAATTTGTGA CCTCGAAAGA
UCD934        ATGCTGGTAC CTTCCAAGCT CAATTTGTGA CCTCGAAGGA
UCD938        ATGCTGGTAC CTTCCAAGCT CAATTTGTGA CCTCGAAAGA
UCD939        ATGCTGGTAC CTTCCAAGCT CAATTTGTGA CCTCGAAAGA
UCD940        ATGCTGGTAC CTTCCAAGCT CAATTTGTGA CCTCGAAAGA
UCD942        ATGCTGGTAC CTTCCAAGCT CAATTTGTGA CCTCGAAAGA
UCD950        ATGCTGGTAC CTTCCAAGCT CAATTTGTGA CCTCGAAGGA
UCD956        ATGCTGGTAC CTTCCAAGCT CAATTTGTGA CCTCGAAAGA
UCD957        ATGCTGGTAC CTTCCAAGCT CAATTTGTGA CCTCGAAGGA 1290       1300       1310       1320
              ....|....| ....|....| ....|....| ....|....|
S288c         ACAGATACCT GTTTCAAACA TCGATTCTAC GAAATTATCA
UCD522        ACAGATACCT GTTTCAAACA TCGATTCTAC GAAATTATCA
UCD932        ACAGATACCT GTTTCAAACA TCGATTCTAC GAAATTATCA
UCD934        ACAGATACCT GTTTCAAACA TCGATTCTAC GAAATTATCA
UCD938        ACAGATACCT GTTTCAAACA TCGATTCTAC GAAATTATCA
UCD939        ACAGATACCT GTTTCAAACA TCGATTCTAC GAAATTATCA
UCD940        ACAGATACCT GTTTCAAACA TCGATTCTAC GAAATTATCA
UCD942        ACAGATACCT GTTTCAAACA TCGATTCTAC GAAATTATCA
UCD950        ACAGATACCT GTTTCAAACA TCGATTCTAC GAAATTATCA
UCD956        ACAGATACCT GTTTCAAACA TCGATTCTAC GAAATTATCA
UCD957        ACAGATACCT GTTTCAAACA TCGATTCTAC GAAATTATCA
```

*Figure 2L*

```
               1330       1340       1350       1360
          ....|....| ....|....| ....|....| ....|....|
S288c     GTCGTTGAAG ATGTCAGTTT ATTGAAGCAT TTAGACGTAG
UCD522    GTCGTTGAAG ATGTCAGTTT ATTGAAGCAT TTAGACGTAG
UCD932    GTCGTTGAAG ATGTCAGTTT ATTGAAGCAT TTAGACGTAG
UCD934    GTCGTTGAAG ATGTCAGTTT ATTGAAGCAT TTAGACGTAG
UCD938    GTCGTTGAAG ATGTCAGTTT ATTGAAGCAT TTAGACGTAG
UCD939    GTCGTTGAAG ATGTCAGTTT ATTGAAGCAT TTAGACGTAG
UCD940    GTCGTTGAAG ATGTCAGTTT ATTGAAGCAT TTAGACGTAG
UCD942    GTCGTTGAAG ATGTCAGTTT ATTGAAGCAT TTAGACGTAG
UCD950    GTCGTTGAAG ATGTCAGTTT ATTGAAGCAT TTAGACGTAG
UCD956    GTCGTTGAAG ATGTCAGTTT ATTGAAGCAT TTAGACGTAG
UCD957    GTCGTTGAAG ATGTCAGTTT ATTGAAGCAT TTAGACGTAG 1370       1380       1390       1400
          ....|....| ....|....| ....|....| ....|....|
S288c     CTGCTACCGT CGCAGAACAA GGTTCAATTG CGTTGGTTTC
UCD522    CTGCTACCGT CGCAGAACAA GGTTCAATTG CGTTGGTTTC
UCD932    CTGCTACCGT CGCAGAACAA GGTTCAATTG CGTTGGTTTC
UCD934    CTGCTACCGT CGCAGAACAA GGTTCAATTG CGTTGGTTTC
UCD938    CTGCTACCGT CGCAGAACAA GGTTCAATTG CGTTGGTTTC
UCD939    CTGCTACCGT CGCAGAACAA GGTTCAATTG CGTTGGTTTC
UCD940    CTGCTACCGT CGCAGAACAA GGTTCAATTG CGTTGGTTTC
UCD942    CTGCTACCGT CGCAGAACAA GGTTCAATTG CGTTGGTTTC
UCD950    CTGCTACCGT CGCAGAACAA GGTTCAATTG CGTTGGTTTC
UCD956    CTGCTACCGT CGCAGAACAA GGTTCAATTG CGTTGGTTTC
UCD957    CTGCTACCGT CGCAGAACAA GGTTCAATTG CGTTGGTTTC 1410       1420       1430       1440
          ....|....| ....|....| ....|....| ....|....|
S288c     CCAAAAGGCA GTTAAAGATT TGGATTTAAA TTCTGTAGAA
UCD522    CCAAAAGGCA GTTAAAGATT TGGATTTAAA TTCTGTAGAA
UCD932    CCAAAAGGCA GTTAAAGATT TGGATTTAAA TTCTGTAGAA
UCD934    CCAAAAGGCA GTTAAAGATT TGGATTTAAA TTCTGTAGAA
UCD938    CCAAAAGGCA GTTAAAGATT TGGCTTTAAA TTCTGTAGAA
UCD939    CCAAAAGGCA GTTAAAGATT TGGATTTAAA TTCTGTAGAA
UCD940    CCAAAAGGCA GTTAAAGATT TGGATTTAAA TTCTGTAGAA
UCD942    CCAAAAGGCA GTTAAAGATT TGGCTTTAAA TTCTGTAGAA
UCD950    CCAAAAGGCA GTTAAAGATT TGGATTTAAA TTCTGTAGAA
UCD956    CCAAAAGGCA GTTAAAGATT TGGATTTAAA TTCTGTAGAA
UCD957    CCAAAAGGCA GTTAAAGATT TGGATTTAAA TTCTGTAGAA
```

*Figure 2M*

```
                1450       1460       1470       1480
            ....|....| ....|....| ....|....| ....|....|
S288c       AGTTACGTCA AGAATTTGGG AATTCCTGAA TCATTCCTAA
UCD522      AGTTACGTCA AGAATTTGGG AATTCCTGAA TCATTCCTAA
UCD932      AGTTACGTCA AGAATTTGGG AATTCCTGAA TCATTCCTAA
UCD934      AGTTACGTCA AGAATTTGGG AATTCCTGAA TCATTCCTAA
UCD938      AGTTACGTCA AGAATTTGGG AATTCCTGAA TCATTCCTAA
UCD939      AGTTACGTCA AGAATTTGGG AATTCCTGAA TCATTCCTAA
UCD940      AGTTACGTCA AGAATTTGGG AATTCCTGAA TCATTCCTAA
UCD942      AGTTACGTCA AGAATTTGGG AATTCCTGAA TCATTCCTAA
UCD950      AGTTACGTCA AGAATTTGGG AATTCCTGAA TCATTCCTAA
UCD956      AGTTACGTCA AGAATTTGGG AATTCCTGAA TCATTCCTAA
UCD957      AGTTACGTCA AGAATTTGGG AATTCCTGAA TCATTCCTAA 1490       1500       1510       1520
            ....|....| ....|....| ....|....| ....|....|
S288c       TATCTATTGC GAAGAAAAAC ATCAAATTGT TTATCATCGA
UCD522      TATCTATTGC GAAGAAAAAC ATCAAATTGT TTATCATCGA
UCD932      TATCTATTGC GAAGAAAAAC ATCAAATTGT TTATCATCGA
UCD934      TATCTATTGC GAAGAAAAAC ATCAAATTGT TTATCATCGA
UCD938      TATCTATTGC GAAGAAAAAC ATCAAATTGT TTATCATCGA
UCD939      TATCTATTGC GAAGAAAAAC ATCAAATTGT TTATCATCGA
UCD940      TATCTATTGC GAAGAAAAAC ATCAAATTGT TTATCATCGA
UCD942      TATCTATTGC GAAGAAAAAC ATCAAATTGT TTATCATCGA
UCD950      TATCTATTGC GAAGAAAAAC ATCAAATTGT TTATCATCGA
UCD956      TATCTATTGC GAAGAAAAAC ATCAAATTGT TTATCATCGA
UCD957      TATCTATTGC GAAGAAAAAC ATCAAATTGT TTATCATCGA 1530       1540       1550       1560
            ....|....| ....|....| ....|....| ....|....|
S288c       TGGTGAGACC ACTAACGACG AGTCCAAATT GTCCTTGTTT
UCD522      TGGTGAGACC AYTAACGACG AGTCCAAATT GTCCTTGTTT
UCD932      TGGTGAGACC ACTAACGACG AGTCCAAATT GTCCTTGTTT
UCD934      TGGTGAGACC ATTAACGACG AGTCCAAATT GTCCTTGTTT
UCD938      TGGTGAGACC ACTAACGACG AGTCCAAATT GTCCTTGTTT
UCD939      TGGTGAGACC ACTAACGACG AGTCCAAATT GTCCTTGTTT
UCD940      TGGTGAGACC ACTAACGACG AGTCCAAATT GTCCTTGTTT
UCD942      TGGTGAGACC ACTAACGACG AGTCCAAATT GTCCTTGTTT
UCD950      TGGTGAGACC ATTAACGACG AGTCCAAATT GTCCTTGTTT
UCD956      TGGTGAGACC ACTAACGACG AGTCCAAATT GTCCTTGTTT
UCD957      TGGTGAGACC ATTAACGACG AGTCCAAATT GTCCTTGTTT
```

*Figure 2N*

```
              1570       1580       1590       1600
          ....|....| ....|....| ....|....| ....|....|
S288c     ATCCAAGCCG TTTTCTGGAA ATTGGCCTTC GGTCTAGATG
UCD522    ATCCAAGCCG TTTTCTGGAA ATTGGCCTTC GGTCTAGATG
UCD932    ATCCAAGCCG TTTTCTGGAA ATTGGCCTTC GGTCTAGATG
UCD934    ATCCAAGCCG TTTTCTGGAA ATTGGCCTTC GGTCTAGATG
UCD938    ATCCAAGCCG TTTTCTGGAA ATTGGCCTTC GGTCTAGATG
UCD939    ATCCAAGCCG TTTTCTGGAA ATTGGCCTTC GGTCTAGATG
UCD940    ATCCAAGCCG TTTTCTGGAA ATTGGCCTTC GGTCTAGATG
UCD942    ATCCAAGCCG TTTTCTGGAA ATTGGCCTTC GGTCTAGATG
UCD950    ATCCAAGCCG TTTTCTGGAA ATTGGCCTTC GGTCTAGATG
UCD956    ATCCAAGCCG TTTTCTGGAA ATTGGCCTTC GGTCTAGATG
UCD957    ATCCAAGCCG TTTTCTGGAA ATTGGCCTTC GGTCTAGATG 1610       1620       1630       1640
          ....|....| ....|....| ....|....| ....|....|
S288c     TCGCAGAATG TACCAACCGT ATCTGGAAAA GCATTGATTC
UCD522    TCGCAGAATG TACCAACCGT ATCTGGAAAA GCATTGATTC
UCD932    TCGCAGAATG TACCAACCGT ATCTGGAAAA GCATTGATTC
UCD934    TCGCAGAATG TACCAACCGT ATCTGGAAAA GCATTGATTC
UCD938    TCGCAGAATG TACCAACCGT ATCTGGAAAA GCATTGATTC
UCD939    TCGCAGAATG TACCAACCGT ATCTGGAAAA GCATTGATTC
UCD940    TCGCAGAATG TACCAACCGT ATCTGGAAAA GCATTGATTC
UCD942    TCGCAGAATG TACCAACCGT ATCTGGAAAA GCATTGATTC
UCD950    TCGCAGAATG TACCAACCGT ATCTGGAAAA GCATTGATTC
UCD956    TCGCAGAATG TACCAACCGT ATCTGGAAAA GCATTGATTC
UCD957    TCGCAGAATG TACCAACCGT ATCTGGAAAA GCATTGATTC 1650       1660       1670       1680
          ....|....| ....|....| ....|....| ....|....|
S288c     AGGTGCAGAC ATTTCAGCAG CCTCGATTTC TGAATTTCTC
UCD522    AGGTGCAGAC ATTTCAGCAG CCTCGATTTC TGAATTTCTC
UCD932    AGGTGCAGAC ATTTCAGCAG CCTCGATTTC TGAATTTCTC
UCD934    AGGTGCAGAC ATTTCAGCAG CCTCGATTTC TGAATTTCTC
UCD938    AGGTGCAGAC ATTTCAGCAG CCTCGATTTC TGAATTTCTC
UCD939    AGGTGCAGAC ATTTCAGCAG CCTCGATTTC TGAATTTCTC
UCD940    AGGTGCAGAC ATTTCAGCAG CCTCGATTTC TGAATTTCTC
UCD942    AGGTGCAGAC ATTTCAGCAG CCTCGATTTC TGAATTTCTC
UCD950    AGGTGCAGAC ATTTCAGCAG CCTCGATTTC TGAATTTCTC
UCD956    AGGTGCAGAC ATTTCAGCAG CCTCGATTTC TGAATTTCTC
UCD957    AGGTGCAGAC ATTTCAGCAG CCTCGATTTC TGAATTTCTC
```

Figure 2O

```
                1690       1700       1710       1720
             ....|....| ....|....| ....|....| ....|....|
S288c        ACTGGTGCAT TCAAAAACTT CCTCAGTGAG GTTCCGCTAG
UCD522       ACTGGTGCAT TCAAAAACTT CCTCAGTGAG GTTCCGCTAG
UCD932       ACTGGTGCAT TCAAAAACTT CCTCAGTGAG GTTCCGCTAG
UCD934       ACTGGTGCAT TCAAAAACTT CCTCAGTGAG GTTCCGCTAG
UCD938       ACTGGTGCAT TCAAAAACTT CCTCAGTGAG GTTCCGCTAG
UCD939       ACTGGTGCAT TCAAAAACTT CCTCAGTGAG GTTCCGCTAG
UCD940       ACTGGTGCAT TCAAAAACTT CCTCAGTGAG GTTCCGCTAG
UCD942       ACTGGTGCAT TCAAAAACTT CCTCAGTGAG GTTCCGCTAG
UCD950       ACTGGTGCAT TCAAAAACTT CCTCAGTGAG GTTCCGCTAG
UCD956       ACTGGTGCAT TCAAAAACTT CCTCAGTGAG GTTCCGCTAG
UCD957       ACTGGTGCAT TCAAAAACTT CCTCAGTGAG GTTCCGCTAG 1730       1740       1750       1760
             ....|....| ....|....| ....|....| ....|....|
S288c        CGCTGTACAC TAAATTTTCT GAAATAAACA TTGAAAAGAA
UCD522       CGCTGTACAC TAAATTTTCT GAAATAAACA TTGAAAAGAA
UCD932       CGCTGTACAC TAAATTTTCT GAAATAAACA TTGAAAAGAA
UCD934       CGCTGTACAC TAAATTTTCT GAAATAAACA TTGAAAAGAA
UCD938       CGCTGTACAC TAAATTTTCT GAAATAAACA TTGAAAAGAA
UCD939       CGCTGTACAC TAAATTTTCT GAAATAAACA TTGAAAAGAA
UCD940       CGCTGTACAC TAAATTTTCT GAAATAAACA TTGAAAAGAA
UCD942       CGCTGTACAC TAAATTTTCT GAAATAAACA TTGAAAAGAA
UCD950       CGCTGTACAC TAAATTTTCT GAAATAAACA TTGAAAAGAA
UCD956       CGCTGTACAC TAAATTTTCT GAAATAAACA TTGAAAAGAA
UCD957       CGCTGTACAC TAAATTTTCT GAAATAAACA TTGAAAAGAA 1770       1780       1790       1800
             ....|....| ....|....| ....|....| ....|....|
S288c        AGAGGATGAG GAAGAGCCTG CAGCTTTACC AATTTTCGTT
UCD522       AGAGGATGAG GAAGAGCCTG CAGCTTTACC AATTTTCGTT
UCD932       AGAGGATGAG GAAGAGCCTG CAGCTTTACC AATTTTCGTT
UCD934       AGAGGATAAG GAAGAGCCTG CAGCTTTACC AATTTTCGTT
UCD938       AGAGGATGAG GAAGAGCCTG CAGCTTTACC AATTTTCGTT
UCD939       AGAGGATCAG GAAGAGCCTG CAGCTTTACC AATTTTCGTT
UCD940       AGAGGATGAG GAAGAGCCTG CAGCTTTACC AATTTTCGTT
UCD942       AGAGGATGAG GAAGAGCCTG CAGCTTTACC AATTTTCGTT
UCD950       AGAGGATAAG GAAGAGCCTG CAGCTTTACC AATTTTCGTT
UCD956       AGAGGATGAG GAAGAGCCTG CAGCTTTACC AATTTTCGTT
UCD957       AGAGGATAAG GAAGAGCCTG CAGCTTTACC AATTTTCGTT
```

Figure 2P

```
                    1810       1820       1830       1840
                ....|....| ....|....| ....|....| ....|....|
        S288c   AATGAAACAT CTTTCCTCCC AAATAACAGT ACCATTGAAG
        UCD522  AATGAAACAT CTTTCCTCCC AAATAACAGT ACCATTGAAG
        UCD932  AATGAAACAT CTTTCCTCCC AAATAACAGT ACCATTGAAG
        UCD934  AATGAAACAT CTTTCCTCCC AAATAACAGT ACCATTGAAG
        UCD938  AATGAAACAT CTTTCCTCCC AAATAACAGT ACCATTGAAG
        UCD939  AATGAAACAT CTTTCCTCCC AAATAACAGT ACCATTGAAG
        UCD940  AATGAAACAT CTTTCCTCCC AAATAACAGT ACCATTGAAG
        UCD942  AATGAAACAT CTTTCCTCCC AAATAACAGT ACCATTGAAG
        UCD950  AATGAAACAT CTTTCCTCCC AAATAACAGT ACCATTGAAG
        UCD956  AATGAAACAT CTTTCCTCCC AAATAACAGT ACCATTGAAG
        UCD957  AATGAAACAT CTTTCCTCCC AAATAACAGT ACCATTGAAG 1850       1860       1870       1880
                ....|....| ....|....| ....|....| ....|....|
        S288c   AAATACCATT ACCTGAGACC TCTGAGATCT CTGATATTGC
        UCD522  AAATACCATT ACCTGAGACC TCTGAGATCT CTGATATTGC
        UCD932  AAATACCATT ACCTGAGACC TCTGAGATCT CTGATATTGC
        UCD934  AAATACCATT ACCTGAGACC TCTGAGATCT CTGATATTGC
        UCD938  AAATACCATT ACCTGAGACC TCTGAGATCT CTGATATTGC
        UCD939  AAATACCATT ACCTGAGACC TCTGAGATCT CTGATATTGC
        UCD940  AAATACCATT ACCTGAGACC TCTGAGATCT CTGATATTGC
        UCD942  AAATACCATT ACCTGAGACC TCTGAGATCT CTGATATTGC
        UCD950  AAATACCATT ACCTGAGACC TCTGAGATCT CTGATATTGC
        UCD956  AAATACCATT ACCTGAGACC TCTGAGATCT CTGATATTGC
        UCD957  AAATACCATT ACCTGAGACC TCTGAGATCT CTGATATTGC 1890       1900       1910       1920
                ....|....| ....|....| ....|....| ....|....|
        S288c   CAAGAAGTTG TCCTTCAAAG AGGCATATGA AGTTGAGAAT
        UCD522  CAAGAAGTTG TCCTTCAAAG AGGCATATGA AGTTGAGAAT
        UCD932  CAAGAAGTTG TCCTTCAAAG AGGCATATGA AGTTGAGAAT
        UCD934  CAAGAAGTTG TCCTTCAAAG AGGCATATGA AGTTGAGAAT
        UCD938  CAAGAAGTTG TCCTTCAAAG AGGCATATGA AGTTGAGAAT
        UCD939  CAAGAAGTTG TCCTTCAAAG AGGCATATGA AGTTGAGAAT
        UCD940  CAAGAAGTTG TCCTTCAAAG AGGCATATGA AGTTGAGAAT
        UCD942  CAAGAAGTTG TCCTTCAAAG AGGCATATGA AGTTGAGAAT
        UCD950  CAAGAAGTTG TCCTTCAAAG AGGCATATGA AGTTGAGAAT
        UCD956  CAAGAAGTTG TCCTTCAAAG AGGCATATGA AGTTGAGAAT
        UCD957  CAAGAAGTTG TCCTTCAAAG AGGCATATGA AGTTGAGAAT
```

Figure 2Q

```
                1930       1940       1950       1960
            ....|....| ....|....| ....|....| ....|....|
S288c       AAACTAAGAC CCGATTTACC CGTCAAGAAC TTCGTCGTGA
UCD522      AAACTAAGAC CCGATTTACC CGTCAAGAAC TTCGTCGTGA
UCD932      AAACTAAGAC CCGATTTACC CGTCAAGAAC TTCGTCGTGA
UCD934      AAACTAAGAC CCGATTTACC CGTCAAGAAC TTCGTCGTGA
UCD938      AAACTAAGAC CCGATTTACC CGTCAAGAAC TTCGTCGTGA
UCD939      AAACTAAGAC CCGATTTACC CGTCAAGAAC TTCGTCGTGA
UCD940      AAACTAAGAC CCGATTTACC CGTCAAGAAC TTCGTCGTGA
UCD942      AAACTAAGAC CCGATTTACC CGTCAAGAAC TTCGTCGTGA
UCD950      AAACTAAGAC CCGATTTACC CGTCAAGAAC TTCGTCGTGA
UCD956      AAACTAAGAC CCGATTTACC CGTCAAGAAC TTCGTCGTGA
UCD957      AAACTAAGAC CCGATTTACC CGTCAAGAAC TTCGTCGTGA 1970       1980       1990       2000
            ....|....| ....|....| ....|....| ....|....|
S288c       AAGTTAAAGA AAATAGACGT GTTACGCCTG CTGATTATGA
UCD522      AAGTTAAAGA AAATAGACGT GTTACGCCTG CTGATTATGA
UCD932      AAGTTAAAGA AAATAGACGT GTTAAGCCTG CTGATTATGA
UCD934      AAGTTAAAGA AAATAGACGT GTTACGCCTG CTGATTATGA
UCD938      AAGTTAAAGA AAATAGACGT GTTACGCCTG CTGATTATGA
UCD939      AAGTTAAAGA AAATAGACGT GTTACGCCTG CTGATTATGA
UCD940      AAGTTAAAGA AAATAGACGT GTTACGCCTG CTGATTATGA
UCD942      AAGTTAAAGA AAATAGACGT GTTACGCCTG CTGATTATGA
UCD950      AAGTTAAAGA AAATAGACGT GTTACGCCTG CTGATTATGA
UCD956      AAGTTAAAGA AAATAGACGT GTTACGCCTG CTGATTATGA
UCD957      AAGTTAAAGA AAATAGACGT GTTACGCCTG CTGATTATGA 2010       2020       2030       2040
            ....|....| ....|....| ....|....| ....|....|
S288c       TAGATATATT TTCCATATTG AATTCGATAT TTCTGGTACT
UCD522      TAGATATATT TTCCATATTG AATTCGATAT TTCTGGTACT
UCD932      TAGATATATT TTCCATATTG AATTCGATAT TTCTGGTACT
UCD934      TAGATATATT TTCCATATTG AATTCGATAT TTCTGGTACT
UCD938      TAGATATATT TTCCATATTG AATTCGATAT TTCTGGTACT
UCD939      TAGATATATT TTCCATATTG AATTCGATAT TTCTGGTACT
UCD940      TAGATATATT TTCCATATTG AATTCGATAT TTCTGGTACT
UCD942      TAGATATATT TTCCATATTG AATTCGATAT TTCTGGTACT
UCD950      TAGATATATT TTCCATATTG AATTCGATAT TTCTGGTACT
UCD956      TAGATATATT TTCCATATTG AATTCGATAT TTCTGGTACT
UCD957      TAGATATATT TTCCATATTG AATTCGATAT TTCTGGTACT
```

Figure 2R

```
                       2050       2060       2070       2080
                  ....|....| ....|....| ....|....| ....|....|
    S288c         GGAATGACTT ATGACATCGG TGAAGCCCTC GGTATTCATG
    UCD522        GGAATGACTT ATGACATCGG TGAAGCCCTC GGTATTCATG
    UCD932        GGAATGACTT ATGACATCGG TGAAGCCCTC GGTATTCATG
    UCD934        GGAATGACTT ATGACATCGG TGAAGCCCTC GGTATTCATG
    UCD938        GGAATGACTT ATGACATCGG TGAAGCCCTC GGTATTCATG
    UCD939        GGAATGACTT ATGACATCGG TGAAGCCCTC GGTATTCATG
    UCD940        GGAATGACTT ATGACATCGG TGAAGCCCTC GGTATTCATG
    UCD942        GGAATGACTT ATGACATCGG TGAAGCCCTC GGTATTCATG
    UCD950        GGAATGACTT ATGACATCGG TGAAGCCCTC GGTATTCATG
    UCD956        GGAATGACTT ATGACATCGG TGAAGCCCTC GGTATTCATG
    UCD957        GGAATGACTT ATGACATCGG TGAAGCCCTC GGTATTCATG 2090       2100       2110       2120
                  ....|....| ....|....| ....|....| ....|....|
    S288c         CCAGAAACAA TGAATCTTTG GTCAAAGAAT TCTTAACCTT
    UCD522        CCAGAAACAA TGAATCTTTG GTCAAAGAAT TCTTAACCTT
    UCD932        CCAGAAACAA TGAATCTTTG GTCAAAGAAT TCTTAACCTT
    UCD934        CCAGAAACAA TGAATCTTTG GTCAAAGAAT TCTTAACCTT
    UCD938        CCAGAAACAA TGAATCTTTG GTCAAAGAAT TCTTAACCTT
    UCD939        CCAGAAACAA TGAATCTTTG GTCAAAGAAT TCTTAACCTT
    UCD940        CCAGAAACAA TGAATCTTTG GTCAAAGAAT TCTTAACCTT
    UCD942        CCAGAAACAA TGAATCTTTG GTCAAAGAAT TCTTAACCTT
    UCD950        CCAGAAACAA TGAATCTTTG GTCAAAGAAT TCTTAACCTT
    UCD956        CCAGAAACAA TGAATCTTTG GTCAAAGAAT TCTTAACCTT
    UCD957        CCAGAAACAA TGAATCTTTG GTCAAAGAAT TCTTAACCTT 2130       2140       2150       2160
                  ....|....| ....|....| ....|....| ....|....|
    S288c         CTATGGTCTA AATGAATCCG ATGTTGTCTT AGTCCCCAAC
    UCD522        CTATGGTCTA AATGAATCCG ATGTTGTCTT AGTCCCCAAC
    UCD932        CTATGGTCTA AATGAATCCG ATGTTGTCTT AGTCCCCAAC
    UCD934        CTATGGTCTA AATGAATCCG ATGTTGTCTT AGTCCCCAAC
    UCD938        CTATGGTCTA AATGAATCCG ATGTTGTCTT AGTCCCCAAC
    UCD939        CTATGGTCTA AATGAATCCG ATGTTGTCTT AGTCCCCAAC
    UCD940        CTATGGTCTA AATGAATCCG ATGTTGTCTT AGTCCCCAAC
    UCD942        CTATGGTCTA AATGAATCCG ATGTTGTCTT AGTCCCCAAC
    UCD950        CTATGGTCTA AATGAATCCG ATGTTGTCTT AGTCCCCAAC
    UCD956        CTATGGTCTA AATGAATCCG ATGTTGTCTT AGTCCCCAAC
    UCD957        CTATGGTCTA AATGAATCCG ATGTTGTCTT AGTCCCCAAC
```

*Figure 2S*

```
              2170       2180       2190       2200
         ....|....| ....|....| ....|....| ....|....|
S288c    AAGGACAACC ACCATTTGTT AGAAACAAGA ACCGTCTTAC
UCD522   AAGGACAACC ACCATTTGTT AGAAACAAGA ACCGTCTTAC
UCD932   AAGGACAACC ACCATTTGTT AGAAACAAGA ACCGTCTTAC
UCD934   AAGGACAACC ACCATTTGTT AGAAACAAGA ACCGTCTTAC
UCD938   AAGGACAACC ACCATTTGTT AGAAACAAGA ACCGTCTTAC
UCD939   AAGGACAACC ACCATTTGTT AGAAACAAGA ACCGTCTTAC
UCD940   AAGGACAACC ACCATTTGTT AGAAACAAGA ACCGTCTTAC
UCD942   AAGGACAACC ACCATTTGTT AGAAACAAGA ACCGTCTTAC
UCD950   AAGGACAACC ACCATTTGTT AGAAACAAGA ACCGTCTTAC
UCD956   AAGGACAACC ACCATTTGTT AGAAACAAGA ACCGTCTTAC
UCD957   AAGGACAACC ACCATTTGTT AGAAACAAGA ACCGTCTTAC 2210       2220       2230       2240
         ....|....| ....|....| ....|....| ....|....|
S288c    AAGCATTTGT GGAAAATTTG GATATTTTCG GTAAACCACC
UCD522   AAGCATTTGT GGAAAATTTG GATATTTTCG GTAAACCACC
UCD932   AAGCATTTGT GGAAAATTTG GATATTTTCG GTAAACCACC
UCD934   AAGCATTTGT GGAAAATTTG GATATTTTCG GTAAACCACC
UCD938   AAGCATTTGT GGAAAATTTG GATATTTTCG GTAAACCACC
UCD939   AAGCATTTGT GGAAAATTTG GATATTTTCG GTAAACCACC
UCD940   AAGCATTTGT GGAAAATTTG GATATTTTCG GTAAACCACC
UCD942   AAGCATTTGT GGAAAATTTG GATATTTTCG GTAAACCACC
UCD950   AAGCATTTGT GGAAAATTTG GATATTTTCG GTAAACCACC
UCD956   AAGCATTTGT GGAAAATTTG GATATTTTCG GTAAACCACC
UCD957   AAGCATTTGT GGAAAATTTG GATATTTTCG GTAAACCACC 2250       2260       2270       2280
         ....|....| ....|....| ....|....| ....|....|
S288c    AAAAAGATTT TACGAATCAT TGATTCCATA TGCCTCTAAC
UCD522   AAAAAGATTT TACGAATCAT TGATTCCATA TGCCTCTAAC
UCD932   AAAAAGATTT TACGAATCAT TGATTCCATA TGCCTCTAAC
UCD934   AAAAAGATTT TACGAATCAT TGATTCCATA TGCCTCTAAC
UCD938   AAAAAGATTT TACGAATCAT TGATTCCATA TGCCTCTAAC
UCD939   AAAAAGATTT TACGAATCAT TGATTCCATA TGCCTCTAAC
UCD940   AAAAAGATTT TACGAATCAT TGATTCCATA TGCCTCTAAC
UCD942   AAAAAGATTT TACGAATCAT TGATTCCATA TGCCTCTAAC
UCD950   AAAAAGATTT TACGAATCAT TGATTCCATA TGCCTCTAAC
UCD956   AAAAAGATTT TACGAATCAT TGATTCCATA TGCCTCTAAC
UCD957   AAAAAGATTT TACGAATCAT TGATTCCATA TGCCTCTAAC
```

*Figure 2T*

```
                 2290       2300       2310       2320
             ....|....| ....|....| ....|....| ....|....|
    S288c    GAAGAGGAGA AGAAAAAATT AGAGGATTTG GTTACTCCTG
    UCD522   GAAGAGGAGA AGAAAAAATT AGAGGATTTG GTTACTCCTG
    UCD932   GAAGAGGAGA AGAAAAAATT AGAGGATTTG GTTACTCCTG
    UCD934   GAAGAGGAGA AGAAAAAATT AGAGGATTTG GTTACTCCTG
    UCD938   GAAGAGGAGA AGAAAAAATT AGAGGATTTG GTTACTCCTG
    UCD939   GAAGAGGAGA AGAAAAAATT AGAGGATTTG GTTACTCCTG
    UCD940   GAAGAGGAGA AGAAAAAATT AGAGGATTTG GTTACTCCTG
    UCD942   GAAGAGGAGA AGAAAAAATT AGAGGATTTG GTTACTCCTG
    UCD950   GAAGAGGAGA AGAAAAAATT AGAGGATTTG GTTACTCCTG
    UCD956   GAAGAGGAGA AGAAAAAATT AGAGGATTTG GTTACTCCTG
    UCD957   GAAGAGGAGA AGAAAAAATT AGAGGATTTG GTTACTCCTG 2330       2340       2350       2360
             ....|....| ....|....| ....|....| ....|....|
    S288c    CCGGTGCAGT AGATTTGAAG AGATTTCAAG ATGTGGAGTA
    UCD522   CCGGTGCAGT AGATTTGAAG AGATTTCAAG ATGTGGAGTA
    UCD932   CCGGTGCAGT AGATTTGAAG AGATTTCAAG ATGTGGAGTA
    UCD934   CCGGTGCAGT AGATTTGAAG AGATTTCAAG ATGTGGAGTA
    UCD938   CCGGTGCAGT AGATTTGAAG AGATTTCAAG ATGTGGAGTA
    UCD939   CCGGTGCAGT AGATTTGAAG AGATTTCAAG ATGTGGAGTA
    UCD940   CCGGTGCAGT AGATTTGAAG AGATTTCAAG ATGTGGAGTA
    UCD942   CCGGTGCAGT AGATTTGAAG AGATTTCAAG ATGTGGAGTA
    UCD950   CCGGTGCAGT AGATTTGAAG AGATTTCAAG ATGTGGAGTA
    UCD956   CCGGTGCAGT AGATTTGAAG AGATTTCAAG ATGTGGAGTA
    UCD957   CCGGTGCAGT AGATTTGAAG AGATTTCAAG ATGTGGAGTA 2370       2380       2390       2400
             ....|....| ....|....| ....|....| ....|....|
    S288c    TTATACATAT GCTGACATTT TTGAATTGTT CCCATCTGTT
    UCD522   TTATACATAT GCTGACATTT TTGAATTGTT CCCATCTGTT
    UCD932   TTATACATAT GCTGACATTT TTGAATTGTT CCCATCTGTT
    UCD934   TTATACATAT GCTGACATTT TTGAATTGTT CCCATCTGTT
    UCD938   TTATACATAT GCTGACATTT TTGAATTGTT CCCATCTGTT
    UCD939   TTATACATAT GCTGACATTT TTGAATTGTT CCCATCTGTT
    UCD940   TTATACATAT GCTGACATTT TTGAATTGTT CCCATCTGTT
    UCD942   TTATACATAT GCTGACATTT TTGAATTGTT CCCATCTGTT
    UCD950   TTATACATAT GCTGACATTT TTGAATTGTT CCCATCTGTT
    UCD956   TTATACATAT GCTGACATTT TTGAATTGTT CCCATCTGTT
    UCD957   TTATACATAT GCTGACATTT TTGAATTGTT CCCATCTGTT
```

Figure 2U

```
                  2410       2420       2430       2440
              ....|....| ....|....| ....|....| ....|....|
S288c         CGCCCATCTC TTGAGGAACT TGTTACTATC ATTGAACCAT
UCD522        CGCCCATCTC TTGAGGAACT TGTTACTATC ATTGAACCAT
UCD932        CGCCCATCTC TTGAGGAACT TGTTACTATC ATTGAACCAT
UCD934        CGCCCATCTC TTGAGGAACT TGTTACTATC ATTGAACCAT
UCD938        CGCCCATCTC TTGAGGAACT TGTTACTATC ATTGAACCAT
UCD939        CGCCCATCTC TTGAGGAACT TGTTACTATC ATTGAACCAT
UCD940        CGCCCATCTC TTGAGGAACT TGTTACTATC ATTGAACCAT
UCD942        CGCCCATCTC TTGAGGAACT TGTTACTATC ATTGAACCAT
UCD950        CGCCCATCTC TTGAGGAACT TGTTACTATC ATTGAACCAT
UCD956        CGCCCATCTC TTGAGGAACT TGTTACTATC ATTGAACCAT
UCD957        CGCCCATCTC TTGAGGAACT TGTTACTATC ATTGAACCAT 2450       2460       2470       2480
              ....|....| ....|....| ....|....| ....|....|
S288c         TGAAGAGAAG AGAATACTCA ATTGCCTCCT CTCAGAAAGT
UCD522        TGAAGAGAAG AGAATACTCA ATTGCCTCCT CTCAGAAAGT
UCD932        TGAAGAGAAG AGAATACTCA ATTGCCTCCT CTCAGAAAGT
UCD934        TGAAGAGAAG AGAATACTCA ATTGCCTCCT CTCAGAAAGT
UCD938        TGAAGAGAAG AGAATACTCA ATTGCCTCCT CTCAGAAAGT
UCD939        TGAAGAGAAG AGAATACTCA ATTGCCTCCT CTCAGAAAGT
UCD940        TGAAGAGAAG AGAATACTCA ATTGCCTCCT CTCAGAAAGT
UCD942        TGAAGAGAAG AGAATACTCA ATTGCCTCCT CTCAGAAAGT
UCD950        TGAAGAGAAG AGAATACTCA ATTGCCTCCT CTCAGAAAGT
UCD956        TGAAGAGAAG AGAATACTCA ATTGCCTCCT CTCAGAAAGT
UCD957        TGAAGAGAAG AGAATACTCA ATTGCCTCCT CTCAGAAAGT 2490       2500       2510       2520
              ....|....| ....|....| ....|....| ....|....|
S288c         TCATCCAAAT GAAGTTCATT TATTGATCGT TGTTGTTGAT
UCD522        TCATCCAAAT GAAGTTCATT TATTGATCGT TGTTGTTGAT
UCD932        TCATCCAAAT GAAGTTCATT TATTGATCGT TGTTGTTGAT
UCD934        TCATCCAAAT GAAGTTCATT TATTGATCGT TGTTGTTGAT
UCD938        TCATCCAAAT GAAGTTCATT TATTGATCGT TGTTGTTGAT
UCD939        TCATCCAAAT GAAGTTCATT TATTGATCGT TGTTGTTGAT
UCD940        TCATCCAAAT GAAGTTCATT TATTGATCGT TGTTGTTGAT
UCD942        TCATCCAAAT GAAGTTCATT TATTGATCGT TGTTGTTGAT
UCD950        TCATCCAAAT GAAGTTCATT TATTGATCGT TGTTGTTGAT
UCD956        TCATCCAAAT GAAGTTCATT TATTGATCGT TGTTGTTGAT
UCD957        TCATCCAAAT GAAGTTCATT TATTGATCGT TGTTGTTGAT
```

Figure 2V

```
               2530       2540       2550       2560
          ....|....| ....|....| ....|....| ....|....|
S288c     TGGGTGGATA ATAAAGGAAG AAAAAGGTAC GGTCAAGCTT
UCD522    TGGGTGGATA ATAAAGGAAG AAAAAGGTAC GGTCAAGCTT
UCD932    TGGGTGGATA ATAAAGGAAG AAAAAGGTAC GGTCAAGCTT
UCD934    TGGGTGGATA ATAAAGGAAG AAAAAGGTAC GGTCAAGCTT
UCD938    TGGGTGGATA ATAAAGGAAG AAAAAGGTAC GGTCAAGCTT
UCD939    TGGGTGGATA ATAAAGGAAG AAAAAGGTAC GGTCAAGCTT
UCD940    TGGGTGGATA ATAAAGGAAG AAAAAGGTAC GGTCAAGCTT
UCD942    TGGGTGGATA ATAAAGGAAG AAAAAGGTAC GGTCAAGCTT
UCD950    TGGGTGGATA ATAAAGGAAG AAAAAGGTAC GGTCAAGCTT
UCD956    TGGGTGGATA ATAAAGGAAG AAAAAGGTAC GGTCAAGCTT
UCD957    TGGGTGGATA ATAAAGGAAG AAAAAGGTAC GGTCAAGCTT 2570       2580       2590       2600
          ....|....| ....|....| ....|....| ....|....|
S288c     CTAAGTATAT CTCAGACCTT GCTGTCGGTT CAGAATTGGT
UCD522    CTAAGTATAT CTCAGACCTT GCTGTCGGTT CAGAATTGGT
UCD932    CTAAGTATAT CTCAGACCTT GCTGTCGGTT CAGAATTGGT
UCD934    CTAAGTATAT CTCAGACCTT GCTGTCGGTT CAGAATTGGT
UCD938    CTAAGTATAT CTCAGACCTT GCTGTCGGTT CAGAATTGGT
UCD939    CTAAGTATAT CTCAGACCTT GCTGTCGGTT CAGAATTGGT
UCD940    CTAAGTATAT CTCAGACCTT GCTGTCGGTT CAGAATTGGT
UCD942    CTAAGTATAT CTCAGACCTT GCTGTCGGTT CAGAATTGGT
UCD950    CTAAGTATAT CTCAGACCTT GCTGTCGGTT CAGAATTGGT
UCD956    CTAAGTATAT CTCAGACCTT GCTGTCGGTT CAGAATTGGT
UCD957    CTAAGTATAT CTCAGACCTT GCTGTCGGTT CAGAATTGGT 2610       2620       2630       2640
          ....|....| ....|....| ....|....| ....|....|
S288c     CGTTAGCGTT AAACCATCTG TTATGAAATT ACCACCATCT
UCD522    CGTTAGCGTT AAACCATCTG TTATGAAATT ACCACCATCT
UCD932    CGTTAGCGTT AAACCATCTG TTATGAAATT ACCACCATCT
UCD934    CGTTAGCGTT AAACCATCTG TTATGAAATT ACCACCATCT
UCD938    CGTTAGCGTT AAACCATCTG TTATGAAATT ACCACCATCT
UCD939    CGTTAGCGTT AAACCATCTG TTATGAAATT ACCACCATCT
UCD940    CGTTAGCGTT AAACCATCTG TTATGAAATT ACCACCATCT
UCD942    CGTTAGCGTT AAACCATCTG TTATGAAATT ACCACCATCT
UCD950    CGTTAGCGTT AAACCATCTG TTATGAAATT ACCACCATCT
UCD956    CGTTAGCGTT AAACCATCTG TTATGAAATT ACCACCATCT
UCD957    CGTTAGCGTT AAACCATCTG TTATGAAATT ACCACCATCT
```

*Figure 2W*

```
             2650       2660       2670       2680
        ....|....| ....|....| ....|....| ....|....|
S288c   CCAAAGCAAC CAGTTATTAT GAGTGGTTTA GGTACTGGTT
UCD522  CCAAAGCAAC CAGTTATTAT GAGTGGTTTA GGTACTGGTT
UCD932  CCAAAGCAAC CAGTTATTAT GAGTGGTTTA GGTACTGGTT
UCD934  CCAAAGCAAC CAGTTATTAT GAGTGGTTTA GGTACTGGTT
UCD938  CCAAAGCAAC CAGTTATTAT GAGTGGTTTA GGTACTGGTT
UCD939  CCAAAGCAAC CAGTTATTAT GAGTGGTTTA GGTACTGGTT
UCD940  CCAAAGCAAC CAGTTATTAT GAGTGGTTTA GGTACTGGTT
UCD942  CCAAAGCAAC CAGTTATTAT GAGTGGTTTA GGTACTGGTT
UCD950  CCAAAGCAAC CAGTTATTAT GAGTGGTTTA GGTACTGGTT
UCD956  CCAAAGCAAC CAGTTATTAT GAGTGGTTTA GGTACTGGTT
UCD957  CCAAAGCAAC CAGTTATTAT GAGTGGTTTA GGTACTGGTT 2690       2700       2710       2720
        ....|....| ....|....| ....|....| ....|....|
S288c   TGGCACCATT CAAGGCCATT GTTGAAGAGA AATTATGGCA
UCD522  TGGCACCATT CAAGGCCATT GTTGAAGAGA AATTATGGCA
UCD932  TGGCACCATT CAAGGCCATT GTTGAAGAGA AATTATGGCA
UCD934  TGGCACCATT CAAGGCCATT GTTGAAGAGA AATTATGGCA
UCD938  TGGCACCATT CAAGGCCATT GTTGAAGAGA AATTATGGCA
UCD939  TGGCACCATT CAAGGCCATT GTTGAAGAGA AATTATGGCA
UCD940  TGGCACCATT CAAGGCCATT GTTGAAGAGA AATTATGGCA
UCD942  TGGCACCATT CAAGGCCATT GTTGAAGAGA AATTATGGCA
UCD950  TGGCACCATT CAAGGCCATT GTTGAAGAGA AATTATGGCA
UCD956  TGGCATCATT CAAGGCCATT GTTGAAGAGA AATTATGGCA
UCD957  TGGCACCATT CAAGGCCATT GTTGAAGAGA AATTATGGCA 2730       2740       2750       2760
        ....|....| ....|....| ....|....| ....|....|
S288c   AAAGCAGCAA GGTTATGAGA TTGGTGAAGT CTTCCTATAT
UCD522  AAAGCAGCAA GGTTATGAGA TTGGTGAAGT CTTCCTATAT
UCD932  AAAGCAGCAA GGTTATGAGA TTGGTGAAGT CTTCCTATAT
UCD934  AAAGCAGCAA GGTTATGAGA TTGGTGAAGT CTTCCTATAT
UCD938  AAAGCAGCAA GGTTATGAGA TTGGTGAAGT CTTCCTATAT
UCD939  AAAGCAGCAA GGTTATGAGA TTGGTGAAGT CTTCCTATAT
UCD940  AAAGCAGCAA GGTTATGAGA TTGGTGAAGT CTTCCTATAT
UCD942  AAAGCAGCAA GGTTATGAGA TTGGTGAAGT CTTCCTATAT
UCD950  AAAGCAGCAA GGTTATGAGA TTGGTGAAGT CTTCCTATAT
UCD956  AAAGCAGCAA GGTTATGAGA TTGGTGAAGT CTTCCTATAT
UCD957  AAAGCAGCAA GGTTATGAGA TTGGTGAAGT CTTCCTATAT
```

*Figure 2X*

```
             2770       2780       2790       2800
        ....|....| ....|....| ....|....| ....|....|
S288c   CTAGGTTCAA GACACAAAAG AGAAGAATAT TTATATGGTG
UCD522  CTAGGTTCAA GACACAAAAG AGAAGAATAT TTATATGGTG
UCD932  CTAGGTTCAA GACACAAAAG AGAAGAATAT TTATATGGTG
UCD934  CTAGGTTCAA GACACAAAAG AGAAGAATAT TTATATGGTG
UCD938  CTAGGTTCAA GACACAAAAG AGAAGAATAT TTATATGGTG
UCD939  CTAGGTTCAA GACACAAAAG AGAAGAATAT TTATATGGTG
UCD940  CTAGGTTCAA GACACAAAAG AGAAGAATAT TTATATGGTG
UCD942  CTAGGTTCAA GACACAAAAG AGAAGAATAT TTATATGGTG
UCD950  CTAGGTTCAA GACACAAAAG AGAAGAATAT TTATATGGTG
UCD956  CTAGGTTCAA GACACAAAAG AGAAGAATAT TTATATGGTG
UCD957  CTAGGTTCAA GACACAAAAG AGAAGAATAT TTATATGGTG 2810       2820       2830       2840
        ....|....| ....|....| ....|....| ....|....|
S288c   AGTTATGGGA GGCTTACAAA GATGCAGGTA TTATCACACA
UCD522  AGTTATGGGA GGCTTACAAA GATGCAGGTA TTATCACACA
UCD932  AGTTATGGGA GGCTTACAAA GATGCAGGTA TTATCACACA
UCD934  AGTTATGGGA GGCTTACAAA GATGCAGGTA TTATCACACA
UCD938  AGTTATGGGA GGCTTACAAA GATGCAGGTA TTATCACACA
UCD939  AGTTATGGGA GGCTTACAAA GATGCAGGTA TTATCACACA
UCD940  AGTTATGGGA GGCTTACAAA GATGCAGGTA TTATCACACA
UCD942  AGTTATGGGA GGCTTACAAA GATGCAGGTA TTATCACACA
UCD950  AGTTATGGGA GGCTTACAAA GATGCAGGTA TTATCACACA
UCD956  AGTTATGGGA GGCTTACAAA GATGCAGGTA TTATCACACA
UCD957  AGTTATGGGA GGCTTACAAA GATGCAGGTA TTATCACACA 2850       2860       2870       2880
        ....|....| ....|....| ....|....| ....|....|
S288c   CATCGGCGCT GCTTTCTCAA GAGACCAACC TCAAAAAATT
UCD522  CATCGGCGCT GCTTTCTCAA GAGACCAACC TCAAAAAATT
UCD932  CATCGGCGCT GCTTTCTCAA GAGACCAACC TCAAAAAATT
UCD934  CATCGGCGCT GCTTTCTCAA GAGACCAACC TCAAAAAATT
UCD938  CATCGGCGCT GCTTTCTCAA GAGACCAACC TCAAAAAATT
UCD939  CATCGGCGCT GCTTTCTCAA GAGACCAACC TCAAAAAATT
UCD940  CATCGGCGCT GCTTTCTCAA GAGACCAACC TCAAAAAATT
UCD942  CATCGGCGCT GCTTTCTCAA GAGACCAACC TCAAAAAATT
UCD950  CATCGGCGCT GCTTTCTCAA GAGACCAACC TCAAAAAATT
UCD956  CATCGGCGCT GCTTTCTCAA GAGACCAACC TCAAAAAATT
UCD957  CATCGGCGCT GCTTTCTCAA GAGACCAACC TCAAAAAATT
```

*Figure 2Y*

```
                2890       2900       2910       2920
            ....|....| ....|....| ....|....| ....|....|
S288c       TACATTCAAG ATCGTATCAA AGAGAATTTG GATGAATTAA
UCD522      TACATTCAAG ATCGTATCAA AGAGAATTTG GATGAATTAA
UCD932      TACATTCAAG ATCGTATCAA AGAGAATTTG GATGAATTAA
UCD934      TACATTCAAG ATCGTATCAA AGAGAATTTG GATGAATTAA
UCD938      TACATTCAAG ATCGTATCAA AGAGAATTTG GATGAATTAA
UCD939      TACATTCAAG ATCGTATCAA AGAGAATTTG GATGAATTAA
UCD940      TACATTCAAG ATCGTATCAA AGAGAATTTG GATGAATTAA
UCD942      TACATTCAAG ATCGTATCAA AGAGAATTTG GATGAATTAA
UCD950      TACATTCAAG ATCGTATCAA AGAGAATTTG GATGAATTAA
UCD956      TACATTCAAG ATCGTATCAA AGAGAATTTG GATGAATTAA
UCD957      TACATTCAAG ATCGTATCAA AGAGAATTTG GATGAATTAA 2930       2940       2950       2960
            ....|....| ....|....| ....|....| ....|....|
S288c       AAACTGCAAT GATTGATAAT AAAGGTTCAT TTTACTTGTG
UCD522      AAACTGCAAT GATTGATAAT AAAGGTTCAT TTTACTTGTG
UCD932      AAACTGCAAT GATTGATAAT AAAGGTTCAT TTTACTTGTG
UCD934      AAACTGCAAT GATTGATAAT AAAGGTTCAT TTTACTTGTG
UCD938      AAACTGCAAT GATTGATAAT AAAGGTTCAT TTTACTTGTG
UCD939      AAACTGCAAT GATTGATAAT AAAGGTTCAT TTTACTTGTG
UCD940      AAACTGCAAT GATTGATAAT AAAGGTTCAT TTTACTTGTG
UCD942      AAACTGCAAT GATTGATAAT AAAGGTTCAT TTTACTTGTG
UCD950      AAACTGCAAT GATTGATAAT AAAGGTTCAT TTTACTTGTG
UCD956      AAACTGCAAT GATTGATAAT AAAGGTTCAT TTTACTTGTG
UCD957      AAACTGCAAT GATTGATAAT AAAGGTTCAT TTTACTTGTG 2970       2980       2990       3000
            ....|....| ....|....| ....|....| ....|....|
S288c       TGGCCCTACT TGGCCAGTTC CAGATATTAC TCAAGCTTTG
UCD522      TGGCCCTACT TGGCCAGTTC CAGATATTAC TCAAGCTTTG
UCD932      TGGCCCTACT TGGCCAGTTC CAGATATTAC TCAAGCTTTG
UCD934      TGGCCCTACT TGGCCAGTTC CAGATATTAC TCAAGCTTTG
UCD938      TGGCCCTACT TGGCCAGTTC CAGATATTAC TCAAGCTTTG
UCD939      TGGCCCTACT TGGCCAGTTC CAGATATTAC TCAAGCTTTG
UCD940      TGGCCCTACT TGGCCAGTTC CAGATATTAC TCAAGCTTTG
UCD942      TGGCCCTACT TGGCCAGTTC CAGATATTAC TCAAGCTTTG
UCD950      TGGCCCTACT TGGCCAGTTC CAGATATTAC TCAAGCTTTG
UCD956      TGGCCCTACT TGGCCAGTTC CAGATATTAC TCAAGCTTTG
UCD957      TGGCCCTACT TGGCCAGTTC CAGATATTAC TCAAGCTTTG
```

Figure 2Z

```
                  3010       3020       3030       3040
             ....|....| ....|....| ....|....| ....|....|
S288c        CAAGACATTC TGGCTAAAGA CGCCGAGGAA AGAGGCATCA
UCD522       CAAGACATTC TGGCTAAAGA CGCCGAGGAA AGAGGCATCA
UCD932       CAAGACATTC TGGCTAAAGA CGCCGAGGAA AGAGGCATCA
UCD934       CAAGACATTC TGGCTAAAGA CGCCGAGGAA AGAGGCATCA
UCD938       CAAGACATTC TGGCTAAAGA CGCCGAGGAA AGAGGCATCA
UCD939       CAAGACATTC TGGCTAAAGA CGCCGAGGAA AGAGGCATCA
UCD940       CAAGACATTC TGGCTAAAGA CGCCGAGGAA AGAGGCATCA
UCD942       CAAGACATTC TGGCTAAAGA CGCCGAGGAA AGAGGCATCA
UCD950       CAAGACATTC TGGCTAAAGA CGCCGAGGAA AGAGGCATCA
UCD956       CAAGACATTC TGGCTAAAGA CGCCGAGGAA AGAGGCATCA
UCD957       CAAGACATTC TGGCTAAAGA CGCCGAGGAA AGAGGCATCA 3050       3060       3070       3080
             ....|....| ....|....| ....|....| ....|....|
S288c        AAGTCGACTT GGATGCCGCA ATTGAAGAAT TAAAGGAAGC
UCD522       AAGTCGACTT GGATGCCGCA ATTGAAGAAT TAAAGGAAGC
UCD932       AAGTCGACTT GGATGCCGCA ATTGAAGAAT TAAAGGAAGC
UCD934       AAGTCGACTT GGATGCCGCA ATTGAAGAAT TAAAGGAAGC
UCD938       AAGTCGACTT GGATGCCGCA ATTGAAGAAT TAAAGGAAGC
UCD939       AAGTCGACTT GGATGCCGCA ATTGAAGAAT TAAAGGAAGC
UCD940       AAGTCGACTT GGATGCCGCA ATTGAAGAAT TAAAGGAAGC
UCD942       AAGTCGACTT GGATGCCGCA ATTGAAGAAT TAAAGGAAGC
UCD950       AAGTCGACTT GGATGCCGCA ATTGAAGAAT TAAAGGAAGC
UCD956       AAGTCGACTT GGATGCCGCA ATTGAAGAAT TAAAGGAAGC
UCD957       AAGTCGACTT GGATGCCGCA ATTGAAGAAT TAAAGGAAGC 3090       3100
             ....|....| ....|....| ....|...
S288c        ATCAAGATAC ATTTTAGAAG TCTACTAA
UCD522       ATCAAGATAC ATTTTAGAAG TCTACTAA
UCD932       ATCAAGATAC ATTTTAGAAG TCTACTAA
UCD934       ATCAAGATAC ATTTTAGAAG TCTACTAA
UCD938       ATCAAGATAC ATTTTAGAAG TCTACTAA
UCD939       ATCAAGATAC ATTTTAGAAG TCTACTAA
UCD940       ATCAAGATAC ATTTTAGAAG TCTACTAA
UCD942       ATCAAGATAC ATTTTAGAAG TCTACTAA
UCD950       ATCAAGATAC ATTTTAGAAG TCTACTAA
UCD956       ATCAAGATAC ATTTTAGAAG TCTACTAA
UCD957       ATCAAGATAC ATTTTAGAAG TCTACTAA
```

Figure 4A

PileUp: Comparison of amino acid sequences of the MET10 protein in strains S288C, UCD932 and UCD950.

```
  MSF: 1036   Type: P   Check: 6465   ..

Name: S288C      Len: 1036   Check: 9124  Weight: 0
 Name: UCD932     Len: 1036   Check: 8702  Weight: 0
 Name: UCD950     Len: 1036   Check: 8639  Weight: 0

1                                                     50
   S288C      MPVEFATNPF GEAKNATSLP KYGTPVTAIS SVLFNNVDSI FAYKSFSQPD
   UCD932     MPVEFATNPF GEAKNATSLP KYGTPVTAIS SVLFNNVDSI FAYKSFSQPD
   UCD950     MPVEFATNPF GEAKNATSLP KYGTPVTAIS SVLFNNVDSI FAYKSFSQPD 51                                                    100
   S288C      LLHQDLKKWS EKRGNESRGK PFFQELDIRS GAGLAPLGFS HGLKNTTAIV
   UCD932     LLHQDLKKWS EKRGNESRGK PFFQELDIRS GAGLAPLGFS HGLKNTTAIV
   UCD950     LLHQDLKKWS EKRGNESRGK PFFQELDIRS GAGLAPLGFS HGLKNTTAIV 101                                                   150
   S288C      APGFSLPYFI NSLKTVSHDG KFLLNVGALN YDNA GSVTN DYVTALDAAS
   UCD932     APGFSLPYFI NSLKTVSHDG KFLLNVGALN YDNA GSVTN DYVTALDAAS
   UCD950     APGFSLPYFI NSLKTVSHDG KFLLNVGALN YDNA GSVTN DYVTALDAAS 151                                                   200
   S288C      KLKYGVVTPI SANEVQSVAL L LAIATFSN NSGAINLFDG LNYSKTVLPL
   UCD932     KLKYGVVTPI SANEVQSVAL L LAIATFSN NSGAINLFDG LNYSKTVLPL
   UCD950     KLKYGVVTPI SANEVQSVAL L LAIATFSN NSGAINLFDG LNYSKTVLPL 201                                                   250
   S288C      VESVPEASIL AKLSKVIAPD AAFDDVLDKF NELTGLRLHN FQYFGAQDAE
   UCD932     VESVPEASIL AKLSKVIAPD AAFDDVLDKF NELTGLRLHN FQYFGAQDAE
   UCD950     VESVPEASIL AKLSKVIAPD AAFDDVLDKF NELTGLRLHN FQYFGAQDAE 251                                                   300
   S288C      TVFITYGSLE SELFNSAISG NNSKIGLINV RVPLPFNVAK FVTHVPSTTK
   UCD932     TVFITYGSLE SELFNSAISG NNSKIGLINV RVPLPFNVAK FVTHVPSTTK
   UCD950     TVFITYGSLE SELFNSAISG NNSKIGLINV RVPLPFNVAK FVTHVPSTTK 301                                                   350
   S288C      QIVVIGQTLD GSSPSFLRSQ VSAALFYHGR TSISVSEYIY QPDFIWSPKA
   UCD932     QIVVIGQTLD GSSPSFLRSQ VSAALFYHGR TSISVSEYIY QPDFIWSPKA
   UCD950     QIVVIGQTLD GSSPSFLRSQ VSAALFYHGR TSISVSEYIY QPDFIWSPKA 351                                                   400
   S288C      VKSIVSSFIP EFTYNADSSF GEGFIYWASD KSINIDVASK LVKALSLEDG
   UCD932     VKSIVSSFIP EFTYNADSSF GEGFIYWASD KSINIDVASK LVKALSLEDG
   UCD950     VKSIVSSFIP EFTYNADSSF GEGFIYWASD KSINIDVASK LVKALSLEDG 401                                                   450
   S288C      KFVSLRTKFD NLANAGTFQA QFVTSKEQIP VSNIDSTKLS VVEDVSLLKH
   UCD932     KFVSLRTKFD NLANAGTFQA QFVTSKEQIP VSNIDSTKLS VVEDVSLLKH
   UCD950     KFVSLRTKFD NLANAGTFQA QFVTSKEQIP VSNIDSTKLS VVEDVSLLKH 451                                                   500
   S288C      LDVAATVAEQ GSIALVSQKA VKDLDLNSVE SYVKNLGIPE SFLISIAKKN
   UCD932     LDVAATVAEQ GSIALVSQKA VKDLDLNSVE SYVKNLGIPE SFLISIAKKN
   UCD950     LDVAATVAEQ GSIALVSQKA VKDLDLNSVE SYVKNLGIPE SFLISIAKKN
```

Figure 4B

```
              501                                                          550
    S288C     IKLFIIDGET KNDESKLSLF IQAVFWKLAF GLDVAECTNR IWKSIDSGAD
    UCD932    IKLFIIDGET KNDESKLSLF IQAVFWKLAF GLDVAECTNR IWKSIDSGAD
    UCD950    IKLFIIDGET INDESKLSLF IQAVFWKLAF GLDVAECTNR IWKSIDSGAD 551                                                          600
    S288C     ISAASISEFL TGAFKNFLSE VPLALYTKFS EINIEKKEDE EEPAALPIFV
    UCD932    ISAASISEFL TGAFKNFLSE VPLALYTKFS EINIEKKEDE EEPAALPIFV
    UCD950    ISAASISEFL TGAFKNFLSE VPLALYTKFS EINIEKKEDK EEPAALPIFV 601                                                          650
    S288C     NETSFLPNNS TIEEIPLPET SEISDIAKKL SFKEAYEVEN KLRPDLPVKN
    UCD932    NETSFLPNNS TIEEIPLPET SEISDIAKKL SFKEAYEVEN KLRPDLPVKN
    UCD950    NETSFLPNNS TIEEIPLPET SEISDIAKKL SFKEAYEVEN KLRPDLPVKN 651                                                          700
    S288C     FVVKVKENRR VRPADYDRYI FHIEFDISGT GMTYDIGEAL GIHARNNESL
    UCD932    FVVKVKENRR VKPADYDRYI FHIEFDISGT GMTYDIGEAL GIHARNNESL
    UCD950    FVVKVKENRR VRPADYDRYI FHIEFDISGT GMTYDIGEAL GIHARNNESL 701                                                          750
    S288C     VKEFLTFYGL NESDVVLVPN KDNHHLLETR TVLQAFVENL DIFGKPPKRF
    UCD932    VKEFLTFYGL NESDVVLVPN KDNHHLLETR TVLQAFVENL DIFGKPPKRF
    UCD950    VKEFLTFYGL NESDVVLVPN KDNHHLLETR TVLQAFVENL DIFGKPPKRF 751                                                          800
    S288C     YESLIPYASN EEEKKKLEDL VTPAGAVDLK RFQDVEYYTY ADIFELFPSV
    UCD932    YESLIPYASN EEEKKKLEDL VTPAGAVDLK RFQDVEYYTY ADIFELFPSV
    UCD950    YESLIPYASN EEEKKKLEDL VTPAGAVDLK RFQDVEYYTY ADIFELFPSV 801                                                          850
    S288C     RPSLEELVTI IEPLKRREYS IASSQKVHPN EVHLLIVVVD WVDNKGRKRY
    UCD932    RPSLEELVTI IEPLKRREYS IASSQKVHPN EVHLLIVVVD WVDNKGRKRY
    UCD950    RPSLEELVTI IEPLKRREYS IASSQKVHPN EVHLLIVVVD WVDNKGRKRY 851                                                          900
    S288C     GQASKYISDL AVGSELVVSV KPSVMKLPPS PKQPVIMSGL GTGLAPFKAI
    UCD932    GQASKYISDL AVGSELVVSV KPSVMKLPPS PKQPVIMSGL GTGLAPFKAI
    UCD950    GQASKYISDL AVGSELVVSV KPSVMKLPPS PKQPVIMSGL GTGLAPFKAI 901                                                          950
    S288C     VEEKLWQKQQ GYEIGEVFLY LGSRHKREEY LYGELWEAYK DAGIITHIGA
    UCD932    VEEKLWQKQQ GYEIGEVFLY LGSRHKREEY LYGELWEAYK DAGIITHIGA
    UCD950    VEEKLWQKQQ GYEIGEVFLY LGSRHKREEY LYGELWEAYK DAGIITHIGA 951                                                         1000
    S288C     AFSRDQPQKI YIQDRIKENL DELKTAMIDN KGSFYLCGPT WPVPDITQAL
    UCD932    AFSRDQPQKI YIQDRIKENL DELKTAMIDN KGSFYLCGPT WPVPDITQAL
    UCD950    AFSRDQPQKI YIQDRIKENL DELKTAMIDN KGSFYLCGPT WPVPDITQAL 1001                          1036
    S288C     QDILAKDAEE RGIKVDLDAA IEELKEASRY ILEVY.
    UCD932    QDILAKDAEE RGIKVDLDAA IEELKEASRY ILEVY.
    UCD950    QDILAKDAEE RGIKVDLDAA IEELKEASRY ILEVY.
```

*Figure 5*

```
   1951                                              2000
 S288c  TTCGTCGTGA AAGTTAAAGA AAATAGACGT GTTA GCCTG CTGATTATGA
UCD932  TTCGTCGTGA AAGTTAAAGA AAATAGACGT GTTAAGCCTG CTGATTATGA
UCD950  TTCGTCGTGA AAGTTAAAGA AAATAGACGT GTTA GCCTG CTGATTATGA

S288c       AAT AGA CGT GTT A G CCT GCT GAT TAT
        UCD932      AAT AGA CGT GTT AAG CCT GCT GAT TAT
        UCD950      AAT AGA CGT GTT A G CCT GCT GAT TAT
        AMINO ACID   N   R   R   V  T/K  P   A   D   Y
```

MET10/YFR030W Domains/Motifs and Signal Peptides

*Figure 7*
A
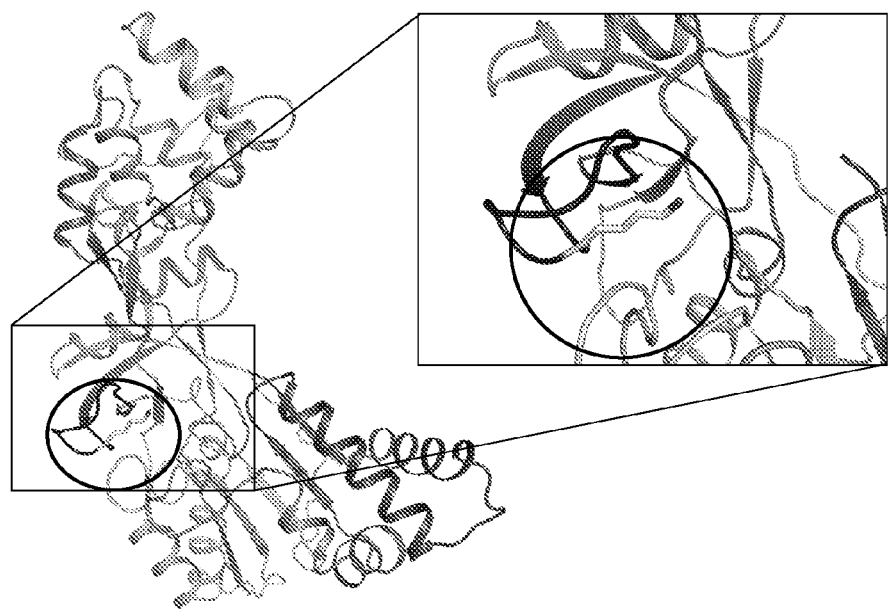
B
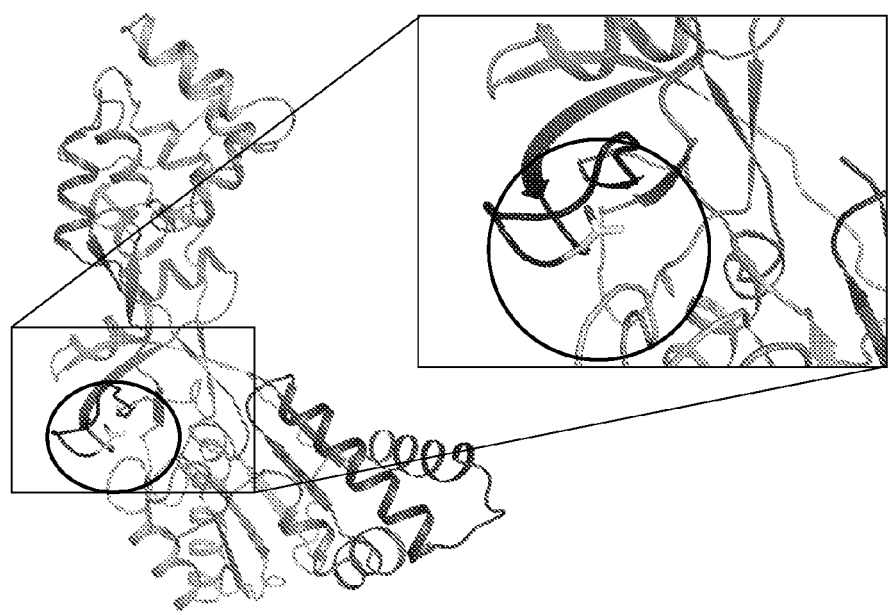

Figure 8

| | | | | | | |
|---|---|---|---|---|---|---|
| UCD_932_Met10 | 628 | KKLSFKEAYE | VENKLRPDLP | VNNFVVKVEE | NRRVPADYD | RNIFHEFDI | 677 |
| S288c_Met10 | 628 | KKLSFKEAYE | VENKLRPDLP | VNNFVVKVEE | NRRVTPADYD | RNIFHEFDI | 677 |
| S._cerevisiae_(carlsbergensis) | 628 | KKLSFKEAYG | VENKLRPDLP | VNNFVVKVEE | NRRVTPADYD | RNIFHEFDI | 677 |
| Kluyveromyces_lactis | 628 | KKLTFQEAYG | VSQQLRPDLP | VNNYVVKVEE | NRRVTPDEYD | RNIFHEFDI | 677 |
| Yarrowia_lipolytica | 634 | KRVVFKEAYG | TENSLRPDIS | TNNIVKVQE | KRRVTPENYE | RNIFHVEFD | 683 |
| Schizosaccharomyces_pombe | 602 | KQIIFPEAYK | KKDALRPDVS | EKVETVHVRA | KRLTPAEYN | RNIFHEFDL | 651 |

SEQUENCE LISTING

```
<160> NUMBER OF SEQ ID NOS: 93

<210> SEQ ID NO 1
<211> LENGTH: 3108
<212> TYPE: DNA
<213> ORGANISM: Saccharomyces cerevisiae
<220> FEATURE:
<223> OTHER INFORMATION: yeast assimilatory sulfite reductase alpha
      subunit (Met 10, MET10), strain UCD932 allele

<400> SEQUENCE: 1
atgccagttg agtttgctac caatcctttt ggcgaggcca aaaatgcaac ttcactgcca      60
aaatatggta cacccgtaac tgccatttca tctgtgctgt tcaataacgt ggactccatt     120
tttgcttaca agtccttttc tcaacccgat ttgttacacc aagatctaaa aaaatggtct     180
gaaaagcgtg gtaacgaatc acgtgggaag ccattttcc aagagctgga tatcagatct      240
ggcgctggtt tggctccttt agggttttct catggattga agaacactac agcaattgtt     300
gctccagggt tttcgctgcc atacttcatt aactctttga aaaccgtctc tcatgatggt     360
aagtttcttt tgaatgttgg tgctttaaac tacgacaatg ctaacggctc tgtcaccaac     420
gattatgtaa ccgcattgga tgctgcttcc aagctgaagt atggtgtcgt gactccgatt     480
tccgctaacg aggtacaaag tgtcgcctta ctgacattgg cgattgccac tttcagtaat     540
```

```
aactccggag ctatcaattt atttgacgga ttaaactact cgaaaaccgt cttgccgttg      600
gtcgaatctg ttcctgaggc atctattttg gcaaaactat ccaaagttat tgcaccagat      660
gctgcctttg atgatgtctt ggataagttt aatgaattga ctggattgag actacataat      720
ttccaatact ttggtgctca ggatgctgaa actgtgttta tcacttatgg gtctttagaa      780
tccgaattgt tcaactctgc gattagtggt aataattcca aaatcgggtt aatcaacgtc      840
agagtaccat tacctttaa cgttgctaag tttgtcactc acgttccatc cactaccaaa       900
caaattgttg ttataggcca aactttggat ggttcttcgc cttctttctt gagatctcaa      960
gtttcagccg ccttatttta ccacggccgc acctcaatta gcgtttctga gtacatctat     1020 caaccgatt tcatttggtc cccaaaagct gtcaaatcaa ttgtatcgtc attcatccct      1080
gaattcactt acaatgccga ttcatctttc ggcgaaggat tcatttattg ggcctctgat     1140
aagagtatca atattgatgt tgcctccaaa cttgtgaaag ctctgtcttt ggaagatggg     1200
aaatttgtgt ctttgagaac gaaatttgat aacttggcta atgctggtac cttccaagct     1260
caatttgtga cctcgaaaga acagatacct gtttcaaaca tcgattctac gaaattatca     1320
gtcgttgaag atgtcagttt attgaagcat ttagacgtag ctgctaccgt cgcagaacaa     1380
ggttcaattg cgttggtttc ccaaaaggca gttaaagatt tggatttaaa ttctgtagaa     1440
agttacgtca agaatttggg aattcctgaa tcattcctaa tatctattgc gaagaaaaac     1500
atcaaattgt ttatcatcga tggtgagacc actaacgacg agtccaaatt gtccttgttt     1560
atccaagccg ttttctggaa attggccttc ggtctagatg tcgcagaatg taccaaccgt     1620
atctggaaaa gcattgattc aggtgcagac atttcagcag cctcgatttc tgaatttctc     1680
actggtgcat tcaaaaactt cctcagtgag gttccgctag cgctgtacac taaattttct     1740
gaaataaaca ttgaaagaa agaggatgag gaagagcctg cagctttacc aatttttcgtt     1800 aatgaaacat ctttcctccc aaataacagt accattgaag aaataccatt acctgagacc     1860
tctgagatct ctgatattgc caagaagttg tccttcaaag aggcatatga agttgagaat     1920
aaactaagac ccgatttacc cgtcaagaac ttcgtcgtga agttaaagaa aaatagacgt     1980
gttaagcctg ctgattatga tagatatatt ttccatattg aattcgatat ttctggtact     2040
ggaatgactt atgacatcgg tgaagccctc ggtattcatg ccagaaacaa tgaatctttg     2100
gtcaaagaat tcttaacctt ctatggtcta atgaatccg atgttgtctt agtccccaac      2160
aaggacaacc accatttgtt agaaacaaga accgtcttac aagcatttgt ggaaaatttg     2220
gatattttcg gtaaaccacc aaaagagttt tacgaatcat tgattccata tgcctctaac     2280
gaagaggaga agaaaaaatt agaggatttg gttactcctg ccggtgcagt agatttgaag     2340
agatttcaag atgtggagta ttatacatat gctgacattt ttgaattgtt cccatctgtt     2400
cgcccatctc ttgaggaact tgttactatc attgaaccat tgaagagaag agaatactca     2460
attgcctcct ctcagaaagt tcatccaaat gaagttcatt tattgatcgt tgttgttgat     2520
tgggtggata taaaggaag aaaaggtac ggtcaagctt ctaagtatat ctcagacctt      2580
gctgtcggtt cagaattggt cgttagcgtt aaaccatctg ttatgaaatt accaccatct     2640
ccaaagcaac cagttattat gagtggttta ggtactggtt tggcaccatt caaggccatt     2700
gttgaagaga attatggca aaagcagcaa ggttatgaga ttggtgaagt cttcctatat      2760
ctaggttcaa gacacaaaag agaagaatat ttatatggtg agttatggga ggcttacaaa     2820
gatgcaggta ttatcacaca catcggcgct gcttttctcaa gagaccaacc tcaaaaaatt     2880
tacattcaag atcgtatcaa agagaatttg gatgaattaa aaactgcaat gattgataat     2940
```

```
aaaggttcat tttacttgtg tggccctact tggccagttc cagatattac tcaagctttg    3000
caagacattc tggctaaaga cgccgaggaa agaggcatca aagtcgactt ggatgccgca    3060
attgaagaat taaaggaagc atcaagatac attttagaag tctactaa                3108

<210> SEQ ID NO 2
<211> LENGTH: 3108
<212> TYPE: DNA
<213> ORGANISM: Saccharomyces cerevisiae
<220> FEATURE:
<223> OTHER INFORMATION: yeast assimilatory sulfite reductase alpha
      subunit (Met 10, MET10), strain UCD950 allele

<400> SEQUENCE: 2
atgccagttg agtttgctac caatcctttt ggcgaggcca aaaatgcaac ttcactgcca      60
aaatatggta cacccgtaac tgccatttca tctgtgctgt tcaataacgt ggactccatt     120
tttgcttaca agtccttttc tcaacccgat ttgttacacc aagatctaaa aaaatggtct     180
gaaaagcgtg gtaacgaatc acgtgggaag ccattttttcc aagagctgga tatcagatct    240
ggcgctggtt tggctccttt agggttttct catggattga agaacactac agcaattgtt     300
gctccagggt tttcgctgcc atacttcatt aactctttga aaaccgtctc tcatgatggt     360
aagtttcttt tgaatgttgg tgcttttaaac tacgacaatg ctaccggctc tgtcaccaac    420
gattatgtaa ccgcattgga tgctgcttcc aagctgaagt atggtgtcgt gactccgatt     480
tccgctaacg aggtacaaag tgtcgcctta ctggcattgg cgattgccac tttcagtaat    540
aactccggag ctatcaattt atttgacgga ttaaactact cgaaaaccgt cttgccgttg     600
gtcgaatctg ttcctgaggc atctattttg gcaaaactat ccaaagttat tgcaccagat     660
gctgcctttg atgatgtctt ggataagttt aatgaattga ctggattgag actacataat    720
ttccaatact tggtgctca ggatgctgaa actgtgttta tcacttatgg gtctttagaa     780
tccgaattgt tcaactctgc gattagtggt aataattcca aaatcgggtt aatcaacgtc    840
agagtaccat taccttttaa cgttgctaag tttgtcactc acgttccatc cactaccaaa    900
caaattgttg ttataggcca aactttggat ggttcttcgc cttctttctt gagatctcaa    960
gtttcagccg ccttatttta ccacggccgc acctcaatta gcgtttctga gtacatctat    1020
caaccagatt tcatttggtc cccaaaaagct gtcaaatcaa ttgtatcgtc attcatccct    1080
gaattcactt acaatgccga ttcatctttc ggcgaaggat tcattattg ggcctctgat     1140 aagagtatca atattgatgt tgcctccaaa cttgtgaaag ctctgtcttt ggaagatggg    1200
aaatttgtgt ctttgagaac gaaatttgat aacttggcta atgctggtac cttccaagct    1260
caatttgtga cctcgaagga acagataccct gtttcaaaca tcgattctac gaaattatca    1320
gtcgttgaag atgtcagttt attgaagcat ttagacgtag ctgctaccgt cgcagaacaa    1380
ggttcaattg cgttggtttc ccaaaaggca gttaaagatt tggatttaaa ttctgtagaa    1440
agttacgtca agaatttggg aattcctgaa tcattcctaa tatctattgc gaagaaaaac    1500
atcaaattgt ttatcatcga tggtgagacc attaacgacg agtccaaatt gtccttgttt    1560
atccaagccg ttttctggaa attggccttc ggtctagatg tcgcagaatg taccaaccgt    1620
atctggaaaa gcattgattc aggtgcagac atttcagcag cctcgatttc tgaatttctc    1680
actggtgcat tcaaaaactt cctcagtgag gttccgctag cgctgtacac taaattttct    1740
gaaataaaca ttgaaagaa agaggataag gaagagcctg cagctttacc aattttcgtt    1800
aatgaaacat cttttcctccc aaataacagt accattgaag aaatcaccatt acctgagacc    1860
```

-continued

```
tctgagatct ctgatattgc caagaagttg tccttcaaag aggcatatga agttgagaat    1920
aaactaagac ccgatttacc cgtcaagaac ttcgtcgtga agttaaaga aaatagacgt    1980 gttacgcctg ctgattatga tagatatatt ttccatattg aattcgatat ttctggtact    2040
ggaatgactt atgacatcgg tgaagccctc ggtattcatg ccagaaacaa tgaatctttg    2100
gtcaaagaat tcttaacctt ctatggtcta aatgaatccg atgttgtctt agtccccaac    2160
aaggacaacc accatttgtt agaaacaaga accgtcttac aagcatttgt ggaaaatttg    2220
gatattttcg gtaaaccacc aaaaagattt tacgaatcat tgattccata tgcctctaac    2280
gaagaggaga agaaaaaatt agaggatttg gttactcctg ccggtgcagt agatttgaag    2340
agatttcaag atgtggagta ttatacatat gctgacattt ttgaattgtt cccatctgtt    2400
cgcccatctc ttgaggaact tgttactatc attgaaccat tgaagagaag agaatactca    2460
attgcctcct ctcagaaagt tcatccaaat gaagttcatt tattgatcgt tgttgttgat    2520
tgggtggata taaaggaag aaaaaggtac ggtcaagctt ctaagtatat ctcagacctt    2580
gctgtcggtt cagaattggt cgttagcgtt aaaccatctg ttatgaaatt accaccatct    2640
ccaaagcaac cagttattat gagtggttta ggtactggtt tggcaccatt caaggccatt    2700
gttgaagaga aattatggca aaagcagcaa ggttatgaga ttggtgaagt cttcctatat    2760
ctaggttcaa gacacaaaag agaagaatat ttatatggtg agttatggga ggcttacaaa    2820
gatgcaggta ttatcacaca catcggcgct gctttctcaa gagaccaacc tcaaaaaatt    2880
tacattcaag atcgtatcaa agagaatttg gatgaattaa aaactgcaat gattgataat    2940
aaaggttcat tttacttgtg tggccctact tggccagttc cagatattac tcaagctttg    3000
caagacattc tggctaaaga cgccgaggaa agaggcatca agtcgacttt ggatgccgca    3060
attgaagaat taaaggaagc atcaagatac attttagaag tctactaa    3108
```

<210> SEQ ID NO 3
<211> LENGTH: 1035
<212> TYPE: PRT
<213> ORGANISM: Artificial Sequence
<220> FEATURE:
<223> OTHER INFORMATION: Description of Artificial Sequence:sulfide
      inactive yeast assimilatory sulfite reductase
      alpha subunit (Met 10, MET10) consensus sequence
<220> FEATURE:
<221> NAME/KEY: MOD_RES
<222> LOCATION: (135)
<223> OTHER INFORMATION: Xaa = Thr or Asn
<220> FEATURE:
<221> NAME/KEY: MOD_RES
<222> LOCATION: (172)
<223> OTHER INFORMATION: Xaa = Ala or Thr
<220> FEATURE:
<221> NAME/KEY: MOD_RES
<222> LOCATION: (511)
<223> OTHER INFORMATION: Xaa = Thr or Ile
<220> FEATURE:
<221> NAME/KEY: MOD_RES
<222> LOCATION: (590)
<223> OTHER INFORMATION: Xaa = Glu or Lys
<220> FEATURE:
<221> NAME/KEY: MOD_RES
<222> LOCATION: (662)
<223> OTHER INFORMATION: Xaa = Ala, Cys, Asp, Glu, Phe, Gly, His, Ile,
      Lys, Leu, Met, Asn, Pro, Gln, Arg, Ser, Val, Trp or
      Tyr, not Thr

<400> SEQUENCE: 3

Met Pro Val Glu Phe Ala Thr Asn Pro Phe Gly Glu Ala Lys Asn Ala
 1               5                  10                  15

Thr Ser Leu Pro Lys Tyr Gly Thr Pro Val Thr Ala Ile Ser Ser Val

```
                    20                  25                  30
Leu Phe Asn Asn Val Asp Ser Ile Phe Ala Tyr Lys Ser Phe Ser Gln
                35                  40                  45

Pro Asp Leu Leu His Gln Asp Leu Lys Lys Trp Ser Glu Lys Arg Gly
        50                  55                  60

Asn Glu Ser Arg Gly Lys Pro Phe Phe Gln Glu Leu Asp Ile Arg Ser
 65                  70                  75                  80

Gly Ala Gly Leu Ala Pro Leu Gly Phe Ser His Gly Leu Lys Asn Thr
                    85                  90                  95

Thr Ala Ile Val Ala Pro Gly Phe Ser Leu Pro Tyr Phe Ile Asn Ser
                100                 105                 110

Leu Lys Thr Val Ser His Asp Gly Lys Phe Leu Leu Asn Val Gly Ala
                115                 120                 125

Leu Asn Tyr Asp Asn Ala Xaa Gly Ser Val Thr Asn Asp Tyr Val Thr
        130                 135                 140

Ala Leu Asp Ala Ala Ser Lys Leu Lys Tyr Gly Val Val Thr Pro Ile
145                 150                 155                 160

Ser Ala Asn Glu Val Gln Ser Val Ala Leu Leu Xaa Leu Ala Ile Ala
                165                 170                 175

Thr Phe Ser Asn Asn Ser Gly Ala Ile Asn Leu Phe Asp Gly Leu Asn
                180                 185                 190

Tyr Ser Lys Thr Val Leu Pro Leu Val Glu Ser Val Pro Glu Ala Ser
            195                 200                 205

Ile Leu Ala Lys Leu Ser Lys Val Ile Ala Pro Asp Ala Ala Phe Asp
        210                 215                 220

Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
                    245                 250                 255

Gly Ser Leu Glu Ser Glu Leu Phe Asn Ser Ala Ile Ser Gly Asn Asn
                260                 265                 270

Ser Lys Ile Gly Leu Ile Asn Val Arg Val Pro Leu Pro Phe Asn Val
            275                 280                 285

Ala Lys Phe Val Thr His Val Pro Ser Thr Thr Lys Gln Ile Val Val
        290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                    325                 330                 335

Glu Tyr Ile Tyr Gln Pro Asp Phe Ile Trp Ser Pro Lys Ala Val Lys
                340                 345                 350

Ser Ile Val Ser Ser Phe Ile Pro Glu Phe Thr Tyr Asn Ala Asp Ser
            355                 360                 365

Ser Phe Gly Glu Gly Phe Ile Tyr Trp Ala Ser Asp Lys Ser Ile Asn
        370                 375                 380

Ile Asp Val Ala Ser Lys Leu Val Lys Ala Leu Ser Leu Glu Asp Gly
385                 390                 395                 400

Lys Phe Val Ser Leu Arg Thr Lys Phe Asp Asn Leu Ala Asn Ala Gly
                    405                 410                 415

Thr Phe Gln Ala Gln Phe Val Thr Ser Lys Glu Gln Ile Pro Val Ser
                420                 425                 430

Asn Ile Asp Ser Thr Lys Leu Ser Val Val Glu Asp Val Ser Leu Leu
            435                 440                 445
```

-continued

```
Lys His Leu Asp Val Ala Ala Thr Val Ala Glu Gln Gly Ser Ile Ala
450                 455                 460
Leu Val Ser Gln Lys Ala Val Lys Asp Leu Asp Leu Asn Ser Val Glu
465                 470                 475                 480
Ser Tyr Val Lys Asn Leu Gly Ile Pro Glu Ser Phe Leu Ile Ser Ile
                485                 490                 495
Ala Lys Lys Asn Ile Lys Leu Phe Ile Ile Asp Gly Glu Thr Xaa Asn
            500                 505                 510
Asp Glu Ser Lys Leu Ser Leu Phe Ile Gln Ala Val Phe Trp Lys Leu
        515                 520                 525
Ala Phe Gly Leu Asp Val Ala Glu Cys Thr Asn Arg Ile Trp Lys Ser
    530                 535                 540
Ile Asp Ser Gly Ala Asp Ile Ser Ala Ala Ser Ile Ser Glu Phe Leu
545                 550                 555                 560
Thr Gly Ala Phe Lys Asn Phe Leu Ser Glu Val Pro Leu Ala Leu Tyr
                565                 570                 575
Thr Lys Phe Ser Glu Ile Asn Ile Glu Lys Lys Glu Asp Xaa Glu Glu
            580                 585                 590
Pro Ala Ala Leu Pro Ile Phe Val Asn Glu Thr Ser Phe Leu Pro Asn
        595                 600                 605
Asn Ser Thr Ile Glu Glu Ile Pro Leu Pro Glu Thr Ser Glu Ile Ser
    610                 615                 620
Asp Ile Ala Lys Lys Leu Ser Phe Lys Glu Ala Tyr Glu Val Glu Asn
625                 630                 635                 640
Lys Leu Arg Pro Asp Leu Pro Val Lys Asn Phe Val Val Lys Val Lys
                645                 650                 655
Glu Asn Arg Arg Val Xaa Pro Ala Asp Tyr Asp Arg Tyr Ile Phe His
            660                 665                 670
Ile Glu Phe Asp Ile Ser Gly Thr Gly Met Thr Tyr Asp Ile Gly Glu
        675                 680                 685
Ala Leu Gly Ile His Ala Arg Asn Asn Glu Ser Leu Val Lys Glu Phe
    690                 695                 700
Leu Thr Phe Tyr Gly Leu Asn Glu Ser Asp Val Val Leu Val Pro Asn
705                 710                 715                 720
Lys Asp Asn His His Leu Leu Glu Thr Arg Thr Val Leu Gln Ala Phe
                725                 730                 735
Val Glu Asn Leu Asp Ile Phe Gly Lys Pro Pro Lys Arg Phe Tyr Glu
            740                 745                 750
Ser Leu Ile Pro Tyr Ala Ser Asn Glu Glu Lys Lys Lys Leu Glu
        755                 760                 765
Asp Leu Val Thr Pro Ala Gly Ala Val Asp Leu Lys Arg Phe Gln Asp
    770                 775                 780
Val Glu Tyr Tyr Thr Tyr Ala Asp Ile Phe Glu Leu Phe Pro Ser Val
785                 790                 795                 800
Arg Pro Ser Leu Glu Glu Leu Val Thr Ile Ile Glu Pro Leu Lys Arg
                805                 810                 815
Arg Glu Tyr Ser Ile Ala Ser Ser Gln Lys Val His Pro Asn Glu Val
            820                 825                 830
His Leu Leu Ile Val Val Asp Trp Val Asp Asn Lys Gly Arg Lys
        835                 840                 845
Arg Tyr Gly Gln Ala Ser Lys Tyr Ile Ser Asp Leu Ala Val Gly Ser
    850                 855                 860
Glu Leu Val Val Ser Val Lys Pro Ser Val Met Lys Leu Pro Pro Ser
865                 870                 875                 880
```

```
Pro Lys Gln Pro Val Ile Met Ser Gly Leu Gly Thr Gly Leu Ala Pro
                885                 890                 895

Phe Lys Ala Ile Val Glu Glu Lys Leu Trp Gln Lys Gln Gly Tyr
            900                 905                 910

Glu Ile Gly Glu Val Phe Leu Tyr Leu Gly Ser Arg His Lys Arg Glu
            915                 920                 925

Glu Tyr Leu Tyr Gly Glu Leu Trp Glu Ala Tyr Lys Asp Ala Gly Ile
        930                 935                 940

Ile Thr His Ile Gly Ala Ala Phe Ser Arg Asp Gln Pro Gln Lys Ile
945                 950                 955                 960

Tyr Ile Gln Asp Arg Ile Lys Glu Asn Leu Asp Glu Leu Lys Thr Ala
                965                 970                 975

Met Ile Asp Asn Lys Gly Ser Phe Tyr Leu Cys Gly Pro Thr Trp Pro
                980                 985                 990

Val Pro Asp Ile Thr Gln Ala Leu Gln Asp Ile Leu Ala Lys Asp Ala
            995                 1000                1005

Glu Glu Arg Gly Ile Lys Val Asp Leu Asp Ala Ala Ile Glu Glu Leu
    1010                1015                1020

Lys Glu Ala Ser Arg Tyr Ile Leu Glu Val Tyr
1025                1030                1035

<210> SEQ ID NO 4
<211> LENGTH: 1035
<212> TYPE: PRT
<213> ORGANISM: Artificial Sequence
<220> FEATURE:
<223> OTHER INFORMATION: Description of Artificial Sequence:modified
      sulfide inactive yeast assimilatory sulfite
      reductase alpha subunit (Met 10, MET10) based on
      strain UCD932 sequence
<220> FEATURE:
<221> NAME/KEY: MOD_RES
<222> LOCATION: (662)
<223> OTHER INFORMATION: Xaa = Ala, Cys, Asp, Glu, Phe, Gly, His, Ile,
      Lys, Leu, Met, Asn, Pro, Gln, Arg, Ser, Val, Trp or
      Tyr, not Thr

<400> SEQUENCE: 4

Met Pro Val Glu Phe Ala Thr Asn Pro Phe Gly Glu Ala Lys Asn Ala
1               5                   10                  15

Thr Ser Leu Pro Lys Tyr Gly Thr Pro Val Thr Ala Ile Ser Ser Val
            20                  25                  30

Leu Phe Asn Asn Val Asp Ser Ile Phe Ala Tyr Lys Ser Phe Ser Gln
        35                  40                  45

Pro Asp Leu Leu His Gln Asp Leu Lys Lys Trp Ser Glu Lys Arg Gly
    50                  55                  60

Asn Glu Ser Arg Gly Lys Pro Phe Gln Glu Leu Asp Ile Arg Ser
65                  70                  75                  80

Gly Ala Gly Leu Ala Pro Leu Gly Phe Ser His Gly Leu Lys Asn Thr
                85                  90                  95

Thr Ala Ile Val Ala Pro Gly Phe Ser Leu Pro Tyr Phe Ile Asn Ser
            100                 105                 110

Leu Lys Thr Val Ser His Asp Gly Lys Phe Leu Leu Asn Val Gly Ala
        115                 120                 125

Leu Asn Tyr Asp Asn Ala Asn Gly Ser Val Thr Asn Asp Tyr Val Thr
    130                 135                 140

Ala Leu Asp Ala Ala Ser Lys Leu Lys Tyr Gly Val Val Thr Pro Ile
145                 150                 155                 160
```

```
Ser Ala Asn Glu Val Gln Ser Val Ala Leu Leu Thr Leu Ala Ile Ala
                165                 170                 175

Thr Phe Ser Asn Asn Ser Gly Ala Ile Asn Leu Phe Asp Gly Leu Asn
            180                 185                 190

Tyr Ser Lys Thr Val Leu Pro Leu Val Glu Ser Val Pro Glu Ala Ser
        195                 200                 205

Ile Leu Ala Lys Leu Ser Lys Val Ile Ala Pro Asp Ala Ala Phe Asp
    210                 215                 220

Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
                245                 250                 255

Gly Ser Leu Glu Ser Glu Leu Phe Asn Ser Ala Ile Ser Gly Asn Asn
            260                 265                 270

Ser Lys Ile Gly Leu Ile Asn Val Arg Val Pro Leu Pro Phe Asn Val
        275                 280                 285

Ala Lys Phe Val Thr His Val Pro Ser Thr Thr Lys Gln Ile Val Val
    290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                325                 330                 335

Glu Tyr Ile Tyr Gln Pro Asp Phe Ile Trp Ser Pro Lys Ala Val Lys
            340                 345                 350

Ser Ile Val Ser Ser Phe Ile Pro Glu Phe Thr Tyr Asn Ala Asp Ser
        355                 360                 365

Ser Phe Gly Glu Gly Phe Ile Tyr Trp Ala Ser Asp Lys Ser Ile Asn
    370                 375                 380

Ile Asp Val Ala Ser Lys Leu Val Lys Ala Leu Ser Leu Glu Asp Gly
385                 390                 395                 400

Lys Phe Val Ser Leu Arg Thr Lys Phe Asp Asn Leu Ala Asn Ala Gly
                405                 410                 415

Thr Phe Gln Ala Gln Phe Val Ser Lys Glu Gln Ile Pro Val Ser
            420                 425                 430

Asn Ile Asp Ser Thr Lys Leu Ser Val Val Glu Asp Val Ser Leu Leu
        435                 440                 445

Lys His Leu Asp Val Ala Ala Thr Val Ala Glu Gln Gly Ser Ile Ala
    450                 455                 460

Leu Val Ser Gln Lys Ala Val Lys Asp Leu Asp Leu Asn Ser Val Glu
465                 470                 475                 480

Ser Tyr Val Lys Asn Leu Gly Ile Pro Glu Ser Phe Leu Ile Ser Ile
                485                 490                 495

Ala Lys Lys Asn Ile Lys Leu Phe Ile Ile Asp Gly Glu Thr Thr Asn
            500                 505                 510

Asp Glu Ser Lys Leu Ser Leu Phe Ile Gln Ala Val Phe Trp Lys Leu
        515                 520                 525

Ala Phe Gly Leu Asp Val Ala Glu Cys Thr Asn Arg Ile Trp Lys Ser
    530                 535                 540

Ile Asp Ser Gly Ala Asp Ile Ser Ala Ala Ser Ile Ser Glu Phe Leu
545                 550                 555                 560

Thr Gly Ala Phe Lys Asn Phe Leu Ser Glu Val Pro Leu Ala Leu Tyr
                565                 570                 575

Thr Lys Phe Ser Glu Ile Asn Ile Glu Lys Lys Glu Asp Glu Glu Glu
            580                 585                 590
```

```
Pro Ala Ala Leu Pro Ile Phe Val Asn Glu Thr Ser Phe Leu Pro Asn
            595                 600                 605

Asn Ser Thr Ile Glu Glu Ile Pro Leu Pro Glu Thr Ser Glu Ile Ser
            610                 615                 620

Asp Ile Ala Lys Lys Leu Ser Phe Lys Glu Ala Tyr Glu Val Glu Asn
625                 630                 635                 640

Lys Leu Arg Pro Asp Leu Pro Val Lys Asn Phe Val Lys Val Lys
                645                 650                 655

Glu Asn Arg Arg Val Xaa Pro Ala Asp Tyr Asp Arg Tyr Ile Phe His
            660                 665                 670

Ile Glu Phe Asp Ile Ser Gly Thr Gly Met Thr Tyr Asp Ile Gly Glu
            675                 680                 685

Ala Leu Gly Ile His Ala Arg Asn Asn Glu Ser Leu Val Lys Glu Phe
            690                 695                 700

Leu Thr Phe Tyr Gly Leu Asn Glu Ser Asp Val Val Leu Val Pro Asn
705                 710                 715                 720

Lys Asp Asn His His Leu Leu Glu Thr Arg Thr Val Leu Gln Ala Phe
                725                 730                 735

Val Glu Asn Leu Asp Ile Phe Gly Lys Pro Pro Lys Arg Phe Tyr Glu
            740                 745                 750

Ser Leu Ile Pro Tyr Ala Ser Asn Glu Glu Lys Lys Lys Leu Glu
            755                 760                 765

Asp Leu Val Thr Pro Ala Gly Ala Val Asp Leu Lys Arg Phe Gln Asp
770                 775                 780

Val Glu Tyr Tyr Thr Tyr Ala Asp Ile Phe Glu Leu Phe Pro Ser Val
785                 790                 795                 800

Arg Pro Ser Leu Glu Gly Leu Val Thr Ile Ile Glu Pro Leu Lys Arg
            805                 810                 815

Arg Glu Tyr Ser Ile Ala Ser Ser Gln Lys Val His Pro Asn Glu Val
            820                 825                 830

His Leu Leu Ile Val Val Val Asp Trp Val Asp Asn Lys Gly Arg Lys
            835                 840                 845

Arg Tyr Gly Gln Ala Ser Lys Tyr Ile Ser Asp Leu Ala Val Gly Ser
            850                 855                 860

Glu Leu Val Val Ser Val Lys Pro Ser Val Met Lys Leu Pro Pro Ser
865                 870                 875                 880

Pro Lys Gln Pro Val Ile Met Ser Gly Leu Gly Thr Gly Leu Ala Pro
                885                 890                 895

Phe Lys Ala Ile Val Glu Glu Lys Leu Trp Gln Lys Gln Gly Tyr
            900                 905                 910

Glu Ile Gly Glu Val Phe Leu Tyr Leu Gly Ser Arg His Lys Arg Glu
            915                 920                 925

Glu Tyr Leu Tyr Gly Glu Leu Trp Glu Ala Tyr Lys Asp Ala Gly Ile
            930                 935                 940

Ile Thr His Ile Gly Ala Ala Phe Ser Arg Asp Gln Pro Gln Lys Ile
945                 950                 955                 960

Tyr Ile Gln Asp Arg Ile Lys Glu Asn Leu Asp Glu Leu Lys Thr Ala
                965                 970                 975

Met Ile Asp Asn Lys Gly Ser Phe Tyr Leu Cys Gly Pro Thr Trp Pro
            980                 985                 990

Val Pro Asp Ile Thr Gln Ala Leu Gln Asp Ile Leu Ala Lys Asp Ala
            995                 1000                1005

Glu Glu Arg Gly Ile Lys Val Asp Leu Asp Ala Ala Ile Glu Glu Leu
```

```
                  1010              1015             1020
Lys Glu Ala Ser Arg Tyr Ile Leu Glu Val Tyr
1025              1030             1035

<210> SEQ ID NO 5
<211> LENGTH: 1035
<212> TYPE: PRT
<213> ORGANISM: Artificial Sequence
<220> FEATURE:
<223> OTHER INFORMATION: Description of Artificial Sequence:sulfide
      inactive yeast assimilatory sulfite reductase
      alpha subunit (Met 10, MET10)
<220> FEATURE:
<221> NAME/KEY: MOD_RES
<222> LOCATION: (135)
<223> OTHER INFORMATION: Xaa = Thr or Asn
<220> FEATURE:
<221> NAME/KEY: MOD_RES
<222> LOCATION: (172)
<223> OTHER INFORMATION: Xaa = Ala or Thr
<220> FEATURE:
<221> NAME/KEY: MOD_RES
<222> LOCATION: (511)
<223> OTHER INFORMATION: Xaa = Thr or Ile
<220> FEATURE:
<221> NAME/KEY: MOD_RES
<222> LOCATION: (590)
<223> OTHER INFORMATION: Xaa = Glu or Lys
<220> FEATURE:
<221> NAME/KEY: MOD_RES
<222> LOCATION: (662)
<223> OTHER INFORMATION: Xaa = Ala, Cys, Asp, Glu, Phe, Gly, His, Ile,
      Lys, Leu, Met, Asn, Pro, Gln, Arg, Val, Trp or Tyr, not
      Thr or Ser

<400> SEQUENCE: 5

Met Pro Val Glu Phe Ala Thr Asn Pro Phe Gly Glu Ala Lys Asn Ala
  1               5                  10                  15

Thr Ser Leu Pro Lys Tyr Gly Thr Pro Val Thr Ala Ile Ser Ser Val
                 20                  25                  30

Leu Phe Asn Asn Val Asp Ser Ile Phe Ala Tyr Lys Ser Phe Ser Gln
             35                  40                  45

Pro Asp Leu Leu His Gln Asp Leu Lys Lys Trp Ser Glu Lys Arg Gly
 50                  55                  60

Asn Glu Ser Arg Gly Lys Pro Phe Phe Gln Glu Leu Asp Ile Arg Ser
 65                  70                  75                  80

Gly Ala Gly Leu Ala Pro Leu Gly Phe Ser His Gly Leu Lys Asn Thr
                 85                  90                  95

Thr Ala Ile Val Ala Pro Gly Phe Ser Leu Pro Tyr Phe Ile Asn Ser
            100                 105                 110

Leu Lys Thr Val Ser His Asp Gly Lys Phe Leu Leu Asn Val Gly Ala
            115                 120                 125

Leu Asn Tyr Asp Asn Ala Xaa Gly Ser Val Thr Asn Asp Tyr Val Thr
130                 135                 140

Ala Leu Asp Ala Ala Ser Lys Leu Lys Tyr Gly Val Val Thr Pro Ile
145                 150                 155                 160

Ser Ala Asn Glu Val Gln Ser Val Ala Leu Xaa Leu Ala Ile Ala
                165                 170                 175

Thr Phe Ser Asn Asn Ser Gly Ala Ile Asn Leu Phe Asp Gly Leu Asn
            180                 185                 190

Tyr Ser Lys Thr Val Leu Pro Leu Val Glu Ser Val Pro Glu Ala Ser
            195                 200                 205

Ile Leu Ala Lys Leu Ser Lys Val Ile Ala Pro Asp Ala Ala Phe Asp
210                 215                 220
```

```
Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
            245                 250                 255

Gly Ser Leu Glu Ser Glu Leu Phe Asn Ser Ala Ile Ser Gly Asn Asn
            260                 265                 270

Ser Lys Ile Gly Leu Ile Asn Val Arg Val Pro Leu Pro Phe Asn Val
        275                 280                 285

Ala Lys Phe Val Thr His Val Pro Ser Thr Thr Lys Gln Ile Val Val
    290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                325                 330                 335

Glu Tyr Ile Tyr Gln Pro Asp Phe Ile Trp Ser Pro Lys Ala Val Lys
            340                 345                 350

Ser Ile Val Ser Ser Phe Ile Pro Glu Phe Thr Tyr Asn Ala Asp Ser
        355                 360                 365

Ser Phe Gly Glu Gly Phe Ile Tyr Trp Ala Ser Asp Lys Ser Ile Asn
370                 375                 380

Ile Asp Val Ala Ser Lys Leu Val Lys Ala Leu Ser Leu Glu Asp Gly
385                 390                 395                 400

Lys Phe Val Ser Leu Arg Thr Lys Phe Asp Asn Leu Ala Asn Ala Gly
                405                 410                 415

Thr Phe Gln Ala Gln Phe Val Thr Ser Lys Glu Gln Ile Pro Val Ser
            420                 425                 430

Asn Ile Asp Ser Thr Lys Leu Ser Val Val Glu Asp Val Ser Leu Leu
        435                 440                 445

Lys His Leu Asp Val Ala Ala Thr Val Ala Glu Gln Gly Ser Ile Ala
    450                 455                 460

Leu Val Ser Gln Lys Ala Val Lys Asp Leu Asp Leu Asn Ser Val Glu
465                 470                 475                 480

Ser Tyr Val Lys Asn Leu Gly Ile Pro Glu Ser Phe Leu Ile Ser Ile
                485                 490                 495

Ala Lys Lys Asn Ile Lys Leu Phe Ile Ile Asp Gly Glu Thr Xaa Asn
            500                 505                 510

Asp Glu Ser Lys Leu Ser Leu Phe Ile Gln Ala Val Phe Trp Lys Leu
        515                 520                 525

Ala Phe Gly Leu Asp Val Ala Glu Cys Thr Asn Arg Ile Trp Lys Ser
    530                 535                 540

Ile Asp Ser Gly Ala Asp Ile Ser Ala Ala Ser Ile Ser Glu Phe Leu
545                 550                 555                 560

Thr Gly Ala Phe Lys Asn Phe Leu Ser Glu Val Pro Leu Ala Leu Tyr
                565                 570                 575

Thr Lys Phe Ser Glu Ile Asn Ile Glu Lys Lys Glu Asp Xaa Glu Glu
            580                 585                 590

Pro Ala Ala Leu Pro Ile Phe Val Asn Glu Thr Ser Phe Leu Pro Asn
        595                 600                 605

Asn Ser Thr Ile Glu Glu Ile Pro Leu Pro Thr Ser Glu Ile Ser
    610                 615                 620

Asp Ile Ala Lys Lys Leu Ser Phe Lys Glu Ala Tyr Glu Val Glu Asn
625                 630                 635                 640

Lys Leu Arg Pro Asp Leu Pro Val Lys Asn Phe Val Val Lys Val Lys
```

```
                645                 650                 655
Glu Asn Arg Arg Val Xaa Pro Ala Asp Tyr Asp Arg Tyr Ile Phe His
            660                 665                 670
Ile Glu Phe Asp Ile Ser Gly Thr Gly Met Thr Tyr Asp Ile Gly Glu
            675                 680                 685
Ala Leu Gly Ile His Ala Arg Asn Asn Glu Ser Leu Val Lys Glu Phe
            690                 695                 700
Leu Thr Phe Tyr Gly Leu Asn Glu Ser Asp Val Val Leu Val Pro Asn
705                 710                 715                 720
Lys Asp Asn His His Leu Leu Glu Thr Arg Thr Val Leu Gln Ala Phe
                725                 730                 735
Val Glu Asn Leu Asp Ile Phe Gly Lys Pro Lys Arg Phe Tyr Glu
            740                 745                 750
Ser Leu Ile Pro Tyr Ala Ser Asn Glu Glu Lys Lys Lys Leu Glu
            755                 760                 765
Asp Leu Val Thr Pro Ala Gly Ala Val Asp Leu Lys Arg Phe Gln Asp
            770                 775                 780
Val Glu Tyr Tyr Thr Tyr Ala Asp Ile Phe Glu Leu Phe Pro Ser Val
785                 790                 795                 800
Arg Pro Ser Leu Glu Glu Leu Val Thr Ile Ile Glu Pro Leu Lys Arg
                805                 810                 815
Arg Glu Tyr Ser Ile Ala Ser Ser Gln Lys Val His Pro Asn Glu Val
            820                 825                 830
His Leu Leu Ile Val Val Asp Trp Val Asp Asn Lys Gly Arg Lys
            835                 840                 845
Arg Tyr Gly Gln Ala Ser Lys Tyr Ile Ser Asp Leu Ala Val Gly Ser
            850                 855                 860
Glu Leu Val Val Ser Val Lys Pro Ser Val Met Lys Leu Pro Pro Ser
865                 870                 875                 880
Pro Lys Gln Pro Val Ile Met Ser Gly Leu Gly Thr Gly Leu Ala Pro
                885                 890                 895
Phe Lys Ala Ile Val Glu Glu Lys Leu Trp Gln Lys Gln Gln Gly Tyr
            900                 905                 910
Glu Ile Gly Glu Val Phe Leu Tyr Leu Gly Ser Arg His Lys Arg Glu
            915                 920                 925
Glu Tyr Leu Tyr Gly Glu Leu Trp Glu Ala Tyr Lys Asp Ala Gly Ile
            930                 935                 940
Ile Thr His Ile Gly Ala Ala Phe Ser Arg Asp Gln Pro Gln Lys Ile
945                 950                 955                 960
Tyr Ile Gln Asp Arg Ile Lys Glu Asn Leu Asp Glu Leu Lys Thr Ala
                965                 970                 975
Met Ile Asp Asn Lys Gly Ser Phe Tyr Leu Cys Gly Pro Thr Trp Pro
            980                 985                 990
Val Pro Asp Ile Thr Gln Ala Leu Gln Asp Ile Leu Ala Lys Asp Ala
            995                 1000                1005
Glu Glu Arg Gly Ile Lys Val Asp Leu Asp Ala Ala Ile Glu Glu Leu
    1010                1015                1020
Lys Glu Ala Ser Arg Tyr Ile Leu Glu Val Tyr
1025                1030                1035

<210> SEQ ID NO 6
<211> LENGTH: 1035
<212> TYPE: PRT
<213> ORGANISM: Artificial Sequence
<220> FEATURE:
```

-continued

```
<223> OTHER INFORMATION: Description of Artificial Sequence:sulfide
      inactive yeast assimilatory sulfite reductase
      alpha subunit (Met 10, MET10)
<220> FEATURE:
<221> NAME/KEY: MOD_RES
<222> LOCATION: (135)
<223> OTHER INFORMATION: Xaa = Thr or Asn
<220> FEATURE:
<221> NAME/KEY: MOD_RES
<222> LOCATION: (172)
<223> OTHER INFORMATION: Xaa = Ala or Thr
<220> FEATURE:
<221> NAME/KEY: MOD_RES
<222> LOCATION: (511)
<223> OTHER INFORMATION: Xaa = Thr or Ile
<220> FEATURE:
<221> NAME/KEY: MOD_RES
<222> LOCATION: (590)
<223> OTHER INFORMATION: Xaa = Glu or Lys
<220> FEATURE:
<221> NAME/KEY: MOD_RES
<222> LOCATION: (662)
<223> OTHER INFORMATION: Xaa = Lys, Arg, His, Gln or Asn

<400> SEQUENCE: 6

Met Pro Val Glu Phe Ala Thr Asn Pro Phe Gly Glu Ala Lys Asn Ala
 1               5                  10                  15

Thr Ser Leu Pro Lys Tyr Gly Thr Pro Val Thr Ala Ile Ser Ser Val
            20                  25                  30

Leu Phe Asn Asn Val Asp Ser Ile Phe Ala Tyr Lys Ser Phe Ser Gln
        35                  40                  45

Pro Asp Leu Leu His Gln Asp Leu Lys Lys Trp Ser Glu Lys Arg Gly
    50                  55                  60

Asn Glu Ser Arg Gly Lys Pro Phe Phe Gln Glu Leu Asp Ile Arg Ser
65                  70                  75                  80

Gly Ala Gly Leu Ala Pro Leu Gly Phe Ser His Gly Leu Lys Asn Thr
                85                  90                  95

Thr Ala Ile Val Ala Pro Gly Phe Ser Leu Pro Tyr Phe Ile Asn Ser
            100                 105                 110

Leu Lys Thr Val Ser His Asp Gly Lys Phe Leu Leu Asn Val Gly Ala
        115                 120                 125

Leu Asn Tyr Asp Asn Ala Xaa Gly Ser Val Thr Asn Asp Tyr Val Thr
    130                 135                 140

Ala Leu Asp Ala Ala Ser Lys Leu Lys Tyr Gly Val Val Thr Pro Ile
145                 150                 155                 160

Ser Ala Asn Glu Val Gln Ser Val Ala Leu Xaa Leu Ala Ile Ala
                165                 170                 175

Thr Phe Ser Asn Asn Ser Gly Ala Ile Asn Leu Phe Asp Gly Leu Asn
            180                 185                 190

Tyr Ser Lys Thr Val Leu Pro Leu Val Glu Ser Val Pro Glu Ala Ser
        195                 200                 205

Ile Leu Ala Lys Leu Ser Lys Val Ile Ala Pro Asp Ala Ala Phe Asp
    210                 215                 220

Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
                245                 250                 255

Gly Ser Leu Glu Ser Glu Leu Phe Asn Ser Ala Ile Ser Gly Asn Asn
            260                 265                 270

Ser Lys Ile Gly Leu Ile Asn Val Arg Val Pro Leu Pro Phe Asn Val
        275                 280                 285
```

```
Ala Lys Phe Val Thr His Val Pro Ser Thr Thr Lys Gln Ile Val Val
290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                325                 330                 335

Glu Tyr Ile Tyr Gln Pro Asp Phe Ile Trp Ser Pro Lys Ala Val Lys
            340                 345                 350

Ser Ile Val Ser Ser Phe Ile Pro Glu Phe Thr Tyr Asn Ala Asp Ser
        355                 360                 365

Ser Phe Gly Glu Gly Phe Ile Tyr Trp Ala Ser Asp Lys Ser Ile Asn
    370                 375                 380

Ile Asp Val Ala Ser Lys Leu Val Lys Ala Leu Ser Leu Glu Asp Gly
385                 390                 395                 400

Lys Phe Val Ser Leu Arg Thr Lys Phe Asp Asn Leu Ala Asn Ala Gly
                405                 410                 415

Thr Phe Gln Ala Gln Phe Val Thr Ser Lys Glu Gln Ile Pro Val Ser
            420                 425                 430

Asn Ile Asp Ser Thr Lys Leu Ser Val Val Glu Asp Val Ser Leu Leu
        435                 440                 445

Lys His Leu Asp Val Ala Ala Thr Val Ala Glu Gln Gly Ser Ile Ala
    450                 455                 460

Leu Val Ser Gln Lys Ala Val Lys Asp Leu Asp Leu Asn Ser Val Glu
465                 470                 475                 480

Ser Tyr Val Lys Asn Leu Gly Ile Pro Glu Ser Phe Leu Ile Ser Ile
                485                 490                 495

Ala Lys Lys Asn Ile Lys Leu Phe Ile Ile Asp Gly Glu Thr Xaa Asn
            500                 505                 510

Asp Glu Ser Lys Leu Ser Leu Phe Ile Gln Ala Val Phe Trp Lys Leu
        515                 520                 525

Ala Phe Gly Leu Asp Val Ala Glu Cys Thr Asn Arg Ile Trp Lys Ser
    530                 535                 540

Ile Asp Ser Gly Ala Asp Ile Ser Ala Ala Ser Ile Ser Glu Phe Leu
545                 550                 555                 560

Thr Gly Ala Phe Lys Asn Phe Leu Ser Glu Val Pro Leu Ala Leu Tyr
                565                 570                 575

Thr Lys Phe Ser Glu Ile Asn Ile Glu Lys Lys Glu Asp Xaa Glu Glu
            580                 585                 590

Pro Ala Ala Leu Pro Ile Phe Val Asn Glu Thr Ser Phe Leu Pro Asn
        595                 600                 605

Asn Ser Thr Ile Glu Glu Ile Pro Leu Pro Thr Ser Glu Ile Ser
    610                 615                 620

Asp Ile Ala Lys Lys Leu Ser Phe Lys Glu Ala Tyr Glu Val Glu Asn
625                 630                 635                 640

Lys Leu Arg Pro Asp Leu Pro Val Lys Asn Phe Val Lys Val Lys
                645                 650                 655

Glu Asn Arg Arg Val Xaa Pro Ala Asp Tyr Arg Tyr Ile Phe His
            660                 665                 670

Ile Glu Phe Asp Ile Ser Gly Thr Gly Met Thr Tyr Asp Ile Gly Glu
        675                 680                 685

Ala Leu Gly Ile His Ala Arg Asn Asn Glu Ser Leu Val Lys Glu Phe
    690                 695                 700

Leu Thr Phe Tyr Gly Leu Asn Glu Ser Asp Val Val Leu Val Pro Asn
705                 710                 715                 720
```

```
Lys Asp Asn His His Leu Leu Glu Thr Arg Thr Val Leu Gln Ala Phe
                725                 730                 735

Val Glu Asn Leu Asp Ile Phe Gly Lys Pro Lys Arg Phe Tyr Glu
            740                 745                 750

Ser Leu Ile Pro Tyr Ala Ser Asn Glu Glu Lys Lys Lys Leu Glu
            755                 760                 765

Asp Leu Val Thr Pro Ala Gly Ala Val Asp Leu Lys Arg Phe Gln Asp
            770                 775                 780

Val Glu Tyr Tyr Thr Tyr Ala Asp Ile Phe Glu Leu Phe Pro Ser Val
785                 790                 795                 800

Arg Pro Ser Leu Glu Glu Leu Val Thr Ile Ile Glu Pro Leu Lys Arg
                805                 810                 815

Arg Glu Tyr Ser Ile Ala Ser Ser Gln Lys Val His Pro Asn Glu Val
                820                 825                 830

His Leu Leu Ile Val Val Asp Trp Val Asp Asn Lys Gly Arg Lys
                835                 840                 845

Arg Tyr Gly Gln Ala Ser Lys Tyr Ile Ser Asp Leu Ala Val Gly Ser
                850                 855                 860

Glu Leu Val Val Ser Val Lys Pro Ser Val Met Lys Leu Pro Pro Ser
865                 870                 875                 880

Pro Lys Gln Pro Val Ile Met Ser Gly Leu Gly Thr Gly Leu Ala Pro
                885                 890                 895

Phe Lys Ala Ile Val Glu Glu Lys Leu Trp Gln Lys Gln Gly Tyr
                900                 905                 910

Glu Ile Gly Glu Val Phe Leu Tyr Leu Gly Ser Arg His Lys Arg Glu
                915                 920                 925

Glu Tyr Leu Tyr Gly Glu Leu Trp Glu Ala Tyr Lys Asp Ala Gly Ile
                930                 935                 940

Ile Thr His Ile Gly Ala Ala Phe Ser Arg Asp Gln Pro Gln Lys Ile
945                 950                 955                 960

Tyr Ile Gln Asp Arg Ile Lys Glu Asn Leu Asp Glu Leu Lys Thr Ala
                965                 970                 975

Met Ile Asp Asn Lys Gly Ser Phe Tyr Leu Cys Gly Pro Thr Trp Pro
                980                 985                 990

Val Pro Asp Ile Thr Gln Ala Leu Gln Asp Ile Leu Ala Lys Asp Ala
                995                 1000                1005

Glu Glu Arg Gly Ile Lys Val Asp Leu Asp Ala Ala Ile Glu Glu Leu
    1010                1015                1020

Lys Glu Ala Ser Arg Tyr Ile Leu Glu Val Tyr
1025                1030                1035

<210> SEQ ID NO 7
<211> LENGTH: 1035
<212> TYPE: PRT
<213> ORGANISM: Artificial Sequence
<220> FEATURE:
<223> OTHER INFORMATION: Description of Artificial Sequence:sulfide
      inactive yeast assimilatory sulfite reductase
      alpha subunit (Met 10, MET10)
<220> FEATURE:
<221> NAME/KEY: MOD_RES
<222> LOCATION: (135)
<223> OTHER INFORMATION: Xaa = Thr or Asn
<220> FEATURE:
<221> NAME/KEY: MOD_RES
<222> LOCATION: (172)
<223> OTHER INFORMATION: Xaa = Ala or Thr
<220> FEATURE:
<221> NAME/KEY: MOD_RES
```

```
<222> LOCATION: (511)
<223> OTHER INFORMATION: Xaa = Thr or Ile
<220> FEATURE:
<221> NAME/KEY: MOD_RES
<222> LOCATION: (590)
<223> OTHER INFORMATION: Xaa = Glu or Lys

<400> SEQUENCE: 7
```

| | | | | | | | | | | | | | | |
|---|---|---|---|---|---|---|---|---|---|---|---|---|---|---|
| Met | Pro | Val | Glu | Phe | Ala | Thr | Asn | Pro | Phe | Gly | Glu | Ala | Lys | Asn | Ala |
| 1 | | | | 5 | | | | | 10 | | | | | 15 | |
| Thr | Ser | Leu | Pro | Lys | Tyr | Gly | Thr | Pro | Val | Thr | Ala | Ile | Ser | Ser | Val |
| | | | 20 | | | | | 25 | | | | | 30 | | |
| Leu | Phe | Asn | Asn | Val | Asp | Ser | Ile | Phe | Ala | Tyr | Lys | Ser | Phe | Ser | Gln |
| | | 35 | | | | | 40 | | | | | 45 | | | |
| Pro | Asp | Leu | Leu | His | Gln | Asp | Leu | Lys | Lys | Trp | Ser | Glu | Lys | Arg | Gly |
| | 50 | | | | | 55 | | | | | 60 | | | | |
| Asn | Glu | Ser | Arg | Gly | Lys | Pro | Phe | Gln | Glu | Leu | Asp | Ile | Arg | Ser |
| 65 | | | | | 70 | | | | | 75 | | | | | 80 |
| Gly | Ala | Gly | Leu | Ala | Pro | Leu | Gly | Phe | Ser | His | Gly | Leu | Lys | Asn | Thr |
| | | | | 85 | | | | | 90 | | | | | 95 | |
| Thr | Ala | Ile | Val | Ala | Pro | Gly | Phe | Ser | Leu | Pro | Tyr | Phe | Ile | Asn | Ser |
| | | | 100 | | | | | 105 | | | | | 110 | | |
| Leu | Lys | Thr | Val | Ser | His | Asp | Gly | Lys | Phe | Leu | Leu | Asn | Val | Gly | Ala |
| | | 115 | | | | | 120 | | | | | 125 | | | |
| Leu | Asn | Tyr | Asp | Asn | Ala | Xaa | Gly | Ser | Val | Thr | Asn | Asp | Tyr | Val | Thr |
| | 130 | | | | | 135 | | | | | 140 | | | | |
| Ala | Leu | Asp | Ala | Ala | Ser | Lys | Leu | Lys | Tyr | Gly | Val | Val | Thr | Pro | Ile |
| 145 | | | | | 150 | | | | | 155 | | | | | 160 |
| Ser | Ala | Asn | Glu | Val | Gln | Ser | Val | Ala | Leu | Leu | Xaa | Leu | Ala | Ile | Ala |
| | | | | 165 | | | | | 170 | | | | | 175 | |
| Thr | Phe | Ser | Asn | Asn | Ser | Gly | Ala | Ile | Asn | Leu | Phe | Asp | Gly | Leu | Asn |
| | | | 180 | | | | | 185 | | | | | 190 | | |
| Tyr | Ser | Lys | Thr | Val | Leu | Pro | Leu | Val | Glu | Ser | Val | Pro | Glu | Ala | Ser |
| | | 195 | | | | | 200 | | | | | 205 | | | |
| Ile | Leu | Ala | Lys | Leu | Ser | Lys | Val | Ile | Ala | Pro | Asp | Ala | Ala | Phe | Asp |
| | 210 | | | | | 215 | | | | | 220 | | | | |
| Asp | Val | Leu | Asp | Lys | Phe | Asn | Glu | Leu | Thr | Gly | Leu | Arg | Leu | His | Asn |
| 225 | | | | | 230 | | | | | 235 | | | | | 240 |
| Phe | Gln | Tyr | Phe | Gly | Ala | Gln | Asp | Ala | Glu | Thr | Val | Phe | Ile | Thr | Tyr |
| | | | | 245 | | | | | 250 | | | | | 255 | |
| Gly | Ser | Leu | Glu | Ser | Glu | Leu | Phe | Asn | Ser | Ala | Ile | Ser | Gly | Asn | Asn |
| | | | 260 | | | | | 265 | | | | | 270 | | |
| Ser | Lys | Ile | Gly | Leu | Ile | Asn | Val | Arg | Val | Pro | Leu | Pro | Phe | Asn | Val |
| | | 275 | | | | | 280 | | | | | 285 | | | |
| Ala | Lys | Phe | Val | Thr | His | Val | Pro | Ser | Thr | Thr | Lys | Gln | Ile | Val | Val |
| | 290 | | | | | 295 | | | | | 300 | | | | |
| Ile | Gly | Gln | Thr | Leu | Asp | Gly | Ser | Ser | Pro | Ser | Phe | Leu | Arg | Ser | Gln |
| 305 | | | | | 310 | | | | | 315 | | | | | 320 |
| Val | Ser | Ala | Ala | Leu | Phe | Tyr | His | Gly | Arg | Thr | Ser | Ile | Ser | Val | Ser |
| | | | | 325 | | | | | 330 | | | | | 335 | |
| Glu | Tyr | Ile | Tyr | Gln | Pro | Asp | Phe | Ile | Trp | Ser | Pro | Lys | Ala | Val | Lys |
| | | | 340 | | | | | 345 | | | | | 350 | | |
| Ser | Ile | Val | Ser | Ser | Phe | Ile | Pro | Glu | Phe | Thr | Tyr | Asn | Ala | Asp | Ser |
| | | 355 | | | | | 360 | | | | | 365 | | | |
| Ser | Phe | Gly | Glu | Gly | Phe | Ile | Tyr | Trp | Ala | Ser | Asp | Lys | Ser | Ile | Asn |
| | 370 | | | | | 375 | | | | | 380 | | | | |

```
Ile Asp Val Ala Ser Lys Leu Val Lys Ala Leu Ser Leu Glu Asp Gly
385                 390                 395                 400

Lys Phe Val Ser Leu Arg Thr Lys Phe Asp Asn Leu Ala Asn Ala Gly
            405                 410                 415

Thr Phe Gln Ala Gln Phe Val Thr Ser Lys Glu Gln Ile Pro Val Ser
        420                 425                 430

Asn Ile Asp Ser Thr Lys Leu Ser Val Val Glu Asp Val Ser Leu Leu
    435                 440                 445

Lys His Leu Asp Val Ala Ala Thr Val Ala Glu Gln Gly Ser Ile Ala
450                 455                 460

Leu Val Ser Gln Lys Ala Val Lys Asp Leu Asp Leu Asn Ser Val Glu
465                 470                 475                 480

Ser Tyr Val Lys Asn Leu Gly Ile Pro Glu Ser Phe Leu Ile Ser Ile
            485                 490                 495

Ala Lys Lys Asn Ile Lys Leu Phe Ile Ile Asp Gly Glu Thr Lys Asn
        500                 505                 510

Asp Glu Ser Lys Leu Ser Leu Phe Ile Gln Ala Val Phe Trp Lys Leu
    515                 520                 525

Ala Phe Gly Leu Asp Val Ala Glu Cys Thr Asn Arg Ile Trp Lys Ser
530                 535                 540

Ile Asp Ser Gly Ala Asp Ile Ser Ala Ala Ser Ile Ser Glu Phe Leu
545                 550                 555                 560

Thr Gly Ala Phe Lys Asn Phe Leu Ser Glu Val Pro Leu Ala Leu Tyr
            565                 570                 575

Thr Lys Phe Ser Glu Ile Asn Ile Glu Lys Lys Glu Asp Xaa Glu Glu
        580                 585                 590

Pro Ala Ala Leu Pro Ile Phe Val Asn Glu Thr Ser Phe Leu Pro Asn
    595                 600                 605

Asn Ser Thr Ile Glu Glu Ile Pro Leu Pro Glu Thr Ser Glu Ile Ser
610                 615                 620

Asp Ile Ala Lys Lys Leu Ser Phe Lys Glu Ala Tyr Glu Val Glu Asn
625                 630                 635                 640

Lys Leu Arg Pro Asp Leu Pro Val Lys Asn Phe Val Lys Val Lys
            645                 650                 655

Glu Asn Arg Arg Val Lys Pro Ala Asp Tyr Asp Arg Tyr Ile Phe His
        660                 665                 670

Ile Glu Phe Asp Ile Ser Gly Thr Gly Met Thr Tyr Asp Ile Gly Glu
    675                 680                 685

Ala Leu Gly Ile His Ala Arg Asn Asn Glu Ser Leu Val Lys Glu Phe
690                 695                 700

Leu Thr Phe Tyr Gly Leu Asn Glu Ser Asp Val Val Leu Val Pro Asn
705                 710                 715                 720

Lys Asp Asn His His Leu Leu Glu Thr Arg Thr Val Leu Gln Ala Phe
            725                 730                 735

Val Glu Asn Leu Asp Ile Phe Gly Lys Pro Pro Lys Arg Phe Tyr Glu
        740                 745                 750

Ser Leu Ile Pro Tyr Ala Ser Asn Glu Glu Lys Lys Lys Leu Glu
    755                 760                 765

Asp Leu Val Thr Pro Ala Gly Ala Val Asp Leu Lys Arg Phe Gln Asp
770                 775                 780

Val Glu Tyr Tyr Thr Tyr Ala Asp Ile Phe Glu Leu Phe Pro Ser Val
785                 790                 795                 800

Arg Pro Ser Leu Glu Glu Leu Val Thr Ile Ile Glu Pro Leu Lys Arg
```

```
                         805                 810                 815
Arg Glu Tyr Ser Ile Ala Ser Ser Gln Lys Val His Pro Asn Glu Val
                820                 825                 830

His Leu Leu Ile Val Val Val Asp Trp Val Asp Asn Lys Gly Arg Lys
            835                 840                 845

Arg Tyr Gly Gln Ala Ser Lys Tyr Ile Ser Asp Leu Ala Val Gly Ser
        850                 855                 860

Glu Leu Val Val Ser Val Lys Pro Ser Val Met Lys Leu Pro Pro Ser
865                 870                 875                 880

Pro Lys Gln Pro Val Ile Met Ser Gly Leu Gly Thr Gly Leu Ala Pro
                885                 890                 895

Phe Lys Ala Ile Val Glu Glu Lys Leu Trp Gln Lys Gln Gln Gly Tyr
            900                 905                 910

Glu Ile Gly Glu Val Phe Leu Tyr Leu Gly Ser Arg His Lys Arg Glu
        915                 920                 925

Glu Tyr Leu Tyr Gly Glu Leu Trp Glu Ala Tyr Lys Asp Ala Gly Ile
    930                 935                 940

Ile Thr His Ile Gly Ala Ala Phe Ser Arg Asp Gln Pro Gln Lys Ile
945                 950                 955                 960

Tyr Ile Gln Asp Arg Ile Lys Glu Asn Leu Asp Glu Leu Lys Thr Ala
                965                 970                 975

Met Ile Asp Asn Lys Gly Ser Phe Tyr Leu Cys Gly Pro Thr Trp Pro
            980                 985                 990

Val Pro Asp Ile Thr Gln Ala Leu Gln Asp Ile Leu Ala Lys Asp Ala
        995                1000                1005

Glu Glu Arg Gly Ile Lys Val Asp Leu Asp Ala Ala Ile Glu Glu Leu
   1010                1015                1020

Lys Glu Ala Ser Arg Tyr Ile Leu Glu Val Tyr
1025                1030                1035

<210> SEQ ID NO 8
<211> LENGTH: 3108
<212> TYPE: DNA
<213> ORGANISM: Saccharomyces cerevisiae
<220> FEATURE:
<223> OTHER INFORMATION: yeast assimilatory sulfite reductase alpha
      subunit (Met 10, MET10), strain S288c allele

<400> SEQUENCE: 8
atgccagttg agtttgctac caatcctttt ggcgaggcca aaaatgcaac ttcactgcca      60
aaatatggta cacccgtaac tgccatttca tctgtgctgt tcaataacgt ggactccatt     120
tttgcttaca agtcctttc tcaacccgat ttgctacacc aagatctaaa aaaatggtct     180
gaaaagcgtg gtaacgaatc acgtgggaag ccatttttcc aagagctgga tatcagatct     240
ggcgctggtt tggctccttt agggttttct catggattga gaacactac agcaattgtt     300 gctccagggt tttcgctgcc atacttcatt aactctttga aaaccgtctc tcatgatggt     360
aagtttcttt tgaatgttgg tgctttaaac tacgacaatg ctaccggctc tgtcaccaac     420
gattatgtaa ccgcattgga tgctgcttcc aagctgaagt atggtgtcgt gactccgatt     480
tccgctaacg aggtacaaag tgtcgcctta ctggcattgg cgattgccac tttcagtaat     540
aactccggag ctatcaattt atttgacgga ttaaactact cgaaaaccgt cttgccgttg     600
gtcgaatctg ttcctgaggc atctattttg gcaaaactat ccaaagttat tgcaccagat     660
gctgcctttg atgatgtctt ggataagttt aatgaattga ctggattgag actacataat     720
ttccaatact tggtgctcca ggatgctgaa actgtgttta tcacttatgg gtctttagaa     780
```

```
tccgaattgt tcaactctgc gattagtggt aataattcca aaatcgggtt aatcaacgtc    840
agagtgccat tacctttta  cgttgctaag tttgtcactc acgttccatc cactaccaaa    900
caaattgttg ttataggcca aactttggat ggttcttcgc cttctttctt gagatctcaa    960
gtttcagccg ccttatttta ccacggccgc acctcaatta gcgtttctga gtacatctat   1020
caaccagatt tcatttggtc cccaaaagct gtcaaatcaa ttgtatcgtc attcatccct   1080
gaattcactt acaatgccga ttcatctttc ggcgaaggat tcatttattg ggcctctgat   1140
aagagtatca atattgatgt tgcctccaaa cttgtgaaag ctctgtcttt ggaagatggg   1200
aaatttgtgt ctttgagaac gaaatttgat aacttggcta atgctggtac cttccaagct   1260
caatttgtga cctcgaaaga acagatacct gtttcaaaca tcgattctac gaaattatca   1320
gtcgttgaag atgtcagttt attgaagcat ttagacgtag ctgctaccgt cgcagaacaa   1380
ggttcaattg cgttggtttc ccaaaaggca gttaaagatt tggatttaaa ttctgtagaa   1440
agttacgtca agaatttggg aattcctgaa tcattcctaa tatctattgc gaagaaaaac   1500
atcaaattgt ttatcatcga tggtgagacc actaacgacg agtccaaatt gtccttgttt   1560
atccaagccg ttttctggaa attggccttc ggtctagatg tcgcagaatg taccaaccgt   1620
atctggaaaa gcattgattc aggtgcagac atttcagcag cctcgatttc tgaatttctc   1680
actggtgcat tcaaaaactt cctcagtgag gttccgctag cgctgtacac taaattttct   1740
gaaataaaca ttgaaaagaa agaggatgag gaagagcctg cagctttacc aattttcgtt   1800
aatgaaacat ctttcctccc aaataacagt accattgaag aaataccatt acctgagacc   1860
tctgagatct ctgatattgc caagaagttg tccttcaaag aggcatatga agttgagaat   1920
aaactaagac ccgatttacc cgtcaagaac ttcgtcgtga agttaaagaa aaatagacgt   1980
gttacgcctg ctgattatga tagatatatt ttccatattg aattcgatat ttctggtact   2040
ggaatgactt atgacatcgg tgaagccctc ggtattcatg ccagaaacaa tgaatctttg   2100
gtcaaagaat tcttaaccttc tatggtcta  aatgaatccg atgttgtctt agtccccaac   2160
aaggacaacc accatttgtt agaaacaaga accgtcttac aagcatttgt ggaaaatttg   2220
gatattttcg gtaaaccacc aaaaagattt tacgaatcat tgattccata tgcctctaac   2280
gaagaggaga agaaaaaatt agaggatttg gttactcctg ccggtgcagt agatttgaag   2340
agatttcaag atgtggagta ttatacatat gctgacattt ttgaattgtt cccatctgtt   2400
cgcccatctc ttgaggaact tgttactatc attgaaccat tgaagagaag agaatactca   2460
attgcctcct ctcagaaagt tcatccaaat gaagttcatt tattgatcgt tgttgttgat   2520
tgggtggata taaaggaag  aaaaaggtac ggtcaagctt ctaagtatat ctcagacctt   2580
gctgtcggtt cagaattggt cgttagcgtt aaaccatctg ttatgaaatt accaccatct   2640
ccaaagcaac cagttattat gagtggtttta ggtactggtt tggcaccatt caaggccatt   2700
gttgaagaga attatggca  aaagcagcaa ggttatgaga ttggtgaagt cttcctatat   2760
ctaggttcaa gacacaaaag agaagaatat ttatatggtg agttatggga ggcttacaaa   2820
gatgcaggta ttatcacaca catcggcgct gctttctcaa gagaccaacc tcaaaaaatt   2880
tacattcaag atcgtatcaa agagaatttg atgaattaa  aaactgcaat gattgataat   2940
aaaggttcat tttacttgtg tggccctact tggccagttc cagatattac tcaagctttg   3000
caagacattc tggctaaaga cgccgaggaa agaggcatca agtcgacttg gatgccgca   3060
attgaagaat taaggaagc  atcaagatac attttagaag tctactaa                3108
```

<210> SEQ ID NO 9
<211> LENGTH: 3108
<212> TYPE: DNA
<213> ORGANISM: Saccharomyces cerevisiae
<220> FEATURE:
<223> OTHER INFORMATION: yeast assimilatory sulfite reductase alpha subunit (Met 10, MET10), strain UCD522 allele

<400> SEQUENCE: 9

```
atgccagttg agtttgctac caatcctttt ggcgaggcca aaaatgcaac ttcactgcca      60
aaatatggta cacccgtaac tgccatttca tctgtgctgt tcaataacgt ggactccatt     120
tttgcttaca agtccttttc tcaacccgat ttgttacacc aagatctaaa aaaatggtct     180
gaaaagcgtg gtaacgaatc acgtgggaag ccattttttcc aagagctgga tatcagatct    240
ggcgctggtt tggctccttt agggttttct catggattga agaacactac agcaattgtt    300
gctccagggt tttcgctgcc atacttcatt aactctttga aaaccgtctc tcatgatggt    360
aagtttcttt tgaatgttgg tgctttaaac tacgacaatg ctaccggctc tgtcaccaac    420
gattatgtaa ccgcattgga tgctgcttcc aagctgaagt atggtgtcgt gactccgatt    480
tccgctaacg aggtacaaag tgtcgcctta ctgacattgg cgattgccac tttcagtaat    540
aactccggag ctatcaattt atttgacgga ttaaactact cgaaaaccgt cttgccgttg    600
gtcgaatctg ttcctgaggc atctattttg gcaaaactat ccaaagttat tgcaccagat    660
gctgcctttg atgatgtctt ggataagttt aatgaattga ctggattgag actacataat    720
ttccaatact tggtgctcca ggatgctgaa actgtgttta tcacttatgg gtctttagaa    780
tccgaattgt tcaactctgc gattagtggt aataattcca aaatcgggtt aatcaacgtc    840
agagtaccat taccttttaa cgttgctaag tttgtcactc acgttccatc cactaccaaa    900
caaattgttg ttataggcca aactttggat ggttcttcgc cttctttctt gagatctcaa    960
gtttcagccg ccttattta ccacggccgc acctcaatta gcgttctga gtacatctat   1020
caaccagatt tcatttggtc cccaaaagct gtcaaatcaa ttgtatcgtc attcatccct   1080
gaattcactt acaatgccga ttcatctttc ggcgaaggat tcatttattg ggcctctgat   1140
aagagtatca atattgatgt tgcctccaaa cttgtgaaag ctctgtcttt ggaagatggg   1200
aaatttgtgt ctttgagaac gaaatttgat aacttggcta atgctggtac cttccaagct   1260
caatttgtga cctcgaarga acagataccg tgtttcaaaca tcgattctac gaaattatca   1320
gtcgttgaag atgtcagttt attgaagcat ttagacgtag ctgctaccgt cgcagaacaa   1380
ggttcaattg cgttggttte ccaaaaggca gttaaagatt tggatttaaa ttctgtagaa   1440
agttacgtca agaatttggg aattcctgaa tcattcctaa tatctattgc gaagaaaaac   1500
atcaaattgt ttatcatcga tggtgagacc aytaacgacg agtccaaatt gtccttgttt   1560
atccaagccg ttttctggaa attggccttc ggtctagatg tcgcagaatg taccaaccgt   1620
atctggaaaa gcattgattc aggtgcagac atttcagcag cctcgatttc tgaatttctc   1680
actggtgcat tcaaaaactt cctcagtgag gttccgctag cgctgtacac taaatttttct   1740
gaaataaaca ttgaaaagaa agaggatgag gaagagcctg cagctttacc aattttcgtt   1800
aatgaaacat ctttcctccc aaataacagt accattgaag aaataccatt acctgagacc   1860
tctgagatct ctgatattgc caagaagttg tccttcaaag aggcatatga agttgagaat   1920
aaactaagac ccgatttacc cgtcaagaac ttcgtcgtga agttaaaga aatagacgt    1980
gttacgcctg ctgattatga tagatatatt ttccatattg aattcgatat ttctggtact   2040
ggaatgactt atgacatcgg tgaagccctc ggtattcatg ccagaaacaa tgaatctttg   2100
```

-continued

```
gtcaaagaat tcttaacctt ctatggtcta aatgaatccg atgttgtctt agtccccaac    2160
aaggacaacc accatttgtt agaaacaaga accgtcttac aagcatttgt ggaaaatttg    2220
gatattttcg gtaaaccacc aaaaagattt tacgaatcat tgattccata tgcctctaac    2280
gaagaggaga agaaaaaatt agaggatttg gttactcctg ccggtgcagt agatttgaag    2340
agatttcaag atgtggagta ttatacatat gctgacattt ttgaattgtt cccatctgtt    2400
cgcccatctc ttgaggaact tgttactatc attgaaccat tgaagagaag agaatactca    2460
attgcctcct ctcagaaagt tcatccaaat gaagttcatt tattgatcgt tgttgttgat    2520
tgggtggata taaaggaag aaaaaggtac ggtcaagctt ctaagtatat ctcagacctt    2580
gctgtcggtt cagaattggt cgttagcgtt aaaccatctg ttatgaaatt accaccatct    2640
ccaaagcaac cagttattat gagtggttta ggtactggtt tggcaccatt caaggccatt    2700
gttgaagaga aattatggca aaagcagcaa ggttatgaga ttggtgaagt cttcctatat    2760
ctaggttcaa gacacaaaag agaagaatat ttatatggtg agttatggga ggcttacaaa    2820
gatgcaggta ttatcacaca catcggcgct gctttctcaa gagaccaacc tcaaaaaatt    2880
tacattcaag atcgtatcaa agagaatttg gatgaattaa aaactgcaat gattgataat    2940
aaaggttcat tttacttgtg tggccctact tggccagttc cagatattac tcaagctttg    3000
caagacattc tggctaaaga cgccgaggaa agaggcatca aagtcgactt ggatgccgca    3060
attgaagaat taaggaagc atcaagatac attttagaag tctactaa                 3108
```

<210> SEQ ID NO 10
<211> LENGTH: 3108
<212> TYPE: DNA
<213> ORGANISM: Saccharomyces cerevisiae
<220> FEATURE:
<223> OTHER INFORMATION: yeast assimilatory sulfite reductase alpha
      subunit (Met 10, MET10), strain UCD934 allele

<400> SEQUENCE: 10

```
atgccagttg agtttgctac caatcctttt ggcgaggcca aaaatgcaac ttcactgcca      60
aaatatggta cacccgtaac tgccatttca tctgtgctgt tcaataacgt ggactccatt     120
tttgcttaca gtcctttttc tcaacccgat tgttacacc aagatctaaa aaaatggtct     180
gaaaagcgtg gtaacgaatc acgtgggaag ccattttttcc aagagctgga tatcagatct    240
ggcgctggtt tggctccttt agggttttct catggattga agaacactac agcaattgtt     300
gctccagggt tttcgctgcc atacttcatt aactctttga aaccgtctc tcatgatggt      360 aagtttcttt tgaatgttgg tgctttaaac tacgacaatg ctaccggctc tgtcaccaac     420
gattatgtaa ccgcattgga tgctgcttcc aagctgaagt atggtgtcgt gactccgatt     480
tccgctaacg aggtacaaag tgtcgcctta ctggcattgg cgattgccac tttcagtaat    540
aactccggag ctatcaattt atttgacgga ttaaactact cgaaaaccgt cttgccgttg    600
gtcgaatctg ttcctgaggc atctattttg gcaaaactat ccaaagttat tgcaccagat    660
gctgcctttg atgatgtctt ggataagttt aatgaattga ctggattgag actacataat    720
ttccaatact ttggtgctca ggatgctgaa actgtgttta tcacttatgg gtcctttagaa   780 tccgaattgt tcaactctgc gattagtggt aataattcca aaatcgggtt aatcaacgtc    840
agagtaccat taccttttaa cgttgctaag tttgtcactc acgttccatc cactaccaaa    900
caaattgttg ttataggcca aactttggat ggttcttcgc cttctttctt gagatctcaa    960
gtttcagccg cctattttta ccacggccgc acctcaatta gcgtttctga gtacatctat   1020
caaccagatt tcatttggtc cccaaaagct gtcaaatcaa ttgtatcgtc attcatccct   1080
```

```
gaattcactt acaatgccga ttcatctttc ggcgaaggat tcatttattg ggcctctgat    1140
aagagtatca atattgatgt tgcctccaaa cttgtgaaag ctctgtcttt ggaagatggg    1200
aaatttgtgt ctttgagaac gaaatttgat aacttggcta atgctggtac cttccaagct    1260
caatttgtga cctcgaagga acagatacct gtttcaaaca tcgattctac gaaattatca    1320
gtcgttgaag atgtcagttt attgaagcat ttagacgtag ctgctaccgt cgcagaacaa    1380
ggttcaattg cgttggtttc ccaaaaggca gttaagatt tggatttaaa ttctgtagaa    1440
agttacgtca agaatttggg aattcctgaa tcattcctaa tatctattgc gaagaaaaac    1500
atcaaattgt ttatcatcga tggtgagacc attaacgacg agtccaaatt gtccttgttt    1560
atccaagccg ttttctggaa attggccttc ggtctagatg tcgcagaatg taccaaccgt    1620
atctggaaaa gcattgattc aggtgcagac atttcagcag cctcgatttc tgaatttctc    1680
actggtgcat tcaaaaactt cctcagtgag gttccgctag cgctgtacac taaattttct    1740
gaaataaaca ttgaaaagaa agaggataag gaagagcctg cagctttacc aattttcgtt    1800
aatgaaacat ctttcctccc aaataacagt accattgaag aaataccatt acctgagacc    1860
tctgagatct ctgatattgc caagaagttg tccttcaaag aggcatatga agttgagaat    1920
aaactaagac ccgatttacc cgtcaagaac ttcgtcgtga agttaaaga aaatagacgt    1980 gttacgcctg ctgattatga tagatatatt ttccatattg aattcgatat ttctggtact    2040
ggaatgactt atgacatcgg tgaagccctc ggtattcatg ccagaaacaa tgaatctttg    2100
gtcaaagaat tcttaacctt ctatggtcta aatgaatccg atgttgtctt agtccccaac    2160
aaggacaacc accatttgtt agaaacaaga accgtcttac aagcatttgt ggaaaatttg    2220 gatatttcg gtaaaccacc aaaaagattt tacgaatcat tgattccata tgcctctaac    2280
gaagaggaga agaaaaaatt agaggatttg gttactcctg ccggtgcagt agatttgaag    2340
agatttcaag atgtggagta ttatacatat gctgacattt ttgaattgtt cccatctgtt    2400
cgcccatctc ttgaggaact tgttactatc attgaaccat tgaagagaag agaatactca    2460
attgcctcct ctcagaaagt tcatccaaat gaagttcatt tattgatcgt tgttgttgat    2520
tgggtggata ataaaggaag aaaaaggtac ggtcaagctt ctaagtatat ctcagacctt    2580
gctgtcggtt cagaattggt cgttagcgtt aaaccatctg ttatgaaatt accaccatct    2640
ccaaagcaac cagttattat gagtggttta ggtactggtt tggcaccatt caaggccatt    2700
gttgaagaga attatggca aaagcagcaa ggttatgaga ttggtgaagt cttcctatat    2760
ctaggttcaa gacacaaaag agaagaatat ttatatggtg agttatggga ggcttacaaa    2820
gatgcaggta ttatcacaca catcggcgct gctttctcaa gagaccaacc tcaaaaaatt    2880
tacattcaag atcgtatcaa agagaatttg gatgaattaa aaactgcaat gattgataat    2940
aaaggttcat tttacttgtg tggccctact tggccagttc cagatattac tcaagctttg    3000
caagacattc tggctaaaga cgccgaggaa agaggcatca aagtcgactt ggatgccgca    3060
attgaagaat taaggaagc atcaagatac attttagaag tctactaa              3108
```

<210> SEQ ID NO 11
<211> LENGTH: 3108
<212> TYPE: DNA
<213> ORGANISM: Saccharomyces cerevisiae
<220> FEATURE:
<223> OTHER INFORMATION: yeast assimilatory sulfite reductase alpha
      subunit (Met 10, MET10), strain UCD938 allele

<400> SEQUENCE: 11

```
atgccagttg agtttgctac caatcctttt ggcgaggcca aaaatgcaac ttcactgcca    60
aaatatggta cacccgtaac tgccatttca tctgtgctgt tcaataacgt ggactccatt   120
tttgcttaca agtccttttc tcaacccgat tgttacacc aagatctaaa aaaatggtct   180
gaaaagcgtg gtaacgaatc acgtgggaag ccatttttcc aagagctgga tatcagatct   240
ggcgctggtt tggctccttt agggttttct catggattga agaacactac agcaattgtt   300
gctccagggt tttcgctgcc atacttcatt aactctttga aaaccgtctc tcatgatggt   360
aagtttcttt tgaatgttgg tgctttaaac tacgacaatg ctaacggctc tgtcaccaac   420
gattatgtaa ccgcattgga tgctgcttcc aagctgaagt atggtgtcgt gactccgatt   480
tccgctaacg aggtacaaag tgtcgcctta ctgacattgg cgattgccac tttcagtaat   540
aactccggag ctatcaattt atttgacgga ttaaactact cgaaaaccgt cttgccgttg   600
gtcgaatctg ttcctgaggc atctattttg gcaaaactat ccaaagttat tgcaccagat   660
gctgcctttg atgatgtctt ggataagttt aatgaattga ctggattgag actacataat   720
ttccaatact ttggtgctca ggatgctgaa actgtgttta tcacttatgg gtctttagaa   780
tccgaattgt tcaactctgc gattagtggt aataattcca aaatcgggtt aatcaacgtc   840
agagtaccat taccttttaa cgttgctaag tttgtcactc acgttccatc cactaccaaa   900
caaattgttg ttataggcca aactttggat ggttcttcgc cttctttctt gagatctcaa   960
gtttcagccg ccttatttta ccacggccgc acctcaatta gcgtttctga gtacatctat  1020
caaccagatt tcatttggtc cccaaaagct gtcaaatcaa ttgtatcgtc attcatccct  1080
gaattcactt acaatgccga ttcatctttc ggcgaaggat tcatttattg ggcctctgat  1140
aagagtatca atattgatgt tgcctccaaa cttgtgaaag ctctgtcttt ggaagatggg  1200
aaatttgtgt ctttgagaac gaaatttgat aacttggcta atgctggtac cttccaagct  1260
caatttgtga cctcgaaaga acagataccct gtttcaaaca tcgattctac gaaattatca  1320
gtcgttgaag atgtcagttt attgaagcat ttagacgtag ctgctaccgt cgcagaacaa  1380
ggttcaattg cgttggtttc ccaaaaggca gttaaagatt tggctttaaa ttctgtagaa  1440
agttacgtca agaatttggg aattcctgaa tcattcctaa tatctattgc gaagaaaaac  1500
atcaaattgt ttatcatcga tggtgagacc actaacgacg agtccaaatt gtccttgttt  1560
atccaagccg ttttctggaa attggccttc ggtctagatg tcgcagaatg taccaaccgt  1620
atctggaaaa gcattgattc aggtgcagac atttcagcag cctcgatttc tgaatttctc  1680
actggtgcat tcaaaaactt cctcagtgag gttccgctag cgctgtacac taaattttct  1740
gaaataaaca ttgaaagaa agaggatgag gaagagcctg cagctttacc aattttcgtt  1800
aatgaaacat ctttcctccc aaataacagt accattgaag aaataccatt acctgagacc  1860
tctgagatct ctgatattgc caagaagttg tccttcaaag aggcatatga agttgagaat  1920
aaactaagac ccgatttacc cgtcaagaac ttcgtcgtga agttaaagaa aaatagacgt  1980
gttacgcctg ctgattatga tagatatatt ttccatattg aattcgatat ttctggtact  2040
ggaatgactt atgacatcgg tgaagccctc ggtattcatg ccagaaacaa tgaatctttg  2100
gtcaaagaat tcttaacctt ctatggtcta aatgaatccg atgttgtctt agtccccaac  2160
aaggacaacc accatttgtt agaaacaaga accgtcttac aagcatttgt ggaaaatttg  2220
gatatttcg gtaaaccacc aaaaagattt tacgaatcat tgattccata tgcctctaac  2280
gaagaggaga agaaaaaatt agaggatttg gttactcctg ccggtgcagt agatttgaag  2340
agatttcaag atgtggagta ttatacatat gctgacattt ttgaattgtt cccatctgtt  2400
```

-continued

```
cgcccatctc ttgaggaact tgttactatc attgaaccat tgaagagaag agaatactca    2460
attgcctcct ctcagaaagt tcatccaaat gaagttcatt tattgatcgt tgttgttgat    2520
tgggtggata taaaggaag aaaaaggtac ggtcaagctt ctaagtatat ctcagacctt     2580
gctgtcggtt cagaattggt cgttagcgtt aaaccatctg ttatgaaatt accaccatct    2640
ccaaagcaac cagttattat gagtggttta ggtactggtt tggcaccatt caaggccatt    2700
gttgaagaga attatggca aaagcagcaa ggttatgaga ttggtgaagt cttcctatat     2760
ctaggttcaa gacacaaaag agaagaatat ttatatggtg agttatggga ggcttacaaa    2820
gatgcaggta ttatcacaca catcggcgct gctttctcaa gagaccaacc tcaaaaaatt    2880
tacattcaag atcgtatcaa agagaatttg gatgaattaa aaactgcaat gattgataat    2940
aaaggttcat tttacttgtg tggccctact tggccagttc cagatattac tcaagctttg    3000
caagacattc tggctaaaga cgccgaggaa agaggcatca aagtcgactt ggatgccgca    3060
attgaagaat taaggaagc atcaagatac attttagaag tctactaa                 3108
```

<210> SEQ ID NO 12
<211> LENGTH: 3108
<212> TYPE: DNA
<213> ORGANISM: Saccharomyces cerevisiae
<220> FEATURE:
<223> OTHER INFORMATION: yeast assimilatory sulfite reductase alpha
subunit (Met 10, MET10), strain UCD939 allele

<400> SEQUENCE: 12

```
atgccagttg agtttgctac caatccttt ggcgaggcca aaaatgcaac ttcactgcca      60
aaatatggta cacccgtaac tgccatttca tctgtgctgt tcaataacgt ggactccatt     120
tttgcttaca gtccttttc tcaacccgat ttgttacacc aagatctaaa aaaatggtct     180
gaaaagcgtg gtaacgaatc acgtgggaag ccattttcc aagagctgga tatcagatct    240
ggcgctggtt tggctccttt agggttttct catggattga agaacactac agcaattgtt    300
gctccagggt tttcgctgcc atacttcatt aactctttga aaaccgtctc tcatgatggt    360
aagtttcttt tgaatgttgg tgcttttaaac tacgacaatg ctaccggctc tgtcaccaac    420
gattatgtaa ccgcattgga tgctgcttcc aagctgaagt atggtgtcgt gactccgatt    480
tccgctaacg aggtacaaag tgtcgcctta ctgrcattgg cgattgccac tttcagtaat    540
aactccggag ctatcaattt atttgacgga ttaaactact cgaaaaccgt cttgccgttg    600
gtcgaatctg ttcctgaggc atctatttg gcaaaactat ccaaagttat tgcaccagat    660 gctgccttg atgatgtctt ggataagttt aatgaattga ctggattgag actacataat    720
ttccaatact ttggtgctca ggatgctgaa actgtgttta tcacttatgg gtctttagaa    780
tccgaattgt tcaactctgc gattagtggt aataattcca aaatcgggtt aatcaacgtc    840
agagtaccat tacccttttaa cgttgctaag tttgtcactc acgttccatc cactaccaaa    900
caaattgttg ttataggcca aactttggat ggttcttcgc cttctttctt gagatctcaa    960
gtttcagccg ccttattta ccacggccgc acctcaatta gcgtttctga gtacatctat   1020
caaccagatt tcatttggtc cccaaaagct gtcaaatcaa ttgtatcgtc attcatccct   1080
gaattcactt acaatgccga ttcatctttc ggcgaaggat tcatttattg ggcctctgat   1140
aagagtatca atattgatgt tgcctccaaa cttgtgaaag ctctgtcttt ggaagatggg   1200
aaatttgtgt ctttgagaac gaaatttgat aacttggcta atgctggtac cttccaagct   1260
caatttgtga cctcgaaaga acagatacct gtttcaaaca tcgattctac gaaattatca   1320
gtcgttgaag atgtcagttt attgaagcat ttagacgtag ctgctaccgt cgcagaacaa   1380
```

```
ggttcaattg cgttggtttc caaaaggca gttaaagatt tggatttaaa ttctgtagaa    1440
agttacgtca agaatttggg aattcctgaa tcattcctaa tatctattgc gaagaaaaac    1500
atcaaattgt ttatcatcga tggtgagacc actaacgacg agtccaaatt gtccttgttt    1560
atccaagccg ttttctggaa attggccttc ggtctagatg tcgcagaatg taccaaccgt    1620
atctggaaaa gcattgattc aggtgcagac atttcagcag cctcgatttc tgaatttctc    1680
actggtgcat tcaaaaactt cctcagtgag gttccgctag cgctgtacac taaattttct    1740
gaaataaaca ttgaaaagaa agaggatcag gaagagcctg cagctttacc aattttcgtt    1800
aatgaaacat ctttcctccc aaataacagt accattgaag aaataccatt acctgagacc    1860
tctgagatct ctgatattgc caagaagttg tccttcaaag aggcatatga agttgagaat    1920
aaactaagac ccgatttacc cgtcaagaac ttcgtcgtga agttaaagaa aaatagacgt    1980
gttacgcctg ctgattatga tagatatatt ttccatattg aattcgatat ttctggtact    2040
ggaatgactt atgacatcgg tgaagccctc ggtattcatg ccagaaacaa tgaatctttg    2100
gtcaaagaat tcttaacctt ctatggtcta aatgaatccg atgttgtctt agtccccaac    2160
aaggacaacc accattgttt agaaacaaga accgtcttac aagcatttgt ggaaaatttg    2220
gatattttcg gtaaaccacc aaaaagattt tacgaatcat tgattccata tgcctctaac    2280
gaagaggaga agaaaaaatt agaggatttg gttactcctg ccggtgcagt agatttgaag    2340
agatttcaag atgtggagta ttatacatat gctgacattt ttgaattgtt cccatctgtt    2400
cgcccatctc ttgaggaact tgttactatc attgaaccat tgaagagaag agaatactca    2460
attgcctcct ctcagaaagt tcatccaaat gaagttcatt tattgatcgt tgttgttgat    2520
tgggtggata taaaggaag aaaaaggtac ggtcaagctt ctaagtatat ctcagacctt    2580
gctgtcggtt cagaattggt cgttagcgtt aaaccatctg ttatgaaatt accaccatct    2640
ccaaagcaac cagttattat gagtggttta ggtactggtt tggcaccatt caaggccatt    2700
gttgaagaga aattatggca aaagcagcaa ggttatgaga ttggtgaagt cttcctatat    2760
ctaggttcaa gacacaaaag agaagaatat ttatatggtg agttatggga ggcttacaaa    2820
gatgcaggta ttatcacaca catcggcgct gctttctcaa gagaccaacc tcaaaaaatt    2880
tacattcaag atcgtatcaa agagaatttg gatgaattaa aaactgcaat gattgataat    2940
aaaggttcat tttacttgtg tggccctact tggccagttc cagatattac tcaagctttg    3000
caagacattc tggctaaaga cgccgaggaa agaggcatca aagtcgactt ggatgccgca    3060
attgaagaat taaggaagc atcaagatac attttagaag tctactaa                 3108
```

<210> SEQ ID NO 13  
<211> LENGTH: 3108  
<212> TYPE: DNA  
<213> ORGANISM: Saccharomyces cerevisiae  
<220> FEATURE:  
<223> OTHER INFORMATION: yeast assimilatory sulfite reductase alpha subunit (Met 10, MET10), strain UCD940 allele

<400> SEQUENCE: 13

```
atgccagttg agtttgctac caatccttt ggcgaggcca aaaatgcaac ttcactgcca    60
aaatatggta cacccgtaac tgccatttca tctgtgctgt tcaataacgt ggactccatt    120
tttgcttaca agtcctttc tcaacccgat tgttacacc aagatctaaa aaaatggtct    180
gaaaagcgtg gtaacgaatc acgtgggaag ccatttttcc aagagctgga tatcagatct    240
ggcgctggtt tggctccttt agggttttct catggattga agaacactac agcaattgtt    300
```

```
gctccagggt tttcgctgcc atacttcatt aactctttga aaaccgtctc tcatgatggt    360
aagtttcttt tgaatgttgg tgcttttaaac tacgacaatg ctamcggctc tgtcaccaac   420
gattatgtaa ccgcattgga tgctgcttcc aagctgaagt atggtgtcgt gactccgatt   480
tccgctaacg aggtacaaag tgtcgcctta ctgacattgg cgattgccac tttcagtaat    540
aactccggag ctatcaattt atttgacgga ttaaactact cgaaaccgt cttgccgttg     600
gtcgaatctg ttcctgaggc atctattttg gcaaaactat ccaaagttat tgcaccagat   660
gctgcctttg atgatgtctt ggataagttt aatgaattga ctggattgag actacataat   720
ttccaatact ttggtgctca ggatgctgaa actgtgttta tcacttatgg gtctttagaa   780
tccgaattgt tcaactctgc gattagtggt aataattcca aaatcgggtt aatcaacgtc   840
agagtaccat tacctttttaa cgttgctaag tttgtcactc acgttccatc cactaccaaa  900
caaattgttg ttataggcca aactttggat ggttcttcgy cttctttctt gagatctcaa   960
gtttcagccg ccttatttta ccacggccgc acctcaatta gcgtttctga gtacatctat  1020
caaccagatt tcatttggtc cccaaaagct gtcaaatcaa ttgtatcgtc attcatccct  1080
gaattcactt acaatgccga ttcatctttc ggcgaaggat tcatttattg ggcctctgat  1140
aagagtatca atattgatgt tgcctccaaa cttgtgaaag ctctgtcttt ggaagatggg  1200
aaatttgtgt ctttgagaac gaaatttgat aacttggcta atgctggtac cttccaagct  1260
caatttgtga cctcgaaaga acagatacct gtttcaaaca tcgattctac gaaattatca  1320
gtcgttgaag atgtcagttt attgaagcat ttagacgtag ctgctaccgt cgcagaacaa  1380
ggttcaattg cgttggtttc ccaaaaggca gttaaagatt tggatttaaa ttctgtagaa  1440
agttacgtca agaatttggg aattcctgaa tcattcctaa tatctattgc gaagaaaaac  1500
atcaaattgt ttatcatcga tggtgagacc actaacgacg agtccaaatt gtccttgttt  1560
atccaagccg ttttctggaa attggccttc ggtctagatg tcgcagaatg taccaaccgt  1620
atctggaaaa gcattgattc aggtgcagac atttcagcag cctcgatttc tgaatttctc  1680
actggtgcat tcaaaaactt cctcagtgag gttccgctag cgctgtacac taaatttttct 1740
gaaataaaca ttgaaaagaa agaggatgag gaagagcctg cagctttacc aattttcgtt  1800
aatgaaacat ctttcctccc aaataacagt accattgaag aaataccatt acctgagacc  1860
tctgagatct ctgatattgc caagaagttg tccttcaaag aggcatatga agttgagaat  1920
aaactaagac ccgatttacc cgtcaagaac ttcgtcgtga agttaaaga aaatagacgt   1980
gttacgcctg ctgattatga tagatatatt ttccatattg aattcgatat ttctggtact  2040
ggaatgactt atgacatcgg tgaagccctc ggtattcatg ccagaaacaa tgaatctttg  2100
gtcaaagaat tcttaacctt ctatggtcta aatgaatccg atgttgtctt agtccccaac  2160
aaggacaacc accatttgtt agaaacaaga accgtcttac aagcatttgt ggaaaatttg  2220
gatattttcg gtaaaccacc aaaaagattt tacgaatcat tgattccata tgcctctaac  2280
gaagaggaga agaaaaaatt agaggatttg gttactcctg ccggtgcagt agatttgaag  2340
agatttcaag atgtggagta ttatacatat gctgacattt ttgaattgtt cccatctgtt  2400
cgcccatctc ttgaggaact tgttactatc attgaaccat gaagagaag agaatactca   2460
attgcctcct ctcagaaagt tcatccaaat gaagttcatt tattgatcgt tgttgttgat  2520
tgggtggata ataaaggaag aaaaaggtac ggtcaagctt ctaagtatat ctcagacctt  2580
gctgtcggtt cagaattggt cgttagcgtt aaaccatctg ttatgaaatt accaccatct  2640
ccaaagcaac cagttattat gagtggttta ggtactggtt tggcaccatt caaggccatt  2700
```

```
gttgaagaga aattatggca aaagcagcaa ggttatgaga ttggtgaagt cttcctatat    2760
ctaggttcaa gacacaaaag agaagaatat ttatatggtg agttatggga ggcttacaaa    2820
gatgcaggta ttatcacaca catcggcgct gctttctcaa gagaccaacc tcaaaaaatt    2880
tacattcaag atcgtatcaa agagaatttg gatgaattaa aaactgcaat gattgataat    2940
aaaggttcat tttacttgtg tggccctact tggccagttc cagatattac tcaagctttg    3000
caagacattc tggctaaaga cgccgaggaa agaggcatca aagtcgactt ggatgccgca    3060
attgaagaat aaaggaagc atcaagatac attttagaag tctactaa              3108
```

<210> SEQ ID NO 14
<211> LENGTH: 3108
<212> TYPE: DNA
<213> ORGANISM: Saccharomyces cerevisiae
<220> FEATURE:
<223> OTHER INFORMATION: yeast assimilatory sulfite reductase alpha
      subunit (Met 10, MET10), strain UCD942 allele

<400> SEQUENCE: 14

```
atgccagttg agtttgctac caatcctttt ggcgaggcca aaaatgcaac ttcactgcca      60
aaatatggta cacccgtaac tgccatttca tctgtgctgt tcaataacgt ggactccatt     120
tttgcttaca agtccttttc tcaacccgat ttgttacacc aagatctaaa aaaatggtct     180
gaaaagcgtg gtaacgaatc acgtgggaag ccatttttcc aagagctgga tatcagatct     240
ggcgctggtt tggctccttt agggttttct catggattga gaacactac agcaattgtt     300 gctccagggt tttcgctgcc atacttcatt aactctttga aaaccgtctc tcatgatggt     360
aagtttcttt tgaatgttgg tgcttaaaac tacgacaatg ctaacggctc tgtcaccaac     420
gattatgtaa ccgcattgga tgctgcttcc aagctgaagt atggtgtcgt gactccgatt     480
tccgctaacg aggtacaaag tgtcgcctta ctgacattgg cgattgccac tttcagtaat     540
aactccggag ctatcaattt atttgacgga ttaaactact cgaaaaccgt cttgccgttg     600
gtcgaatctg ttcctgaggc atctatttg gcaaaactat ccaaagttat tgcaccagat     660
gctgcctttg atgatgtctt ggataagttt aatgaattga ctggattgag actacataat     720
ttccaatact ttggtgctca ggatgctgaa actgtgttta tcacttatgg gtctttagaa     780
tccgaattgt tcaactctgc gattagtggt aataattcca aaatcgggtt aatcaacgtc     840
agagtaccat taccttttaa cgttgctaag tttgtcactc acgttccatc cactaccaaa     900
caaattgttg ttataggcca aactttggat ggttcttcgc cttcttttctt gagatctcaa     960 gtttcagccg ccttattta ccacggccgc acctcaatta gcgtttctga gtacatctat    1020
caaccagatt tcatttggtc cccaaaagct gtcaaatcaa ttgtatcgtc attcatccct    1080
gaattcactt acaatgccga ttcatctttc ggcgaaggat tcatttattg ggcctctgat    1140
aagagtatca atattgatgt tgcctccaaa cttgtgaaag ctctgtcttt ggaagatggg    1200
aaatttgtgt ctttgagaac gaaatttgat aacttggcta atgctggtac cttccaagct    1260
caatttgtga cctcgaaaga acagatacct gtttcaaaca tcgattctac gaaattatca    1320
gtcgttgaag atgtcagttt attgaagcat ttagacgtag ctgctaccgt cgcagaacaa    1380
ggttcaattg cgttggtttc ccaaaaggca gttaaagatt tggctttaaa ttctgtagaa    1440
agttacgtca agaatttggg aattcctgaa tcattcctaa tatctattgc gaagaaaaac    1500
atcaaattgt ttatcatcga tggtgagacc actaacgacg agtccaaatt gtccttgttt    1560
atccaagccg ttttctggaa attggccttc ggtctagatg tcgcagaatg taccaaccgt    1620
atctggaaaa gcattgattc aggtgcagac atttcagcag cctcgatttc tgaatttctc    1680
```

-continued

```
actggtgcat tcaaaaactt cctcagtgag gttccgctag cgctgtacac taaattttct   1740
gaaataaaca ttgaaaagaa agaggatgag gaagagcctg cagctttacc aattttcgtt   1800
aatgaaacat ctttcctccc aaataacagt accattgaag aaataccatt acctgagacc   1860
tctgagatct ctgatattgc caagaagttg tccttcaaag aggcatatga agttgagaat   1920
aaactaagac ccgatttacc cgtcaagaac ttcgtcgtga agttaaaga aaatagacgt    1980 gttacgcctg ctgattatga tagatatatt ttccatattg aattcgatat ttctggtact   2040
ggaatgactt atgacatcgg tgaagccctc ggtattcatg ccagaaacaa tgaatctttg   2100
gtcaaagaat tcttaacctt ctatggtcta atgaatccg atgttgtctt agtccccaac    2160
aaggacaacc accatttgtt agaaacaaga accgtcttac aagcatttgt ggaaatttg    2220 gatattttcg gtaaaccacc aaaaagattt tacgaatcat tgattccata tgcctctaac   2280
gaagaggaga agaaaaaatt agaggatttg gttactcctg ccggtgcagt agatttgaag   2340
agatttcaag atgtggagta ttatacatat gctgacattt ttgaattgtt cccatctgtt   2400
cgcccatctc ttgaggaact tgttactatc attgaaccat tgaagagaag agaatactca   2460
attgcctcct ctcagaaagt tcatccaaat gaagttcatt tattgatcgt tgttgttgat   2520
tgggtggata ataaaggaag aaaaaggtac ggtcaagctt ctaagtatat ctcagacctt   2580
gctgtcggtt cagaattggt cgttagcgtt aaaccatctg ttatgaaatt accaccatct   2640
ccaaagcaac cagttattat gagtggttta ggtactggtt tggcaccatt caaggccatt   2700
gttgaagaga aattatggca aaagcagcaa ggttatgaga ttggtgaagt cttcctatat   2760
ctaggttcaa gacacaaaag agaagaatat ttatatggtg agttatggga ggcttacaaa   2820
gatgcaggta ttatcacaca catcggcgct gctttctcaa gagaccaacc tcaaaaaatt   2880
tacattcaag atcgtatcaa agagaatttg gatgaattaa aaactgcaat gattgataat   2940
aaaggttcat tttacttgtg tggccctact tggccagttc cagatattac tcaagctttg   3000
caagacattc tggctaaaga cgccgaggaa agaggcatca aagtcgactt ggatgccgca   3060
attgaagaat taaggaagc atcaagatac attttagaag tctactaa              3108
```

<210> SEQ ID NO 15
<211> LENGTH: 3108
<212> TYPE: DNA
<213> ORGANISM: Saccharomyces cerevisiae
<220> FEATURE:
<223> OTHER INFORMATION: yeast assimilatory sulfite reductase alpha
      subunit (Met 10, MET10), strain UCD956 allele

<400> SEQUENCE: 15

```
atgccagttg agtttgctac caatcctttt ggcgaggcca aaaatgcaac ttcactgcca    60
aaatatggta cacccgtaac tgccatttca tctgtgctgt tcaataacgt ggactccatt   120
tttgcttaca agtccttttc tcaacccgat ttgttacacc aagatctaaa aaaatggtct   180
gaaaagcgtg gtaacgaatc acgtgggaag ccattttttcc aagagctgga tatcagatct   240
ggcgctggtt tggctccttt agggttttct catggattga agaacactac agcaattgtt   300
gctccagggt tttcgctgcc atacttcatt aactctttga aaaccgtctc tcatgatggt   360
aagtttcttt tgaatgttgg tgcttttaaac tacgacaatg ctaccggctc tgtcaccaac   420
gattatgtaa ccgcattgga tgctgcttcc aagctgaagt atggtgtcgt gactccgatt   480
tccgctaacg aggtacaaag tgtcgcctta ctgacattgg cgattgccac tttcagtaat   540
aactccggag ctatcaattt atttgacgga ttaaactact cgaaaaccgt cttgccgttg   600
```

```
gtcgaatctg ttcctgaggc atctattttg gcaaaactat ccaaagttat tgcaccagat    660
gctgcctttg atgatgtctt ggataagttt aatgaattga ctggattgag actacataat    720
ttccaatact ttggtgctca ggatgctgaa actgtgttta tcacttatgg gtctttagaa    780
tccgaattgt tcaactctgc gattagtggt aataattcca aaatcgggtt aatcaacgtc    840
agagtaccat taccttttaa cgttgctaag tttgtcactc acgttccatc cactaccaaa    900
caaattgttt tataggcca aactttggat ggttcttcgc cttctttctt gagatctcaa    960
gtttcagccg ccttatttta ccacggccgc acctcaatta gcgtttctga gtacatctat    1020
caaccagatt tcatttggtc cccaaaagct gtcaaatcaa ttgtatcgtc attcatccct    1080
gaattcactt acaatgccga ttcatctttc ggcgaaggat tcatttattg ggcctctgat    1140
aagagtatca atattgatgt tgcctccaaa cttgtgaaag ctctgtcttt ggaagatggg    1200
aaatttgtgt cttttgagaac gaaatttgat aacttggcta atgctggtac cttccaagct    1260
caatttgtga cctcgaaaga acagatacct gtttcaaaca tcgattctac gaaattatca    1320
gtcgttgaag atgtcagttt attgaagcat ttagacgtag ctgctaccgt cgcagaacaa    1380
ggttcaattg cgttggtttc ccaaaaggca gttaaagatt tggatttaaa ttctgtagaa    1440
agttacgtca agaatttggg aattcctgaa tcattcctaa tatctattgc gaagaaaaac    1500
atcaaattgt ttatcatcga tggtgagacc actaacgacg agtccaaatt gtccttgttt    1560
atccaagccg ttttctggaa attggccttc ggtctagatg tcgcagaatg taccaaccgt    1620
atctggaaaa gcattgattc aggtgcagac atttcagcag cctcgatttc tgaatttctc    1680
actggtgcat tcaaaaactt cctcagtgag gttccgctag cgctgtacac taaattttct    1740
gaaataaaca ttgaaaagaa agaggatgag gaagagcctg cagctttacc aattttcgtt    1800
aatgaaacat ctttcctccc aaataacagt accattgaag aaataccatt acctgagacc    1860
tctgagatct ctgatattgc caagaagttg tccttcaaag aggcatatga agttgagaat    1920
aaactaagac ccgatttacc cgtcaagaac ttcgtcgtga agttaaagaa aaatagacgt    1980
gttacgcctg ctgattatga tagatatatt ttccatattg aattcgatat ttctggtact    2040
ggaatgactt atgacatcgg tgaagccctc ggtattcatg ccagaaacaa tgaatctttg    2100
gtcaaagaat tcttaacctt ctatggtcta aatgaatccg atgttgtctt agtccccaac    2160
aaggacaacc accattgtt agaaacaaga accgtcttac aagcatttgt ggaaaatttg    2220
gatattttcg gtaaaccacc aaaaagattt tacgaatcat tgattccata tgcctctaac    2280
gaagaggaga agaaaaaatt agaggatttg gttactcctg ccggtgcagt agatttgaag    2340
agatttcaag atgtggagta ttatacatat gctgacattt ttgaattgtt cccatctgtt    2400 cgccatctc ttgaggaact tgttactatc attgaaccat tgaagagaag agaatactca    2460
attgcctcct ctcagaaagt tcatccaaat gaagttcatt tattgatcgt tgttgttgat    2520
tgggtggata taaaggaag aaaaaggtac ggtcaagctt ctaagtatat ctcagacctt    2580
gctgtcggtt cagaattggt cgttagcgtt aaaccatctg ttatgaaatt accaccatct    2640
ccaaagcaac cagttattat gagtggttta ggtactggtt tggcatcatt caaggccatt    2700
gttgaagaga aattatggca aaagcagcaa ggttatgaga ttggtgaagt cttcctatat    2760
ctaggttcaa gacacaaaag agaagaatat ttatatggtg agttatggga ggcttacaaa    2820
gatgcaggta ttatcacaca catcggcgct gctttctcaa gagaccaacc tcaaaaaatt    2880
tacattcaag atcgtatcaa agagaatttg atgaattaa aaactgcaat gattgataat    2940
aaaggttcat tttacttgtg tggccctact tggccagttc cagatattac tcaagctttg    3000
```

| | |
|---|---|
| caagacattc tggctaaaga cgccgaggaa agaggcatca aagtcgactt ggatgccgca | 3060 |
| attgaagaat taaaggaagc atcaagatac attttagaag tctactaa | 3108 |

<210> SEQ ID NO 16
<211> LENGTH: 3108
<212> TYPE: DNA
<213> ORGANISM: Saccharomyces cerevisiae
<220> FEATURE:
<223> OTHER INFORMATION: yeast assimilatory sulfite reductase alpha subunit (Met 10, MET10), strain UCD957 allele

<400> SEQUENCE: 16

| | |
|---|---|
| atgccagttg agtttgctac caatccttt ggcgaggcca aaatgcaac ttcactgcca | 60 |
| aaatatggta cacccgtaac tgccatttca tctgtgctgt tcaataacgt ggactccatt | 120 |
| tttgcttaca agtcctttc tcaacccgat ttgttacacc aagatctaaa aaaatggtct | 180 |
| gaaaagcgtg gtaacgaatc acgtgggaag ccatttttcc aagagctgga tatcagatct | 240 |
| ggcgctggtt tggctccttt agggttttct catggattga agaacactac agcaattgtt | 300 |
| gctccagggt tttcgctgcc atacttcatt aactctttga aaccgtctc tcatgatggt | 360 |
| aagtttcttt tgaatgttgg tgcttttaaac tacgacaatg ctaccggctc tgtcaccaac | 420 |
| gattatgtaa ccgcattgga tgctgcttcc aagctgaagt atggtgtcgt gactccgatt | 480 |
| tccgctaacg aggtacaaag tgtcgcctta ctggcattgg cgattgccac tttcagtaat | 540 |
| aactccggag ctatcaattt atttgacgga ttaaactact cgaaaaccgt cttgccgttg | 600 |
| gtcgaatctg ttcctgaggc atctattttg gcaaaactat ccaaagttat tgcaccagat | 660 |
| gctgcctttg atgatgtctt ggataagttt aatgaattga ctggattgag actacataat | 720 |
| ttccaatact ttggtgctca ggatgctgaa actgtgtta tcacttatgg gtctttagaa | 780 |
| tccgaattgt tcaactctgc gattagtggt ataattcca aaatcgggtt aatcaacgtc | 840 |
| agagtaccat tacctttaa cgttgctaag tttgtcactc acgttccatc cactaccaaa | 900 |
| caaattgttg ttataggcca aactttggat ggttcttcgc cttctttctt gagatctcaa | 960 |
| gtttcagccg cctattttta ccacggccgc acctcaatta gcgtttctga gtacatctat | 1020 |
| caaccagatt tcatttggtc cccaaaagct gtcaaatcaa ttgtatcgtc attcatccct | 1080 |
| gaattcactt acaatgccga ttcatctttc ggcgaaggat tcatttattg ggcctctgat | 1140 |
| aagagtatca atattgatgt tgcctccaaa cttgtgaaag ctctgtctt ggaagatggg | 1200 |
| aaatttgtgt ctttgagaac gaaatttgat aacttggcta atgctggtac cttccaagct | 1260 |
| caatttgtga cctcgaagga acagatacct gtttcaaaca tcgattctac gaaattatca | 1320 |
| gtcgttgaag atgtcagttt attgaagcat ttagacgtag ctgctaccgt cgcagaacaa | 1380 |
| ggttcaattg cgttggtttc ccaaaaggca gttaaagatt tggatttaaa ttctgtagaa | 1440 |
| agttacgtca agaatttggg aattcctgaa tcattcctaa tatctattgc gaagaaaaac | 1500 |
| atcaaattgt ttatcatcga tggtgagacc attaacgacg agtccaaatt gtccttgttt | 1560 |
| atccaagccg tttctggaa attggccttc ggtctagatg tcgcagaatg taccaaccgt | 1620 |
| atctggaaaa gcattgattc aggtgcagac atttcagcag cctcgatttc tgaatttctc | 1680 |
| actggtgcat tcaaaaactt cctcagtgag gttccgctag cgctgtacac taaattttct | 1740 |
| gaaataaaca ttgaaagaa agaggataag gaagagcctg cagctttacc aattttcgtt | 1800 |
| aatgaaacat ctttcctccc aaataacagt accattgaag aaataccatt acctgagacc | 1860 |
| tctgagatct ctgatattgc caagaagttg tccttcaaag aggcatatga agttgagaat | 1920 |
| aaactaagac ccgatttacc cgtcaagaac ttcgtcgtga agttaaaga aaatagacgt | 1980 |

```
gttacgcctg ctgattatga tagatatatt ttccatattg aattcgatat ttctggtact    2040
ggaatgactt atgacatcgg tgaagccctc ggtattcatg ccagaaacaa tgaatctttg    2100
gtcaaagaat tcttaacctt ctatggtcta aatgaatccg atgttgtctt agtccccaac    2160
aaggacaacc accatttgtt agaaacaaga accgtcttac aagcatttgt ggaaaatttg    2220
gatattttcg gtaaaccacc aaaaagattt tacgaatcat tgattccata tgcctctaac    2280
gaagaggaga agaaaaaatt agaggatttg gttactcctg ccggtgcagt agatttgaag    2340
agatttcaag atgtggagta ttatacatat gctgacattt ttgaattgtt cccatctgtt    2400
cgcccatctc ttgaggaact tgttactatc attgaaccat gaagagaag agaatactca    2460 attgcctcct ctcagaaagt tcatccaaat gaagttcatt tattgatcgt tgttgttgat    2520
tgggtggata ataaaggaag aaaaaggtac ggtcaagctt ctaagtatat ctcagacctt    2580
gctgtcggtt cagaattggt cgttagcgtt aaaccatctg ttatgaaatt accaccatct    2640
ccaaagcaac cagttattat gagtggttta ggtactggtt tggcaccatt caaggccatt    2700
gttgaagaga aattatggca aaagcagcaa ggttatgaga ttggtgaagt cttcctatat    2760
ctaggttcaa gacacaaaag agaagaatat ttatatggtg agttatggga ggcttacaaa    2820
gatgcaggta ttatcacaca catcggcgct gctttctcaa gagaccaacc tcaaaaaatt    2880
tacattcaag atcgtatcaa agagaatttg gatgaattaa aaactgcaat gattgataat    2940
aaaggttcat tttacttgtg tggccctact tggccagttc cagatattac tcaagctttg    3000
caagacattc tggctaaaga cgccgaggaa agaggcatca aagtcgactt ggatgccgca    3060
attgaagaat taaggaagc atcaagatac attttagaag tctactaa                  3108
```

<210> SEQ ID NO 17
<211> LENGTH: 1035
<212> TYPE: PRT
<213> ORGANISM: Saccharomyces cerevisiae
<220> FEATURE:
<223> OTHER INFORMATION: yeast assimilatory sulfite reductase alpha
      subunit (Met 10, MET10), strain S288c allele

<400> SEQUENCE: 17

```
Met Pro Val Glu Phe Ala Thr Asn Pro Phe Gly Glu Ala Lys Asn Ala
 1               5                  10                  15

Thr Ser Leu Pro Lys Tyr Gly Thr Pro Val Thr Ala Ile Ser Ser Val
            20                  25                  30

Leu Phe Asn Asn Val Asp Ser Ile Phe Ala Tyr Lys Ser Phe Ser Gln
        35                  40                  45

Pro Asp Leu Leu His Gln Asp Leu Lys Lys Trp Ser Glu Lys Arg Gly
    50                  55                  60

Asn Glu Ser Arg Gly Lys Pro Phe Gln Glu Leu Asp Ile Arg Ser
 65                  70                  75              80

Gly Ala Gly Leu Ala Pro Leu Gly Phe Ser His Gly Leu Lys Asn Thr
                85                  90                  95

Thr Ala Ile Val Ala Pro Gly Phe Ser Leu Pro Tyr Phe Ile Asn Ser
           100                 105                 110

Leu Lys Thr Val Ser His Asp Gly Lys Phe Leu Leu Asn Val Gly Ala
       115                 120                 125

Leu Asn Tyr Asp Asn Ala Thr Gly Ser Val Thr Asn Asp Tyr Val Thr
   130                 135                 140

Ala Leu Asp Ala Ala Ser Lys Leu Lys Tyr Gly Val Val Thr Pro Ile
145                 150                 155                 160
```

```
Ser Ala Asn Glu Val Gln Ser Val Ala Leu Leu Ala Leu Ala Ile Ala
                165                 170                 175

Thr Phe Ser Asn Asn Ser Gly Ala Ile Asn Leu Phe Asp Gly Leu Asn
            180                 185                 190

Tyr Ser Lys Thr Val Leu Pro Leu Val Glu Ser Val Pro Glu Ala Ser
        195                 200                 205

Ile Leu Ala Lys Leu Ser Lys Val Ile Ala Pro Asp Ala Ala Phe Asp
    210                 215                 220

Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
                245                 250                 255

Gly Ser Leu Glu Ser Glu Leu Phe Asn Ser Ala Ile Ser Gly Asn Asn
            260                 265                 270

Ser Lys Ile Gly Leu Ile Asn Val Arg Val Pro Leu Pro Phe Asn Val
        275                 280                 285

Ala Lys Phe Val Thr His Val Pro Ser Thr Thr Lys Gln Ile Val Val
    290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                325                 330                 335

Glu Tyr Ile Tyr Gln Pro Asp Phe Ile Trp Ser Pro Lys Ala Val Lys
            340                 345                 350

Ser Ile Val Ser Ser Phe Ile Pro Glu Phe Thr Tyr Asn Ala Asp Ser
        355                 360                 365

Ser Phe Gly Glu Gly Phe Ile Tyr Trp Ala Ser Asp Lys Ser Ile Asn
    370                 375                 380

Ile Asp Val Ala Ser Lys Leu Val Lys Ala Leu Ser Leu Glu Asp Gly
385                 390                 395                 400

Lys Phe Val Ser Leu Arg Thr Lys Phe Asp Asn Leu Ala Asn Ala Gly
                405                 410                 415

Thr Phe Gln Ala Gln Phe Val Thr Ser Lys Glu Gln Ile Pro Val Ser
            420                 425                 430

Asn Ile Asp Ser Thr Lys Leu Ser Val Val Glu Asp Val Ser Leu Leu
        435                 440                 445

Lys His Leu Asp Val Ala Ala Thr Val Ala Glu Gln Gly Ser Ile Ala
    450                 455                 460

Leu Val Ser Gln Lys Ala Val Lys Asp Leu Asp Leu Asn Ser Val Glu
465                 470                 475                 480

Ser Tyr Val Lys Asn Leu Gly Ile Pro Glu Ser Phe Leu Ile Ser Ile
                485                 490                 495

Ala Lys Lys Asn Ile Lys Leu Phe Ile Ile Asp Gly Glu Thr Thr Asn
            500                 505                 510

Asp Glu Ser Lys Leu Ser Leu Phe Ile Gln Ala Val Phe Trp Lys Leu
        515                 520                 525

Ala Phe Gly Leu Asp Val Ala Glu Cys Thr Asn Arg Ile Trp Lys Ser
    530                 535                 540

Ile Asp Ser Gly Ala Asp Ile Ser Ala Ala Ser Ile Ser Glu Phe Leu
545                 550                 555                 560

Thr Gly Ala Phe Lys Asn Phe Leu Ser Glu Val Pro Leu Ala Leu Tyr
                565                 570                 575

Thr Lys Phe Ser Glu Ile Asn Ile Glu Lys Lys Glu Asp Glu Glu Glu
            580                 585                 590
```

-continued

Pro Ala Ala Leu Pro Ile Phe Val Asn Glu Thr Ser Phe Leu Pro Asn
            595                 600                 605

Asn Ser Thr Ile Glu Glu Ile Pro Leu Pro Glu Thr Ser Glu Ile Ser
            610                 615                 620

Asp Ile Ala Lys Lys Leu Ser Phe Lys Glu Ala Tyr Glu Val Glu Asn
625                 630                 635                 640

Lys Leu Arg Pro Asp Leu Pro Val Lys Asn Phe Val Lys Val Lys
            645                 650                 655

Glu Asn Arg Arg Val Thr Pro Ala Asp Tyr Asp Arg Tyr Ile Phe His
            660                 665                 670

Ile Glu Phe Asp Ile Ser Gly Thr Gly Met Thr Tyr Asp Ile Gly Glu
            675                 680                 685

Ala Leu Gly Ile His Ala Arg Asn Asn Glu Ser Leu Val Lys Glu Phe
            690                 695                 700

Leu Thr Phe Tyr Gly Leu Asn Glu Ser Asp Val Val Leu Val Pro Asn
705                 710                 715                 720

Lys Asp Asn His His Leu Leu Glu Thr Arg Thr Val Leu Gln Ala Phe
            725                 730                 735

Val Glu Asn Leu Asp Ile Phe Gly Lys Pro Pro Lys Arg Phe Tyr Glu
            740                 745                 750

Ser Leu Ile Pro Tyr Ala Ser Asn Glu Glu Lys Lys Lys Leu Glu
            755                 760                 765

Asp Leu Val Thr Pro Ala Gly Ala Val Asp Leu Lys Arg Phe Gln Asp
            770                 775                 780

Val Glu Tyr Tyr Thr Tyr Ala Asp Ile Phe Glu Leu Phe Pro Ser Val
785                 790                 795                 800

Arg Pro Ser Leu Glu Gly Leu Val Thr Ile Ile Glu Pro Leu Lys Arg
            805                 810                 815

Arg Glu Tyr Ser Ile Ala Ser Ser Gln Lys Val His Pro Asn Glu Val
            820                 825                 830

His Leu Leu Ile Val Val Val Asp Trp Val Asp Asn Lys Gly Arg Lys
            835                 840                 845

Arg Tyr Gly Gln Ala Ser Lys Tyr Ile Ser Asp Leu Ala Val Gly Ser
            850                 855                 860

Glu Leu Val Val Ser Val Lys Pro Ser Val Met Lys Leu Pro Pro Ser
865                 870                 875                 880

Pro Lys Gln Pro Val Ile Met Ser Gly Leu Gly Thr Gly Leu Ala Pro
            885                 890                 895

Phe Lys Ala Ile Val Glu Glu Lys Leu Trp Gln Lys Gln Gly Tyr
            900                 905                 910

Glu Ile Gly Glu Val Phe Leu Tyr Leu Gly Ser Arg His Lys Arg Glu
            915                 920                 925

Glu Tyr Leu Tyr Gly Glu Leu Trp Glu Ala Tyr Lys Asp Ala Gly Ile
            930                 935                 940

Ile Thr His Ile Gly Ala Ala Phe Ser Arg Asp Gln Pro Gln Lys Ile
945                 950                 955                 960

Tyr Ile Gln Asp Arg Ile Lys Glu Asn Leu Asp Glu Leu Lys Thr Ala
            965                 970                 975

Met Ile Asp Asn Lys Gly Ser Phe Tyr Leu Cys Gly Pro Thr Trp Pro
            980                 985                 990

Val Pro Asp Ile Thr Gln Ala Leu Gln Asp Ile Leu Ala Lys Asp Ala
            995                 1000                1005

Glu Glu Arg Gly Ile Lys Val Asp Leu Asp Ala Ala Ile Glu Glu Leu

```
                1010            1015            1020
Lys Glu Ala Ser Arg Tyr Ile Leu Glu Val Tyr
1025            1030            1035

<210> SEQ ID NO 18
<211> LENGTH: 1035
<212> TYPE: PRT
<213> ORGANISM: Saccharomyces cerevisiae
<220> FEATURE:
<223> OTHER INFORMATION: yeast assimilatory sulfite reductase alpha
      subunit (Met 10, MET10), strain UCD932 allele

<400> SEQUENCE: 18

Met Pro Val Glu Phe Ala Thr Asn Pro Phe Gly Glu Ala Lys Asn Ala
  1               5                  10                  15

Thr Ser Leu Pro Lys Tyr Gly Thr Pro Val Thr Ala Ile Ser Ser Val
             20                  25                  30

Leu Phe Asn Asn Val Asp Ser Ile Phe Ala Tyr Lys Ser Phe Ser Gln
         35                  40                  45

Pro Asp Leu Leu His Gln Asp Leu Lys Lys Trp Ser Glu Lys Arg Gly
     50                  55                  60

Asn Glu Ser Arg Gly Lys Pro Phe Phe Gln Glu Leu Asp Ile Arg Ser
 65                  70                  75                  80

Gly Ala Gly Leu Ala Pro Leu Gly Phe Ser His Gly Leu Lys Asn Thr
                 85                  90                  95

Thr Ala Ile Val Ala Pro Gly Phe Ser Leu Pro Tyr Phe Ile Asn Ser
            100                 105                 110

Leu Lys Thr Val Ser His Asp Gly Lys Phe Leu Leu Asn Val Gly Ala
        115                 120                 125

Leu Asn Tyr Asp Asn Ala Asn Gly Ser Val Thr Asn Asp Tyr Val Thr
    130                 135                 140

Ala Leu Asp Ala Ala Ser Lys Leu Lys Tyr Gly Val Val Thr Pro Ile
145                 150                 155                 160

Ser Ala Asn Glu Val Gln Ser Val Ala Leu Leu Thr Leu Ala Ile Ala
                165                 170                 175

Thr Phe Ser Asn Asn Ser Gly Ala Ile Asn Leu Phe Asp Gly Leu Asn
            180                 185                 190

Tyr Ser Lys Thr Val Leu Pro Leu Val Glu Ser Val Pro Glu Ala Ser
        195                 200                 205

Ile Leu Ala Lys Leu Ser Lys Val Ile Ala Pro Asp Ala Ala Phe Asp
    210                 215                 220

Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
                245                 250                 255

Gly Ser Leu Glu Ser Glu Leu Phe Asn Ser Ala Ile Ser Gly Asn Asn
            260                 265                 270

Ser Lys Ile Gly Leu Ile Asn Val Arg Val Pro Leu Pro Phe Asn Val
        275                 280                 285

Ala Lys Phe Val Thr His Val Pro Ser Thr Thr Lys Gln Ile Val Val
    290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                325                 330                 335

Glu Tyr Ile Tyr Gln Pro Asp Phe Ile Trp Ser Pro Lys Ala Val Lys
```

-continued

```
            340                 345                 350
Ser Ile Val Ser Ser Phe Ile Pro Glu Phe Thr Tyr Asn Ala Asp Ser
            355                 360                 365
Ser Phe Gly Glu Gly Phe Ile Tyr Trp Ala Ser Asp Lys Ser Ile Asn
    370                 375                 380
Ile Asp Val Ala Ser Lys Leu Val Lys Ala Leu Ser Leu Glu Asp Gly
385                 390                 395                 400
Lys Phe Val Ser Leu Arg Thr Lys Phe Asp Asn Leu Ala Asn Ala Gly
                405                 410                 415
Thr Phe Gln Ala Gln Phe Val Thr Ser Lys Glu Gln Ile Pro Val Ser
            420                 425                 430
Asn Ile Asp Ser Thr Lys Leu Ser Val Val Glu Asp Val Ser Leu Leu
        435                 440                 445
Lys His Leu Asp Val Ala Ala Thr Val Ala Glu Gln Gly Ser Ile Ala
            450                 455                 460
Leu Val Ser Gln Lys Ala Val Lys Asp Leu Asp Leu Asn Ser Val Glu
465                 470                 475                 480
Ser Tyr Val Lys Asn Leu Gly Ile Pro Glu Ser Phe Leu Ile Ser Ile
                485                 490                 495
Ala Lys Lys Asn Ile Lys Leu Phe Ile Asp Gly Glu Thr Thr Asn
            500                 505                 510
Asp Glu Ser Lys Leu Ser Leu Phe Ile Gln Ala Val Phe Trp Lys Leu
        515                 520                 525
Ala Phe Gly Leu Asp Val Ala Glu Cys Thr Asn Arg Ile Trp Lys Ser
            530                 535                 540
Ile Asp Ser Gly Ala Asp Ile Ser Ala Ala Ser Ile Ser Glu Phe Leu
545                 550                 555                 560
Thr Gly Ala Phe Lys Asn Phe Leu Ser Glu Val Pro Leu Ala Leu Tyr
                565                 570                 575
Thr Lys Phe Ser Glu Ile Asn Ile Glu Lys Lys Glu Asp Glu Glu
            580                 585                 590
Pro Ala Ala Leu Pro Ile Phe Val Asn Glu Thr Ser Phe Leu Pro Asn
        595                 600                 605
Asn Ser Thr Ile Glu Glu Ile Pro Leu Pro Glu Thr Ser Glu Ile Ser
    610                 615                 620
Asp Ile Ala Lys Lys Leu Ser Phe Lys Glu Ala Tyr Glu Val Glu Asn
625                 630                 635                 640
Lys Leu Arg Pro Asp Leu Pro Val Lys Asn Phe Val Val Lys Val Lys
                645                 650                 655
Glu Asn Arg Arg Val Lys Pro Ala Asp Tyr Asp Arg Tyr Ile Phe His
            660                 665                 670
Ile Glu Phe Asp Ile Ser Gly Thr Gly Met Thr Tyr Asp Ile Gly Glu
        675                 680                 685
Ala Leu Gly Ile His Ala Arg Asn Asn Glu Ser Leu Val Lys Glu Phe
            690                 695                 700
Leu Thr Phe Tyr Gly Leu Asn Glu Ser Asp Val Val Leu Val Pro Asn
705                 710                 715                 720
Lys Asp Asn His His Leu Leu Glu Thr Arg Thr Val Leu Gln Ala Phe
                725                 730                 735
Val Glu Asn Leu Asp Ile Phe Gly Lys Pro Pro Lys Arg Phe Tyr Glu
            740                 745                 750
Ser Leu Ile Pro Tyr Ala Ser Asn Glu Glu Glu Lys Lys Lys Leu Glu
        755                 760                 765
```

```
Asp Leu Val Thr Pro Ala Gly Ala Val Asp Leu Lys Arg Phe Gln Asp
        770                 775                 780

Val Glu Tyr Tyr Thr Tyr Ala Asp Ile Phe Glu Leu Phe Pro Ser Val
785                 790                 795                 800

Arg Pro Ser Leu Glu Glu Leu Val Thr Ile Ile Glu Pro Leu Lys Arg
                805                 810                 815

Arg Glu Tyr Ser Ile Ala Ser Ser Gln Lys Val His Pro Asn Glu Val
            820                 825                 830

His Leu Leu Ile Val Val Val Asp Trp Val Asp Asn Lys Gly Arg Lys
        835                 840                 845

Arg Tyr Gly Gln Ala Ser Lys Tyr Ile Ser Asp Leu Ala Val Gly Ser
    850                 855                 860

Glu Leu Val Val Ser Val Lys Pro Ser Val Met Lys Leu Pro Pro Ser
865                 870                 875                 880

Pro Lys Gln Pro Val Ile Met Ser Gly Leu Gly Thr Gly Leu Ala Pro
                885                 890                 895

Phe Lys Ala Ile Val Glu Glu Lys Leu Trp Gln Lys Gln Gln Gly Tyr
            900                 905                 910

Glu Ile Gly Glu Val Phe Leu Tyr Leu Gly Ser Arg His Lys Arg Glu
        915                 920                 925

Glu Tyr Leu Tyr Gly Glu Leu Trp Glu Ala Tyr Lys Asp Ala Gly Ile
    930                 935                 940

Ile Thr His Ile Gly Ala Ala Phe Ser Arg Asp Gln Pro Gln Lys Ile
945                 950                 955                 960

Tyr Ile Gln Asp Arg Ile Lys Glu Asn Leu Asp Glu Leu Lys Thr Ala
                965                 970                 975

Met Ile Asp Asn Lys Gly Ser Phe Tyr Leu Cys Gly Pro Thr Trp Pro
            980                 985                 990

Val Pro Asp Ile Thr Gln Ala Leu Gln Asp Ile Leu Ala Lys Asp Ala
        995                 1000                1005

Glu Glu Arg Gly Ile Lys Val Asp Leu Asp Ala Ala Ile Glu Glu Leu
    1010                1015                1020

Lys Glu Ala Ser Arg Tyr Ile Leu Glu Val Tyr
1025                1030                1035

<210> SEQ ID NO 19
<211> LENGTH: 1035
<212> TYPE: PRT
<213> ORGANISM: Saccharomyces cerevisiae
<220> FEATURE:
<223> OTHER INFORMATION: yeast assimilatory sulfite reductase alpha
      subunit (Met 10, MET10), strain UCD950 allele

<400> SEQUENCE: 19

Met Pro Val Glu Phe Ala Thr Asn Pro Phe Glu Ala Lys Asn Ala
 1               5                  10                  15

Thr Ser Leu Pro Lys Tyr Gly Pro Val Thr Ala Ile Ser Ser Val
                20                  25                  30

Leu Phe Asn Asn Val Asp Ser Ile Phe Ala Tyr Lys Ser Phe Ser Gln
            35                  40                  45

Pro Asp Leu Leu His Gln Asp Leu Lys Lys Trp Ser Glu Lys Arg Gly
        50                  55                  60

Asn Glu Ser Arg Gly Lys Pro Phe Phe Gln Glu Leu Asp Ile Arg Ser
65                  70                  75                  80

Gly Ala Gly Leu Ala Pro Leu Gly Phe Ser His Gly Leu Lys Asn Thr
                85                  90                  95
```

```
Thr Ala Ile Val Ala Pro Gly Phe Ser Leu Pro Tyr Phe Ile Asn Ser
            100                 105                 110

Leu Lys Thr Val Ser His Asp Gly Lys Phe Leu Leu Asn Val Gly Ala
        115                 120                 125

Leu Asn Tyr Asp Asn Ala Thr Gly Ser Val Thr Asn Asp Tyr Val Thr
    130                 135                 140

Ala Leu Asp Ala Ala Ser Lys Leu Lys Tyr Gly Val Val Thr Pro Ile
145                 150                 155                 160

Ser Ala Asn Glu Val Gln Ser Val Ala Leu Leu Ala Leu Ala Ile Ala
                165                 170                 175

Thr Phe Ser Asn Asn Ser Gly Ala Ile Asn Leu Phe Asp Gly Leu Asn
            180                 185                 190

Tyr Ser Lys Thr Val Leu Pro Leu Val Glu Ser Val Pro Glu Ala Ser
    195                 200                 205

Ile Leu Ala Lys Leu Ser Lys Val Ile Ala Pro Asp Ala Ala Phe Asp
210                 215                 220

Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
                245                 250                 255

Gly Ser Leu Glu Ser Glu Leu Phe Asn Ser Ala Ile Ser Gly Asn Asn
            260                 265                 270

Ser Lys Ile Gly Leu Ile Asn Val Arg Val Pro Leu Pro Phe Asn Val
    275                 280                 285

Ala Lys Phe Val Thr His Val Pro Ser Thr Thr Lys Gln Ile Val Val
290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                325                 330                 335

Glu Tyr Ile Tyr Gln Pro Asp Phe Ile Trp Ser Pro Lys Ala Val Lys
            340                 345                 350

Ser Ile Val Ser Ser Phe Ile Pro Glu Phe Thr Tyr Asn Ala Asp Ser
    355                 360                 365

Ser Phe Gly Glu Gly Phe Ile Tyr Trp Ala Ser Asp Lys Ser Ile Asn
370                 375                 380

Ile Asp Val Ala Ser Lys Leu Val Lys Ala Leu Ser Leu Glu Asp Gly
385                 390                 395                 400

Lys Phe Val Ser Leu Arg Thr Lys Phe Asp Asn Leu Ala Asn Ala Gly
                405                 410                 415

Thr Phe Gln Ala Gln Phe Val Thr Ser Lys Glu Gln Ile Pro Val Ser
            420                 425                 430

Asn Ile Asp Ser Thr Lys Leu Ser Val Val Glu Asp Val Ser Leu Leu
    435                 440                 445

Lys His Leu Asp Val Ala Ala Thr Val Ala Glu Gln Gly Ser Ile Ala
450                 455                 460

Leu Val Ser Gln Lys Ala Val Lys Asp Leu Asp Leu Asn Ser Val Glu
465                 470                 475                 480

Ser Tyr Val Lys Asn Leu Gly Ile Pro Glu Ser Phe Leu Ile Ser Ile
                485                 490                 495

Ala Lys Lys Asn Ile Lys Leu Phe Ile Asp Gly Glu Thr Ile Asn
            500                 505                 510

Asp Glu Ser Lys Leu Ser Leu Phe Ile Gln Ala Val Phe Trp Lys Leu
    515                 520                 525
```

```
Ala Phe Gly Leu Asp Val Ala Glu Cys Thr Asn Arg Ile Trp Lys Ser
        530                 535                 540

Ile Asp Ser Gly Ala Asp Ile Ser Ala Ser Ile Ser Glu Phe Leu
545                 550                 555                 560

Thr Gly Ala Phe Lys Asn Phe Leu Ser Glu Val Pro Leu Ala Leu Tyr
                565                 570                 575

Thr Lys Phe Ser Glu Ile Asn Ile Glu Lys Lys Glu Asp Lys Glu Glu
                580                 585                 590

Pro Ala Ala Leu Pro Ile Phe Val Asn Glu Thr Ser Phe Leu Pro Asn
                595                 600                 605

Asn Ser Thr Ile Glu Glu Ile Pro Leu Pro Glu Thr Ser Glu Ile Ser
        610                 615                 620

Asp Ile Ala Lys Lys Leu Ser Phe Lys Glu Ala Tyr Glu Val Glu Asn
625                 630                 635                 640

Lys Leu Arg Pro Asp Leu Pro Val Lys Asn Phe Val Val Lys Val Lys
                645                 650                 655

Glu Asn Arg Arg Val Thr Pro Ala Asp Tyr Asp Arg Tyr Ile Phe His
        660                 665                 670

Ile Glu Phe Asp Ile Ser Gly Thr Gly Met Thr Tyr Asp Ile Gly Glu
        675                 680                 685

Ala Leu Gly Ile His Ala Arg Asn Asn Glu Ser Leu Val Lys Glu Phe
        690                 695                 700

Leu Thr Phe Tyr Gly Leu Asn Glu Ser Asp Val Val Leu Val Pro Asn
705                 710                 715                 720

Lys Asp Asn His His Leu Leu Glu Thr Arg Thr Val Leu Gln Ala Phe
                725                 730                 735

Val Glu Asn Leu Asp Ile Phe Gly Lys Pro Pro Lys Arg Phe Tyr Glu
                740                 745                 750

Ser Leu Ile Pro Tyr Ala Ser Asn Glu Glu Lys Lys Lys Leu Glu
        755                 760                 765

Asp Leu Val Thr Pro Ala Gly Ala Val Asp Leu Lys Arg Phe Gln Asp
        770                 775                 780

Val Glu Tyr Tyr Thr Tyr Ala Asp Ile Phe Glu Leu Phe Pro Ser Val
785                 790                 795                 800

Arg Pro Ser Leu Glu Glu Leu Val Thr Ile Ile Glu Pro Leu Lys Arg
                805                 810                 815

Arg Glu Tyr Ser Ile Ala Ser Ser Gln Lys Val His Pro Asn Glu Val
                820                 825                 830

His Leu Leu Ile Val Val Val Asp Trp Val Asp Asn Lys Gly Arg Lys
        835                 840                 845

Arg Tyr Gly Gln Ala Ser Lys Tyr Ile Ser Asp Leu Ala Val Gly Ser
        850                 855                 860

Glu Leu Val Val Ser Val Lys Pro Ser Val Met Lys Leu Pro Pro Ser
865                 870                 875                 880

Pro Lys Gln Pro Val Ile Met Ser Gly Leu Gly Thr Gly Leu Ala Pro
                885                 890                 895

Phe Lys Ala Ile Val Glu Glu Lys Leu Trp Gln Lys Gln Gly Tyr
        900                 905                 910

Glu Ile Gly Glu Val Phe Leu Tyr Leu Gly Ser Arg His Lys Arg Glu
        915                 920                 925

Glu Tyr Leu Tyr Gly Glu Leu Trp Glu Ala Tyr Lys Asp Ala Gly Ile
        930                 935                 940

Ile Thr His Ile Gly Ala Ala Phe Ser Arg Asp Gln Pro Gln Lys Ile
```

```
                                945                 950                 955                 960
      Tyr Ile Gln Asp Arg Ile Lys Glu Asn Leu Asp Glu Leu Lys Thr Ala
                        965                 970                 975

Met Ile Asp Asn Lys Gly Ser Phe Tyr Leu Cys Gly Pro Thr Trp Pro
              980                 985                 990

Val Pro Asp Ile Thr Gln Ala Leu Gln Asp Ile Leu Ala Lys Asp Ala
                  995                 1000                1005

Glu Glu Arg Gly Ile Lys Val Asp Leu Asp Ala Ala Ile Glu Glu Leu
          1010                1015                1020

Lys Glu Ala Ser Arg Tyr Ile Leu Glu Val Tyr
      1025                1030                1035

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence:DNA sequence
      surrounding residue 662 of yeast assimilatory
      sulfite reductase alpha subunit (Met 10, MET10),
      strain S288c and UCD950 alleles

<400> SEQUENCE: 20
ttcgtcgtga aagttaaaga aaatagacgt gttacgcctg ctgattatga                50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence:DNA sequence
      surrounding residue 662 of yeast assimilatory
      sulfite reductase alpha subunit (Met 10, MET10),
      strain UCD932 allele

<400> SEQUENCE: 21
ttcgtcgtga aagttaaaga aaatagacgt gttaagcctg ctgattatga                50

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:DNA sequence
      surrounding residue 662 of yeast assimilatory
      sulfite reductase alpha subunit (Met 10, MET10),
      strain S288c and UCD950 alleles

<400> SEQUENCE: 22
aatagacgtg ttacgcctgc tgattat                                         27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence:DNA sequence
      surrounding residue 662 of yeast assimilatory
      sulfite reductase alpha subunit (Met 10, MET10),
      strain UCD932 allele

<400> SEQUENCE: 23
aatagacgtg ttaagcctgc tgattat                                         27

<210> SEQ ID NO 24
<211> LENGTH: 9
```

```
<212> TYPE: PRT
<213> ORGANISM: Artificial Sequence
<220> FEATURE:
<223> OTHER INFORMATION: Description of Artificial Sequence:amino acid
      sequence surrounding residue 662 of yeast
      assimilatory sulfite reductase alpha subunit (Met
      10, MET10), strains S288c, UCD932 and UCD950 alleles
<220> FEATURE:
<221> NAME/KEY: MOD_RES
<222> LOCATION: (5)
<223> OTHER INFORMATION: Xaa = Thr or Lys

<400> SEQUENCE: 24

Asn Arg Arg Val Xaa Pro Ala Asp Tyr
  1               5

<210> SEQ ID NO 25
<211> LENGTH: 50
<212> TYPE: PRT
<213> ORGANISM: Artificial Sequence
<220> FEATURE:
<223> OTHER INFORMATION: Description of Artificial Sequence:subsequence
      of yeast assimilatory sulfite reductase alpha subunit
      (Met 10, MET10) catalytic region of Saccharomyces
      cerevisiae strain UCD932

<400> SEQUENCE: 25

Lys Lys Leu Ser Phe Lys Glu Ala Tyr Glu Val Glu Asn Lys Leu Arg
  1               5                  10                  15

Pro Asp Leu Pro Val Lys Asn Phe Val Val Lys Val Lys Glu Asn Arg
             20                  25                  30

Arg Val Lys Pro Ala Asp Tyr Asp Arg Tyr Ile Phe His Ile Glu Phe
         35                  40                  45

Asp Ile
     50

<210> SEQ ID NO 26
<211> LENGTH: 50
<212> TYPE: PRT
<213> ORGANISM: Artificial Sequence
<220> FEATURE:
<223> OTHER INFORMATION: Description of Artificial Sequence:subsequence
      of yeast assimilatory sulfite reductase alpha subunit
      (Met 10, MET10) catalytic region of Saccharomyces
      cerevisiae strain S288c

<400> SEQUENCE: 26

Lys Lys Leu Ser Phe Lys Glu Ala Tyr Glu Val Glu Asn Lys Leu Arg
  1               5                  10                  15

Pro Asp Leu Pro Val Lys Asn Phe Val Val Lys Val Lys Glu Asn Arg
             20                  25                  30

Arg Val Thr Pro Ala Asp Tyr Asp Arg Tyr Ile Phe His Ile Glu Phe
         35                  40                  45

Asp Ile
     50

<210> SEQ ID NO 27
<211> LENGTH: 50
<212> TYPE: PRT
<213> ORGANISM: Artificial Sequence
<220> FEATURE:
<223> OTHER INFORMATION: Description of Artificial Sequence:subsequence
      of yeast assimilatory sulfite reductase alpha subunit
      (Met 10, MET10) catalytic region of Saccharomyces
      cerevisiae (carlsbergensis)

<400> SEQUENCE: 27
```

```
Lys Lys Leu Ser Phe Lys Glu Ala Tyr Gly Val Glu Asn Lys Leu Arg
  1               5                  10                  15

Pro Asp Leu Pro Val Lys Asn Phe Val Val Lys Val Lys Glu Asn Arg
             20                  25                  30

Arg Val Thr Pro Ala Asp Tyr Asp Arg Tyr Ile Phe His Ile Glu Phe
             35                  40                  45

Asp Ile
     50

<210> SEQ ID NO 28
<211> LENGTH: 50
<212> TYPE: PRT
<213> ORGANISM: Artificial Sequence
<220> FEATURE:
<223> OTHER INFORMATION: Description of Artificial Sequence:subsequence
      of yeast assimilatory sulfite reductase alpha subunit
      (Met 10, MET10) catalytic region of Kluyveromyces
      lactis

<400> SEQUENCE: 28

Lys Lys Leu Thr Phe Gln Glu Ala Tyr Gly Val Ser Gln Gln Leu Arg
  1               5                  10                  15

Pro Asp Leu Pro Val Asn Asn Tyr Val Val Lys Val Lys Glu Asn Arg
             20                  25                  30

Arg Val Thr Pro Asp Asp Tyr Asp Arg Tyr Ile Phe His Ile Glu Phe
             35                  40                  45

Asp Ile
     50

<210> SEQ ID NO 29
<211> LENGTH: 50
<212> TYPE: PRT
<213> ORGANISM: Artificial Sequence
<220> FEATURE:
<223> OTHER INFORMATION: Description of Artificial Sequence:subsequence
      of yeast assimilatory sulfite reductase alpha subunit
      (Met 10, MET10) catalytic region of Yarowwia
      lipolytica

<400> SEQUENCE: 29

Lys Arg Val Val Phe Lys Glu Ala Tyr Gly Thr Glu Asn Ser Leu Arg
  1               5                  10                  15

Pro Asp Ile Ser Thr Lys Asn Phe Val Val Lys Val Gln Glu Lys Arg
             20                  25                  30

Arg Val Thr Pro Glu Asn Tyr Asp Arg Asn Ile Phe His Val Glu Phe
             35                  40                  45

Asp Ile
     50

<210> SEQ ID NO 30
<211> LENGTH: 50
<212> TYPE: PRT
<213> ORGANISM: Artificial Sequence
<220> FEATURE:
<223> OTHER INFORMATION: Description of Artificial Sequence:subsequence
      of yeast assimilatory sulfite reductase alpha subunit
      (Met 10, MET10) catalytic region of
      Schizosaccharomyces pombe

<400> SEQUENCE: 30

Lys Gln Ile Ile Phe Pro Glu Ala Tyr Lys Lys Asp Ala Leu Arg
  1               5                  10                  15

Pro Asp Val Ser Glu Lys Val Phe Thr Val His Val Arg Ala Asn Lys
             20                  25                  30
```

Arg Leu Thr Pro Ala Glu Tyr Asn Arg Asn Ile Phe His Ile Glu Phe
            35                  40                  45

Asp Leu
    50

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence:conserved
      yeast motif in sulfite active sulfite reductase
      catalytic region
<220> FEATURE:
<221> NAME/KEY: MOD_RES
<222> LOCATION: (1)
<223> OTHER INFORMATION: Xaa = Asn or Lys
<220> FEATURE:
<221> NAME/KEY: MOD_RES
<222> LOCATION: (2)
<223> OTHER INFORMATION: Xaa = Arg or Lys
<220> FEATURE:
<221> NAME/KEY: MOD_RES
<222> LOCATION: (4)
<223> OTHER INFORMATION: Xaa = Val or Leu
<220> FEATURE:
<221> NAME/KEY: MOD_RES
<222> LOCATION: (7)
<223> OTHER INFORMATION: Xaa = Ala, Asp or Glu
<220> FEATURE:
<221> NAME/KEY: MOD_RES
<222> LOCATION: (8)
<223> OTHER INFORMATION: Xaa = Asp, Asn or Glu
<220> FEATURE:
<221> NAME/KEY: MOD_RES
<222> LOCATION: (12)
<223> OTHER INFORMATION: Xaa = Tyr or Asn
<220> FEATURE:
<221> NAME/KEY: MOD_RES
<222> LOCATION: (16)
<223> OTHER INFORMATION: Xaa = Ile or Val
<220> FEATURE:
<221> NAME/KEY: MOD_RES
<222> LOCATION: (20)
<223> OTHER INFORMATION: Xaa = Ile or Leu

<400> SEQUENCE: 31

Xaa Xaa Arg Xaa Thr Pro Xaa Xaa Tyr Asx Arg Xaa Ile Phe His Xaa
  1               5                  10                  15

Glu Phe Asp Xaa
            20

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence:conserved
      yeast motif in sulfite inactive sulfite reductase
      catalytic region
<220> FEATURE:
<221> NAME/KEY: MOD_RES
<222> LOCATION: (1)
<223> OTHER INFORMATION: Xaa = Asn or Lys
<220> FEATURE:
<221> NAME/KEY: MOD_RES
<222> LOCATION: (2)
<223> OTHER INFORMATION: Xaa = Arg or Lys
<220> FEATURE:
<221> NAME/KEY: MOD_RES
<222> LOCATION: (4)
<223> OTHER INFORMATION: Xaa = Val or Leu
<220> FEATURE:
<221> NAME/KEY: MOD_RES

```
<222> LOCATION: (5)
<223> OTHER INFORMATION: Xaa = Ala, Cys, Asp, Glu, Phe, Gly, His, Ile,
      Lys, Leu, Met, Asn, Pro, Gln, Arg, Ser, Val, Trp or
      Tyr, not Thr
<220> FEATURE:
<221> NAME/KEY: MOD_RES
<222> LOCATION: (7)
<223> OTHER INFORMATION: Xaa = Ala, Asp or Glu
<220> FEATURE:
<221> NAME/KEY: MOD_RES
<222> LOCATION: (8)
<223> OTHER INFORMATION: Xaa = Asp, Asn or Glu
<220> FEATURE:
<221> NAME/KEY: MOD_RES
<222> LOCATION: (12)
<223> OTHER INFORMATION: Xaa = Tyr or Asn
<220> FEATURE:
<221> NAME/KEY: MOD_RES
<222> LOCATION: (16)
<223> OTHER INFORMATION: Xaa = Ile or Val
<220> FEATURE:
<221> NAME/KEY: MOD_RES
<222> LOCATION: (20)
<223> OTHER INFORMATION: Xaa = Ile or Leu

<400> SEQUENCE: 32

Xaa Xaa Arg Xaa Xaa Pro Xaa Xaa Tyr Asx Arg Xaa Ile Phe His Xaa
 1               5                  10                  15

Glu Phe Asp Xaa
            20

<210> SEQ ID NO 33
<211> LENGTH: 1035
<212> TYPE: PRT
<213> ORGANISM: Artificial Sequence
<220> FEATURE:
<223> OTHER INFORMATION: Description of Artificial Sequence:sulfide
      inactive yeast assimilatory sulfite reductase
      alpha subunit (Met 10, MET10)
<220> FEATURE:
<221> NAME/KEY: MOD_RES
<222> LOCATION: (135)
<223> OTHER INFORMATION: Xaa = Thr or Asn
<220> FEATURE:
<221> NAME/KEY: MOD_RES
<222> LOCATION: (172)
<223> OTHER INFORMATION: Xaa = Ala or Thr
<220> FEATURE:
<221> NAME/KEY: MOD_RES
<222> LOCATION: (511)
<223> OTHER INFORMATION: Xaa = Thr or Ile
<220> FEATURE:
<221> NAME/KEY: MOD_RES
<222> LOCATION: (590)
<223> OTHER INFORMATION: Xaa = Glu or Lys
<220> FEATURE:
<221> NAME/KEY: MOD_RES
<222> LOCATION: (662)
<223> OTHER INFORMATION: Xaa = Ala, Cys, Asp, Glu, Phe, Gly, His, Ile,
      Lys, Leu, Met, Asn, Pro, Gln, Arg, Ser, Val or Trp, not
      Thr, Ser or Tyr

<400> SEQUENCE: 33

Met Pro Val Glu Phe Ala Thr Asn Pro Phe Gly Glu Ala Lys Asn Ala
 1               5                  10                  15

Thr Ser Leu Pro Lys Tyr Gly Thr Pro Val Thr Ala Ile Ser Ser Val
            20                  25                  30

Leu Phe Asn Asn Val Asp Ser Ile Phe Ala Tyr Lys Ser Phe Ser Gln
        35                  40                  45

Pro Asp Leu Leu His Gln Asp Leu Lys Lys Trp Ser Glu Lys Arg Gly
    50                  55                  60

Asn Glu Ser Arg Gly Lys Pro Phe Phe Gln Glu Leu Asp Ile Arg Ser
```

```
              65                  70                  75                  80
Gly Ala Gly Leu Ala Pro Leu Gly Phe Ser His Gly Leu Lys Asn Thr
                     85                  90                  95

Thr Ala Ile Val Ala Pro Gly Phe Ser Leu Pro Tyr Phe Ile Asn Ser
                    100                 105                 110

Leu Lys Thr Val Ser His Asp Gly Lys Phe Leu Leu Asn Val Gly Ala
                115                 120                 125

Leu Asn Tyr Asp Asn Ala Xaa Gly Ser Val Thr Asn Asp Tyr Val Thr
            130                 135                 140

Ala Leu Asp Ala Ala Ser Lys Leu Lys Tyr Gly Val Val Thr Pro Ile
145                 150                 155                 160

Ser Ala Asn Glu Val Gln Ser Val Ala Leu Leu Xaa Leu Ala Ile Ala
                165                 170                 175

Thr Phe Ser Asn Asn Ser Gly Ala Ile Asn Leu Phe Asp Gly Leu Asn
                180                 185                 190

Tyr Ser Lys Thr Val Leu Pro Leu Val Glu Ser Val Pro Glu Ala Ser
                195                 200                 205

Ile Leu Ala Lys Leu Ser Lys Val Ile Ala Pro Asp Ala Ala Phe Asp
    210                 215                 220

Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
                    245                 250                 255

Gly Ser Leu Glu Ser Glu Leu Phe Asn Ser Ala Ile Ser Gly Asn Asn
                260                 265                 270

Ser Lys Ile Gly Leu Ile Asn Val Arg Val Pro Leu Pro Phe Asn Val
    275                 280                 285

Ala Lys Phe Val Thr His Val Pro Ser Thr Thr Lys Gln Ile Val Val
290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                    325                 330                 335

Glu Tyr Ile Tyr Gln Pro Asp Phe Ile Trp Ser Pro Lys Ala Val Lys
                340                 345                 350

Ser Ile Val Ser Ser Phe Ile Pro Glu Phe Thr Tyr Asn Ala Asp Ser
                355                 360                 365

Ser Phe Gly Glu Gly Phe Ile Tyr Trp Ala Ser Asp Lys Ser Ile Asn
    370                 375                 380

Ile Asp Val Ala Ser Lys Leu Val Lys Ala Leu Ser Leu Glu Asp Gly
385                 390                 395                 400

Lys Phe Val Ser Leu Arg Thr Lys Phe Asp Asn Leu Ala Asn Ala Gly
                    405                 410                 415

Thr Phe Gln Ala Gln Phe Val Ser Lys Glu Gln Ile Pro Val Ser
                420                 425                 430

Asn Ile Asp Ser Thr Lys Leu Ser Val Val Glu Asp Val Ser Leu Leu
                435                 440                 445

Lys His Leu Asp Val Ala Ala Thr Val Ala Glu Gln Gly Ser Ile Ala
                450                 455                 460

Leu Val Ser Gln Lys Ala Val Lys Asp Leu Asp Leu Asn Ser Val Glu
465                 470                 475                 480

Ser Tyr Val Lys Asn Leu Gly Ile Pro Glu Ser Phe Leu Ile Ser Ile
                    485                 490                 495
```

```
Ala Lys Lys Asn Ile Lys Leu Phe Ile Ile Asp Gly Glu Thr Xaa Asn
                500                 505                 510
Asp Glu Ser Lys Leu Ser Leu Phe Ile Gln Ala Val Phe Trp Lys Leu
            515                 520                 525
Ala Phe Gly Leu Asp Val Ala Glu Cys Thr Asn Arg Ile Trp Lys Ser
        530                 535                 540
Ile Asp Ser Gly Ala Asp Ile Ser Ala Ala Ser Ile Ser Glu Phe Leu
545                 550                 555                 560
Thr Gly Ala Phe Lys Asn Phe Leu Ser Glu Val Pro Leu Ala Leu Tyr
                565                 570                 575
Thr Lys Phe Ser Glu Ile Asn Ile Glu Lys Lys Glu Asp Xaa Glu Glu
            580                 585                 590
Pro Ala Ala Leu Pro Ile Phe Val Asn Glu Thr Ser Phe Leu Pro Asn
        595                 600                 605
Asn Ser Thr Ile Glu Glu Ile Pro Leu Pro Glu Thr Ser Glu Ile Ser
        610                 615                 620
Asp Ile Ala Lys Lys Leu Ser Phe Lys Glu Ala Tyr Glu Val Glu Asn
625                 630                 635                 640
Lys Leu Arg Pro Asp Leu Pro Val Lys Asn Phe Val Val Lys Val Lys
                645                 650                 655
Glu Asn Arg Arg Val Xaa Pro Ala Asp Tyr Asp Arg Tyr Ile Phe His
            660                 665                 670
Ile Glu Phe Asp Ile Ser Gly Thr Gly Met Thr Tyr Asp Ile Gly Glu
        675                 680                 685
Ala Leu Gly Ile His Ala Arg Asn Asn Glu Ser Leu Val Lys Glu Phe
        690                 695                 700
Leu Thr Phe Tyr Gly Leu Asn Glu Ser Asp Val Val Leu Val Pro Asn
705                 710                 715                 720
Lys Asp Asn His His Leu Leu Glu Thr Arg Thr Val Leu Gln Ala Phe
                725                 730                 735
Val Glu Asn Leu Asp Ile Phe Gly Lys Pro Pro Lys Arg Phe Tyr Glu
            740                 745                 750
Ser Leu Ile Pro Tyr Ala Ser Asn Glu Glu Lys Lys Lys Leu Glu
        755                 760                 765
Asp Leu Val Thr Pro Ala Gly Ala Val Asp Leu Lys Arg Phe Gln Asp
        770                 775                 780
Val Glu Tyr Tyr Thr Tyr Ala Asp Ile Phe Glu Leu Phe Pro Ser Val
785                 790                 795                 800
Arg Pro Ser Leu Glu Glu Leu Val Thr Ile Ile Glu Pro Leu Lys Arg
                805                 810                 815
Arg Glu Tyr Ser Ile Ala Ser Ser Gln Lys Val His Pro Asn Glu Val
            820                 825                 830
His Leu Leu Ile Val Val Val Asp Trp Val Asp Asn Lys Gly Arg Lys
        835                 840                 845
Arg Tyr Gly Gln Ala Ser Lys Tyr Ile Ser Asp Leu Ala Val Gly Ser
        850                 855                 860
Glu Leu Val Val Ser Val Lys Pro Ser Val Met Lys Leu Pro Pro Ser
865                 870                 875                 880
Pro Lys Gln Pro Val Ile Met Ser Gly Leu Gly Thr Gly Leu Ala Pro
                885                 890                 895
Phe Lys Ala Ile Val Glu Glu Lys Leu Trp Gln Lys Gln Gln Gly Tyr
            900                 905                 910
Glu Ile Gly Glu Val Phe Leu Tyr Leu Gly Ser Arg His Lys Arg Glu
        915                 920                 925
```

```
Glu Tyr Leu Tyr Gly Glu Leu Trp Glu Ala Tyr Lys Asp Ala Gly Ile
        930                 935                 940

Ile Thr His Ile Gly Ala Ala Phe Ser Arg Asp Gln Pro Gln Lys Ile
945                 950                 955                 960

Tyr Ile Gln Asp Arg Ile Lys Glu Asn Leu Asp Glu Leu Lys Thr Ala
                965                 970                 975

Met Ile Asp Asn Lys Gly Ser Phe Tyr Leu Cys Gly Pro Thr Trp Pro
            980                 985                 990

Val Pro Asp Ile Thr Gln Ala Leu Gln Asp Ile Leu Ala Lys Asp Ala
        995                 1000                1005

Glu Glu Arg Gly Ile Lys Val Asp Leu Asp Ala Ala Ile Glu Glu Leu
    1010                1015                1020

Lys Glu Ala Ser Arg Tyr Ile Leu Glu Val Tyr
1025                1030                1035

<210> SEQ ID NO 34
<211> LENGTH: 1035
<212> TYPE: PRT
<213> ORGANISM: Artificial Sequence
<220> FEATURE:
<223> OTHER INFORMATION: Description of Artificial Sequence:sulfide
      inactive yeast assimilatory sulfite reductase
      alpha subunit (Met 10, MET10)
<220> FEATURE:
<221> NAME/KEY: MOD_RES
<222> LOCATION: (135)
<223> OTHER INFORMATION: Xaa = Thr or Asn
<220> FEATURE:
<221> NAME/KEY: MOD_RES
<222> LOCATION: (172)
<223> OTHER INFORMATION: Xaa = Ala or Thr
<220> FEATURE:
<221> NAME/KEY: MOD_RES
<222> LOCATION: (511)
<223> OTHER INFORMATION: Xaa = Thr or Ile
<220> FEATURE:
<221> NAME/KEY: MOD_RES
<222> LOCATION: (590)
<223> OTHER INFORMATION: Xaa = Glu or Lys
<220> FEATURE:
<221> NAME/KEY: MOD_RES
<222> LOCATION: (662)
<223> OTHER INFORMATION: Xaa = large or bulky amino acid, Lys, Arg, His,
      Gln, Asn, Glu, Asp, Ile, Leu, Val, Phe, Tyr or Trp

<400> SEQUENCE: 34

Met Pro Val Glu Phe Ala Thr Asn Pro Phe Gly Glu Ala Lys Asn Ala
1               5                   10                  15

Thr Ser Leu Pro Lys Tyr Gly Thr Pro Val Thr Ala Ile Ser Ser Val
            20                  25                  30

Leu Phe Asn Asn Val Asp Ser Ile Phe Ala Tyr Lys Ser Phe Ser Gln
        35                  40                  45

Pro Asp Leu Leu His Gln Asp Leu Lys Lys Trp Ser Glu Lys Arg Gly
    50                  55                  60

Asn Glu Ser Arg Gly Lys Pro Phe Phe Gln Glu Leu Asp Ile Arg Ser
65                  70                  75                  80

Gly Ala Gly Leu Ala Pro Leu Gly Phe Ser His Gly Leu Lys Asn Thr
                85                  90                  95

Thr Ala Ile Val Ala Pro Gly Phe Ser Leu Pro Tyr Phe Ile Asn Ser
            100                 105                 110

Leu Lys Thr Val Ser His Asp Gly Lys Phe Leu Leu Asn Val Gly Ala
        115                 120                 125

Leu Asn Tyr Asp Asn Ala Xaa Gly Ser Val Thr Asn Asp Tyr Val Thr
```

```
            130                 135                 140
Ala Leu Asp Ala Ala Ser Lys Leu Lys Tyr Gly Val Val Thr Pro Ile
145                 150                 155                 160

Ser Ala Asn Glu Val Gln Ser Val Ala Leu Leu Xaa Leu Ala Ile Ala
                165                 170                 175

Thr Phe Ser Asn Asn Ser Gly Ala Ile Asn Leu Phe Asp Gly Leu Asn
                180                 185                 190

Tyr Ser Lys Thr Val Leu Pro Leu Val Glu Ser Val Pro Glu Ala Ser
                195                 200                 205

Ile Leu Ala Lys Leu Ser Lys Val Ile Ala Pro Asp Ala Ala Phe Asp
210                 215                 220

Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
                245                 250                 255

Gly Ser Leu Glu Ser Glu Leu Phe Asn Ser Ala Ile Ser Gly Asn Asn
                260                 265                 270

Ser Lys Ile Gly Leu Ile Asn Val Arg Val Pro Leu Pro Phe Asn Val
                275                 280                 285

Ala Lys Phe Val Thr His Val Pro Ser Thr Thr Lys Gln Ile Val Val
290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                325                 330                 335

Glu Tyr Ile Tyr Gln Pro Asp Phe Ile Trp Ser Pro Lys Ala Val Lys
                340                 345                 350

Ser Ile Val Ser Ser Phe Ile Pro Glu Phe Thr Tyr Asn Ala Asp Ser
                355                 360                 365

Ser Phe Gly Glu Gly Phe Ile Tyr Trp Ala Ser Asp Lys Ser Ile Asn
                370                 375                 380

Ile Asp Val Ala Ser Lys Leu Val Lys Ala Leu Ser Leu Glu Asp Gly
385                 390                 395                 400

Lys Phe Val Ser Leu Arg Thr Lys Phe Asp Asn Leu Ala Asn Ala Gly
                405                 410                 415

Thr Phe Gln Ala Gln Phe Val Thr Ser Lys Glu Gln Ile Pro Val Ser
                420                 425                 430

Asn Ile Asp Ser Thr Lys Leu Ser Val Val Glu Asp Val Ser Leu Leu
                435                 440                 445

Lys His Leu Asp Val Ala Ala Thr Val Ala Glu Gln Gly Ser Ile Ala
450                 455                 460

Leu Val Ser Gln Lys Ala Val Lys Asp Leu Asp Leu Asn Ser Val Glu
465                 470                 475                 480

Ser Tyr Val Lys Asn Leu Gly Ile Pro Glu Ser Phe Leu Ile Ser Ile
                485                 490                 495

Ala Lys Lys Asn Ile Lys Leu Phe Ile Ile Asp Gly Glu Thr Xaa Asn
                500                 505                 510

Asp Glu Ser Lys Leu Ser Leu Phe Ile Gln Ala Val Phe Trp Lys Leu
                515                 520                 525

Ala Phe Gly Leu Asp Val Ala Glu Cys Thr Asn Arg Ile Trp Lys Ser
                530                 535                 540

Ile Asp Ser Gly Ala Asp Ile Ser Ala Ala Ser Ile Ser Glu Phe Leu
545                 550                 555                 560
```

```
Thr Gly Ala Phe Lys Asn Phe Leu Ser Glu Val Pro Leu Ala Leu Tyr
                565             570                 575
Thr Lys Phe Ser Glu Ile Asn Ile Glu Lys Lys Glu Asp Xaa Glu Glu
                580             585                 590
Pro Ala Ala Leu Pro Ile Phe Val Asn Glu Thr Ser Phe Leu Pro Asn
                595             600                 605
Asn Ser Thr Ile Glu Glu Ile Pro Leu Pro Glu Thr Ser Glu Ile Ser
            610             615                 620
Asp Ile Ala Lys Lys Leu Ser Phe Lys Glu Ala Tyr Glu Val Glu Asn
625             630                 635                 640
Lys Leu Arg Pro Asp Leu Pro Val Lys Asn Phe Val Val Lys Val Lys
                645                 650                 655
Glu Asn Arg Arg Val Xaa Pro Ala Asp Tyr Asp Arg Tyr Ile Phe His
                660             665                 670
Ile Glu Phe Asp Ile Ser Gly Thr Gly Met Thr Tyr Asp Ile Gly Glu
            675             680                 685
Ala Leu Gly Ile His Ala Arg Asn Asn Glu Ser Leu Val Lys Glu Phe
            690             695             700
Leu Thr Phe Tyr Gly Leu Asn Glu Ser Asp Val Val Leu Val Pro Asn
705             710                 715                 720
Lys Asp Asn His His Leu Leu Glu Thr Arg Thr Val Leu Gln Ala Phe
                725                 730                 735
Val Glu Asn Leu Asp Ile Phe Gly Lys Pro Lys Arg Phe Tyr Glu
                740             745                 750
Ser Leu Ile Pro Tyr Ala Ser Asn Glu Glu Lys Lys Lys Leu Glu
                755             760                 765
Asp Leu Val Thr Pro Ala Gly Ala Val Asp Leu Lys Arg Phe Gln Asp
            770             775                 780
Val Glu Tyr Tyr Thr Tyr Ala Asp Ile Phe Glu Leu Phe Pro Ser Val
785             790                 795                 800
Arg Pro Ser Leu Glu Glu Leu Val Thr Ile Ile Glu Pro Leu Lys Arg
                805             810                 815
Arg Glu Tyr Ser Ile Ala Ser Ser Gln Lys Val His Pro Asn Glu Val
                820             825                 830
His Leu Leu Ile Val Val Val Asp Trp Val Asp Asn Lys Gly Arg Lys
                835             840                 845
Arg Tyr Gly Gln Ala Ser Lys Tyr Ile Ser Asp Leu Ala Val Gly Ser
                850             855                 860
Glu Leu Val Val Ser Val Lys Pro Ser Val Met Lys Leu Pro Pro Ser
865             870                 875                 880
Pro Lys Gln Pro Val Ile Met Ser Gly Leu Gly Thr Gly Leu Ala Pro
                885             890                 895
Phe Lys Ala Ile Val Glu Glu Lys Leu Trp Gln Lys Gln Gly Tyr
                900             905                 910
Glu Ile Gly Glu Val Phe Leu Tyr Leu Gly Ser Arg His Lys Arg Glu
                915             920                 925
Glu Tyr Leu Tyr Gly Glu Leu Trp Glu Ala Tyr Lys Asp Ala Gly Ile
            930             935                 940
Ile Thr His Ile Gly Ala Ala Phe Ser Arg Asp Gln Pro Gln Lys Ile
945             950                 955                 960
Tyr Ile Gln Asp Arg Ile Lys Glu Asn Leu Asp Glu Leu Lys Thr Ala
                965                 970                 975
Met Ile Asp Asn Lys Gly Ser Phe Tyr Leu Cys Gly Pro Thr Trp Pro
                980             985                 990
```

-continued

Val Pro Asp Ile Thr Gln Ala Leu Gln Asp Ile Leu Ala Lys Asp Ala
        995                 1000                1005

Glu Glu Arg Gly Ile Lys Val Asp Leu Asp Ala Ala Ile Glu Glu Leu
    1010                1015                1020

Lys Glu Ala Ser Arg Tyr Ile Leu Glu Val Tyr
1025                1030                1035

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:PCR primer
      HOM2-F

<400> SEQUENCE: 35
cacttaagta cacatacaaa                                               20

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence:PCR primer
      HOM2-R

<400> SEQUENCE: 36
gggtcagcga gagaatt                                                  17

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence:PCR primer
      HOM6-F

<400> SEQUENCE: 37
cctggtggta aagttggg                                                 18

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:PCR primer
      HOM6-R

<400> SEQUENCE: 38
gattgtagaa gattgagtag                                               20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:PCR primer
      SER33-F

<400> SEQUENCE: 39
ggaatctccc aggtttaat                                                19

<210> SEQ ID NO 40
<211> LENGTH: 17
<212> TYPE: DNA
<213> ORGANISM: Artificial Sequence

```
<220> FEATURE:
<223> OTHER INFORMATION: Description of Artificial Sequence:PCR primer
      SER33-R

<400> SEQUENCE: 40
gggcaatcaa aggctat                                                     17

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence:PCR primer
      MET1-F

<400> SEQUENCE: 41
cgctaataaa ctcgctacaa aag                                              23

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence:PCR primer
      MET1-R

<400> SEQUENCE: 42
cgtccttttt gctcaatatc c                                                21

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence:PCR primer
      MET5-F

<400> SEQUENCE: 43
gctgcaagca gttatataaa gtg                                              23

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence:PCR primer
      MET5-R

<400> SEQUENCE: 44
aaaaccgaac tagccgaag                                                   19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence:PCR primer
      MET8-F

<400> SEQUENCE: 45
aaaatcgcta caaagtccg                                                   19

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence:PCR primer
```

MET8-R

<400> SEQUENCE: 46
gcattgttgt tcgttctcc					19

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence:PCR primer
      PCR-MET10-F

<400> SEQUENCE: 47
cggatcccca atcaccataa cactt					25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence:PCR primer
      PCR-MET10-R

<400> SEQUENCE: 48
gccgcggtag ggtcttcagg acgag					25

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence:PCR primer
      MET10-F-KO

<400> SEQUENCE: 49
caaatagttt cgtttagatg g					21

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:PCR primer
      MET10-R-KO

<400> SEQUENCE: 50
gtataatgtg atggttagtt					20

<210> SEQ ID NO 51
<211> LENGTH: 58
<212> TYPE: DNA
<213> ORGANISM: Artificial Sequence
<220> FEATURE:
<223> OTHER INFORMATION: Description of Artificial Sequence:PCR primer
      MET10-hphMX-F

<400> SEQUENCE: 51
actgtgttta tcacttatgg gtctttagaa tccgaattgt attttgatgg ccgcacgg					58

<210> SEQ ID NO 52
<211> LENGTH: 63
<212> TYPE: DNA
<213> ORGANISM: Artificial Sequence
<220> FEATURE:
<223> OTHER INFORMATION: Description of Artificial Sequence:PCR primer
      MET10-hphMX-R

```
<400> SEQUENCE: 52
aacaattcaa aaatgtcagc atatgtataa tactccacat aatcgacagc agtatagcga    60
cca                                                                  63

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence:PCR
      confirmation primer JKKanRE

<400> SEQUENCE: 53
gggcgacagt cacatcat                                                  18

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence:PCR
      confirmation primer HYGROB CHK_R

<400> SEQUENCE: 54
tgacggtgtc gtccatcac                                                 19

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence:MET
      sequencing primer MET1-S1F

<400> SEQUENCE: 55
tggggagagt tctggtatgc aag                                            23

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence:MET
      sequencing primer MET1-S2F

<400> SEQUENCE: 56
cagatggtta tctcagataa tggag                                          25

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence:MET
      sequencing primer MET1-S3F

<400> SEQUENCE: 57
tttcttcaaa gatcacggat atatt                                          25

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence:MET
      sequencing primer MET1-S1R
```

```
<400> SEQUENCE: 58
gctatatcac gttgagtagc gg                                         22

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence:MET
      sequencing primer MET1-S2R

<400> SEQUENCE: 59
ggtactacac cctctgtgac agtt                                       24

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence:MET
      sequencing primer MET1-S3R

<400> SEQUENCE: 60
ctcagttttt ggcattgcca                                            20

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence:MET
      sequencing primer MET5-S1F

<400> SEQUENCE: 61
cctaataaac ttccattggt gatta                                      25

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence:MET
      sequencing primer MET5-S2F

<400> SEQUENCE: 62
ccgttttaca gggtgtctct aaga                                       24

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:MET
      sequencing primer MET5-S3F

<400> SEQUENCE: 63
gacgcgatct tgacgaagct                                            20

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence:MET
      sequencing primer MET5-S4F

<400> SEQUENCE: 64
```

```
gaatctggtt actggccatt gt                                           22
```

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence:MET
      sequencing primer MET5-S5F

<400> SEQUENCE: 65

```
ctgaaaaatg acaccgactt gg                                           22
```

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence:MET
      sequencing primer MET5-S6F

<400> SEQUENCE: 66

```
tggcttgctc tggatcactt                                              20
```

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence:MET
      sequencing primer MET5-S7F

<400> SEQUENCE: 67

```
cgatgtcggt ttagttgcta tagtt                                        25
```

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence:MET
      sequencing primer MET5-S8F

<400> SEQUENCE: 68

```
tggtaatcaa catttggtta tctct                                        25
```

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence:MET
      sequencing primer MET5-S1R

<400> SEQUENCE: 69

```
gggcaaccag tcattctcat aa                                           22
```

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence:MET
      sequencing primer MET5-S2R

<400> SEQUENCE: 70

```
cttcgacacc catatcatct acag                                         24
```

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence:MET
      sequencing primer MET5-S3R

<400> SEQUENCE: 71
caattttccc atatcagcga                                           20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence:MET
      sequencing primer MET5-S4R

<400> SEQUENCE: 72
catcatcaac agcagcgccg                                           20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence:MET
      sequencing primer MET5-S5R

<400> SEQUENCE: 73
ctgatcgaag gcagccttgc                                           20

<210> SEQ ID NO 74
<211> LENGTH: 25
<212> TYPE: DNA
<213> ORGANISM: Artificial Sequence
<220> FEATURE:
<223> OTHER INFORMATION: Description of Artificial Sequence:MET
      sequencing primer MET5-S6R

<400> SEQUENCE: 74
catatggctc tgaatcaatc aataa                                     25

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence:MET
      sequencing primer MET5-S7R

<400> SEQUENCE: 75
ttcacaactt ttttgacaga agaa                                      24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence:MET
      sequencing primer MET5-S8R

<400> SEQUENCE: 76
cgttagcaat ctccaaggta ggaa                                      24

<210> SEQ ID NO 77

```
<211> LENGTH: 24
<212> TYPE: DNA
<213> ORGANISM: Artificial Sequence
<220> FEATURE:
<223> OTHER INFORMATION: Description of Artificial Sequence:MET
      sequencing primer MET8-S1F

<400> SEQUENCE: 77
gcagtgactt caaagacgaa tacc                                           24

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence:MET
      sequencing primer MET8-S2F

<400> SEQUENCE: 78
ctggaggacg ctgtcgtcaa                                                20

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence:MET
      sequencing primer MET8-S1R

<400> SEQUENCE: 79
tcatctctta ctagagcgcc aa                                             22

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence:MET
      sequencing primer MET8-S2R

<400> SEQUENCE: 80
ggtcccagtt cggattgata a                                              21

<210> SEQ ID NO 81
<211> LENGTH: 17
<212> TYPE: DNA
<213> ORGANISM: Artificial Sequence
<220> FEATURE:
<223> OTHER INFORMATION: Description of Artificial Sequence:MET
      sequencing primer MET10-SEQ1-F

<400> SEQUENCE: 81
agtcatcttc gagcaaa                                                   17

<210> SEQ ID NO 82
<211> LENGTH: 17
<212> TYPE: DNA
<213> ORGANISM: Artificial Sequence
<220> FEATURE:
<223> OTHER INFORMATION: Description of Artificial Sequence:MET
      sequencing primer MET10-SEQ2-F

<400> SEQUENCE: 82
tcatgatggt aagtttc                                                   17

<210> SEQ ID NO 83
<211> LENGTH: 19
<212> TYPE: DNA
```

```
<213> ORGANISM: Artificial Sequence
<220> FEATURE:
<223> OTHER INFORMATION: Description of Artificial Sequence:MET
      sequencing primer MET10-SEQ3-F

<400> SEQUENCE: 83
tcaacgtcag agtgccatt                                             19

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence:MET
      sequencing primer MET10-SEQ4-F

<400> SEQUENCE: 84
atcagtcgtt gaagatgtc                                             19

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence:MET
      sequencing primer MET10-SEQ5-F

<400> SEQUENCE: 85
ctgagatctc tgatattgc                                             19

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence:MET
      sequencing primer MET10-SEQ6-F

<400> SEQUENCE: 86
tgcagtagat ttgaagagat                                            20

<210> SEQ ID NO 87
<211> LENGTH: 16
<212> TYPE: DNA
<213> ORGANISM: Artificial Sequence
<220> FEATURE:
<223> OTHER INFORMATION: Description of Artificial Sequence:MET
      sequencing primer MET10-SEQ7-F

<400> SEQUENCE: 87
cacacacatc ggcgct                                                16

<210> SEQ ID NO 88
<211> LENGTH: 17
<212> TYPE: DNA
<213> ORGANISM: Artificial Sequence
<220> FEATURE:
<223> OTHER INFORMATION: Description of Artificial Sequence:MET
      sequencing primer MET10-SEQ1-R

<400> SEQUENCE: 88
cggagtcacg acaccat                                               17

<210> SEQ ID NO 89
<211> LENGTH: 19
<212> TYPE: DNA
<213> ORGANISM: Artificial Sequence
<220> FEATURE:
```

```
<223> OTHER INFORMATION: Description of Artificial Sequence:MET
      sequencing primer MET10-SEQ2-R

<400> SEQUENCE: 89
ggctgaaact tgagatctc                                            19

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence:MET
      sequencing primer MET10-SEQ3-R

<400> SEQUENCE: 90
cttgacgtaa ctttctacag                                           20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence:MET
      sequencing primer MET10-SEQ4-R

<400> SEQUENCE: 91
tcataatcag caggcgtaac                                           20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence:MET
      sequencing primer MET10-SEQ5-R

<400> SEQUENCE: 92
cttctcttca atggttcaat                                           20

<210> SEQ ID NO 93
<211> LENGTH: 17
<212> TYPE: DNA
<213> ORGANISM: Artificial Sequence
<220> FEATURE:
<223> OTHER INFORMATION: Description of Artificial Sequence:MET
      sequencing primer MET10-SEQ6-R

<400> SEQUENCE: 93
agtagggcca gacaagt                                              17
```

COMPOSITIONS AND METHODS FOR REDUCING H₂S LEVELS IN FERMENTED BEVERAGES

CROSS-REFERENCES TO RELATED APPLICATIONS

This application is the U.S. National Stage entry under §371 of International Application No. PCT/US2008/056847, filed Mar. 13, 2008, which claims the benefit of U.S. Provisional Patent Application No. 60/918,616, filed Mar. 16, 2007, and U.S. Provisional Application No. 60/959,366, filed Jul. 12, 2007 the entire disclosure of each application is hereby incorporated by reference for all purposes.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The production of volatile sulfur compounds such as hydrogen sulfide ($H_2S$) during alcoholic fermentation is an issue that affects the brewing and winemaking industries. Hydrogen sulfide ($H_2S$) is an undesirable by-product of the sulfate reduction pathway (FIG. 1). It is formed in *Saccharomyces cerevisiae* under fermentation conditions. Production of $H_2S$ by *S. cerevisiae* strains ranges from 0 ug/L to 290 ug/L, well above the human detection threshold of 11 ng/L (Amoore and Hautala 1983). Its undesirable quality stems from the fact that it introduces a rotten egg odor characteristic to wines and although $H_2S$ is a volatile compound and can be removed by aeration, it has the potential to form mercaptans and thiols which will persist in the wine due to the low pH (Thoukis 1962). Mercaptans and thiols present themselves as onion or canned vegetable aromas and where volatile $H_2S$ can be managed, removal of other undesired sulfur compounds is technically difficult and strips the wine of other flavor compounds.

The formation of hydrogen sulfide by *Saccharomyces cerevisae* is a well-documented problem in the wine, beer and sake industry (Acree et al. 1972, Eschenbruch et al. 1978, Giudici and Kunkee 1994, Jiranek et al. 1995, Rauhut and Kurbel 1994, Walker and Simpson 1993). Nutritional factors such as levels of nitrogen, vitamins and cofactors (Giudici and Kunkee 1994, Jiranek et al. 1995) and environmental factors such as temperature, pH, levels of elemental sulfur (Rauhut and Kurbel 1994), presence of sulfur dioxide (Stratford and Rose 1985) and levels of organic compounds containing sulfur (Acree et al. 1972) have been associated with the production of volatile sulfur compounds in fermented beverages. The differences in production of volatile sulfur compounds have also been attributed to differences in yeast strain metabolism (Acree et al. 1972, Spiropoulos et al. 2000).

There are at least six different classes of yeast strain behavior with respect to hydrogen sulfide formation: 1) elevated levels under all conditions; 2) low levels under all conditions; 3) elevated production below and above a threshold level of nitrogen; reduced production during a 'window' of nitrogen levels with sulfide increasing at nitrogen levels above or below this window; 4) elevated production in response to limiting micronutrient levels irrespective of nitrogen content; 5) elevated sulfide production only when limited for both nitrogen and micronutrients; and 6) elevated sulfide production with increased rate of fermentation, which may be related to fermentation rate and carbon dioxide evolution or to some other factor such as increased heat production (Spiropoulos 2000, Jiranek 1995, Giudici 1994, Linderholm 2006).

The existing method for stripping sulfides from wine is copper fining. Copper addition can lead to the catalysis of deleterious compositional changes as well as increase the amount of waste produced by wineries requiring special treatment, ultimately resulting in higher production costs for wineries and higher wine costs for the consumer. Further, use of copper as a fining agent may lead to high residual copper levels in wine. The Trade and Tax Bureau allows a residual copper level of 0.5 mg/L for wine (See, e.g., the worldwide website at regulations.justia.com/view/89060/). Winemakers who use copper to remove hydrogen sulfide must then take measures to reduce the copper levels in the wine. Given the adverse health effects associated with excessive copper ingestion, particularly neurological disorders such as Alzheimers, the World Health Organization has recommended dietary restrictions on consumption of this compound (See, the worldwide website at who.int/water_sanitation_health/dwq/chemicals/copper.pdf). The availability of commercial yeast strains unable to produce hydrogen sulfide or which produce reduced levels of hydrogen sulfide will eliminate the need for copper treatment of wines.

Thus, there is a need in the art for compositions and methods for reducing $H_2S$ levels in fermented beverages. The present invention meets these and other needs.

BRIEF SUMMARY OF THE INVENTION

The present invention provides compositions and methods for reducing $H_2S$ levels in fermented beverages.

One aspect of the invention provides methods for reducing or eliminating $H_2S$ levels in fermentation product or medium. In some embodiments, the methods comprise contacting the fermentation product or medium with a yeast strain, yeast cell or yeast culture comprising a polynucleotide encoding a modified MET10 polypeptide that does not catalyze the release of free hydrogen sulfide from sulfite (i.e., a "sulfide inactive" MET10 polypeptide), wherein the amino acid at position 662 of the MET10 polypeptide is not threonine. In some embodiments, the polynucleotide encodes a MET10 polypeptide of SEQ ID NO:3, wherein X at position 662 is not threonine. In some embodiments, the polynucleotide comprises SEQ ID NO:1.

With respect to the embodiments of a sulfide inactive MET10 polypeptide, in some embodiments, the amino acid residue at position 662 of the MET10 polypeptide is not threonine or serine. In some embodiments, the amino acid residue at position 662 of the MET10 polypeptide is Ala, Cys, Asp, Glu, Phe, Gly, His, Ile, Lys, Leu, Met, Asn, Pro, Gln, Arg, Ser, Val, Trp or Tyr (SEQ ID NO:3). In some embodiments, the amino acid residue at position 662 of the MET10 polypeptide is Ala, Cys, Asp, Glu, Phe, Gly, His, Ile, Lys, Leu, Met, Asn, Pro, Gln, Arg, Val, Trp or Tyr (SEQ ID NO:5). In some embodiments, the amino acid residue at position 662 is selected from the group consisting of Lys, Arg, His, Gln and Asn (SEQ ID NO:6). In some embodiments, the amino acid residue at position 662 is Lys (SEQ ID NO:7).

In some embodiments, the sulfide inactive MET10 polypeptide or MET10 polynucleotide is a yeast MET10. In some embodiments, the sulfide inactive MET10 polypeptide shares at least about 90%, 91%, 92%, 93%, 94%, 95%, 96%, 97%, 98%, 99%, or higher sequence identity with a MET10 of SEQ ID NO:3 or SEQ ID NO:4, wherein X at position 662 is as described above and herein. In some embodiments, the polynucleotide encoding a sulfide inactive MET10 polypeptide shares at least about 90%, 91%, 92%, 93%, 94%, 95%, 96%, 97%, 98%, 99%, or higher sequence identity with SEQ ID NO:1.

In some embodiments, the yeast cell does not also express a sulfide active MET10 polypeptide capable of converting sulfite into sulfide. In some embodiments, the fermentation product is wine, beer or champagne. In some embodiments, the fermentation media may be selected from the group consisting of a must (e.g., a grape juice must) and a wort.

With respect to the embodiments of yeast cells, in some embodiments, the yeast strain may be a *Saccharomyces cerevisiae* strain. In some embodiments, the yeast strain can be any commercially available strain for use with making beer or wine, as described herein. Oftentimes, the parent strain or originating strain is a hydrogen sulfide producer that has been rendered a hydrogen sulfide non-producer by replacement of the nucleic acid encoding a sulfide active MET10 polypeptide with a nucleic acid encoding a sulfide inactive MET10 polypeptide. Exemplary *S. cerevisiae* wine strains include, without limitation, Prise de Mousse, Premier Cuveé, French Red, Montrachet, Lallemand K1, Bordeaux, UCD522, UCD940, Ba25, Ba126, Ba137, Ba220, Bb23, Bb25, Ba30, Bb32, Bb19 and Bb22. Further embodiments of yeast cells are as described herein.

Another aspect of the invention provides isolated polynucleotides comprising a nucleic acid sequence that encodes a MET10 polypeptide that does not catalyze the conversion of sulfite into sulfide, wherein the amino acid at position 662 of the MET10 polypeptide is not threonine. In some embodiments the amino acid at position 662 of the MET10 polypeptide is not threonine or serine (SEQ ID NO:5). The embodiments of the sulfide inactive MET10 polypeptide encoded by the polynucleotides are as described above and herein. In some embodiments, the isolated polynucleotide encoding a sulfide inactive MET10 polypeptide shares at least about 90%, 91%, 92%, 93%, 94%, 95%, 96%, 97%, 98%, 99% sequence identity with SEQ ID NO:1. In some embodiments, the isolated polynucleotide comprises the nucleic acid sequence provided in SEQ ID NO:1 or a complement thereof.

In a related aspect, the invention provides expression cassettes and expression vectors comprising a polynucleotide encoding a MET10 polypeptide that does not catalyze the conversion of sulfite into sulfide, wherein the amino acid at position 662 of the MET10 polypeptide is not threonine (SEQ ID NO:3), and wherein the polynucleotide is operably linked to an expression control sequence. Further embodiments of the sulfide inactive MET10 polypeptide are as described above and herein. Further provided are host cells comprising the expression vectors or expression cassettes. The host cells can be yeast cells, for example, *Saccharomyces cerevisiae* cells. Further embodiments of the yeast cells are as described above and herein. In some embodiments, the expression cassette or expression vector comprise a promoter that promotes expression in a yeast cell.

In a related aspect, the invention provides improved yeast cells that do not produce detectable hydrogen sulfide or produce low levels of hydrogen sulfide, the improved cells comprising an exogenous polynucleotide encoding a MET10 polypeptide that does not catalyze the conversion of sulfite to sulfide, wherein the amino acid at position 662 of the MET10 polypeptide is not threonine (SEQ ID NO:3), wherein a parent cell of the improved yeast cell produces hydrogen sulfide. In some embodiments, the amino acid at position 662 of the MET10 polypeptide is not threonine or serine (SEQ ID NO:5). Further embodiments of the sulfide inactive MET10 polypeptides and yeast cells are as described above and herein.

In a further aspect, the invention provides improved yeast cell cultures that produce reduced levels of or do not produce detectable hydrogen sulfide, the improved culture comprising a population of yeast cells, the yeast cells comprising an exogenous polynucleotide encoding a MET10 polypeptide that does not catalyze the conversion of sulfite to sulfide, wherein the amino acid at position 662 of the MET10 polypeptide is not threonine (SEQ ID NO:3), wherein the improved yeast cell culture produces no or reduced hydrogen sulfide in comparison to a culture of parent cells. In some embodiments, the amino acid at position 662 of the MET10 polypeptide is not threonine or serine (SEQ ID NO:5). Further embodiments of the sulfide inactive MET10 polypeptides and yeast cells are as described above and herein.

In another aspect, the invention provides methods of producing an improved yeast cell that does not produce detectable hydrogen sulfide, the method comprising replacing an endogenous nucleic acid encoding a sulfide active MET10 polypeptide with a nucleic acid encoding a sulfide inactive MET10 polypeptide by introducing into a parent of the improved yeast cell an exogenous polynucleotide encoding a sulfide inactive MET10 polypeptide that does not catalyze the conversion of sulfite to sulfide, wherein the amino acid at position 662 of the sulfide inactive MET10 polypeptide is not threonine (SEQ ID NO:3), wherein the parent of the improved yeast cell produces hydrogen sulfide. In some embodiments, the amino acid at position 662 of the MET10 polypeptide is not threonine or serine (SEQ ID NO:5). In some embodiments, the nucleic acid encoding the sulfide inactive MET10 polypeptide is introduced recombinantly. In some embodiments, the nucleic acid encoding the sulfide inactive MET10 polypeptide is introduced by back-crossing. Further embodiments of the sulfide inactive MET10 polypeptides and yeast cells are as described above and herein.

In another aspect, the invention provides fermentation products, e.g., wine, beer, champagne, with no detectable hydrogen sulfide or low levels of hydrogen sulfide, or residue therefrom, wherein the fermentation products are produced according to the methods described herein.

A further embodiment of the invention provides isolated polynucleotides capable of distinguishing between the sequences provided in SEQ ID NO:1 or a complement thereof and a nucleic acid encoding a wild type MET10, expression vectors comprising the polynucleotides operably linked to an expression control sequence, and host cells (e.g., *Saccharomyces cerevisiae* cells) comprising the expression vector.

A further embodiment of the invention provides isolated polynucleotides comprising one or more substitutions (e.g., at least two, three, four or more substitutions) in SEQ ID NO:1, wherein the one or more substitutions are selected from: an A→C at position 404, an A→G at position 514, an A→G at position 1278, and a C→T at position 1532, a G→A at position 1768, and an A→C at position 1985, expression vectors comprising the polynucleotides operably linked to an expression control sequence, and host cells (e.g., *Saccharomyces cerevisiae* cells) comprising the expression vector.

Yet another embodiment of the invention provides isolated polynucleotides comprising one or more substitutions (e.g., at least two, three, four or more substitutions) in SEQ ID NO:2, wherein the one or more substitutions are selected from the group consisting of: a C→A at position 404, a G→A at position 514, a G→A at position 1278, and a T→C at position 1532, an A→G at position 1768, and a C→A at position 1985, expression vectors comprising the polynucleotides operably linked to an expression control sequence, and host cells (e.g., *Saccharomyces cerevisiae* cells) comprising the expression vector.

BRIEF DESCRIPTION OF THE DRAWINGS

FIGS. 2A-2Z set forth a sequence alignment of the MET10 allele in various *Saccharomyces* strains (SEQ ID NOS:8, 9, 1, 10-14, 2, 15 and 16, respectively). Nucleic acid changes that result in codon changes are highlighted.

FIGS. 4A-B illustrate the amino acid sequence alignment of the MET10 gene in various *Saccharomyces* strains (S288C=SEQ ID NO:17; UCD932=SEQ ID NO:18; UCD950=SEQ ID NO:19). Amino acid differences between the different strains are highlighted.

FIG. 5 illustrates the amino acid changes surrounding residue 662 in the MET10 protein. DNA sequences of MET10 alleles from S288C (SEQ ID NO:20), UCD932 (SEQ ID NO:21) and UCD950 (SEQ ID NO:20) aligned near nucleotide 1985 with the key mutation highlighted and bolded. The codons (SEQ ID NOS:22 and 23) and corresponding amino acid sequence (SEQ ID NO:24) (highlighted in light gray) are shown in the inset. The change from a C to an A results in the corresponding change of a threonine residue to a lysine at position 662 of the protein.

FIG. 7 illustrates the structural features of the sulfite reductase domain and illustrates the impact of the change of the threonine residue for a lysine on the structural features of the protein. Structural ribbon models of the MET10 protein based on structural homology prediction are depicted. Only the predicted sulfite reductase domain from lysine 633 to tyrosine 1035 is shown with the region around residue 662 enlarged in the inset. The predicted structure for UCD932 (Figure A) highlights the lysine at residue 662 while the predicted structure for UCD950 (Figure B) highlights the Threonine at residue 662.

FIG. 8 illustrates an alignment of a subsequence of MET10 protein from some industrially relevant yeast species (UCD 932 Met10=SEQ ID NO:25; S288c Met10=SEQ ID NO:26; *S. cerevisiae* (carlsbergensis)=SEQ ID NO:27; *Kluyveromyces lactis*=SEQ ID NO:28; *Yarowwia lipolytica*=SEQ ID NO:29; *Schizosaccharomyces pombe*=SEQ ID NO:30) whose sequences in the sulfite reductase catalytic region are known. Amino acid residues conserved throughout the aligned species are in bold. Amino acid residues conserved in the most related species are shaded. The threonine at position 662 or within the motif (N/K)(R/K)R(V/L)TP(A/D/E)(D/N/E)Y(D/N)R(Y/N)IFH(I/V)EFD(I/L) (SEQ ID NO:31) is conserved in the active MET10 polypeptide throughout all yeast species aligned.

BRIEF DESCRIPTION OF THE TABLES

Figure 1:
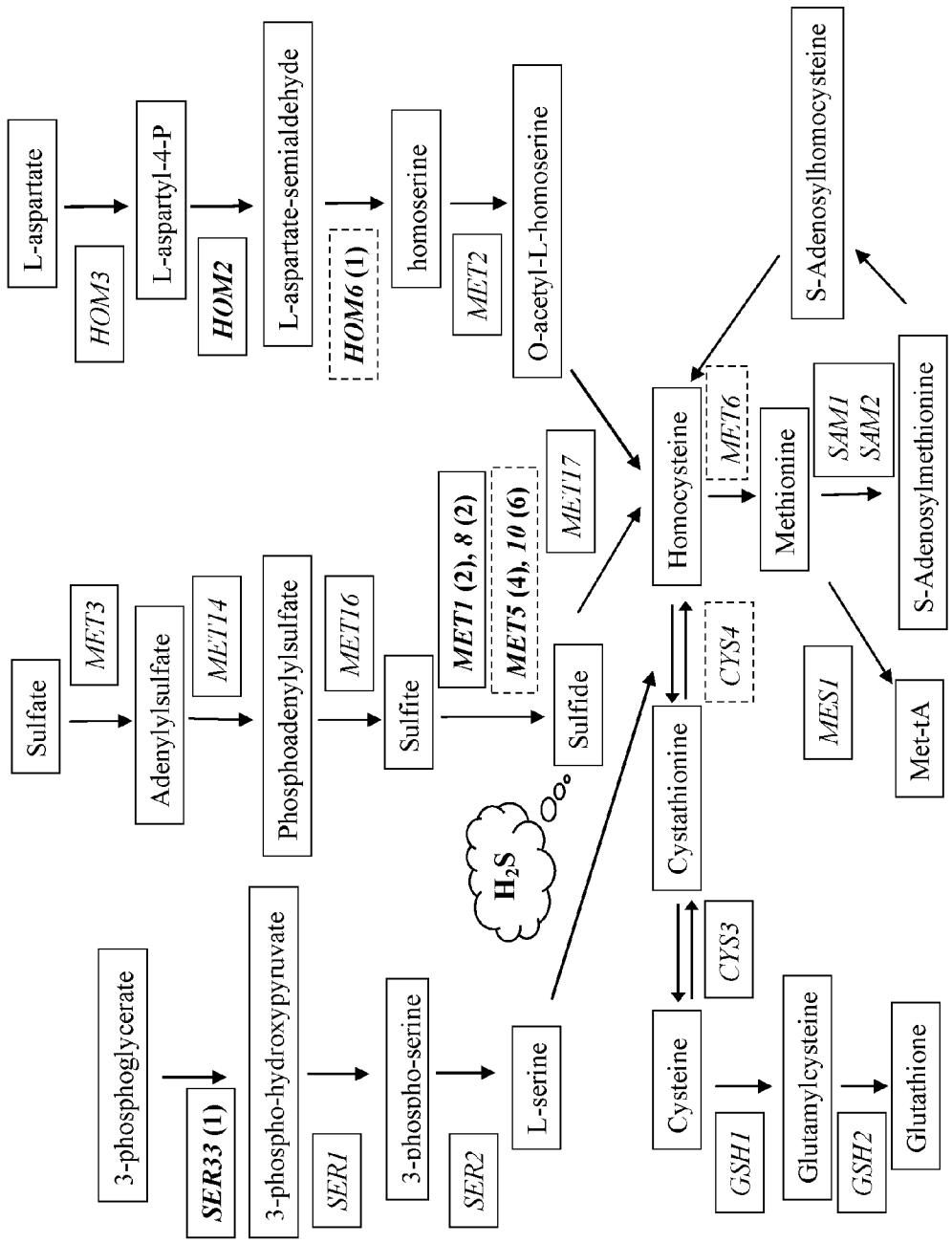
FIG. 1 illustrates the sulfate reduction pathway. Sequence analysis conducted for genes is in bold, number of alleles found is in ( ) alleles found in UCD932 are outlined with dotted lines.

Table 1 sets forth a list of native and industrial yeast strains.
Table 2 sets forth composition for a modified Triple M (MMM) media.
Table 3 sets forth results from the analysis of native yeast isolates grown on BiGGY plates and MMM.
Table 4 sets forth additional yeast strains.
Table 5 sets forth sequences for PCR primers for amplifying, inter alfa, MET10.
Table 6 sets forth sets forth sequences for sequencing primers for inter alfa, MET10.
Table 7 sets forth results summarizing $H_2S$ production from yeast strains transformed with MET10.
Table 8 sets forth amino acid differences in MET10 alleles.
Table 9 sets forth results summarizing $H_2S$ production by additional yeast strains transformed with MET10.
Table 10 sets forth results summarizing $H_2S$ production by yeast strains transformed with MET10.
Table 11 sets forth results summarizing $H_2S$ production by yeast strains transformed with MET10 alleles.

DETAILED DESCRIPTION OF THE INVENTION

I. Introduction

The present invention provides compositions and methods for reducing $H_2S$ levels in fermented beverages. The invention is based in part on the discovery that a MET10 polypeptide with an amino acid residue at position 662 that is other than a threonine does not catalyze the conversion of sulfite to free or released hydrogen sulfide. This is exemplified by the expression of a sulfide inactive MET10 polypeptide from the MET10 allele in yeast strain UCD932 in which a single nucleotide change at position 1985 in the MET10 gene results in an amino acid change at position 662 from threonine to lysine in the catalytic domain of the MET10 protein.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook and Russell, Molecular Cloning, A Laboratory Manual (3d ed., Cold Spring Harbor Laboratory Press 2001); Ausubel, et al., eds., Current Protocols in Molecular Biology (John Wiley & Sons 1987-2008)), which are provided throughout this document. The nomenclature used herein and the laboratory procedures in analytical chemistry, and organic synthesis described below are those well known and commonly employed in the art. Standard techniques, or modifications thereof, are used for chemical syntheses and chemical analyses.

"Fermentation media" or "fermentation medium" as used herein refers to an unfermented mixture prior to addition of yeast. Fermentation media include, e.g., musts and worts. Fermentation media may further comprise an additional sugar source (e.g., honey, cane sugar, beet sugar, corn sugar, fructose, sucrose, or glucose); acid (e.g., citric acid, malic acid, tartaric acid, and mixtures thereof) and yeast nutrients (e.g., diammonium phosphate or another nitrogen source, vitamins, and the like).

A "must" as used herein refers to an unfermented mixture of fruit juice, stem fragments, fruit skins, seeds and/or pulp produced by mashing the fruit. Any fruits containing fermentable sugar such as, for example, grapes, apples, cherries, peaches, nectarines, plums, apricots, pears, persimmons, pineapples, mangoes, kiwis, strawberries, raspberries, blueberries, elderberries, blackberries, cranberries, figs, and loquats can be used. The fruits may be dried, boiled, poached, or otherwise processed prior to mashing. A must may comprise two or more fruits.

"Wort" as used herein refers to an unfermented liquid produced by mashing grains and/or grain hulls. Any grains containing fermentable sugar such as, for example, barley, wheat, rye, barley, rice, corn and oats can be used. The grains may be roasted, flaked, or otherwise processed prior to mashing. A wort may be produced from a mixture comprising two or more grains.

Figure 6:
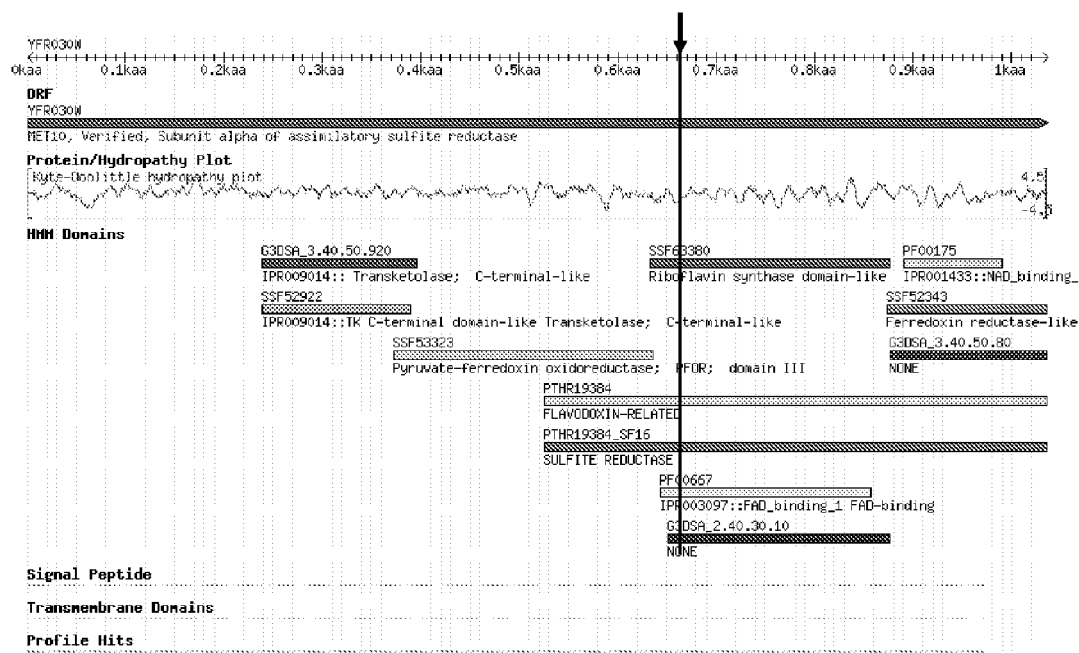
FIG. 6 illustrates the location of the 662 amino acid residue with respect to the known and predicted functional domains of the MET10 protein. A map of the known motifs and domains of the MET10 protein is depicted. The position of the altered base at position 662 is marked by the black arrow. The mutation resides within the sulfite reductase domain of the protein. Data from the world wide web at //db.yeastgenome.org/cgi-bin/protein/domainPage.pl?dbid=S000001926.

"Met10" and "MET10" as used herein refers to the a subunit of assimilatory sulfite reductase of *Saccharomyces*. Functionally, a MET10 polypeptide catalyzes the conversion of sulfite into sulfide. Structurally, MET10 polypeptides, particularly yeast MET10 polypeptides, have been characterized. MET10 polypeptides contain a conserved sulfite reductase catalytic domain at the C-terminal portion, as well as FAD and NAD binding domains. The center portion of the polypeptide contains a pyruvate-ferredoxin oxidoreductase domain. In sulfide active MET10 polypeptides, that are capable of catalyzing the conversion of sulfite to free or released hydrogen sulfide, the amino acid residue at position 662 has been conserved, and is usually a threonine or sometimes a serine, particularly in yeast. Identified MET10 polypeptide domains are depicted in FIG. 6.

As used herein, "MET10" refers to nucleic acids and polypeptide polymorphic variants, alleles, mutants, and interspecies homologs that: (1) have an amino acid sequence that has greater than about 80% amino acid sequence identity, for example, 85%, 90%, 91%, 92%, 93%, 94%, 95%, 96%, 97%, 98% or 99% or greater amino acid sequence identity, preferably over a region of at least about 25, 50, 100, 200, 500, 1000, or more amino acids, or over its full length, to a reference amino acid sequence encoded by a MET10 nucleic acid (for a yeast MET10 nucleic acid sequence, see, e.g. SEQ ID NO: 1, FIG. 2, and the exemplified GenBank accession numbers below); (2) bind to antibodies, e.g., polyclonal antibodies, raised against an immunogen comprising an amino acid sequence of a MET10 polypeptide (e.g., encoded by SEQ ID NO: 1), and conservatively modified variants thereof; (3) specifically hybridize under stringent hybridization conditions to an anti-sense strand corresponding to a nucleic acid sequence encoding a MET10 protein, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, or over its full length, to a MET10 reference nucleic acid sequence. The nucleic acids and proteins of the invention include both naturally occurring or recombinant molecules. In some embodiments, the MET10 polypeptides and MET10 polynucleotides are from yeast. Exemplified MET10 amino acid and nucleic acid sequences are set forth in Genbank Accession Nos. EF058164, EF058165, EF058166, EF058167, EF058168, EF058169, EF058170, EF058171, EF058172, EF058173.

As used herein, a "sulfied active MET10" polypeptide is capable of catalyzing the conversion of sulfite to hydrogen sulfide. In yeast, a sufide active MET10 polypeptide may have a serine or theonine residue at amino acid position 662. In yeast strains, the amino acid at position 662 i *S. cerevisiae* is conserved as a threonine or a serine and resides in the followingmotif in the sulfitereductase catalytic region: (N/K)(R/K)R(V/L)TP(A/D/E)(D/N/E)Y(D/N)R(Y/N)IFH(I/V)EFD(I/L)(SEQ ID NO:31). See, FIG. 8.

As used herein, a "sulfide inactive MET10" polypeptide does not catalyze the conversion of sulfite to free or released hydrogen sulfide. In yeast, a sulfide inactive MET10 polypeptide will not have a threonine at amino acid position 662 or within the motif (N/K)(R/K)R(V/L)XP(A/D/E)(D/N/E)Y(D/N)R(Y/N)IFH(I/V)EFD(I/L) (SEQ ID NO:32), i.e., wherein X is not T. In some embodiments, a sulfide inactive MET10 polypeptide will not have a threonine or a serine residue at amino acid position 662. In some embodiments, the sulfide inactive MET10 polypeptide will have a Ala, Cys, Asp, Glu, Phe, Gly, His, Ile, Lys, Leu, Met, Asn, Pro, Gln, Arg, Ser, Val, Trp or Tyr at position 662 (SEQ ID NO:3). In some embodiments, the amino acid residue at position 662 in a sulfide inactive MET10 polypeptide does not have a hydroxyl group, for example, is not Thr, Ser, or Tyr (SEQ ID NO:33). In some embodiments, the amino acid residue at position 662 in a sulfide inactive MET10 polypeptide is a large or bulky amino acid, for example, Lys, Arg, His, Gln, Asn, Glu, Asp, Ile, Leu, Val, Phe, Tyr, or Trp (SEQ ID NO:34). In some embodiments, the amino acid residue at position 662 in a sulfide inactive MET10 polypeptide is a basic or positively charged amino acid, for example, Lys, Arg, His, Gln or Asn (SEQ ID NO:6). In some embodiments, the amino acid residue at position 662 is Lys (SEQ ID NO:7).

As used herein, an "exogenous" MET10 nucleic acid sequence or amino acid sequence is introduced into a parent yeast cell or parent yeast strain by the action of man. The introduction into the yeast cell of the exogenous nucleic acid sequence or exogenous amino acid sequence can be by any means known in the art, including recombinant methods or classical yeast breeding methods (e.g., back-crossing).

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A nucleic acid "capable of distinguishing" as used herein refers to a polynucleotide(s) that (1) specifically hybridizes under stringent hybridization conditions to an anti-sense strand corresponding to a nucleic acid sequence encoding a MET10 protein, and conservatively modified variants thereof; or (2) has a nucleic acid sequence that has greater than about 80%, 85%, 90%, 95%, preferably greater than about 96%, 97%, 98%, 99%, or higher nucleotide sequence identity, preferably over a region of at least about 25, 50, 100, 200, 500, 1000, or more nucleotides, to a MET10 nucleic acid.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point I for the specific sequence at a defined ionic strength Ph. The $T_m$ is the temperature (under defined ionic strength, Ph, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at Ph 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated MET10 nucleic acid is separated from open reading frames that flank the MET10 gene and encode proteins other than MET10. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "heterologous" when used with reference to portions of a nucleic acid indicates that the nucleic acid comprises two or more subsequences that are divergent from each other, which can arise naturally in the population via spontaneous mutation or genomic rearrangement, or may be artificially introduced. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are divergent or not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, ÿ-carboxyglutamate, and O-phosphoserine. Amino acid analogs refers to compounds that have the same basic chemical structure as a naturally occurring amino acid, i.e., an y carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region a region of SEQ ID NO:1), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to MET10 nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (See, the worldwide website at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=-4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=-4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)).

One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

By "host cell" is meant a cell that contains an expression vector and supports the replication or expression of the expression vector. Host cells may be, for example, prokaryotic cells such as *E. coli* or eukaryotic cells such as yeast.

III. Nucleic Acids Encoding MET10

A. General Recombinant DNA Methods

This invention relies on routine techniques in the field of recombinant and classical genetics. Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook and Russell, Molecular Cloning, A Laboratory Manual (3d ed., Cold Spring Harbor Laboratory Press 2001); Ausubel et al., eds., Current Protocols in Molecular Biology (John Wiley & Sons 1987-2008); and Kriegler, Gene Transfer and Expression: A Laboratory Manual (1990).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. Cloning Methods for the Isolation of Nucleotide Sequences Encoding MET10

In general, the nucleic acid sequences encoding MET10 and related nucleic acid sequence homologues are cloned from cDNA and genomic DNA libraries or isolated using amplification techniques with oligonucleotide primers. For example, MET10 sequences are typically isolated from nucleic acid (genomic or cDNA) libraries by hybridizing with a nucleic acid probe, the sequence of which can be derived from SEQ ID NO:1, or a subsequence thereof. MET10 RNA and cDNA can be isolated from any yeast strain.

MET10 polymorphic variants, alleles, and interspecies homologues that are substantially identical to MET10 can be isolated using MET10 nucleic acid probes and oligonucleotides under stringent hybridization conditions, by screening libraries. Alternatively, expression libraries can be used to clone MET10 polymorphic variants, alleles, and interspecies homologues, by detecting expressed homologues immunologically with antisera or purified antibodies made against the core domain of MET10 which also recognize and selectively bind to the MET10 homologue.

To make a cDNA library, MET10 mRNA may be purified from any yeast strain The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, Gene 25:263-269 (1983); Sambrook et al., supra; Ausubel et al., supra).

For a genomic library, the DNA is extracted from the tissue and either mechanically sheared or enzymatically digested to yield fragments of about 1-8 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, Science 196:180-182 (1977). Colony hybridization is carried out as generally described in Grunstein et al., *PNAS USA.*, 72:3961-3965 (1975).

An alternative method of isolating MET10 nucleic acids and their homologues combines the use of synthetic oligonucleotide primers and amplification of an RNA or DNA template (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of MET10 directly from mRNA, from cDNA, from genomic libraries or cDNA libraries. Degenerate oligonucleotides can be designed to amplify MET10 homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of MET10 encoding mRNA in physiological samples, for nucleic acid sequencing, or for other purposes. Genes amplified by the PCR reaction can be purified from agarose gels and cloned into an appropriate vector.

Amplification techniques using primers can also be used to amplify and isolate MET10 NA or RNA. For example, nucleic acids encoding MET10 or fragments thereof may be obtained by amplification of a yeast cDNA library or reverse transcribed from yeast RNA using isolated nucleic acid primer pairs having the sequences: set forth in Table 5.

These primers can be used, e.g., to amplify either the full length sequence or a probe of one to several hundred nucleotides, which is then used to screen a cDNA library for full-length MET10.

Gene expression of MET10 can also be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like.

Synthetic oligonucleotides can be used to construct recombinant MET10 genes for use as probes or for expression of protein. This method is performed using a series of overlapping oligonucleotides usually 40-120 by in length, representing both the sense and non-sense strands of the gene. These DNA fragments are then annealed, ligated and cloned. Alternatively, amplification techniques can be used with precise primers to amplify a specific subsequence of the MET10 gene. The specific subsequence is then ligated into an expression vector. MET10 chimeras can be made, which combine, e.g., a portion of MET10 with a portion of a heterologous MET10 to create a chimeric, functional MET10.

The gene encoding a sulfide inactive MET10 polypeptide is typically cloned into intermediate vectors before transformation into prokaryotic or eukaryotic cells for replication and/or expression. These intermediate vectors are typically prokaryote vectors, e.g., plasmids, or shuttle vectors. Isolated nucleic acids encoding sulfide inactive MET10 proteins comprise a nucleic acid sequence encoding a sulfide inactive MET10 protein and subsequences, interspecies homologues, alleles and polymorphic variants thereof. In some embodiments, the isolated nucleic acid encoding a sulfide inactive MET10 protein is SEQ ID NO:1 or a complement thereof.

C. Expression of a Sulfide Inactive MET10 Polypeptide

To obtain high level expression of a cloned gene, such as those cDNAs encoding a sulfide inactive MET10 polypeptide, one typically subclones a nucleic acid sequence of a sulfide inactive MET10 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the sulfide inactive MET10 protein are available in, e.g., *E. coli, Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the sulfide inactive MET10 encoding nucleic acid in host cells. A typical expression cassette thus contains a promoter operably linked to the nucleic acid sequence encoding a sulfide inactive MET10 and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

D. Host Cells and Methods of Their Production

The invention also provides host cells that produce no hydrogen sulfide or low levels of hydrogen sulfide and express an exogenous sulfide inactive MET10 polypeptide, as described herein. An exogenous polynucleotide encoding a sulfide inactive MET10 polypeptide, wherein the amino acid at position 662 is not a threonine or a serine, is introduced into the parental host cell by methods known in the art, e.g., using recombinant or genetic crossing methods. In some embodiments, the host cells do not also express a sulfide active MET10 polypeptide, i.e., because the coding sequence for the active MET10 polypeptide has been knocked out and replaced with the coding sequence for a sulfide inactive MET10 polypeptide.

Host cells that produce low or decreased or reduced levels of hydrogen sulfide produce 50% or less $H_2S$ in comparison to the parent strain before introducing the nucleic acid encoding the sulfide inactive MET10 polypeptide. In some embodiments, host cells that produce low or decreased levels of hydrogen sulfide produce 40%, 30%, 25%, 20%, or less $H_2S$ in comparison to the parent strain before introducing the nucleic acid encoding the sulfide inactive MET10 polypeptide.

The host cells can be, for example, eukaryotic or prokaryotic. The host cells can be bacterial, mammalian, yeast or insect cells. In some embodiments the host cell is a yeast cell, for example, a *S. cerevisiae, Kluyveromyces lactis, Yarowwia lipolytica*, or *Schizosaccharomyces pombe* yeast cell. Yeast cells used in the production of fermented beverages, e.g., wine, port, Madeira, beer, champagne, etc. (e.g., "wine yeast," "beer yeast," "champagne yeast," etc.) find use for the introduction of a nucleic acid encoding an exogenous sulfide inactive MET10 polypeptide. Yeast cell strains for use in making fermented beverages, and which are candidates for MET10 inactivation (i.e., they are hydrogen sulfide producers), are commercially available from numerous sources, including without limitation, Lallemand (Lalvin) (Petaluma, CA; on the web at lallemandwine.us/products/yeast_chart.php) Red Star (on the web at redstaryeast.net/), White Labs (Boulder, CO; on the web at whitelabs.com/yeast_search.html), Wyeast (Odell, OR; on the web at wyeastlab.com), Kitzinger's, J. Laffort, Vierka, Gervin, SB Active, Unican, Siebel Inst., and Fermentis (on the web at fermentis.com/FO/EN/00-Home/10-10_home.asp). See, e.g., the worldwide web at winemaking.jackkeller.net/strains.asp for a representative list of wine and champagne yeast strains and at byo.com/referenceguide/yeaststrains/ for a representative list of beer yeast strains.

In some embodiments, the yeast cell strain is a *S. cerevisiae* strain. In some embodiments, the *S. cerevisiae* yeast cell strain is a wine yeast, for example, selected from Prise de Mousse, Premier Cuveé, French Red, Montrachet, Lallemand K1, Bordeaux, UCD522, UCD940, Ba25, Ba126, Ba137, Ba220, Bb23, Bb25, Ba30, Bb32, Bb19 and Bb22. See, e.g., U.S. Patent No. 6,140,108, the entire disclosure of which is hereby incorporated herein by reference for all purposes. Additional yeast strains that are candidates for MET10 inactivation, i.e., for the introduction of a nucleic acid encoding a sulfide inactive MET10 polypeptide, are listed in Tables 1, 3 and 4.

Standard transfection methods are used to produce bacterial, mammalian, yeast or insect cell lines that express large quantities of a sulfide inactive MET10 protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing sulfide inactive MET10. Host cells improved to produce no hydrogen sulfide (i.e., null $H_2S$ producers), will generally also have the active MET10 knocked-out, replaced or mutated. For example, the nucleic acid encoding a sulfide active MET10 in the parent strain can be mutated at the codon (nucleic acid positions 1984-1986) encoding the amino acid at position 662 so that this codon does not encode a threonine (or a serine). Homologous recombination techniques also find use in replacing a nucleic acid encoding a sulfide active MET10 polypeptide with a nucleic acid sequence encoding a sulfide inactive MET10 polypeptide, as described herein. See, e.g., FIG. 3 and Baudin, et al., *Nucleic Acids Res* (1993) 21(14):3329.

After the expression vector is introduced into the cells, the transfected cells are cultured under conditions favoring expression of sulfide inactive MET10, which is recovered from the culture using standard techniques identified below.

An exogenous MET10 nucleic acid encoding the inactive enzyme can also be transferred into novel genetic backgrounds using classical yeast genetic technologies of spore isolation, mating of spores of the opposite mating type, and isolation of the resulting diploid strains. Several rounds of genetic crosses may be used to isolate the novel MET10 allele in a different strain background. Recombinant tools need not be used for the creation of the modified strains. Exemplified methods for introducing a nucleic acid encoding a sulfide inactive MET10 polypeptide into a yeast host cell using classical yeast genetic technologies are described, for example, in U.S. Pat. No. 6,140,108.

E. Purification of MET10 Protein

Either naturally occurring or recombinant MET10 protein can be purified for use in functional assays. Naturally occurring MET10 proteins are purified, e.g., from yeast and any other source of a MET10 homologue. Recombinant MET10 is purified from any suitable expression system.

MET10 may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al., supra).

A number of procedures can be employed when recombinant MET10 protein is being purified. For example, proteins having established molecular adhesion properties can be reversibly fused to MET10. With the appropriate ligand, MET10 can be selectively adsorbed to a purification column and then freed from the column in a relatively pure form. The fused protein is then removed by enzymatic activity. Finally, MET10 could be purified using immunoaffinity columns.

IV. Determining whether a Yeast Strain will Produce $H_2S$ by Detecting MET10 Nucleic Acid Sequences In one embodiment of the invention, methods of determining whether a particular yeast strain is an $H_2S$ producer are provided. According to the methods of the invention, the MET10 allele of the yeast strain is analyzed and compared to the MET10 alleles disclosed herein to determine whether the yeast strain is a high, low, or non-producer of $H_2S$. Determination of the presence or absence of a particular MET10 allele is generally performed by analyzing a nucleic acid sample that is obtained from a yeast (e.g., of the genus *Saccharomyces*) to be analyzed. Often, the nucleic acid sample comprises genomic DNA. It is also possible to analyze RNA samples for the presence of MET10 alleles.

Detection techniques for evaluating nucleic acids for the presence of a single base change involve procedures well known in the field of molecular genetics. Further, many of the methods involve amplification of nucleic acids. Ample guidance for performing the methods is provided in the art. Exemplary references include manuals such as PCR Technology: PRINCIPLES AND APPLICATIONS FOR DNA AMPLIFICATION (ed. H. A. Erlich, Freeman Press, NY, N.Y., 1992); PCR PROTOCOLS: A GUIDE TO METHODS AND APPLICATIONS (eds. Innis, et al., Academic Press, San Diego, Calif., 1990); CURRENT PROTOCOLS IN MOLECULAR BIOLOGY, Ausubel, 1994-2008, Wiley Interscience, including supplemental updates through April 2004; Sambrook & Russell, *Molecular Cloning, A Laboratory Manual* (3rd Ed, 2001).

Methods for detecting single base changes well known in the art often entail one of several general protocols: hybridization using sequence-specific oligonucleotides, primer extension, sequence-specific ligation, sequencing, or electrophoretic separation techniques, e.g., singled-stranded conformational polymorphism (SSCP) and heteroduplex analysis. Exemplary assays include 5' nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and matrix-assisted laser desorption ionization (MALDI) mass spectrometry. In addition to these frequently used methodologies for analysis of nucleic acid samples to detect single base changes, any method known in the art can be used to detect the presence of the MET10 mutations described herein.

Although the methods typically employ PCR steps, other amplification protocols may also be used. Suitable amplification methods include ligase chain reaction (see, e.g., Wu & Wallace, Genomics 4:560-569, 1988); strand displacement assay (see, e.g., Walker et al., Proc. Natl. Acad. Sci. USA 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., Proc. Natl. Acad. Sci. USA 86:1173-1177, 1989); and self-sustained sequence replication (3SR) (Guatelli et al., Proc. Natl. Acad. Sci. USA 87:1874-1878, 1990; WO 92/08800). Alternatively, methods that amplify the probe to detectable levels can be used, such as Qβ-replicase amplification (Kramer & Lizardi, Nature 339:401-402, 1989; Lomeli et al., Clin. Chem. 35:1826-1831, 1989). A review of known amplification methods is provided, for example, by Abramson and Myers in Current Opinion in Biotechnology 4:41-47, 1993.

In some embodiments, the MET10 allele is detected using oligonucleotide primers and/or probes. Oligonucleotides can be prepared by any suitable method, including chemical synthesis. Oligonucleotides can be synthesized using commercially available reagents and instruments. Alternatively, they can be purchased through commercial sources. Methods of synthesizing oligonucleotides are well known in the art (see, e.g., Narang et al., Meth. Enzymol. 68:90-99, 1979; Brown et al., Meth. Enzymol. 68:109-151, 1979; Beaucage et al., Tetrahedron Lett. 22:1859-1862, 1981; and the solid support method of U.S. Pat. No. 4,458,066).

A. PCR Identification of MET10 Alleles

In some embodiments, PCR is used to amplify nucleic acids encoding MET10 alleles. A general overview of the applicable technology can be found in PCR Protocols: A Guide to Methods and Applications (Innis et al. eds. (1990)) and PCR Technology: Principles and Applications for DNA Amplification (Erlich, ed. (1992)). In addition, amplification technology is described in U.S. Pat. Nos. 4,683,195 and 4,683,202.

PCR permits the copying, and resultant amplification of a target nucleic acid, e.g., a nucleic acid encoding MET10. Briefly, a target nucleic acid, e.g. DNA from a sample comprising yeast strains of interest, is combined with a sense and antisense primers, dNTPs, DNA polymerase and other reaction components. (See, Innis et al., supra) The sense primer can anneal to the antisense strand of a DNA sequence of interest. The antisense primer can anneal to the sense strand of the DNA sequence, downstream of the location where the sense primer anneals to the DNA target. In the first round of amplification, the DNA polymerase extends the antisense and sense primers that are annealed to the target nucleic acid. The first strands are synthesized as long strands of indiscriminate length. In the second round of amplification, the antisense and sense primers anneal to the parent target nucleic acid and to the complementary sequences on the long strands. The DNA polymerase then extends the annealed primers to form strands of discrete length that are complementary to each other. The subsequent rounds serve to predominantly amplify the DNA molecules of the discrete length.

In general, PCR and other methods of amplification use primers which anneal to either end of the DNA of interest. For example, nucleic acids encoding MET10 alleles or fragments thereof may be amplified using isolated nucleic acid primer pairs having the sequences set forth in Table 5.

B. Detection of Amplified Products

Amplified products can be detected using any means known in the art, including, e.g., restriction fragment length polymorphism (RFLP) analysis; denaturing gel electrophoresis (see, e.g., Erlich, ed., PCR TECHNOLOGY, PRINCIPLES AND APPLICATIONS FOR DNA AMPLIFICATION, W. H. Freeman and Co, New York, 1992, Chapter 7), direct sequencing, and HPLC-based analysis. Suitable sequence methods include e.g., dideoxy sequencing-based methods and Maxam and Gilbert sequence (see, e.g., Sambrook and Russell, supra). Suitable HPLC-based analyses include, e.g., denaturing HPLC (dH-PLC) as described in e.g., Premstaller and Oefner, LC-GC Europe 1-9 (July 2002); Bennet et al., BMC Genetics 2:17 (2001); Schrimi et al., Biotechniques 28(4):740 (2000); and Nairz et al., PNAS USA 99(16):10575-10580 (2002); and ion-pair reversed phase HPLC-electrospray ionization mass spectrometry (ICEMS) as described in e.g., Oberacher et al.; Hum. Mutat. 21(1):86 (2003). Other methods for characterizing single base changes in MET10 alleles include, e.g., single base extensions (see, e.g., Kobayashi et al, Mol. Cell. Probes, 9:175-182, 1995); single-strand conformation polymorphism analysis, as described, e.g., in Orita et al., Proc. Nat. Acad. Sci. 86, 2766-2770 (1989), allele specific oligonucleotide hybridization (ASO) (e.g., Stoneking et al., Am. J. Hum. Genet. 48:70-382, 1991; Saiki et al., Nature 324, 163-166, 1986; EP 235,726; and WO 89/11548); and sequence-specific amplification or primer extension methods as described in, for example, WO 93/22456; U.S. Pat. Nos. 5,137,806; 5,595,890; 5,639,611; and U.S. Pat. No. 4,851,331; 5'-nuclease assays, as described in U.S. Pat. Nos. 5,210,015; 5,487,972; and 5,804,375; and Holland et al., 1988, Proc. Natl. Acad. Sci. USA 88:7276-7280.

V. Methods for Reducing $H_2S$ Levels in Fermented Beverages

Yeast strains comprising the MET10 nucleic sequences described herein can be used to reduce $H_2S$ levels in fermented beverages (e.g., wine and beer).

According to the methods of the invention, yeast cells transformed with an exogenous nucleic acid sequence encoding a sulfide inactive MET10 polypeptide, as described herein, are contacted with a fermentation medium (e.g., a must or a wort) and the mixture is incubated for a suitable amount of time (e.g., 2, 3, 4, 5, 6, 7, 8, 9, 10, 11, 12, 13, or 14 days) in a suitable first fermentation vessel (e.g., a tank, barrel, crock, jar, pail or polyethylene container) at a suitable temperature (e.g., about 70-75° F.) for fermentation to proceed. The liquid may then be transferred to a second fermentation vessel. The second vessel may or may not be sealed and the contents are incubated for a suitable amount of time (e.g., 2, 3, 4, 5, 6, 7, or 8 weeks) at a suitable temperature (e.g., about 60-65° F.) for anaerobic fermentation and aging to proceed. The liquid is then transferred to a third vessel for racking (i.e., clarification). The third vessel is sealed and sediment is allowed to settle for a suitable amount of time (e.g., 2, 3, 4, 5, 6, 7, or 8 weeks). Racking may be repeated one, two, three or more times prior to bottling the fermented beverage. The native MET10 allele may be replaced either using recombinant DNA technologies or crossed in through classical breeding strategies. The UCD932 MET10 allele confers a white colony color on BiGGY agar, allowing this allele to be followed in genetic crosses and to be readily screened during production to demonstrate successful implantation of the strain.

When the wine is clear and all fermentation and pre-bottle aging has stopped, siphon into wine bottles and cork the bottles securely. Leave corked bottles upright for 3-5 days and then store them on their side at 55 degrees Fahrenheit for six months (white wine) to a year (red wine) before sampling. If not up to expectations, allow to age another year or more.

The yeast may be transformed using any method know in the art including, e.g., Liac/SS carrier DNA/PEG method described by Gietz and Woods *Methods in Enzymology* 350: 87-96 (2002); Agatep et al., *Technical Tips Online* Transformation of *Saccharomyces cerevisiae* by the lithium acetate/single-stranded carrier DNA/polyethylene glycol (LiAc/ss-DNA/PEG) protocol (1998); and the yeast two hybrid method described in Gietz et al., *Mol Cell Biochem* 172:67-79 (1997). Methods for preparing yeast cells that are competent for transformation are set forth in, e.g., Dohmen et al. (1991) Yeast 7: 691-692.

VI. Kits

MET10 and its homologues are useful tools for more specific and sensitive identification of yeast strains that are low $H_2S$ producers. For example, nucleic acids that specifically hybridize to MET10 nucleic acids, such as MET10 probes and primers (e.g., as set forth in Table 5), MET10 nucleic acids (e.g. as set forth in FIG. 2), are used to identify yeast strains that are low $H_2S$ producers.

The invention also provides kits and solutions for detecting the MET10 alleles described herein. For example, the invention provides kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of samples in the same vessel. Such kits allow for ready detection of amplification products of the invention into standard or portable amplification devices. The kits can also include written instructions for the use of the kit to amplify and control for amplification of a target sample.

Kits can include, for instance, amplification reagents comprising primers sufficient to amplify at least one MET10 allele, and at least one probe for amplifying and detecting the polynucleotide sequence. In addition, the kit can include nucleotides (e.g., A, C, G and T), a DNA polymerase and appropriate buffers, salts and other reagents to facilitate amplification reactions.

In some embodiments, the kits comprise vessels such as sample processing cartridges useful for rapid amplification of a sample as described in Belgrader, et al., *Biosensors and Bioelectronics* 14:849-852 (2000); Belgrader, et al., *Science*, 284:449-450 (1999); and Northrup, M. A., et al. "A New Generation of PCR Instruments and Nucleic Acid Concentration Systems" in PCR PROTOCOLS (Sninsky, J. J. et al (eds.)) Academic, San Diego, Chapter 8 (1998)).

EXAMPLES

The following examples are offered to illustrate, but not to limit the claimed invention.

Example 1

Identification of Genes Affecting $H_2S$ Production

To better understand the mechanisms and pathways through which $H_2S$ is formed, and to develop future prevention or management strategies, a screen of the yeast deletion strain set, comprised of 4,827 mutants, was performed to identify genes affecting $H_2S$ production. A collection of native isolates of wine fermentations (Mortimer 1994) was screened in order to define the basis of the bias of colony color versus actual $H_2S$ production. In addition, a yeast null mutant collection whose parental strain is a non-$H_2S$ producer was screened for genes that when mutated resulted in elevated $H_2S$ formation. The possible additive effects on $H_2S$ formation of these mutations were also evaluated.

Materials and Methods

Yeast strains and culture conditions. The yeast strains used for this study and whose results are presented are listed in Table 1. Yeast strains were maintained and grown on yeast extract peptone dextrose medium with 2% glucose (YPD) (Sherman et al. 1974). The same medium (YPD) with geneticin (G418, 0.2 mg/ml) was used for maintenance of deletion strains carrying the $G418^R$ marker.

TABLE 1

Native and Industrial Yeast Strains

| Strains | Known genotypes or descriptions | Reference or Source |
| --- | --- | --- |
| UCD522 | Industrial isolates | UCD |
| UCD713 | Industrial isolates | UCD |
| UCD819 | Industrial isolates | UCD |
| UCD932 (Ba2) | Native isolates | UCD |
| UCD933 | Native isolates | UCD |
| UCD934 (Ba25) | Native isolates | UCD |
| UCD935 | Native isolates | UCD |
| UCD936 | Native isolates | UCD |
| UCD937 | Native isolates | UCD |
| UCD938 (Ba86) | Native isolates | UCD |
| UCD939 (Ba99) | Native isolates | UCD |
| UCD940 (Ba111) | Native isolates | UCD |
| UCD941 | Native isolates | UCD |
| UCD942 (Ba126) | Native isolates | UCD |
| UCD943 | Native isolates | UCD |
| UCD944 | Native isolates | UCD |

TABLE 1-continued

Native and Industrial Yeast Strains

| Strains | Known genotypes or descriptions | Reference or Source |
|---|---|---|
| UCD945 | Native isolates | UCD |
| UCD946 | Native isolates | UCD |
| UCD947 | Native isolates | UCD |
| UCD948 | Native isolates | UCD |
| UCD949 | Native isolates | UCD |
| UCD950 (Ba196) | Native isolates | UCD |
| UCD951 | Native isolates | UCD |
| UCD952 | Native isolates | UCD |
| UCD953 | Native isolates | UCD |
| UCD954 | Native isolates | UCD |
| UCD955 | Native isolates | UCD |
| UCD956 (Ba224) | Native isolates | UCD |
| UCD957 (Ba229) | Native isolates | UCD |
| UCD958 | Native isolates | UCD |
| YLR303W BY4742 | MATα his3Δ1 leu2Δ0 lys2Δ0 ura3Δ0met17::G418 | Open Biosystems |
| YGR155W BY4742 | MATα his3Δ1 leu2Δ0 lys2Δ0 ura3Δ0cys4::G418 | Open Biosystems |
| YHL031C BY4742 | MATα his3Δ1 leu2Δ0 lys2Δ0 ura3Δgos1::G418 | Open Biosystems |
| YER060W-A BY4742 | MATα his3Δ1 leu2Δ0 lys2Δ0 ura3Δ0fcy22::G418 | Open Biosystems |
| YGR138C BY4742 | MATα his3Δ1 leu2Δ0 lys2Δ0 ura3Δ0tpo2::G418 | Open Biosystems |
| YDR158W BY4742 | MATα his3Δ1 leu2Δ0 lys2Δ0 ura3Δ0hom2::G418 | Open Biosystems |
| YJR139C BY4742 | MATα his3Δ1 leu2Δ0 lys2Δ0 ura3Δ0hom6::G418 | Open Biosystems |
| YNL315C BY4742 | MATα his3Δ1 leu2Δ0 lys2Δ0 ura3Δ0atp11::G418 | Open Biosystems |
| YIL074C BY4742 | MATα his3Δ1 leu2Δ0 lys2Δ0 ura3Δ0ser33::G418 | Open Biosystems |
| YNL031C BY4742 | MATα his3Δ1 leu2Δ0 lys2Δ0 ura3Δ0hht2::G418 | Open Biosystems |
| YBR095C BY4742 | MATα his3Δ1 leu2Δ0 lys2Δ0 ura3Δ0rxt2::G418 | Open Biosystems |
| YLR384C BY4742 | MATα his3Δ1 leu2Δ0 lys2Δ0 ura3Δ0iki3::G418 | Open Biosystems |
| YPL035C BY4742 | MATα his3Δ1 leu2Δ0 lys2Δ0 ura3Δ0ypl035c::G418 | Open Biosystems |
| YDL047W BY4742 | MATα his3Δ1 leu2Δ0 lys2Δ0 ura3Δ0sit4::G418 | Open Biosystems |
| YBL046W BY4742 | MATα his3Δ1 leu2Δ0 lys2Δ0 ura3Δ0psy4::G418 | Open Biosystems |
| YGL029W BY4742 | MATα his3Δ1 leu2Δ0 lys2Δ0 ura3Δ0cgr1::G418 | Open Biosystems |

DNA and Genetic Manipulations. Genetic manipulations including crosses, sporulation and tetrad analysis were carried out using standard procedures (Gunthrie 1991). Gene deletions were confirmed by PCR using the upstream forward primer and an internal reverse primer to the KanMX disruption marker—JKKanRE. Amplification conditions were as follows: 30 cycles of 94° C. for 2 min., 92° C. for 45 s, 56° C. for 30 s, 72° C. for 1 min and a final extension at 72° C. for 7 min. Primer sequences are listed in Table 5.

Screen of deletion set and native strains. The deletion set (Open Biosystems, Huntsville, Ala.) and collection of native isolates were screened on BiGGY agar, a bismuth glucose glycine yeast agar (Nickerson 1953). They were also screened in synthetic grape juice medium "Minimal Must Media" (MMM) (Spiropoulos et al. 2000) initially with 123 mg of nitrogen equivalents/liter. The nitrogen level was generated using 0.2 g of L-arginine/liter and 0.5 g of ammonium phosphate/liter.

Analysis of hydrogen sulfide formation. Hydrogen sulfide production was evaluated using the lead acetate method (Spiropoulos et al. 2000; Giudici, P., and R. E. Kunkee, 1994). Hydrogen sulfide formation was initially detected using paper strips (2×10 cm, 3 mm Whatman filter paper) which had been previously treated with 50 μL of 5% lead acetate solution and allowed to dry at room temperature. The lead acetate strips were folded in half and inserted into 50 mL culture tubes with the culture tube cap securing either end of the strip, enclosing the mid-portion of the lead acetate strip in the gaseous environment over the liquid medium. Hydrogen sulfide formation was qualitatively measured by degree of blackening of the lead acetate strip. This screen was conducted by Carrie Findleton as part of her MS thesis dissertation.

All positives were confirmed using a more sensitive and semi-quantitative method. A Whatman filter paper strip (1.5× 8.0 cm, 3 mm) was rolled and placed in a 1 ml bulb-less plastic pipette and treated with 250 μl of a 3% lead acetate solution. The paper was allowed to dry at room temperature and the plastic lead acetate column was then attached to the 50 mL culture tube with a silicone stopper. Hydrogen sulfide formation was measured by mm of darkening on the paper.

In subsequent experiments, to quantify $H_2S$ production, packed lead acetate columns were used, in which each mm of blackening on the column denoted 4 μg/L $H_2S$. Lead acetate columns were purchased from Figasa International Inc. (Seoul, Korea).

Fermentation conditions. To identify yeast strains and nutritional conditions impacting in hydrogen sulfide formation, yeast cultures were grown in 5 mL of modified Triple M Medium in 50 mL culture tubes at 25° C. on shaker tables at 120 rpm. The synthetic grape juice medium "Minimal Must Medium" (MMM) (Giudici et al. 1993) was used and modified from the original recipe to produce seven different nitrogen and micronutrient compositions. Arginine, ammonium phosphate, and Casamino acids additions were manipulated to adjust nitrogen concentration, and YNB (Yeast Nitrogen Base without Amino Acids and Ammonium Sulfate) additions were adjusted to control for nutrient and vitamin concentration. Triple M modifications are illustrated in Table 2.

TABLE 2

Modified Triple M Medium Composition

| MMM Variety | Arginine (g/liter) | Ammonium Phosphate (g/liter) | Casamino acids (g/liter) | YNB (g/liter) |
|---|---|---|---|---|
| 433 g nitrogen equivalents/liter | 0.8 | 1 | 2 | 1.7 |
| 123 g nitrogen equivalents/liter | 0.2 | 0.1 | 2 | 1.7 |
| 123 g nitrogen equivalents/liter and ⅕ YNB | 0.2 | 0.1 | 2 | 0.34 |
| 65 g nitrogen equivalents/liter, no Casamino acids | 0.2 | 0.03 | 0 | 1.7 |
| 65 g nitrogen equivalents/liter | 0.107 | 0.015 | 1 | 1.7 |
| 65 g nitrogen equivalents/liter and ½ YNB | 0.107 | 0.015 | 1 | 0.85 |
| 65 g nitrogen equivalents/liter and ⅓ YNB | 0.107 | 0.015 | 1 | 0.567 |

Yeast inocula were obtained from plated yeast colonies. This procedure may have resulted in some variation in cell number at inoculation, but was necessary due to the large number of yeast strains involved in the preliminary screening process. Hydrogen sulfide formation was evaluated after four days by degree of blackening of the lead acetate strip. Strains that did not grow in four days were repeated to insure there was no other variable that resulted in the absence of growth.

For selected strains of interest, hydrogen sulfide formation was quantified using lead acetate columns. For this purpose, fermentations were conducted in 500-mL Erlenmeyer flasks, containing 300 mL MMM, with a lead acetate column secured to the top of the flask in a rubber stopper. For this purpose, 123 mg/L nitrogen MMM was used to more accurately emulate low nitrogen grape juice conditions. Fermentations were initiated at a density of $1.33 \times 10^5$ cells/ml by inoculation with stationary-phase cells from a culture pre-grown in Triple M Medium of the same composition. The fermentations performed in triplicate, incubated at 25° C. and 120 rpm, and monitored over seven days by weight loss and darkening on the lead acetate column.

Screening of the deletion set and native isolates on BiGGY agar. To assess the $H_2S$ production of the deletion strains and native isolates they were initially all plated on BiGGY agar and the color of the colonies evaluated. The colony colors were white, light tan, tan (deletion set parental strain color), light brown, brown or black (Linderholm et al. 2006). From the deletion set, four colonies were white, 258 were light tan, 4478 were tan, 59 were light brown, 28 were brown and one colony was black ranging in colony color from light to dark.

Screening of native and commercial isolates in synthetic juice. Thirty native isolates were screened in synthetic juice MMM with 123 mg/L nitrogen to evaluate $H_2S$ production versus colony color. Non-$H_2S$-producers (i.e., UCD932, UCD713 UCD819, UCD938, UCD942, UCD954 and UCD956) had colony colors ranging from white to light brown. Strains producing $H_2S$ ranged from light tan (3) to tan (10) to light brown (5) to brown (5). The darkest colonies (brown) ranged from 2-6 mm of $H_2S$ and are in the mid range of production. The three highest producers (over 10 mm) are light tan, tan and light brown on BiGGY. Native isolates on BiGGY and in MAIM are shown in Table 3.

TABLE 3

Native isolates on BiGGY and in MMM

| Strain | Colony color | $H_2S$ (mm) |
|---|---|---|
| UCD522 | Tan | 4 |
| UCD713 | Tan | 0 |
| UCD819 | Tan | 0 |
| UCD932 | White | 0 |

TABLE 3-continued

Native isolates on BiGGY and in MMM

| Strain | Colony color | $H_2S$ (mm) |
|---|---|---|
| UCD933 | Brown | 3 |
| UCD934 | Tan | 5.5 |
| UCD935 | Tan | 10.5 |
| UCD936 | Brown | 2 |
| UCD937 | Light Tan | Trace |
| UCD938 | Tan | 0 |
| UCD939 | Light Tan | 14.5 |
| UCD940 | Brown | 6 |
| UCD941 | Brown | 2 |
| UCD942 | Light Tan | 0 |
| UCD943 | Light Brown | 3.5 |
| UCD944 | Light Brown | Trace |
| UCD945 | Tan | 8 |
| UCD946 | Tan | 2 |
| UCD947 | Tan | 1.75 |
| UCD948 | Tan | 2.5 |
| UCD949 | Light Tan | Trace |
| UCD950 | Light Brown | 19 |
| UCD951 | Tan | 5.5 |
| UCD952 | Tan | 8 |
| UCD953 | Light Brown | Trace |
| UCD954 | Light Brown | 0 |
| UCD955 | Brown | 4 |
| UCD956 | White | 0 |
| UCD957 | Tan | 9 |
| UCD958 | Light Brown | 1 |

Example 2

Identification of Mutations in the MET10 Allele of UCD932

As set forth in Example 1 above, UCD932 was identified as a yeast strain which produces little to undetectable hydrogen sulfide under a variety of environmental conditions. This strain also produces white colonies on BiGGY agar, associated with low sulfite reductase activity. A screen of the deletion set of strains for S. cerevisiae yielded four possible mutations resulting in white colonies, all encoding for components of sulfite reductase. Genetic crosses revealed that the white colony BiGGY phenotype in UCD932 was due to an alteration of the MET10 gene. The MET10 deletion strain was a methionine auxotroph but UCD932 is not a methionine auxotroph, indicating that sulfite reductase activity is still retained by the cell. To define the genetic basis of this low sulfide production ability, the MET10 and several other genes in the sulfate reduction pathway, identified as possibly playing a role in the suppression of $H_2S$ in S. cerevisiae, (Linderholm et al. 2006) were sequenced. This would allow for identification of alleles that could be replaced in $H_2S$ producing wine strains to eliminate the undesirable sulfide characteristic.

Materials and Methods

Yeast strains and culture conditions. The yeast strains used for this study are listed in Table 4. Yeast strains were maintained and grown on yeast extract peptone dextrose medium with 2% glucose (YPD) (Sherman et al. 1974). The same medium (YPD) with geneticin (G418, 0.2 mg/ml) or hygromycin (Hph, 0.3 mg/ml) were used for maintenance of deletion strains carrying the G418$^R$ or HphMX marker. Minimal media (YNB) was made with 0.67% yeast nitrogen base without amino acids and supplemented with casamino acids as recommended (Sherman). Selective-met dropout media were made similar to YNB without the methionine.

plated onto BiGGY agar and incubated at 30° C. for 48 hours. The resulting colonies were assessed for color.

Sequence Analysis. The sequence analysis of MET10, HOM2, HOM6, SER33, MET1, MET5 and MET8 were performed in 169 native and industrial strains of yeast. Chromosomal DNA was extracted from the cell pellets using the smash and grab protocol (Hoffman and Winston 1987) and amplification of the genes was carried out using High Fidelity Platinum Taq (Invitrogen, Carlsbad, Calif.) and primers PCR-MET10-F/PCR-MET10-R for MET10, HOM2-F/HOM2-R for HOM2, HOM6-F/HOM6-R for HOM6, SER33-F/SER33-R for SER33, MET1-F/MET1-R for MET1, MET5-

TABLE 4

Additional yeast strains

| Strains | Known genotypes or descriptions | Reference or Source |
| --- | --- | --- |
| UCD932 (Ba2) | Native isolates | UCD |
| UCD934 (Ba25) | Native isolates | UCD |
| UCD938 (Ba86) | Native isolates | UCD |
| UCD939 (Ba99) | Native isolates | UCD |
| UCD940 (Ba111) | Native isolates | UCD |
| UCD942 (Ba126) | Native isolates | UCD |
| UCD950 (Ba196) | Native isolates | UCD |
| UCD956 (Ba224) | Native isolates | UCD |
| UCD957 (Ba229) | Native isolates | UCD |
| UCD522 | Industrial isolates | UCD |
| YKR069W BY4742 | MATα his3Δ1 leu2Δ0 lys2Δ0 ura3Δ0met1::G418 | Open Biosystems |
| YJR137C BY4742 | MATα his3Δ1 leu2Δ0 lys2Δ0 ura3Δ0met5::G418 | Open Biosystems |
| YBR213W BY4742 | MATα his3Δ1 leu2Δ0 lys2Δ0 ura3Δ0met8::G418 | Open Biosystems |
| YFR030W BY4742 | MATα his3Δ1 leu2Δ0 lys2Δ0 ura3Δ0met10::G418 | Open Biosystems |
| ALY38 | UCD932 MET10$^{S288C}$ | This Study |
| ALY39 | UCD932 MET10$^{UCD932}$ | This Study |
| ALY95 | UCD932 MET10$^{UCD950}$ | This Study |
| ALY72 | BY4742 MET10$^{UCD950}$ | This Study |
| ALY40 | UCD950 MET10$^{S288C}$ | This Study |
| ALY41 | UCD950 MET10$^{UCD932}$ | This Study |
| ALY126 | UCD950 MET10$^{UCD950}$ | This Study |
| ALY127 | UCD939 MET10$^{UCD939}$ | This Study |
| ALY128 | UCD939 MET10$^{S288C}$ | This Study |
| ALY130 | UCD940 MET10$^{S288C}$ | This Study |
| ALY129 | UCD940 MET10$^{UCD940}$ | This Study |
| ALY131 | UCD940 MET10$^{UCD932}$ | This Study |
| ALY132-1A | UCD522 MET10::KanMX4 | This Study |
| ALY133-1B | UCD522 MET10$^{S288C}$ | This Study |
| ALY134-1C | UCD522 MET10$^{S288C}$ | This Study |
| ALY135-1D | UCD522 MET10::KanMX4 | This Study |
| ALY136-1A | UCD522 MET10$^{UCD522}$ | This Study |
| ALY137-1B | UCD522 MET10::hphNT1 | This Study |
| ALY138-1C | UCD522 MET10::hphNT1 | This Study |
| ALY139-1D | UCD522 MET10$^{UCD522}$ | This Study |
| ALY140-1A | UCD522 MET10$^{UCD932}$ | This Study |
| ALY141-1B | UCD522 MET10$^{UCD932}$ | This Study |
| ALY142-1C | UCD522 MET10::KanMX4 | This Study |
| ALY143-1D | UCD522 MET10::KanMX4 | This Study |

Screen of deletion set. The yeast deletion set (Open Biosystems, Huntsville, Ala.) was screened on BiGGY agar, a bismuth glucose glycine yeast agar (Nickerson 1953), supplemented with casamino acids (Sherman 1974). Each strain was F/MET5-R for MET5 and MET8-F/MET9-R for MET8 (Table 5). Amplification conditions were as follows: 30 cycles of 94° C. for 1 min., 94° C. for 30 s, 50° C. for 30 s, 68° C. for 4 min. and a final extension at 68° C. for 7 min.

TABLE 5

PCR Primers

| Primer | Sequence (5' → 3') | SEQ ID NO: |
|---|---|---|
| HOM2 | | |
| HOM2-F | CACTTAAGTACACATACAAA | 35 |
| HOM2-R | GGGTCAGCGAGAGAATT | 36 |
| HOM6 | | |
| HOM6-F | CCTGGTGGTAAAGTTGGG | 37 |
| HOM6-R | GATTGTAGAAGATTGAGTAG | 38 |
| SER33 | | |
| SER33-F | GGAATCTCCCAGGTTTAAT | 39 |
| SER33-R | GGGCAATCAAAGGCTAT | 40 |
| MET1 | | |
| MET1-F | CGCTAATAAACTCGCTACAAAG | 41 |
| MET1-R | CGTCCTTTTTGCTCAATATCC | 42 |
| MET5 | | |
| MET5-F | GCTGCAAGCAGTTATATAAAGTG | 43 |
| MET5-R | AAAACCGAACTAGCCGAAG | 44 |
| MET8 | | |
| MET8-F | AAAATCGCTACAAAGTCCG | 45 |
| MET8-R | GCATTGTTGTTCGTTCTCC | 46 |
| MET10 primers | | |
| PCR-MET10-F | CGGATCCCCAATCACCATAACACTT | 47 |
| PCR-MET10-R | GCCGCGGTAGGGTCTTCAGGACGAG | 48 |
| MET10-F-KO | CAAATAGTTTCGTTTAGATGG | 49 |
| MET10-R-KO | GTATAATGTGATGGTTAGTT | 50 |
| MET10-hphMX-F | ACTGTGTTTATCACTTATGGGTCTTTAGAATCCGAATTGTATTTTGATGGCCGCACGG | 51 |
| MET10-hphMX-R | AACAATTCAAAAATGTCAGCATATGTATAATACTCCACATAATCGACAGCAGTATAGCGACCA | 52 |
| Confirmation primers | | |
| JKKanRE | GGGCGACAGTCACATCAT | 53 |
| HYGROB ChK_R | TGACGGTGTCGTCCATCAC | 54 |

All sequencing was carried out at the College of Biological Sciences Sequencing Facility at the University of California, Davis by using an ABI 3730 capillary electrophoresis genetic analyzer and ABI BigDye Terminator version 3.1 cycle sequencing chemistry (Foster City, Calif.), primers used are listed in Table 6. Sequence data were edited and analyzed with BioEdit sequence Alignment Editor (version 5.0.9; Nucleic Acids Symp. Ser. 41:95-98).

TABLE 6

MET Sequencing Primers

| Primer | Sequence (5' → 3') | SEQ ID NO: |
|---|---|---|
| MET1 | | |
| MET1-S1F | TGGGGAGAGTTCTGGTATGCAAG | 55 |
| MET1-S2F | CAGATGGTTATCTCAGATAATGGAG | 56 |
| MET1-S3F | TTTCTTCAAAGATCACGGATATATT | 57 |
| MET1-S1R | GCTATATCACGTTGAGTAGCGG | 58 |
| MET1-S2R | GGTACTACACCCTCTGTGACAGTT | 59 |
| MET1-S3R | CTCAGTTTTTGGCATTGCCA | 60 |
| MET5 | | |
| MET5-S1F | CCTAATAAACTTCCATTGGTGATTA | 61 |
| MET5-S2F | CCGTTTTACAGGGTGTCTCTAAGA | 62 |
| MET5-S3F | GACGCGATCTTGACGAAGCT | 63 |
| MET5-S4F | GAATCTGGTTACTGGCCATTGT | 64 |
| MET5-S5F | CTGAAAAATGACACCGACTTGG | 65 |
| MET5-S6F | TGGCTTGCTCTGGATCACTT | 66 |
| MET5-S7F | CGATGTCGGTTTAGTTGCTATAGTT | 67 |
| MET5-S8F | TGGTAATCAACATTTGGTTATCTCT | 68 |
| MET5-S1R | GGGCAACCAGTCATTCTCATAA | 69 |
| MET5-S2R | CTTCGACACCCATATCATCTACAG | 70 |
| MET5-S3R | CAATTTTCCCATATCAGCGA | 71 |
| MET5-S4R | CATCATCAACAGCAGCGCCG | 72 |
| MET5-S5R | CTGATCGAAGGCAGCCTTGC | 73 |
| MET5-S6R | CATATGGCTCTGAATCAATCAATAA | 74 |
| MET5-S7R | TTCACAACTTTTTTGACAGAAGAA | 75 |
| MET5-S8R | CGTTAGCAATCTCCAAGGTAGGAA | 76 |
| MET8 | | |
| MET8-S1F | GCAGTGACTTCAAAGACGAATACC | 77 |
| MET8-S2F | CTGGAGGACGCTGTCGTCAA | 78 |
| MET8-S1R | TCATCTCTTACTAGAGCGCCAA | 79 |
| MET8-S2R | GGTCCCAGTTCGGATTGATAA | 80 |
| MET10 | | |
| MET10 SEQ1-F | AGTCATCTTCGAGCAAA | 81 |
| MET10 SEQ2-F | TCATGATGGTAAGTTTC | 82 |
| MET10 SEQ3-F | TCAACGTCAGAGTGCCATT | 83 |
| MET10 SEQ4-F | ATCAGTCGTTGAAGATGTC | 84 |
| MET10 SEQ5-F | CTGAGATCTCTGATATTGC | 85 |
| MET10 SEQ6-F | TGCAGTAGATTTGAAGAGAT | 86 |
| MET10 SEQ7-F | CACACACATCGGCGCT | 87 |
| MET10 SEQ1-R | CGGAGTCACGACACCAT | 88 |
| MET10 SEQ2-R | GGCTGAAACTTGAGATCTC | 89 |
| MET10 SEQ3-R | CTTGACGTAACTTTCTACAG | 90 |
| MET10 SEQ4-R | TCATAATCAGCAGGCGTAAC | 91 |
| MET10 SEQ5-R | CTTCTCTTCAATGGTTCAAT | 92 |
| MET10 SEQ6-R | AGTAGGGCCAGACAAGT | 93 |

GenBank Accession numbers for these sequences are: UCD932 MET10 (EF058164), UCD938 MET10 (EF058165), UCD939 MET10 (EF058166), UCD940 MET10 (EF058167), UCD942 MET10 (EF058168), UCD956 (EF058169), UCD522 MET10 (EF058170), UCD957 MET10 (EF058171), UCD934 MET10 (EF058172), UCD950MET10 (EF058173), UCD932 SER33 (EF058174), UCD939 SER33 (EF058175), UCD940 SER33 (EF058176), UCD956 SER33 (EF058177), UCD950 SER33 (EF058178), UCD932 HOME (EF058179), UCD932 MET1 (EF058180), UCD939 MET1 (EF058181), UCD940 MET1 (EF058182), UCD950 MET1 (EF058183), UCD956 MET1 (EF058184), UCD956 MET5 (EF058185), UCD932 MET5 (EF058186), UCD940 MET5 (EF058187), UCD939 MET5 (EF058188), UCD932 MET8 (EF058189), UCD939 MET8 (EF058190), UCD940 MET8 (EF058191), UCD950MET8 (EF058192), UCD956MET8 (EF058193).

Genetic Manipulations. Genetic manipulations including crosses, sporulation and tetrad analysis were carried out using standard procedures (Guthrie 1991).

Plasmids, DNA manipulations, and transformation methods. The plasmids pAL51 (MET10$^{S288C}$), pAL52 (MET10$^{UCD932}$) were used in this study. Primers, PCR-MET10-F/PCR-MET10-R (Table 5), carrying the restriction sites BamHI and SacII were designed to amplify MET10 from yeast strain UCD932 and S288C chromosomal DNA (Invitrogen, Carlsbad, Calif.). Plasmid pYC130 (Olesen et al. 2000), is a centromeric vector carrying the selectable marker G418$^R$ was digested with BamHI and SacII (New England Biolabs, Ipswich, Mass.) to allow for the ligation of MET10. The resulting plasmids, pAL51 (MET10$^{S288C}$), pAL52 (MET10$^{UCD932}$) were used for transformation. Gene deletions of MET10 were created using a PCR-based technique, FIG. 3 (Baudin 1993). A KanMX containing deletion cassette (Yeast Deletion collection) with overhangs of non-coding regions on either side of MET10 was PCR amplified using primers, MET10-F-KO/MET10-R-KO, and the linear PCR fragment was transformed into yeast diploid strains UCD522, UCD932, UCD939, UCD940 and UCD950. By homologous recombination one copy of the intact MET10 was replaced with the knockout cassette generating strains carrying a copy of both an intact copy of MET10 and a KanMX marker. All of the strains, except UCD522MET10/KanMX, were then sporulated and those homologous for G418$^R$ were used for further experiments. Gene deletions were confirmed by PCR using the upstream forward primer and an internal reverse primer to the KanMX disruption marker—JKKanRE.

To knockout the remaining intact copy of MET10 in UCD522 MET10/KanMX, a HphMX cassette was amplified from BamHI linearized pYC140 (Hansen et al. 2003) using primers MET10-hphMX-F/MET10-hphMX-R, and the linear PCR fragment was transformed into ALY29. A methionine auxotrophic colony displaying both G418$^R$ and Hph$^R$ was selected and the HphMX deletion confirmed by PCR using the upstream forward primer and an internal reverse primer to the HphMX disruption marker—HYGROB CHK_R.

Allele swaps of MET10 were also created using a PCR-based technique (FIG. 3) (Baudin 1993). Alleles of MET10 were amplified from S288C, UCD932, UCD939, UCD940, UCD950 and UCD522 using primers MET10-F-KO/MET10-R-KO. The linear PCR fragments amplified from S288C and UCD932 were then transformed into the methionine auxotrophic strains. The other fragments were transformed into individual strains to create the corresponding control strains.

Strains displaying ability to grow on methionine auxotrophic plates were selected and sporulated to create strains homologous for MET10 for further experiments. *S. cerevisiae* was transformed using the lithium acetate method adapted from the Schiestl and Gietz (1989) and *E. coli* was transformed using the method described by Inoue et al. (Inoue et al. 1990). *E. coli* INVαF' (Invitrogen, Carlsbad, Calif.) was used for plasmid preparations. Luria-Bertani medium (Miller 1972) with ampicillin was used for selection for transformed *E. coli* cells.

Fermentation conditions. In the fermentation experiments, the synthetic grape juice medium "Minimal Must Media" (MMM) (Spiropoulos et al. 2000) was used with 208 mg of nitrogen equivalents/liter. The nitrogen level was generated using 0.2 g of L-arginine/liter and 0.5 g of ammonium phosphate/liter. Fermentations were initiated at a density of 1.33× 10$^5$ cells/ml by inoculation with stationary-phase cells from a culture pre-grown in MAIM starter medium. Fermentations were conducted in 500-ml Erlenmeyer flasks containing 300 ml of medium. Each flask was outfitted with a silicone stopper with a lead acetate tube attached. The flasks were incubated at 25° C. with shaking at 120 rpm. Fermentations were monitored for seven days using weight loss as an estimate of $CO_2$ production.

Results

Characterization of hydrogen sulfide production of the deletion strains. In order to assess the hydrogen sulfide production of the entire set of deletion strains they were initially all plated on BiGGY agar and the color of the colonies evaluated. The colonies were white, light tan, tan (parental strain color), light brown, brown or black. Four colonies were white, 258 were light tan, 4478 were tan, 59 were light brown, 28 were brown and one colony was black. The four deletants yielding white colonies were in MET10, MET8, MET5 or MET1. We also identified HOM2, HOM6 and SER33 as possibly playing a role in the suppression of hydrogen sulfide formation (Linderholm et al. 2006).

Identification of the gene responsible for whiteness in a native strain. UCD932, a native strain isolated from Italy (Mortimer et al. 1994) is a white non-H$_2$S producer on BiGGY agar. To identify the gene that is responsible for its white phenotype, it was mated with each of the white deletion strains. Only one strain failed to complement the white phenotype of UCD932, YFRO30W BY4742.

When a vector carrying the wild type copy of MET10, pAL51 (MET10$^{S288C}$), was transformed into UCD932, it resulted in a strain of UCD932 producing tan colonies but did not lead to sulfide formation (Table 7). This suggested that more than one gene, possibly in combination with MET10, is responsible for the low-H$_2$S production phenotype of UCD932.

TABLE 7

Properties of Hydrogen Sulfide Production Fermentations Transformed with MET10

| Strains[a] | Maximum Fermentation Rate (g/h)[b,c,d] | Total H$_2$S (μg) |
|---|---|---|
| UCD932 vector | 0.437 | <1 |
| UCD932pMET10$^{S288C}$ | 0.446 | <1 |
| UCD932pMET10$^{UCD932}$ | 0.408 | <1 |

[a]Vector: pYC130; pMET10$^{S288C}$: pAL51; pMET10$^{UCD932}$: pAL52
[b]The maximum fermentation rate was calculated from the fermentation rate data by using time points corresponding to the steepest decline in weight.
[c]Values represent the average of independent determinations of two replicates.
[d]Fermentations reached dryness (defined by <0.5% sugar remaining).

Sequence analysis of genes in the sulfate reduction pathway. It was demonstrated previously that UCD932 carries mutations in CYS4 and MET6, both encoding for important enzymes in the sulfate reduction pathway (Linderholm et al. 2006). However, introducing wild type alleles to this background did not alter the low H$_2$S producing characteristic. It was therefore interesting to identify what other mutations this strain might carry in other genes in the pathway. Several genes from the sulfate reduction pathway, MET10, HOM2, HOM6, SER33, MET1, MET5 and MET8 were sequenced from UCD932 as well as from several other native and industrial strains that vary in color on BiGGY agar and in H$_2$S production in synthetic juice (Spiropoulos et al. 2000) to assess the genetic diversity of the sulfate reduction pathway (a sequence alignment of MET10 from various *Saccharomyces* strains is found in FIG. 2). MET10p amino acid differences is shown in Table 8.

TABLE 8

MET10p Amino acid differences

| Amino acid positions | 135 | 172 | 314 | 475 | 511 | 590 | 662 | 896 |
|---|---|---|---|---|---|---|---|---|
| Consensus | T | None | P | D | None | None | T | P |
| Modification[a] (Strains) | N (UCD932) T or N (UCD940) | T (UCD522, 932, 940, 938, 942, 956) A (S288C, UCD934, 957, 950) A or T (UCD939) | P or S (UCD940) | A (UCD938, 942) | I (UCD934, 950, 957) T (S288C, UCD932, 938, 939, 940, 942, 956) T or I (UCD522) | K (UCD934, 950, 957) E (S288C, UCD522, 932, 938, 940, 942, 956) Q (UCD939) | K (UCD932) | S (UCD956) |

[a]Strains with two amino acid possibilities indicate that the strain carries two alleles.

Sequence analysis of MET10 (a component of the enzyme sulfite reductase) demonstrated that it is not conserved amongst yeast strains (Table 9). Six alleles, different from that of S288C, were found in the ten strains that were sequenced. They were loosely grouped by color on BiGGY and $H_2S$ production. UCD934, UCD957 and UCD950, tan $H_2S$ producers, carried the identical allele. UCD938 and UCD942, tan non-$H_2S$ producers carried the same allele. UCD522 and UCD940, brown $H_2S$ producers, were heterozygous but both alleles were identical for those found in other strains. UCD932 and UCD956, white non-$H_2S$ producers, and UCD939, a tan $H_2S$ producer, each carried different alleles.

TABLE 9

Properties of Hydrogen Sulfide Production Fermentations with different MET10

| Strains | Allele | Maximum Fermentation Rate (g/h)[abc] | Total $H_2S$ (µg) |
|---|---|---|---|
| UCD932 | MET10$^{S288C}$ | 0.37 | <1 |
|  | MET10$^{UCD932}$ | 0.34 | <1 |
|  | MET10$^{UCD950}$ | 0.41 | <1 |
| BY4742 | MET10$^{UCD950}$ | 0.26 | <1 |
| UCD950 | MET10$^{S288C}$ | 0.42 | 32 |
|  | MET10$^{UCD932}$ | 0.40 | <1 |
|  | MET10$^{UCD950}$ | 0.41 | 29 |
| UCD939 | MET10$^{S288C}$ | 0.46 | <1 |
|  | MET10$^{UCD932}$ | not viable |  |
|  | MET10$^{UCD939}$ | 0.35 | 41 |
| UCD940 | MET10$^{S288C}$ | 0.40 | 54 |
|  | MET10$^{UCD932}$ | 0.42 | <1 |
|  | MET10$^{UCD940}$ | 0.42 | 49 |

[a]The maximum fermentation rate was calculated from the fermentation rate data by using time points corresponding to the steepest decline in weight.
[b]Values represent the average of independent determinations of two replicates.
[c]Fermentations reached dryness (defined by <0.5% sugar remaining).

The other genes in the sulfate reduction pathway were shown to be more conserved. There were no differences in the amino acid or DNA sequence in HOM2 (encodes for aspartic beta semi-aldehyde dehydrogenase), one amino acid difference in HOME (encodes for homoserine dehydrogenase) in UCD932, one amino acid difference in SER33 (encodes for 3-phosphoglycerate dehydrogenase) between S288C and all of the other wine strains and several amino acid differences in MET1, MET5 and MET8 (all components of the sulfite reductase enzyme)).

Figure 3:
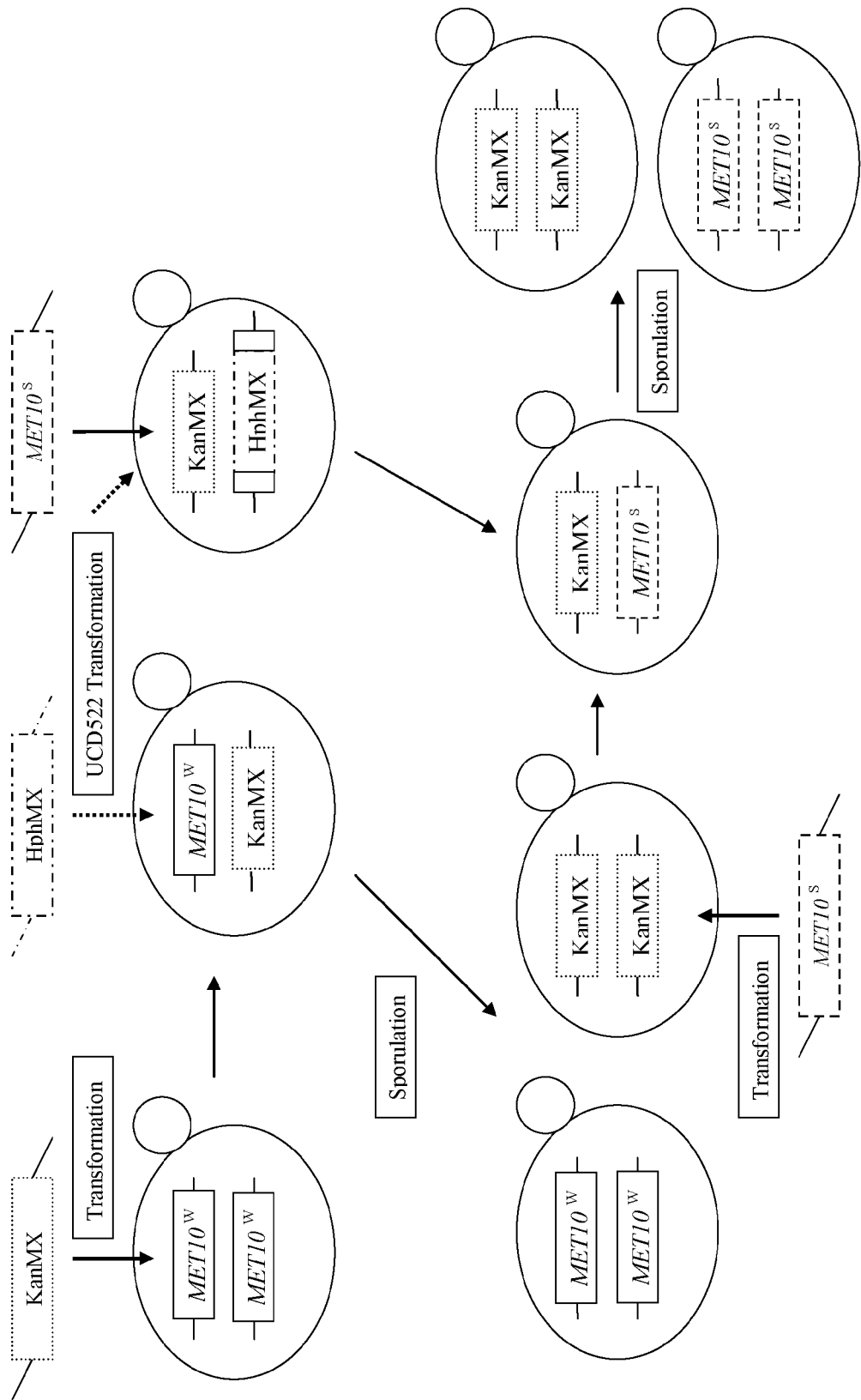
FIG. 3 illustrates an exemplary gene swapping technique. MET10$^S$=S288C allele. MET10$^W$=Wine strain allele.

Swapping of MET10 alleles. The genetic diversity of MET10 alleles and the apparent correlation with $H_2S$ production and colony color supported the hypothesis that genes in the sulfate reduction pathway may be responsible for $H_2S$ phenotype in wine strains, since color on BiGGY agar is loosely correlated with $H_2S$ production through detection of sulfite reductase activity. The effect of MET10 on $H_2S$ production in $H_2S$ producing strains was therefore evaluated. The MET10 alleles of $H_2S$ producing yeast strains were replaced with the allele MET10$^{UCD932}$ (FIG. 3). The native MET10 genes in UCD950, UCD940, UCD939, UCD522 and UCD932 were deleted with a KanMX or HphMX cassette and then the KanMX or HphMX cassettes were replaced with a MET10 allele from UCD932, S288C or their own alleles as a control. All of the strains carrying the MET10$^{UCD932}$ fermented at the same rate as the parental and control strains but became non-$H_2S$ producers and were lighter in color on BiGGY agar. The strains carrying an allele from either S288C or their own allele maintained their $H_2S$ producing phenotype (Table 9).

UCD939 strains carrying the MET10$^{UCD932}$ allele were not restored to methionine prototrophs, in contrast to the other wine and commercial isolates. This may be explained by the presence of other mutations that this strain carries in the sulfate reduction pathway. UCD939 has two mutations in the genes encoding other subunits in the sulfite reductase enzyme. The addition of a third mutation may lower the activity of the sulfite reductase enzyme drastically so there is decreased sulfide available to be incorporated into sulfur containing amino acids, such as methionine or cysteine. Thus the strain cannot grow on plates without methionine. There may also be effects of the accumulation of toxic intermediates upstream of sulfite reductase because the repression of the sulfate pathway has been relieved by the absence of sulfur containing amino acids such as S-adenosyl methionine. However the strain was viable when the MET10$^{S288c}$ allele was substituted for its own allele, the color of the strain on BiGGY changed from tan to white and its $H_2S$ production was significantly reduced.

UCD522, a commercial wine strain that has been characterized as an aneuploid (Bakalinsky and Snow 1990) an imbalance of chromosome number leading to cell death upon sporulation. Therefore both alleles needed to be individually disrupted (FIG. 3) as opposed to knocking out one allele then sporulating the strain to gain a homologous knockout as was done with the other strains. A MET10 allele was transformed into the knockout strains and then it was sporulated to gain two strains that were G418$^R$/hphNT1$^R$ and two strains that carried the MET10 allele. Each strain was used in the experiments to observe if there were any inconsistencies due to the genetic manipulations (Table 10). The strains fermented to completion and behaved as expected in terms of $H_2S$ production. Each of the strains carrying the drug resistant marker were methionine auxotrophs and did not produce $H_2S$. The strains carrying either the MET10$^{S288C}$ or MET10$^{UCD522}$ allele produced $H_2S$ and the strain carrying the MET10$^{UCD932}$ did not produce $H_2S$.

TABLE 10

Properties of Hydrogen Sulfide Production Fermentations of Heterologous strain UCD522

| Strains[a] | Allele | Maximum Fermentation Rate (g/h)[b,c,d] | Total $H_2S$ (µg) |
|---|---|---|---|
| UCD522-1A | met10Δ::KanMX4 | 0.35 | <1 |
| UCD522-1B | MET10$^{S288C}$ | 0.35 | 16 |
| UCD522-1C | MET10$^{S288C}$ | 0.42 | 33 |
| UCD522-1D | met10Δ::KanMX4 | 0.24 | <1 |
| UCD522-1A | MET10$^{UCD522}$ | 0.43 | 26 |
| UCD522-1B | met10Δ::hphNT1 | 0.24 | <1 |
| UCD522-1C | met10Δ::hphNT1 | 0.34 | <1 |
| UCD522-1D | MET10$^{UCD522}$ | 0.38 | 4 |
| UCD522-1A | MET10$^{UCD932}$ | 0.36 | <1 |
| UCD522-1B | MET10$^{UCD932}$ | 0.37 | <1 |
| UCD522-1C | met10Δ::KanMX4 | 0.36 | <1 |
| UCD522-1D | met10Δ::KanMX4 | 0.22 | <1 |

[a]A, B, C, D- designate the different spores.
[b]The maximum fermentation rate was calculated from the fermentation rate data by using time points corresponding to the steepest decline in weight.
[c]Values represent the average of independent determinations of two replicates.
[d]Fermentations reached dryness (defined by <0.5% sugar remaining).

We also replaced the KanMX cassette in YFR030W BY4742 and UCD932 with the MET10 allele from UCD950 and both are tan on BiGGY agar but neither are $H_2S$ producers. Crosses between BY4742 or UCD932 and UCD950 indicated that there are at least four to five alleles segregating for $H_2S$ production.

Discussion

One of the possibilities for the observed naturally arising differences in sulfide production in *S. cerevsiae* is the occurrence of genetic alterations of the expression or activity of enzymes in the sulfate reduction pathway. The sulfate reduction pathway displays complex regulation (Mountain et al. 1991) and an increase in one enzymatic activity may be buffered by changes in the activity of other proteins within the pathway.

Previous research in our lab identified, in a native non-$H_2S$ producer UCD932, several alleles within the sulfate reduction pathway. However, we demonstrated that those particular alleles alone are not responsible for the $H_2S$ phenotype (Linderholm et al. 2006). In our screen of the deletion collection for suppressors of $H_2S$ formation, we identified several other genes in the sulfate reduction pathway in that role, HOM2, HOM6, SER33, MET1, MET5, MET8 and MET10 (Linderholm et al. 2006). When those genes were sequenced in UCD932 and other native and industrial yeast strains that vary in $H_2S$ production, it was revealed that UCD932 carried different alleles in five of the nine genes, including CYS4 and METE (Linderholm et al. 2006). There were many alleles of MET10 found within the collection of strains that was sequenced.

In this study it was demonstrated that MET10 plays an important in the role of $H_2S$ formation, while it alone is not responsible for the non-$H_2S$ formation phenotype in UCD932; it dramatically alters the $H_2S$ phenotype in other $H_2S$ producing strains. In the experiments described above, MET10$^{UCD932}$ was successfully swapped for native alleles in three $H_2S$ producing strains and this changed them into non-$H_2S$ producers. These results have many positive implications for the wine industry because of the ability to construct commercial strains with reduced sulfur production in any genetic background by transferring the appropriate alleles or to predict the $H_2S$ production characteristic for any strain of *Saccharomyces cerevisiae*. Both techniques would be quite simple and useful for winemakers.

The experiments to swap in MET10$^{UCD932}$ in UCD939 were unsuccessful; UCD939 MET10$^{UCD932}$ was not viable on plates deficient in methionine. However it can be explained by other mutations that it carries in the sulfate reduction pathway. UCD939 carries two mutations in the genes encoding other subunits in the sulfite reductase enzyme and although it was not a methionine auxotroph, the addition of a third mutation may lower the activity drastically so it becomes a methionine auxotroph because enzymes downstream cannot boost their activity enough to compensate. The regulation of sulfate reduction by sulfur containing amino acids may also fall apart because the strain can no longer produce methionine and toxic intermediates can accumulate above the sulfite reductase enzymes and also make the strain unviable.

UCD522 was characterized as an aneuploid strain (Bakalinsky and Snow 1990). When the MET10 gene was sequenced in UCD522 it was observed that UCD522 is a heterozygous strain, it carries two alleles of MET10. There may have some type of association between the components that led to the inability to genetically manipulate it like the other strains. It is possible that some type of complex forms between the MET10 alleles or proteins it encodes that does not allow it to segregrate appropriately during sporulation if only one of the alleles is deleted. However when each allele is replaced individually, the strain can sporulate properly. The UCD522 MET10$^{UCD932}$ was sporulated to give two strains that were G418$^R$/hphNT1$^R$ and methionine auxotrophs and two strains that were drug sensitive and carried the MET10 allele. Each strain fermented to completion and their $H_2S$ characteristic was as expected.

Example 3

Further Characterization of the MET10p Allele of UCD 932

As demonstrated in Examples above, the MET10 allele present in the yeast strain UCD932 is able to convert a high hydrogen sulfide ($H_2S$) producing strain into a strain that produces no detectable $H_2S$. This was clearly shown with the high producing strains UCD522 and UCD950, which produced no detectable $H_2S$ when carrying the MET10 allele from UCD932. The ability to convert a strain to a low $H_2S$ producer has implications in any industry that uses yeast including the wine, brewing, and fuel ethanol industries. In addition to presenting a problem for the final product by adding a strong rotten egg smell, the $CO_2$ created in the fermentation is often a useful byproduct, either to be sold as the gas itself or to be used as a motor gas for the movement of product (brewing). Therefore preventing the gas from smelling of rotten eggs has clear benefits.

The previous work determined that the MET10 alleles from UCD932 and UCD950 differ by six nucleotides, five of those changes result in changes in the primary protein sequence (see, FIG. 2). To further characterize the UCD932 MET10 allele, the native alleles of MET10 were cloned into the shuttle vector pUG6. The Quick Change PCR mutagenesis technique was used to make single nucleotide changes (see, e.g., Cormack, B. and Castano, I. (2002) Introduction of Point Mutations into Cloned Genes. Methods in Enzymology (350) 199-218). In separate reactions, the technique was used to convert one nucleotide difference into the similar nucleotide of the other allele. For example, UCD932 MET10 has an adenine at position 404 while UCD950 has a cytosine. The change of the UCD950 cytosine at position 1985 for an adenine was found to be necessary and sufficient for the loss of sulfide production in the UCD950 background. (Table 11) The conversion of the adenine in the UCD932 allele to the cytosine of 950 eliminated the ability of the UCD932 protein to eliminate sulfide production (Table 11). Therefore the single change of the threonine at position 662 to a lysine residue results in the creation of a modified Met10 protein leading to reduced sulfide release.

TABLE 11

$H_2S$ Production by Different MET10 Alleles

| MET10 Allele | Nucleotide at 1985 | Strain Background | Produces $H_2S$? |
|---|---|---|---|
| UCD932 | Adenine | UCD522 | No |
| UCD932 | Adenine | UCD932 | No |
| UCD932 | Adenine | UCD940 | No |
| UCD932 | Adenine | UCD950 | No |
| UCD950 | Cytosine | UCD522 | Yes |
| UCD950 | Cytosine | UCD932 | No* |
| UCD950 | Cytosine | UCD940 | Yes |
| UCD950 | Cytosine | UCD950 | Yes |
| UCD932 1985 A-C | Cytosine | UCD522 | Yes |
| UCD932 1985 A-C | Cytosine | UCD932 | No* |
| UCD932 1985 A-C | Cytosine | UCD940 | Yes |
| UCD932 1985 A-C | Cytosine | UCD950 | Yes |
| UCD950 1985 C-A | Adenine | UCD522 | No |
| UCD950 1985 C-A | Adenine | UCD932 | No |
| UCD950 1985 C-A | Adenine | UCD940 | No |
| UCD950 1985 C-A | Adenine | UCD950 | No |

*The 932 strain background has other determinants of $H_2S$ production and does not produce $H_2S$ under any conditions testes.

Example 4

Allelic Differences at Position 1985 of the MET10 Gene Determine Hydrogen Sulfide Production by *Saccharomyces cerevisiae*

The MET10 allele of strain UCD932 leads to the inability to produce hydrogen sulfide ($H_2S$) when used in an allele replacement strategy to replace the native allele in commercial and native isolates of wine yeast. This allele was found to contain several base pair changes leading to differences in amino acid sequence of the encoded protein. These amino acid changes have been evaluated to determine which one(s) impact the ability to produce $H_2S$.

To identify the exact mutation or combination of mutations responsible for these dramatic differences in $H_2S$ production, we cloned the MET10 alleles from UCD932 and UCD950 and systematically converted each single base difference to the base of the opposite allele using Site Directed Mutagenesis. The resulting alleles were identical to the parent allele with the exception of the single swapped base change. The modified alleles were then inserted back into both strains and BiGGY agar was used as an indicator of a change in sulfite reduction and likely $H_2S$ production. A single base change at position 1985 was identified by this screen as the mutation responsible for the change in colony color. These strains were examined for $H_2S$ production in duplicate during small scale fermentations in synthetic wine juice. 10 mL of synthetic wine media was inoculated with the respective strains and $H_2S$ was detected by the use of lead acetate columns after four days of fermentation. The unchanged UCD950 MET10 allele and the UCD932 allele with the mutation to the UCD950 allele at position 1985 (932 MET10 1985 A-C) resulted in $H_2S$ production while the unchanged allele UCD932 MET10 and the UCD950 allele with the change to UCD932 at position 1985 (950 MET10 1985C-A) resulted in no detectable $H_2S$ production. These results indicate that the single base change at position 1985 is a key determinant of the difference in $H_2S$ production of these alleles. These results were then strengthened by examining the production of $H_2S$ when the single mutant alleles were place into two high $H_2S$ producing commercial strains UCD522 and UCD940. Both of these strains produced $H_2S$ with the 932 MET10 1985A-C allele but no $H_2S$ was detected with the 950 MET10 1985C-A allele. The results are summarized in Table 11, above.

This study demonstrates that a single base pair change at position 1985 in the MET10 allele dictates the production of hydrogen sulfide. The nucleotide difference at 1985 changes the encoded amino acid, thus any change in the surrounding nucleotide sequence that changes the encoded amino acid will likely also eliminate $H_2S$ production. The threonine present in the high producing alleles may act as regulatory point that changes the flux of the pathway as amino acid residues containing a phosphate group can be regulated via phosphorylation. Amino acid residue 662 is predicted to be within the sulfite reductase catalytic domain (FIG. 6). Analysis of the putative structure of the protein with this change (FIG. 7) indicates that the overall structure of the protein is unaltered, but the local area of the active site surrounding this residue change is affected. Thus this change modifies the protein structure only slightly.

REFERENCES

Acree, T. E., E. P. Sonoff, and D. F. Splittstoesser. 1972. Effect of yeast strain and type of sulfur compound on hydrogen sulfide production. *Am. J. Enol. Vitic.* 23:6-9.

Amoore, J. E. and E. Hautala. 1983. Odor as an aid to chemical safety: Odor thresholds compared with threshold limit values and volatilities for 214 chemicals in air and water dilution. *J. Appl. Toxicol.* 3:272-290.

Bakalinsky, A. T. and R. Snow. 1990. The chromosomal constitution of wine strains of *Saccharomyces cerevisiae*. *Yeast.* 6:367-382.

Baudin, A., O. Ozier-Kalogeropoulos, A. Denouel, F. Lacroute, and C. Cullin. 1993. A simple and efficient method for direct gene deletion in *Saccharomyces cerevisiae*. *Nucleic Acids Res.* 21(14): 3329-3330.

Bohlscheid, J. C. and C. G. Edwards. 2004. Interactive effects of nitrogen and biotin on yeast growth, fermentation rate, and volatile production. *Am. J. Enol. Vitic.* 55:310 A.

Eschenbruch, R., P. Bonish and B. M. Fisher. 1978. The production of $H_2S$ by pure culture wine yeasts. *Vitis* 17:67-74.

Giudici, P. and R. E. Kunkee. 1994. The effect of nitrogen deficiency and sulfur-containing amino acids on the reduction of sulfate to hydrogen sulfide by wine yeasts. *Am. J. Enol. Vitic.* 45(1): p. 107-112.

Guthrie C. and G. R. Fink. 1991. *Methods in Enzymology* 194:3-21.

Hansen J., T. Felding, P. F. Johannesen, J Piskur, C. L. Christensen and K. Olesen. 2003. Further development of the cassette-based pYC plasmid system by incorporation of the dominant hph, nat and AUR1-C gene markers and the lacZ reporter system. *FEMS Yeast Research.* 4:323-327.

Hoffman, C. S., and F. Winston. 1987. A Ten-minute DNA preparation from yeast efficiently releases autonomous plasmids for transformation of *Escherichia coli*. *Gene* (Amsterdam). 57:267-272.

Inoue, H., H. Nojima, and H. Okayama. 1990. High efficiency transformation of *Escherichia coli* with plasmids. Gene 96:23-28.

Jiranek, V., P. Langridge and P. A. Henschke. 1995. Regulation of hydrogen sulfide liberation in wine-producing *Saccharomyces cerevisiae* strains by assimilable nitrogen. *Appl. Environ. Microbiol.* 61:461-467.

Linderholm, A. L., T. L. Olineka, Y. Hong and L. F. Bisson. 2006. Allele diversity among genes of the sulfate reduction pathway in wine strains of *Saccharomyces cerevisiae*. *Am. J. Enol. Vitic.* 57(4):431-440.

Miller, J. H. 1972. Experiments in molecular genetics, p. 431-435. Cold Spring Harbor Laboratory Press, Plainview, N.Y.

Mortimer R. K., P Romano, G. Suzzi and M. Posinelli. 1994. Genome renewal: A new phenomenon revealed from a genetic study of 43 strains of *Saccharomyces cerevisiae* derived from natural fermentation of grape musts. Yeast. 10(12): p. 1543-1552.

Mountain, H. A., A. Bystrom, J. T. Larsen and C. Korch. 1991. Four major transcriptional responses in the methionine/threonine biosynthetic pathway of *Saccharomyces cerevisiae*. Yeast 7:781-803.

Nickerson, W. J. 1953. Reduction of inorganic substances by yeast. 1. Extracellular reduction of sulfite by species of *Candida*. *The Journal of Infectious Diseases*. 93: 43-48.

Olesen K., P. Franke Johannesen, L. Hoffmann, S. Bech Sørensen, C. Gjermansen and J. Hansen. 2000. The pYC plasmids, a series of cassette-based yeast plasmid vectors providing means of counter-selection. Yeast 16(11):1035-43.

Rauhut, D. and H. Kurbel. 1994. The production of H$_2$S from elemental sulfur residues during fermentation and its influence on the formation of sulfur metabolites causing off-flavors in wines. Wein-Wissenschaft. 49:27-36.

Schiestl, R. H., and R. D. Gietz 1989. High efficiency transformation of intact cells using single stranded nucleic acids as a carrier. *Curr. Genet.* 16:339-346.

Sherman, F., G. R. Fink, and J. B. Hinks. 1986. Methods in yeast genetics. Cold Spring Harbor Laboratory, Cold Springs New York.

Sherman, F., G. R. Fink and C. W. Lawrence. 1974. Methods in yeast genetics: a laboratory manual. Cold Spring Harbor Laboratory, Cold Spring Harbor, N.Y.

Spiropoulos, A., J. Tanaka and L. F. Bisson. 2000. Characterization of hydrogen sulfide formation in commercial and natural wine isolates of *Saccharomyces*. *Am. J. Enol. Vitic.* 51(3): 233-248.

Spiropoulos, A. and L. F. Bisson. 2000. MET17 and hydrogen sulfide formation in *Saccharomyces cerevisiae*. *Appl. Environ. Microbiol.* 66(10):4421-4426.

Stratford, M. and A. H. Rose. 1985. Hydrogen sulfide production from sulfite by *Saccharomyces cerevisiae*. *J. Gen. Microbiol.* 131:1417-1424.

Thoukis, G. and L. A. Stern. 1962. A review and some studies of the effect of sulfur on the formation of off-odors in wine. *Am. J. Enol. Vitic.* 13(3):133-140.

Tokuyama, T., H. Kuraishi, K. Aida and T. Uemura. 1973. Hydrogen sulfide evolution due to panthothenic acid deficiency in the yeast requiring this vitamin, with special reference to the effect of adenosine triphosphate on yeast cysteine desulfhydrase. *J. Gen. Appl. Microbiol.* 19:439-466.

Wainwright, T. 1970. Hydrogen sulphide production by yeast under conditions of methionine, pantothenate or vitamin B6 deficiency. *J. Gen. Microbiol.* 61:107-119.

Walker, M. D. and W. J. Simpson. 1993. Production of volatile sulphur compounds by ale and lager brewing strains of *Saccharomyces cerevisiae*. *Letts. Appl. Microbiol.* 16:40-4.

It is understood that the examples and embodiments described herein are for illustrative purposes only and that various modifications or changes in light thereof will be suggested to persons skilled in the art and are to be included within the spirit and purview of this application and scope of the appended claims. All publications, accession numbers, patents, and patent applications cited herein are hereby incorporated by reference in their entirety for all purposes.

---

What is claimed is:

1. A method for producing fermentation products with reduced H$_2$S, the method comprising fermenting a fermentation medium with a *Saccharomyces cerevisiae* yeast cell comprising a polynucleotide encoding a *Saccharomyces* MET10 polypeptide that does not catalyze the conversion of sulfite into sulfide, wherein the MET10 polypeptide comprises a sulfite reductase catalytic domain, and wherein the amino acid at position 662 of the MET10 polypeptide is not threonine.

2. The method of claim 1, wherein the polynucleotide encodes a MET10 polypeptide of SEQ ID NO:3, wherein X at position 662 is not threonine.

3. The method of claim 1, wherein the polynucleotide encodes a MET10 polypeptide of SEQ ID NO:3, wherein X at position 662 is lysine.

4. The method of claim 1, wherein the polynucleotide shares at least 95% sequence identity with a nucleic acid sequence of SEQ ID NO:1.

5. The method of claim 1, wherein a fermentation product having no detectable levels of H$_2$S is produced, wherein the fermentation product is a beverage.

6. The method of claim 1, wherein the yeast cell is a wine yeast strain selected from the group consisting of: Premier Cuveé, French Red, Montrachet, Lallemand K1, and Bordeaux.

7. The method of claim 1, wherein the fermentation medium is selected from the group consisting of: a juice, a must and a wort.

8. The method of claim 1, wherein the fermentation medium is a grape juice must.

9. The method of claim 5, wherein a fermentation product having no detectable levels of H$_2$S is produced, wherein the fermentation product is a beverage selected from the group consisting of: wine, beer, champagne, port and Madeira.

10. The method of claim 1, wherein the amino acid at position 662 of the MET10 polypeptide is selected from the group consisting of Ala, Cys, Asp, Glu, Phe, Gly, His, Ile, Lys, Leu, Met, Asn, Pro, Gln, Arg, Val, Tip or Tyr.

11. The method of claim 1, wherein the amino acid at position 662 of the MET10 polypeptide is selected from the group consisting of Lys, Arg, His, Gln, Asn, Glu, Asp, Ile, Leu, Val, Phe, Tyr, or Trp.

12. The method of claim 1, wherein the amino acid at position 662 of the MET10 polypeptide is selected from the group consisting of Lys, Arg, His, Gln or Asn.

13. The method of claim 1, wherein the *Saccharomyces cerevisiae* yeast cell is a methionine prototroph.

14. A method for producing fermentation products with reduced $H_2S$, the method comprising fermenting a fermentation medium with a *Saccharomyces cerevisiae* yeast cell comprising a polynucleotide encoding a *Saccharomyces* MET10 polypeptide having at least 95% sequence identity with the nucleic acid sequence of SEQ ID NO: 1, wherein the amino acid at position 662 of the MET10 olypeptide is not threonine.

15. The method of claim 14, wherein the polynucleotide encodes a MET10 polypeptide of SEQ ID NO:3, wherein X at position 662 is not threonine.

16. The method of claim 14, wherein the polynucleotide encodes a MET10 polypeptide of SEQ ID NO:3, wherein X at position 662 is lysine.

17. The method of claim 14, wherein a fermentation product having no detectable levels of $H_2S$ is produced, wherein the fermentation product is a beverage selected from the group consisting of:
wine, beer, champagne, port and Madeira.

18. The method of claim 17, wherein the yeast cell is a wine yeast strain selected from the group consisting of: Premier Cuveé, French Red, Montrachet, Lallemand K1, and Bordeaux.

19. The method of claim 14, wherein the fermentation medium is selected from the group consisting of: a juice, a must and a wort.

20. The method of claim 14, wherein the fermentation medium is a grape juice must.

21. The method of claim 14, wherein a fermentation product having no detectable levels of $H_2S$ is produced, wherein the fermentation product is a beverage.

22. The method of claim 14, wherein the amino acid at position 662 of the MET10 polypeptide is selected from the group consisting of Ala, Cys, Asp, Glu, Phe, Gly, His, Ile, Lys, Leu, Met, Asn, Pro, Gln, Arg, Val, Trp or Tyr.

23. The method of claim 14, wherein the amino acid at position 662 of the MET10 polypeptide is selected from the group consisting of Lys, Arg, His, Gln, Asn, Glu, Asp, Ile, Leu, Val, Phe, Tyr, or Trp.

24. The method of claim 14, wherein the amino acid at position 662 of the MET10 polypeptide is selected from the group consisting of Lys, Arg, His, Gln or Asn.

25. The method of claim 14, wherein the *Saccharomyces cerevisiae* yeast cell is a methionine prototroph.

* * * * *